(12) United States Patent
Hofmeister et al.

(10) Patent No.: US 6,911,453 B2
(45) Date of Patent: Jun. 28, 2005

(54) SUBSTITUTED 4-PHENYLTETRAHYDROISOQUINOLINIUM, PROCESS FOR THEIR PREPARATION, THEIR USE AS A MEDICAMENT, AND MEDICAMENT CONTAINING THEM

(75) Inventors: Armin Hofmeister, Oppenheim (DE); Uwe Heinelt, Wiesbaden (DE); Hans-Jochen Lang, Hofheim (DE); Markus Bleich, Hünfelden-Dauborn (DE); Klaus Wirth, Kriftel (DE); Michael Gekle, Würzburg (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/309,352

(22) Filed: Dec. 4, 2002

(65) Prior Publication Data

US 2004/0044211 A1 Mar. 4, 2004

Related U.S. Application Data

(60) Provisional application No. 60/353,513, filed on Feb. 1, 2002.

(30) Foreign Application Priority Data

Dec. 5, 2001 (DE) .......................................... 101 59 714

(51) Int. Cl.$^7$ ...................... C07D 217/00; A61K 31/47
(52) U.S. Cl. ...................................... 514/307; 546/144
(58) Field of Search .......................... 546/144; 514/307

(56) References Cited

U.S. PATENT DOCUMENTS 3,666,763 A 5/1972 Grethe et al.

FOREIGN PATENT DOCUMENTS

| EP | 1 113 007 A1 | 7/2001 |
|---|---|---|
| WO | WO01/32624 A1 | 5/2001 |
| WO | WO01/32625 A1 | 5/2001 |
| WO | WO01/79186 A1 | 10/2001 |
| WO | WO 03/000194 | 1/2003 |

OTHER PUBLICATIONS

Freter et al, Journal of Heterocyclic Chemistry, vol. 17, No. 10, pp. 159–169, 1970.*

T. Sattelkau et al., "An Efficient Synthesis of the Potent Dopamine D$_1$ Agonist Dinapsoline by Construction and Selective Reduction of 2'-Azadimethoxybenzanthrone", Synthesis, No. 2, pp. 262–266, (2001).

Esameldin et al., "Alkaloids from *Crinum macowanii*", Biochemical Systematics and Ecology 29, pp. 749–750, 2001.

Ruchirawat et al., "Synthesis of 4–Aryltetrahydroisoquinolines : Application to the Synthesis of Cherylline", Heterocycles, vol. 55, No. 4, pp. 635–640, 2001.

Honda et al., "Palladium–Catalyzed Intramolecular δ–Lactam Formation of Aryl Halides and Amide–Enolates: Syntheses of Cherylline and Latifine", Organic Letters, vol. 3, No. 4, pp. 631–633, 2001.

D.T.A. Youssef, "Further alkaloids from the flowers of *Pancratium maritimum*", Pharmazie, vol. 54, No. 7, pp. 535–537, 1999.

Couture et al., "Base–induced Cyclization of Trimethoxy–o–Aroyldiphenylphosphoryl methylbenzamide : a Formal Synthesis of (±) Cherylline and (±) Cherylline Dimethylether", Tetrahedron Letters, vol. 37, No. 21, pp. 3697–3700, 1996.

Hara et al., "A Novel Ring Cleavage and Recyclization of N–Cyanomethyl–1,2,3,4–tetrahydroisoquinolinium Methiodides: A Biomimetic Synthesis of Litebamine", Tetrahedron vol. 51, No. 37, pp. 10189–10204, 1995.

\* cited by examiner

*Primary Examiner*—Zinna Northington Davis
(74) *Attorney, Agent, or Firm*—Raymond & Parker, III

(57) ABSTRACT

The invention relates to compounds of the formula I

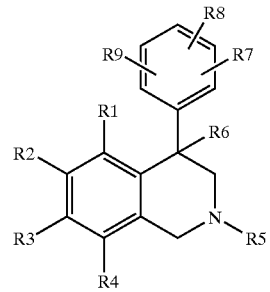

in which R1 to R9 are as defined herein. In one embodiment, these compounds may be used as antihypertensives, for reducing or preventing ischemia-induced damage, as medicaments for surgical intervention for the treatment of ischemias of the nervous system, of stroke and of cerebral edema, of shock, of impaired respiratory drive, for the treatment of snoring, as laxative, as agent against ectoparasites, to prevent the formation of gallstones, as antiatherosclerotics, agents against late complications of diabetes, cancers, fibrotic disorders, endothelial dysfunction, organ hypertrophies and hyperplasias. In one embodiment, the compounds may be inhibitors of the cellular sodium-proton antiporter and influence serum lipoproteins and thus be used for the prophylaxis and for the regression of atherosclerotic lesions.

28 Claims, No Drawings

SUBSTITUTED 4-PHENYLTETRAHYDROISOQUINOLINIUM, PROCESS FOR THEIR PREPARATION, THEIR USE AS A MEDICAMENT, AND MEDICAMENT CONTAINING THEM

This application claims the benefit of foreign priority under 35 U.S.C. §119 of German Patent Application No. 10159714.2, filed on Dec. 5, 2001, the contents of which are incorporated by reference herein, and the benefit of priority of U.S. Provisional Application No. 60/353,513, filed on Feb. 1, 2002.

Substituted 4-phenyltetra hydroisoquinolines, process for their preparation, their use as medicament, and medicament containing them.

The invention relates to compounds of the formula I

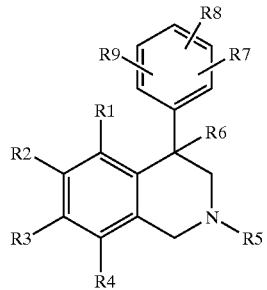

I wherein:

R1, R2, R3 and R4 are independently of one another H, F, Cl, Br, I, CN, $NO_2$, OH, $NH_2$, $C_aH_{2a+1}$, $C_{qq}H_{2qq-1}$, $OC_bH_{2b+1}$, COOR10, OCOR10, COR10 or $O_x$—$(CH_2)_y$-phenyl; wherein
  a and b are independently of one another 1, 2, 3, 4, 5, 6, 7 or 8, wherein the groups $C_aH_{2a+1}$ and $OC_bH_{2b+1}$ independently of one another are unsubstituted or substituted where one or more H atoms are replaced by F atoms;
  qq is 3, 4, 5, 6, 7 or 8, wherein the group CqqH2qq-1 is unsubstituted or substituted where one or more H atoms are replaced by F atoms;
  R10 is H or $C_cH_{2c+1}$;
    c is 1, 2, 3, 4, 5, 6, 7 or 8, wherein the group CcH2c+1 is unsubstituted or substituted where one or more H atoms are replaced by F atoms;
  x is zero or 1;
  y is zero, 1, 2, 3 or 4; where the phenyl ring in the group $O_x$—$(CH_2)_y$— phenyl is unsubstituted or substituted by 1–3 independently chosen from F, Cl, Br, CN, $NO_2$, OH, $NH_2$ and $C_dH_{2d+1}$,
    d is 1, 2, 3 or 4, wherein the group $C_dH_{2d+1}$ is unsubstituted or substituted where one or more H atoms are replaced by F atoms;
or
R1, R2, R3 and R4 are independently of one another chosen from a heteroaryl with at least one heteroatom chosen from 1, 2, 3 or 4 N atoms, 1 oxygen atom and 1 S atom, present as ring atoms; or
R1, R2, R3 and R4 are independently of one another CONR11R12 or NR11R12; wherein
  R11 and R12 are independently of one another H, $C_eH_{2e+1}$, $C_{rr}H_{2rr-1}$;
    e is 1, 2, 3, 4, 5, 6, 7 or 8;
    rr is 3, 4, 5, 6, 7, or 8, wherein the groups $C_eH_{2e+1}$ and $C_{rr}H_{2rr-1}$ independently of one another are unsubstituted or substituted where one or more H atoms are replaced by F atoms and/or one or more $CH_2$ groups are replaced by O or NR13;
    R13 is H or $C_fH_{2f+1}$;
      f is 1, 2, 3 or 4, wherein the group $C_fH_{2f+1}$ is unsubstituted or substituted where one or more H atoms are replaced by F atoms;
    or
    R13 and a $CH_2$ group of R11 or R12 together with the N atom to which they are bonded form a 5- or 6-membered ring;
  or
  R11 and R12 together with the N atom to which they are bonded form a 5-, 6- or 7-membered ring; or
  R11 and R12 are independently of one another COR14, CSR14 or $SO_2$R14; wherein
    R14 is $C_gH_{2g+1}$;
      g is 1, 2, 3, 4, 5, 6, 7 or 8, wherein the group $C_gH_{2g+1}$ is unsubstituted or substituted where one or more H atoms are replaced by F atoms, and/or one or more $CH_2$ groups are replaced by O or NR13;
or
R1, R2, R3 and R4 are independently of one another —$O_h$—$SO_j$—R15, with
  h is zero or 1;
  j is zero, 1 or 2;
  R15 is $C_kH_{2k+1}$, OH, $OC_lH_{2l+1}$ or NR17R18;
    k is 1, 2, 3, 4, 5, 6, 7 or 8, wherein the group $C_kH_{2k+1}$ is unsubstituted or substituted where one or more H atoms are replaced by F atoms;
    l is 1, 2, 3, 4, 5, 6, 7 or 8, wherein the group $OC_lH_{2l+1}$ is unsubstituted or substituted where one or more H atoms are replaced by F atoms;
    R17 and R18 are independently of one another H or $C_mH_{2m+1}$;
      m is 1, 2, 3, 4, 5, 6, 7 or 8, wherein the group $C_mH_{2m+1}$ is unsubstituted or substituted where one or more H atoms is replaced by F atoms and/or one or more $CH_2$ groups are replaced by O, CO, CS or NR19;
        R19 is H or $C_nH_{2n+1}$;
          n is 1, 2, 3 or 4, wherein the group $C_nH_{2n+1}$ is unsubstituted or substituted where one or more H atoms are replaced by F atoms; or
        R19 and a $CH_2$ group of R17 or R18 together with the N atom to which they are bonded form a 5- or 6-membered ring;
      or
    R17 and R18 together with the N atom to which they are bonded form a 5-, 6- or 7-membered ring;
but where R2 does not equal H in any of the foregoing definitions, R5 is H, $C_pH_{2p+1}$, $C_{ss}H_{2ss-1}$, COR20 or $SO_2$R20; wherein
  p is 1, 2, 3, 4, 5, 6, 7 or 8,
  ss is 3, 4, 5, 6, 7 or 8,
  R20 is $C_qH_{2q+1}$;
    q is 1, 2, 3, 4, 5, 6, 7 or 8, wherein the groups $C_pH_{2p+1}$, $C_{ss}H_{2ss-1}$ and $C_qH_{2q+1}$ independently of one another are unsubstituted or substituted where one or more H atoms are replaced by F atoms and/or one or more $CH_2$ groups are replaced by O or NR21;
    R21 is H or $C_rH_{2r+1}$;
      r is 1, 2, 3 or 4; wherein the group $C_rH_{2r+1}$ is unsubstituted or substituted where one or more H atoms are replaced by F atoms;

R6 is H, F, Cl, Br, I, $C_sH_{2s+1}$, $C_{dd}H_{2dd-1}$, OH, $OC_tH_{2t+1}$ or OCOR22; wherein s and t are independently of one another 1, 2, 3, 4, 5, 6, 7 or 8;

dd is 3, 4, 5, 6, 7 or 8, wherein the groups $C_sH_{2s+1}$, $C_{dd}H_{2dd-1}$ and $OC_tH_{2t+1}$ independently of one another are unsubstituted or substituted where one or more H atoms are replaced by F atoms;

R22 is $C_uH_{2u+1}$;
 u 1, 2, 3 or 4, wherein the group $C_uH_{2u+1}$ is unsubstituted or substituted where one or more H atoms are replaced by F atoms;

R7, R8 and R9 are independently of one another —$O_v$—$SO_w$—R23; wherein
 v is zero or 1;
 w is zero, 1 or 2;
 R23 is $C_{nn}H_{2nn+1}$, $C_{mm}H_{2mm-1}$, OH, $OC_{pp}H_{2pp+1}$ or NR25R26;
  nn and pp are independently of one another 1, 2, 3, 4, 5, 6, 7 or 8,
  mm is 3, 4, 5, 6, 7 or 8, wherein the groups $C_{nn}H_{2nn+1}$, $C_{mm}H_{2mm-1}$ and $OC_{pp}H_{2pp+1}$ independently of one another are unsubstituted or substituted where one or more H atoms are replaced by F atoms;
 R25 and R26 are independently of one another H, CN, $C_zH_{2z+1}$, or $C_{zz}H_{2zz-1}$;
  z is 1, 2, 3, 4, 5, 6, 7 or 8;
  zz is 3, 4, 5, 6, 7 or 8, wherein the group $C_zH_{2z+1}$ is unsubstituted or substituted where one or more H atoms are replaced by F atoms and,
   wherein the group $C_zH_{2z+1}$, is unsubstituted or substituted where one or more H atoms are replaced by F atoms and/or one or more $CH_2$ groups are replaced by O, CO, CS or NR27;
  R27 is H or $C_{aa}H_{2aa+1}$;
   aa is 1, 2, 3 or 4, wherein the group $C_{aa}H_{2aa+1}$ is unsubstituted or substituted where one or more H atoms are replaced by F atoms;
  or
  R27 and a $CH_2$ group of R25 or R26 together with the N atom to which they are bonded form a 5- or 6-membered ring;
 or
 R25 and R26 together with the N atom to which they are bonded form a 5-, 6- or 7-membered ring;
or
R7, R8 and R9 are independently of one another NR32COR30, NR32CSR30 or NR32SO$_{bb}$R30;
 R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
 R32 and R33 are independently of one another H or $C_hH_{2h+1}$;
 bb is 2 or 3;
 cc is 1, 2, 3, 4, 5, 6, 7 or 8;
 yy is 3, 4, 5, 6, 7 or 8;
 h is 1, 2, 3, 4, 5, 6, 7 or 8,
 wherein the group $C_hH_{2h+1}$ is unsubstituted or substituted where one or more H atoms are replaced by F atoms, and
 wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group are replaced by O;
 R31 is H, $C_{kk}H_{2kk+1}$, COR65 or $SO_2$ R65;
  kk is 1, 2, 3, or 4; wherein the group $C_{kk}H_{2kk+1}$ is unsubstituted or substituted where one or more H atoms are replaced by F atoms,
  R65 is H, or $C_{xx}H_{2xx+1}$;
   xx is 1, 2, 3 or 4, wherein the group $C_{xx}H_{2xx+1}$ is unsubstituted or substituted where one or more H atoms are replaced by F atoms;
 or
 R31 together with a $CH_2$ group of R30 forms a 5-, 6- or 7-membered ring; or
 R30 is a 5- or 6-membered heteroaryl with at least one hetero atom chosen from 1, 2, 3 or 4 N atoms, zero, 1 S atom and 1 O atom, which is unsubstituted or substituted by up to three substituents chosen from F, Cl, Br, I, $C_{oo}H_{2oo+1}$, and NR70R71;
 R70 and R71 are independently of one another H, $C_{uu}H_{2uu+1}$ or COR72;
 R72 is H, or $C_{vv}H_{2vv+1}$;
 oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;
or
R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42,
 ee and ff are independently of one another 1, 2, 3, 4, 5, 6, 7 or 8;
 ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
 R40 and R41 are independently of one another H, $C_{tt}H_{2tt+1}$ or $C(NH)NH_2$;
  tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;
  R44 is H or $C_{gg}H_{2gg+1}$;
   gg is 1, 2, 3, 4, 5, 6, 7 or 8, wherein the group $C_{gg}H_{2gg+1}$ is unnsubstituted or substituted where one or more H atoms are replaced by F atoms
  or
  R44 forms a 5- or 6-membered ring together with a ($CH_2$) group of R40 or R41 and the N atom to which they are bound;
 or
 R40 and R41 with the N atom to which they are bonded form a 5- or 6-membered ring;
 R42 is H or $C_{hh}H_{2hh+1}$;
  hh is 1, 2, 3, 4, 5, 6, 7 or 8, wherein the group $C_{hh}H_{2hh+1}$ is unnsubstituted or substituted where one or more H atoms are replaced by F atoms;
with the proviso that two substituents chosen from the group R7, R8 and R9 can not simultaneously be OH and $OCH_3$, and that at least one of the substituents R7, R8 and R9 is chosen from CONR40R41, —$O_v$—$SO_w$—R23, NR32COR30, NR32CSR30 and NR32SO$_{bb}$R30;
and the pharmaceutically acceptable salts and trifluoroacetates thereof.

In another embodiment, compounds of the formula I are chosen from:
 R1, R2, R3 and R4 are independently of one another, H, F, Cl, Br, I, CN, $NO_2$, OH, $NH_2$, $C_aH_{2a+1}$, cycloalkyl with 3, 4, 5 or 6 C atoms, $OC_bH_{2b+1}$, or COOR10; wherein a and b are independently of one another 1, 2, 3 or 4, wherein the group $C_aH_{2a+1}$ is unsubstituted or substituted where one or more H atoms are replaced by F atoms;

R10 is H or $C_cH_{2c+1}$;

c is 1, 2, 3 or 4, wherein the group $C_cH_{2c+1}$ is unsubstituted or substituted where one or more H atoms are replaced by F atoms; or R1, R2, R3 and R4 are independently of one another a 5- or 6-membered heteroaryl choawn from pyridyl, imidazolyl, pyrazolyl, pyrrolyl, triazolyl, tetrazolyl, thiazolyl and oxazolyl; or R1, R2, R3 and R4 are independently of one another CONR11R12 or NR11R12; wherein R11 and R12 are independently of one another H, $C_eH_{2e+1}$, $C_{rr}H_{2rr-1}$;

e is 1, 2, 3 or 4, rr is 3, 4, 5 or 6, wherein the groups $C_eH_{2e+1}$ and $C_{rr}H_{2rr-1}$ independently of one another are unsubstituted or substituted where one or more H atoms are replaced by F atoms;

or

R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R11 and R12 together with the N atom to which they are bonded form a pyrrolidine, piperidine, N-methylpiperazine, piperazine or morpholine ring; or R11 and R12 are independently of one another COR14, CSR14, CONHR14, CSNHR14 or $SO_2R14$; wherein R14 is $C_gH_{2g+1}$;

g is 1, 2, 3 or 4, wherein the group $C_gH_{2g+1}$ is unsbustituted or substituted where one or more H atoms are replaced by F atoms;

or

R1, R2, R3 and R4 are independently of one another $OSO_3H$, $SO_3H$, $SO_2R_{15}$; wherein R15 is $C_kH_{2k+1}$, $OC_lH_{2l+1}$ or NR17R18;

k is 1, 2, 3 or 4, wherein the group $C_kH_{2k+1}$ is unsubstituted or substituted where one ore more H atoms are replaced by F atoms;

l is 1, 2, 3 or 4, wherein the group $OC_lH_{2l+1}$ is unsubstituted or substituted where one or more H atoms are replaced by F atoms;

R17 and R18 are independently of one another H, or $C_mH_{2m+1}$, in which the first $CH_2$ group bonded to the nitrogen of NR17R18 is replaced by CO and the second $CH_2$ group is replaced by NR19;

m 1, 2, 3, 4 or 5, wherein the group $C_mH_{2m+1}$ is unsubstituted or substituted where one or more H atoms is replaced by F atoms;

R19 is H or $C_nH_{2n+1}$;

n is 1, 2, 3 or 4, wherein the group $C_nH_{2n+1}$ is unsubstituted or substituted where one or more H atoms is replaced by F atoms;

or

R17 and R18 together with the N atom to which they are bonded form a 5- or 6-membered ring;

but where R2 does not equal H in any of the foregoing definitions,

R5 is H, or $C_pH_{2p+1}$;

p is 1, 2, 3 or 4, wherein the group $C_pH_{2p+1}$ is unsubstituted or substituted where one or more H atoms is replaced by F atoms;

R6 is H, $C_sH_{2s+1}$, $OC_tH_{2t+1}$ or OCOR22;

s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;

R22 is $C_uH_{2u+1}$;

u is 1, 2, 3 or 4; wherein the group $C_uH_{2u+1}$ is unsubstituted or substituted where one or more H atoms is replaced by F atoms;

R7, R8 and R9 are independently of one another $OSO_3H$, $SO_3H$ or $SO_2R23$; wherein R23 is $C_{nn}H_{2nn+1}$, $C_{mm}H_{2mm-1}$, $OC_{pp}H_{2pp+1}$ or NR25R26;

nn and pp are independently of one another 1, 2, 3, 4 or 5, mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;

R25 and R26 are independently of one another H, CN, or $C_zH_{2z+1}$, in which a first $CH_2$ group bonded to the nitrogen of NR25R26 is replaced by CO or CS and a second $CH_2$ is replaced by NR27;

z is 1, 2, 3, 4, 5 or 6; wherein the group $C_zH_{2z+1}$ is unsubstituted or substituted where one or more H atoms are replaced by F atoms;

R27 is H or $C_{aa}H_{2aa+1}$;

aa is 1, 2, 3 or 4, wherein the group $C_{aa}H_{2aa+1}$ is unsubstituted or substituted where one or more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5- or 6-membered ring;

or

R7, R8 and R9 are independently of one another NR32COR30, NR32CSR30 or $NR32SO_2R30$; wherein R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;

cc is 1, 2, 3, 4, 5, 6, 7 or 8;

yy is 3, 4, 5 or 6;

h is 1, 2, 3 or 4; wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups to be replaced by NR31 and/or one $CH_2$ group to be replaced by O;

R31 is H, $C_{kk}H_{2kk+1}$, COR65 or $SO_2$ R65;

kk is 1, 2, 3, or 4, wherein the group $C_{kk}H_{2kk+1}$ is unsubstituted or substituted where one or more H atoms are replaced by F atoms, R65 is H, or $C_{xx}H_{2xx+1}$;

xx is 1, 2, 3 or 4, wherein the group $C_{xx}H_{2xx+1}$ is unsubstituted where one or more H atoms are replaced by F atoms;

or

R31 together with a $CH_2$ group of R30 and the N atom to which they are jointly bonded form form a 5- or 6-membered ring; or R30 is a 5- or 6-membered heteroaryl chosen from pyridyl, imidazolyl, pyrazolyl, pyrrolyl, triazolyl, tetrazolyl, thienyl, thiazolyl and oxazolyl, which is unsubstituted or substituted by up to three substituents chosen from F, Cl, Br, I, $C_{oo}H_{2oo+1}$, and NR70R71,
R70 and R71 are independently of one another H, $C_{uu}H_{2uu+1}$ or COR72;
R72 is H, or $C_{vv}H_{2vv+1}$;
oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;

or

R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;
ee and ff are independently of one another 1, 2, 3 or 4;
ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are independently of one another H, $C_{tt}H_{2tt+1}$, or $C(NH)NH_2$;
tt is 1, 2, 3, 4, 5, 6, 7 or 8, wherein the group $C_{tt}H_{2tt+1}$ is unsubstituted or substituted where one or more H atoms are replaced by F atoms;

or

R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl; or
R40 and R41 together with the N atom to which they are bonded form a ring chosen from pyrrolidine, piperidine, N-methylpiperazine, piperazine and morpholine;
R42 is H or $C_{hh}H_{2hh+1}$;
hh is 1, 2, 3 or 4, wherein the group $C_{hh}H_{2hh+1}$ is unsubstituted or substituted where one or more H atoms are replaced by F atoms;
with the proviso that two substituents chosen from the group R7, R8 and R9 can not simultaneously be OH and $OCH_3$, and that at least one of the substituents R7, R8 and R9 is chosen from CONR40R41, $—O_y—SO_w—R^{23}$, NR32COR30, NR32CSR30 and $NR32SO_{bb}R30$;
and the pharmaceutically acceptable salts and trifluoroacetates thereof.

In another embodiment, compounds of the formula I are chosen from:
R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein
a and b are independently of one another 1, 2, 3 or 4, wherein the groups $C_aH_{2a+1}$ and $OC_bH_{2b+1}$ independenly of one another are unsubstituted or substituted where one or more H atoms are replaced by F atoms;

or

R1, R2, R3 and R4 are independently of one another NR11R12;
R11 and R12 are independently of one another H, $C_eH_{2e+1}$, or $C_{rr}H_{2rr-1}$;
e is 1, 2, 3 or 4,
rr is 3, 4, 5 or 6, wherein the groups $C_eH_{2e+1}$ and $C_{rr}H_{2rr-1}$ independenly of one another are unsubtituted or substituted where one or more H atoms are replaced by F atoms;

or

R11 and R12 together with the N atom to which they are bonded form a ring chosen from pyrrolidine, piperidine, N-methylpiperazine, piperazine and morpholine; or
R11 and R12 are independently of one another COR14, CSR14, CONHR14, CSNHR14 or $SO_2R14$; wherein
R14 is $C_gH_{2g+1}$;
g is 1, 2, 3 or 4, wherein the group $C_gH_{2g+1}$ is unsubstituted or substituted where one or more H atoms are replaced by F atoms;

or

R1, R2, R3 and R4 are independently of one another $OSO_3H$, $SO_3H$, or $SO_2R15$;
R15 is $C_kH_{2k+1}$ or NR17R18;
k is 1, 2, 3 or 4, wherein the group $C_kH_{2k+1}$ is unsubstituted or substituted where one or more H atoms are replaced by F atoms;
R17 and R18 are independently of one another H or $C_mH_{2m+1}$;
m is 1, 2, 3, 4 or 5, wherein the group $C_mH_{2m+1}$ is unsubstituted or substituted where one ore more H atoms are replaced by F atoms;

or

R17 and R18 together with the N atom to which they are bonded form a 5- or 6-membered ring;
but where R2 does not equal H in any of the foregoing definitions;
R5 is methyl or trifluoromethyl;
R6 is H;
R7, R8 and R9 are independently of one another $OSO_3H$, $SO_3H$ or $SO_2R23$; wherein
R23 is $C_{nn}H_{2nn+1}$ or NR25R26;
nn is 1, 2, 3, 4 or 5, wherein the group $C_{nn}H_{2nn+1}$ is unsubstituted or substituted where one ore more H atoms are replaced by F atoms;
R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;
z is 1, 2, 3, 4, 5 or 6, wherein the group $C_zH_{2z+1}$ is unsubstituted or substituted where one ore more H atoms are replaced by F atoms;
R27 is H or $C_{aa}H_{2aa+1}$;
aa is 1, 2, 3 or 4, wherein the group $C_{aa}H_{2aa+1}$ is unsubstituted or substituted where one ore more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5- or 6-membered ring, or R7, R8 and R9 are independently of one another NR32COR30, NR32CSR30 or $NR32SO_2R30$;
R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
R32 and R33 are H, methyl or $CF_3$;
cc is 1, 2, 3, 4, 5, 6, 7 or 8;
yy is 3, 4, 5 or 6; wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group is replaced by O R31 is H, methyl, ethyl, $CF_3$, $CH_2CF_3$, acetyl or propionyl, methanesulfonyl or ethanesulfonyl; or R31 together with a $CH_2$ group of R30 and the N atom to which they are jointly bonded form a 5- or 6-membered ring;

or

R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl;

or

R7, R8 and R9 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;
ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are H, $C_{tt}H_{2tt+1}$ or $C(NH)NH_2$;
tt is 1, 2, 3 or 4, wherein the group $C_{tt}H_{2tt+1}$ is unsubstituted or substituted where one or more H atoms are replaced by F atoms;

or

R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;

R42 is H or $C_{hh}H_{2hh+1}$;
hh is 1, 2, 3 or 4, wherein the $C_{hh}H_{2hh+1}$ is unsubstituted or substituted where one or more H atoms are replaced by F atoms;

with the proviso that two substituents chosen from the group R7, R8 and R9 can not simultaneously be OH and $OCH_3$, and that at least one of the substituents R7, R8 and R9 is chosen from CONR40R41, $—O_v—SO_w—R^{23}$, NR32COR30, NR32CSR30 and $NR32SO_{bb}R30$;

and the pharmaceutically acceptable salts and trifluoroacetates thereof.

In another embodiment, compounds of the formula I are chosen from:

R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$;

a and b are independently of one another 1, 2, 3 or 4, wherein the groups $C_aH_{2a+1}$ and $OC_bH_{2b+1}$ independently of one another are unsubstituted or substituted where one or more H atoms to be replaced by F atoms;

or

R1, R2, R3 and R4 are independently of one another NR11R12; wherein

R11 and R12 are independently of one another H, $C_eH_{2e+1}$, or $C_rH_{2rr-1}$;
e is 1, 2, 3 or 4,
rr is 3, 4, 5 or 6, wherein the groups $C_eH_{2e+1}$ and $C_{rr}H_{2rr-1}$ independently of one another are unsubstituted or substituted where one or more H atoms are replaced by F atoms;

or

R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or $SO_2R14$;

R14 is $C_gH_{2g+1}$;
g is 1, 2, 3 or 4, wherein the group $C_gH_{2g+1}$ is unsubstituted or substituted where one or more H atoms to be replaced by F atoms;

or

R1, R2, R3 and R4 are independently of one another $OSO_3H$, $SO_3H$, or $SO_2R15$; wherein R15 is $C_kH_{2k+1}$ or NR17R18;
k is 1, 2, 3 or 4, wherein the group $C_kH_{2k+1}$ is unsubstituted or substituted where one or more H atoms to be replaced by F atoms;

R17 and R18 are independently of one another H or $C_mH_{2m+1}$;
m is 1, 2, 3, 4 or 5, wherein the group $C_mH_{2m+1}$ is unsubstituted or substituted where one or more H atoms to be replaced by F atoms;

or

R17 and R18 together with the N atom to which they are bonded form a 5- or 6-membered ring;

but where R2 does not equal H in any of the foregoing definitions,

R5 is methyl or trifluoromethyl;
R6 is H;
R7, R8 and R9 are independently of one another $OSO_3H$, $SO_3H$ or $SO_2R23$;

R23 is $C_{nn}H_{2nn+1}$ or NR25R26;
nn is 1, 2, 3, 4 or 5, wherein the group $C_{nn}H_{2nn+1}$ is unsubstituted or substituted where one or more H atoms to be replaced by F atoms;

R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;
z is 1, 2, 3, 4, 5 or 6, wherein the group $C_zH_{2z+1}$ is unsubstituted or substituted where one or more H atoms to be replaced by F atoms;

R27 is H or $C_{aa}H_{2aa+1}$;
aa is 1, 2, 3 or 4, wherein the group $C_{aa}H_{2aa+1}$ is unsubstituted or substituted where one or more H atoms to be replaced by F atoms;

or

R27 and a $CH_2$ group of R25 or R26 together with the N atom to which they are bonded form a 5- or 6-membered ring; or R25 and R26 together with the N atom to which they are bonded form a 5- or 6-membered ring, or R7, R8 and R9 are independently of one another NR32COR30, NR32CSR30 or $NR32SO_2R30$;

R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H, methyl or $CF_3$;

cc is 1, 2, 3, 4, 5, 6, 7 or 8;
yy is 3, 4, 5 or 6; wherein wherein the groups $C_{cc}CH_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group are replaced by O;

R31 is H, methyl, ethyl, $CF_3$, $CH_2CF_3$, acetyl or propionyl, methanesulfonyl or ethanesulfonyl; or R31 together with a $CH_2$ group of R30 and the N atom to which they are jointly bonded form a 5- or 6-membered ring;

or

R30 is pyridyl, imidazolyl, pyrazolyl, pyrrolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl;

or

R7, R8 and R9 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;
ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms to be replaced by F atoms;

R40 and R41 is H, $C_{tt}H_{2tt+1}$ or $C(NH)NH_2$;
tt is 1, 2, 3 or 4, wherein the group $C_{tt}H_{2tt+1}$ is unsubstituted or substituted where one or more H atoms to be replaced by F atoms;

or

R40 and R41 are independently of one another hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;

R42 is H or $C_{hh}H_{2hh+1}$;
hh is 1, 2, 3 or 4, wherein the group $C_{hh}H_{2hh+1}$ is unsubstituted or substituted where one or more H atoms to be replaced by F atoms;

with the proviso that two substituents chosen from the group R7, R8 and R9 can not simultaneously be OH and $OCH_3$, and that at least one of the substituents R7, R8 and R9 is chosen from —$O_v$—$SO_w$— R23, NR32COR30, NR32CSR30 and NR32SO$_{bb}$R30;

and the pharmaceutically acceptable salts and trifluoroacetates thereof.

In another embodiment, compounds of the invention are chosen from the following:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-N,N-dimethyl-benzenesulfonamide;
5) 4-(4-bromo-phenyl)-6,8-dichloro-2-methyl-1,2,3,4-tetrahydroisoquinoline;
6) 4-(6,8-dichloro-2-methyl-1,2,3,4-tetrahydro-isoquinolin-4-yl)-benzoic acid;
7) 4-(6,8-dichloro-2-methyl-1,2,3,4-tetrahydroisoquinolin-4-yl)-N-ethyl-benzamide;
8) 4-(6,8-dichloro-2-methyl-1,2,3,4-tetrahydroisoquinolin-4-yl)-N-propyl-benzamide;
9) 4-(6,8-dichloro-2-methyl-1,2,3,4-tetrahydro-isoquinolin-4-yl)-N-(2-dimethylamino-ethyl)-benzamide;
10) 6,8-dichloro-2-methyl-4-(4-morpholin-4-yl-phenyl)-1,2,3,4-tetrahydroisoquinoline;
11) [4-(6,8-dichloro-2-methyl-1,2,3,4-tetrahydroisoquinolin-4-yl)-phenyl]-diethyl-amine
12) 6,8-dichloro-2-methyl-4-(4-piperidin-1-yl-phenyl)-1,2,3,4-tetrahydroisoquinoline;
13) 6,8-dichloro-2-methyl-4-(4-pyrrolidin-1-yl-phenyl)-1,2,3,4-tetrahydroisoquinoline;
14) 6,8-dichloro-2-methyl-4-[4-(4-methyl-piperazin-1-yl)-phenyl]-1,2,3,4-tetrahydro-isoquinoline;
15) 6,8-dichloro-2-cyclopropyl-4-phenyl-1,2,3,4-tetrahydroisoquinoline;
16) 4-(6,8-dichloro-2-methyl-1,2,3,4-tetrahydro-isoquinolin-4-yl)-phenylamine;
17) 1-[4-(6,8-dichloro-2-methyl-1,2,3,4-tetrahydroisoquinolin-4-yl)-phenyl]-3-propylurea;
18) 1-[4-(6,8-dichloro-2-methyl-1,2,3,4-tetrahydroisoquinolin-4-yl)-phenyl]-3-methyl-thiourea;
19) 1-[4-(6,8-dichloro-2-methyl-1,2,3,4-tetrahydroisoquinolin-4-yl)-phenyl]-3-ethyl-urea;
20) N-[4-(6-methanesulfonyl-2-methyl-1,2,3,4-tetrahydroisoquinolin-4-yl)-phenyl]-acetamide;
21) N-[4-(2,6,8-trimethyl-1,2,3,4-tetrahydro-isoquinolin-4-yl)-phenyl]-acetamide;
22) N-[4-(6-bromo-8-chloro-2-methyl-1,2,3,4-tetrahydroisoquinolin-4-yl)-phenyl]-acetamide;
23) N-[4-(8-chloro-2-methyl-6-pyrrolidin-1-yl-1,2,3,4-tetrahydro-isoquinolin-4-yl)-phenyl]-acetamide;
24) N-[4-(8-chloro-2-methyl-6-morpholin-4-yl-1,2,3,4-tetrahydro-isoquinolin-4-yl)-phenyl]-acetamide;
25) N-{4-[8-chloro-2-methyl-6-(4-methyl-piperazin-1-yl)-1,2,3,4-tetrahydro-isoquinolin-4-yl]-phenyl}-acetamide;
26) N-{4-[8-chloro-6-(cyclopropylmethyl-amino)-2-methyl-1,2,3,4-tetrahydro-isoquinolin-4-yl]-phenyl}-acetamide;
27) 5-(6,8-dichloro-2-methyl-1,2,3,4-tetrahydro-isoquinolin-4-yl)-2-hydroxy-benzoic acid;
28) 5-(6,8-dichloro-2-methyl-1,2,3,4-tetrahydro-isoquinolin-4-yl)-2-hydroxy-N-methyl-benzamide;
29) 5-(6,8-dichloro-2-methyl-1,2,3,4-tetrahydro-isoquinolin-4-yl)-N-ethyl-2-hydroxy-benzamide;
30) 5-(6,8-dichloro-2-methyl-1,2,3,4-tetrahydro-isoquinolin-4-yl)-N-(2-dimethylamino-ethyl)-2-hydroxy-benzamide;
31) N-[5-(6,8-dichloro-2-methyl-1,2,3,4-tetrahydro-isoquinolin-4-yl)-2-hydroxy-benzoyl]-guanidine;
32) N-[3-(6,8-dichloro-2-methyl-1,2,3,4-tetrahydro-isoquinolin-4-yl)-phenyl]-acetamide;
33) 3-(6,8-dichloro-2-methyl-1,2,3,4-tetrahydro-isoquinolin-4-yl)-phenylamine;
34) 2-(6,8-dichloro-2-methyl-1,2,3,4-tetrahydro-isoquinolin-4-yl)-phenylamine;
35) N-[4-(6,8-dichloro-2-methyl-1,2,3,4-tetrahydro-isoquinolin-4-yl)-phenyl]-propionamide;
36) N-[4-(6,8-dichloro-2-methyl-1,2,3,4-tetrahydro-isoquinolin-4-yl)-phenyl]-butyramide;
37) N-[4-(6,8-dichloro-2-methyl-1,2,3,4-tetrahydro-isoquinolin-4-yl)-phenyl]pentanamide;
38) N-[4-(6,8-dichloro-2-methyl-1,2,3,4-tetrahydro-isoquinolin-4-yl)-phenyl]-isobutyramide;
39) N-[4-(6,8-dichloro-2-methyl-1,2,3,4-tetrahydro-isoquinolin-4-yl)-phenyl]-2,2-dimethyl-propionamide;
40) N-[4-(6,8-dichloro-2-methyl-1,2,3,4-tetrahydro-isoquinolin-4-yl)-phenyl]-cyclopropanecarboxamide;
41) N-[4-(6,8-dichloro-2-methyl-1,2,3,4-tetrahydro-isoquinolin-4-yl)-phenyl]-cyclobutanecarboxamide;

42) N-[4-(6,8-dichloro-2-methyl-1,2,3,4-tetrahydro-isoquinolin-4-yl)-phenyl]-cyclopentanecarboxamide;
43) N-[4-(6,8-dichloro-2-methyl-1,2,3,4-tetrahydro-isoquinolin-4-yl)-phenyl]-2,2,2-trifluoro-acetamide;
44) N-[4-(6,8-dichloro-2-methyl-1,2,3,4-tetrahydro-isoquinolin-4-yl)-phenyl]-1-acetylpiperidine-4-carboxamide;
45) N-[4-(6,8-dichloro-2-methyl-1,2,3,4-tetrahydro-isoquinolin-4-yl)-phenyl]-nicotinamide;
46) N-[4-(6,8-dichloro-2-methyl-1,2,3,4-tetrahydro-isoquinolin-4-yl)-phenyl]-methane-sulfonamide;
47) N-[4-(6,8-dichloro-2-methyl-1,2,3,4-tetrahydro-isoquinolin-4-yl)-phenyl]-ethanesulfonamide;
48) N',N'-dimethylamino-N-[4-(6,8-dichloro-2-methyl-1,2,3,4-tetrahydro-isoquinolin-4-yl)-phenyl]-sulfamide;
49) N-[3-(6,8-dichloro-2-methyl-1,2,3,4-tetrahydro-isoquinolin-4-yl)-phenyl]-propionamide;
50) N-[3-(6,8-dichloro-2-methyl-1,2,3,4-tetrahydro-isoquinolin-4-yl)-phenyl]-butyramide;
51) N-[3-(6,8-dichloro-2-methyl-1,2,3,4-tetrahydro-isoquinolin-4-yl)-phenyl]-pentanamide;
52) N-[3-(6,8-dichloro-2-methyl-1,2,3,4-tetrahydro-isoquinolin-4-yl)-phenyl]-isobutyramide;
53) N-[3-(6,8-dichloro-2-methyl-1,2,3,4-tetrahydro-isoquinolin-4-yl)-phenyl]-2,2-dimethyl-propionamide;
54) N-[3-(6,8-dichloro-2-methyl-1,2,3,4-tetrahydro-isoquinolin-4-yl)-phenyl]-cyclopropanecarboxamide;
55) N-[3-(6,8-dichloro-2-methyl-1,2,3,4-tetrahydro-isoquinolin-4-yl)-phenyl]-cyclobutanecarboxamide;
56) N-[3-(6,8-dichloro-2-methyl-1,2,3,4-tetrahydro-isoquinolin-4-yl)-phenyl]-cyclopentanecarboxamide;
57) N-[3-(6,8-dichloro-2-methyl-1,2,3,4-tetrahydro-isoquinolin-4-yl)-phenyl]-2,2,2-trifluoro-acetamide;
58) N-[3-(6,8-dichloro-2-methyl-1,2,3,4-tetrahydro-isoquinolin-4-yl)-phenyl]-1-acetylpiperidine-4-carboxamide;
59) N-[3-(6,8-dichloro-2-methyl-1,2,3,4-tetrahydro-isoquinolin-4-yl)-phenyl]-nicotinamide;
60) N-[3-(6,8-dichloro-2-methyl-1,2,3,4-tetrahydro-isoquinolin-4-yl)-phenyl]-methane-sulfonamide;
61) N-[3-(6,8-dichloro-2-methyl-1,2,3,4-tetrahydro-isoquinolin-4-yl)-phenyl]-ethanesulfonamide;
62) N',N'-dimethylamino-N-[3-(6,8-dichloro-2-methyl-1,2,3,4-tetrahydro-isoquinolin-4-yl)-phenyl]-sulfamide;
63) N-[2-(6,8-dichloro-2-methyl-1,2,3,4-tetrahydro-isoquinolin-4-yl)-phenyl]-propionamide;
64) N-[2-(6,8-dichloro-2-methyl-1,2,3,4-tetrahydro-isoquinolin-4-yl)-phenyl]-butyramide;
65) N-[2-(6,8-dichloro-2-methyl-1,2,3,4-tetrahydro-isoquinolin-4-yl)-phenyl]-pentanamide;
66) N-[2-(6,8-dichloro-2-methyl-1,2,3,4-tetrahydro-isoquinolin-4-yl)-phenyl]-isobutyramide;
67) N-[2-(6,8-dichloro-2-methyl-1,2,3,4-tetrahydro-isoquinolin-4-yl)-phenyl]-2,2-dimethyl-propionamide;
68) N-[2-(6,8-dichloro-2-methyl-1,2,3,4-tetrahydro-isoquinolin-4-yl)-phenyl]-cyclopropanecarboxamide;
69) N-[2-(6,8-dichloro-2-methyl-1,2,3,4-tetrahydro-isoquinolin-4-yl)-phenyl]-cyclobutanecarboxamide;
70) N-[2-(6,8-dichloro-2-methyl-1,2,3,4-tetrahydro-isoquinolin-4-yl)-phenyl]-cyclopentanecarboxamide;
71) N-[2-(6,8-dichloro-2-methyl-1,2,3,4-tetrahydro-isoquinolin-4-yl)-phenyl]-2,2,2-trifluoro-acetamide;
72) N-[2-(6,8-dichloro-2-methyl-1,2,3,4-tetrahydro-isoquinolin-4-yl)-phenyl]-1-acetylpiperidine-4-carboxamide;
73) N-[2-(6,8-Dichloro-2-methyl-1,2,3,4-tetrahydro-isoquinolin-4-yl)-phenyl]-methane-sulfonamide;
74) N-[2-(6,8-dichloro-2-methyl-1,2,3,4-tetrahydro-isoquinolin-4-yl)-phenyl]-ethanesulfonamide;
75) N',N'-dimethylamino-N-[2-(6,8-dichloro-2-methyl-1,2,3,4-tetrahydro-isoquinolin-4-yl)-phenyl]-sulfamide;
76) 1-[3-(6,8-dichloro-2-methyl-1,2,3,4-tetrahydro-isoquinolin-4-yl)-phenyl]-3-ethyl-urea;
77) 1-[3-(6,8-dichloro-2-methyl-1,2,3,4-tetrahydro-isoquinolin-4-yl)-phenyl]-3-methyl-thiourea;
78) 1-[2-(6,8-dichloro-2-methyl-1,2,3,4-tetrahydro-isoquinolin-4-yl)-phenyl]-3-ethyl-urea;
79) 1-[2-(6,8-dichloro-2-methyl-1,2,3,4-tetrahydro-isoquinolin-4-yl)-phenyl]-3-methyl-thiourea;
80) N-{5-[4-(6,8-dichloro-2-methyl-1,2,3,4-tetrahydro-isoquinolin-4-yl)-phenylsulfamoyl]-4-methyl-thiazol-2-yl}-acetamide;
81) N-{5-[3-(6,8-dichloro-2-methyl-1,2,3,4-tetrahydro-isoquinolin-4-yl)-phenylsulfamoyl]-4-methyl-thiazol-2-yl}-acetamide;
82) N-[4-(6,8-dichloro-2-methyl-1,2,3,4-tetrahydro-isoquinolin-4-yl)-phenyl]-1,2-dimethyl-1H-imidazole-4-sulfonamide;
83) N-[3-(6,8-dichloro-2-methyl-1,2,3,4-tetrahydro-isoquinolin-4-yl)-phenyl]-1,2-dimethyl-1H-imidazole-4-sulfonamide;
84) N-[4-(6,8-dichloro-2-methyl-1,2,3,4-tetrahydro-isoquinolin-4-yl)-phenyl]-5-chloro-1,3-dimethyl-1H-pyrazole-4-sulfonamide;
85) N-[3-(6,8-dichloro-2-methyl-1,2,3,4-tetrahydro-isoquinolin-4-yl)-phenyl]-5-chloro-1,3-dimethyl-1H-pyrazole-4-sulfonamide;
86) N-[4-(6,8-dichloro-2-methyl-1,2,3,4-tetrahydro-isoquinolin-4-yl)-phenyl]-5-bromo-thiophene-2-sulfonamide;
87) N-[3-(6,8-dichloro-2-methyl-1,2,3,4-tetrahydro-isoquinolin-4-yl)-phenyl]-5-bromo-thiophene-2-sulfonamide;
88) N-[4-(6,8-dichloro-2-methyl-1,2,3,4-tetrahydro-isoquinolin-4-yl)-phenyl]-C,C,C-trifluoro-methanesulfonamide;
89) N-[3-(6,8-dichloro-2-methyl-1,2,3,4-tetrahydro-isoquinolin-4-yl)-phenyl]-C,C,C-trifluoro-methanesulfonamide;
90) 4-(6,8-dichloro-2-methyl-1,2,3,4-tetrahydro-isoquinolin-4-yl)-phenyl]-2,2,2-trifluoroethanesulfonamide;
91) 3-(6,8-dichloro-2-methyl-1,2,3,4-tetrahydro-isoquinolin-4-yl)-phenyl]-2,2,2-trifluoroethanesulfonamide;
92) N-ethyl-N'-4-(6,8-Dichloro-2-methyl-1,2,3,4-tetrahydro-isoquinolin-4-yl)-benzenesulfonylurea;
93) 2-chloro-5-(6,8-dichloro-2-methyl-1,2,3,4-tetrahydro-isoquinolin-4-yl)-benzenesulfonamide;
94) 2-methyl-4-phenyl-6,8-bis-trifluoromethyl-1,2,3,4-tetrahydro-isoquinoline;
95) 2-Amino-N-[4-(6,8-dichloro-2-methyl-1,2,3,4-tetrahydro-isoquinolin-4-yl)-phenyl]-acetamide;
96) N-[4-(6,8-Dichloro-2-methyl-1,2,3,4-tetrahydro-isoquinolin-4-yl)-phenyl]-2-methylamino-acetamide;
97) N-[4-(6,8-Dichloro-2-methyl-1,2,3,4-tetrahydro-isoquinolin-4-yl)-phenyl]-2-dimethylamino-acetamide;
98) 2-Amino-N-[4-(6,8-dichloro-2-methyl-1,2,3,4-tetrahydro-isoquinolin-4-yl)-phenyl]-propionamide;
99) 2-Amino-N-[4-(6,8-dichloro-2-methyl-1,2,3,4-tetrahydro-isoquinolin-4-yl)-phenyl]-butyramide;
100) 2,6-Diamino-hexanoic acid [4-(6,8-dichloro-2-methyl-1,2,3,4-tetrahydro-isoquinolin-4-yl)-phenyl]-amide;
101) Pyrrolidine-2-carboxylic acid [4-(6,8-dichloro-2-methyl-1,2,3,4-tetrahydro-isoquinolin-4-yl)-phenyl]-amide;

102) N-[4-(6,8-Dichloro-2-methyl-1,2,3,4-tetrahydro-isoquinolin-4-yl)-phenyl]-isonicotinamide;
103) 1H-Pyrrole-3-carboxylic acid [4-(6,8-dichloro-2-methyl-1,2,3,4-tetrahydro-isoquinolin-4-yl)-phenyl]-amide;
104) 1H-Pyrrole-2-carboxylic acid [4-(6,8-dichloro-2-methyl-1,2,3,4-tetrahydro-isoquinolin-4-yl)-phenyl]-amide;
105) 1-Methyl-piperidine-4-carboxylic acid [4-(6,8-dichloro-2-methyl-1,2,3,4-tetrahydro-isoquinolin-4-yl)-phenyl]-amide;
106) 1,4-Dimethyl-1H-pyrrole-2-carboxylic acid [4-(6,8-dichloro-2-methyl-1,2,3,4-tetrahydro-isoquinolin-4-yl)-phenyl]-amide;
107) 4-Nitro-1H-pyrrole-2-carboxylic acid [4-(6,8-dichloro-2-methyl-1,2,3,4-tetrahydro-isoquinolin-4-yl)-phenyl]-amide;
108) 2,5-Dimethyl-1H-pyrrole-3-carboxylic acid [4-(6,8-dichloro-2-methyl-1,2,3,4-tetrahydro-isoquinolin-4-yl)-phenyl]-amide;
109) 1H-Imidazole-4-carboxylic acid [4-(6,8-dichloro-2-methyl-1,2,3,4-tetrahydro-isoquinolin-4-yl)-phenyl]-amide;
110) 1-Methanesulfonyl-piperidine-4-carboxylic acid [4-(6,8-dichloro-2-methyl-1,2,3,4-tetrahydro-isoquinolin-4-yl)-phenyl]-amide;
111) 3,5-Dimethyl-1H-pyrazole-4-carboxylic acid [4-(6,8-dichloro-2-methyl-1,2,3,4-tetrahydro-isoquinolin-4-yl)-phenyl]-amide;
112) 1H-Pyrazole-4-carboxylic acid [4-(6,8-dichloro-2-methyl-1,2,3,4-tetrahydro-isoquinolin-4-yl)-phenyl]-amide;
113) 3-Trifluoromethyl-1H-pyrazole-4-carboxylic acid [4-(6,8-dichloro-2-methyl-1,2,3,4-tetrahydro-isoquinolin-4-yl)-phenyl]-amide;
114) N-[3-(6,8-Dichloro-2-methyl-1,2,3,4-tetrahydro-isoquinolin-4-yl)-phenyl]-2-methylamino-acetamide;
115) N-[3-(6,8-Dichloro-2-methyl-1,2,3,4-tetrahydro-isoquinolin-4-yl)-phenyl]-2-dimethylamino-acetamide;
116) 2-Amino-N-[3-(6,8-dichloro-2-methyl-1,2,3,4-tetrahydro-isoquinolin-4-yl)-phenyl]-propionamide;
117) 2-Amino-N-[3-(6,8-dichloro-2-methyl-1,2,3,4-tetrahydro-isoquinolin-4-yl)-phenyl]-butyramide;
118) 2,6-Diamino-hexanoic acid [3-(6,8-dichloro-2-methyl-1,2,3,4-tetrahydro-isoquinolin-4-yl)-phenyl]-amide;
119) Pyrrolidine-2-carboxylic acid [3-(6,8-dichloro-2-methyl-1,2,3,4-tetrahydro-isoquinolin-4-yl)-phenyl]-amide;
120) N-[3-(6,8-Dichloro-2-methyl-1,2,3,4-tetrahydro-isoquinolin-4-yl)-phenyl]-isonicotinamide;
121) 1H-Pyrrole-3-carboxylic acid [3-(6,8-dichloro-2-methyl-1,2,3,4-tetrahydro-isoquinolin-4-yl)-phenyl]-amide;
122) 1H-Pyrrole-2-carboxylic acid [3-(6,8-dichloro-2-methyl-1,2,3,4-tetrahydro-isoquinolin-4-yl)-phenyl]-amide;
123) 1-Methyl-piperidine-4-carboxylic acid [3-(6,8-dichloro-2-methyl-1,2,3,4-tetrahydro-isoquinolin-4-yl)-phenyl]-amide;
124) 1,4-Dimethyl-1H-pyrrole-2-carboxylic acid [3-(6,8-dichloro-2-methyl-1,2,3,4-tetrahydro-isoquinolin-4-yl)-phenyl]-amide;
125) 4-Nitro-1H-pyrrole-2-carboxylic acid [3-(6,8-dichloro-2-methyl-1,2,3,4-tetrahydro-isoquinolin-4-yl)-phenyl]-amide;
126) 2,5-Dimethyl-1H-pyrrole-3-carboxylic acid [3-(6,8-dichloro-2-methyl-1,2,3,4-tetrahydro-isoquinolin-4-yl)-phenyl]-amide;
127) 1H-Imidazole-4-carboxylic acid [3-(6,8-dichloro-2-methyl-1,2,3,4-tetrahydro-isoquinolin-4-yl)-phenyl]-amide;
128) 1-Methanesulfonyl-piperidine-4-carboxylic acid [3-(6,8-dichloro-2-methyl-1,2,3,4-tetrahydro-isoquinolin-4-yl)-phenyl]-amide;
129) 3,5-Dimethyl-1H-pyrazole-4-carboxylic acid [3-(6,8-dichloro-2-methyl-1,2,3,4-tetrahydro-isoquinolin-4-yl)-phenyl]-amide;
130) 1H-Pyrazole-4-carboxylic acid [3-(6,8-dichloro-2-methyl-1,2,3,4-tetrahydro-isoquinolin-4-yl)-phenyl]-amide;
131) 3-Trifluoromethyl-1H-pyrazole-4-carboxylic acid [3-(6,8-dichloro-2-methyl-1,2,3,4-tetrahydro-isoquinolin-4-yl)-phenyl]-amide;
132) 1-[2-(6,8-Dichloro-2-methyl-1,2,3,4-tetrahydro-isoquinolin-4-yl)-phenyl]-3-ethyl-thiourea;
133) 1-[4-(6,8-Dichloro-2-methyl-1,2,3,4-tetrahydro-isoquinolin-4-yl)-phenyl]-3-ethyl-thiourea;
134) 1-[3-(6,8-Dichloro-2-methyl-1,2,3,4-tetrahydro-isoquinolin-4-yl)-phenyl]-3-ethyl-thiourea;
135) 3-[3-(6,8-Dichloro-2-methyl-1,2,3,4-tetrahydro-isoquinolin-4-yl)-phenyl]-1,1-dimethyl-urea;
136) 4-Methyl-piperazine-1-carboxylic acid [3-(6,8-dichloro-2-methyl-1,2,3,4-tetrahydro-isoquinolin-4-yl)-phenyl]-amide;
137) Piperidine-1-carboxylic acid [3-(6,8-dichloro-2-methyl-1,2,3,4-tetrahydro-isoquinolin-4-yl)-phenyl]-amide;
138) Morpholine-4-carboxylic acid [3-(6,8-dichloro-2-methyl-1,2,3,4-tetrahydro-isoquinolin-4-yl)-phenyl]-amide;
139) Pyrrolidine-1-carboxylic acid [3-(6,8-dichloro-2-methyl-1,2,3,4-tetrahydro-isoquinolin-4-yl)-phenyl]-amide;
140) 3-[3-(6,8-Dichloro-2-methyl-1,2,3,4-tetrahydro-isoquinolin-4-yl)-phenyl]-1,1-diethyl-urea;
141) 1-[3-(6,8-Dichloro-2-methyl-1,2,3,4-tetrahydro-isoquinolin-4-yl)-phenyl]-3-methyl-urea;
142) 1-[3-(6,8-Dichloro-2-methyl-1,2,3,4-tetrahydro-isoquinolin-4-yl)-phenyl]-3-(2-dimethylamino-ethyl)-urea;
143) 1-[3-(6,8-Dichloro-2-methyl-1,2,3,4-tetrahydro-isoquinolin-4-yl)-phenyl]-3-(tetrahydro-furan-3-yl)-urea;
144) 1-[3-(6,8-Dichloro-2-methyl-1,2,3,4-tetrahydro-isoquinolin-4-yl)-phenyl]-3-(tetrahydro-pyran-4-yl)-urea;
145) 3-[3-(6,8-Dichloro-2-methyl-1,2,3,4-tetrahydro-isoquinolin-4-yl)-phenyl]-1-methyl-1-(1-methyl-piperidin-4-yl)-urea;
146) 3-[3-(6,8-Dichloro-2-methyl-1,2,3,4-tetrahydro-isoquinolin-4-yl)-phenyl]-1-(3-dimethylamino-propyl)-1-methyl-urea;
147) 3-[3-(6,8-Dichloro-2-methyl-1,2,3,4-tetrahydro-isoquinolin-4-yl)-phenyl]-1-(2-dimethylamino-ethyl)-1-methyl-urea;
148) 1-[3-(6,8-Dichloro-2-methyl-1,2,3,4-tetrahydro-isoquinolin-4-yl)-phenyl]-3-(3-dimethylamino-propyl)-urea;
149) 1-[3-(6,8-Dichloro-2-methyl-1,2,3,4-tetrahydro-isoquinolin-4-yl)-phenyl]-3-(2-methoxy-ethyl)-urea;
150) 1-[3-(6,8-Dichloro-2-methyl-1,2,3,4-tetrahydro-isoquinolin-4-yl)-phenyl]-3-pyridin-3-yl-urea;
151) 1-[3-(6,8-Dichloro-2-methyl-1,2,3,4-tetrahydro-isoquinolin-4-yl)-phenyl]-3-pyridin-4-yl-urea;
152) 4-Methyl-piperazine-1-carboxylic acid [2-(6,8-dichloro-2-methyl-1,2,3,4-tetrahydro-isoquinolin-4-yl)-phenyl]-amide;

153) 1-[2-(6,8-Dichloro-2-methyl-1,2,3,4-tetrahydro-isoquinolin-4-yl)-phenyl]-3-methyl-urea;
154) 3-[2-(6,8-Dichloro-2-methyl-1,2,3,4-tetrahydro-isoquinolin-4-yl)-phenyl]-1,1-dimethyl-urea;
155) 3-[2-(6,8-Dichloro-2-methyl-1,2,3,4-tetrahydro-isoquinolin-4-yl)-phenyl]-1,1-diethyl-urea;
156) Piperidine-1-carboxylic acid [2-(6,8-dichloro-2-methyl-1,2,3,4-tetrahydro-isoquinolin-4-yl)-phenyl]-amide;
157) Morpholine-4-carboxylic acid [2-(6,8-dichloro-2-methyl-1,2,3,4-tetrahydro-isoquinolin-4-yl)-phenyl]-amide;
158) Pyrrolidine-1-carboxylic acid [2-(6,8-dichloro-2-methyl-1,2,3,4-tetrahydro-isoquinolin-4-yl)-phenyl]-amide;
159) 1-[2-(6,8-Dichloro-2-methyl-1,2,3,4-tetrahydro-isoquinolin-4-yl)-phenyl]-3-(2-dimethylamino-ethyl)-urea;
160) 4-Methyl-piperazine-1-carboxylic acid [4-(6,8-dichloro-2-methyl-1,2,3,4-tetrahydro-isoquinolin-4-yl)-phenyl]-amide;
161) Pyrrolidine-1-carboxylic acid [4-(6,8-dichloro-2-methyl-1,2,3,4-tetrahydro-isoquinolin-4-yl)-phenyl]-amide;
162) 1-[4-(6,8-Dichloro-2-methyl-1,2,3,4-tetrahydro-isoquinolin-4-yl)-phenyl]-3-methyl-urea;
163) 3-[4-(6,8-Dichloro-2-methyl-1,2,3,4-tetrahydro-isoquinolin-4-yl)-phenyl]-1,1-dimethyl-urea;
164) 3-[4-(6,8-Dichloro-2-methyl-1,2,3,4-tetrahydro-isoquinolin-4-yl)-phenyl]-1,1-diethyl-urea;
165) 1-[4-(6,8-Dichloro-2-methyl-1,2,3,4-tetrahydro-isoquinolin-4-yl)-phenyl]-3-(2-dimethylamino-ethyl)-urea;
166) Piperidine-1-carboxylic acid [4-(6,8-dichloro-2-methyl-1,2,3,4-tetrahydro-isoquinolin-4-yl)-phenyl]-amide;
167) Morpholine-4-carboxylic acid [4-(6,8-dichloro-2-methyl-1,2,3,4-tetrahydro-isoquinolin-4-yl)-phenyl]-amide;
168) N-[4-(6,8-Dichloro-2-methyl-1,2,3,4-tetrahydro-isoquinolin-4-yl)-phenyl]-formamide;
169) [4-(6,8-Dichloro-2-methyl-1,2,3,4-tetrahydro-isoquinolin-4-yl)-phenyl]-methyl-amine;
170) 1-[4-(6,8-Dichloro-2-methyl-1,2,3,4-tetrahydro-isoquinolin-4-yl)-phenyl]-1,3-dimethyl-urea;
171) 4-Methyl-piperazine-1-carboxylic acid [4-(6,8-dichloro-2-methyl-1,2,3,4-tetrahydro-isoquinolin-4-yl)-phenyl]-methyl-amide;
172) 1-[4-(6,8-Dichloro-2-methyl-1,2,3,4-tetrahydro-isoquinolin-4-yl)-phenyl]-1,3,3-trimethyl-urea;
173) Piperidine-1-carboxylic acid [4-(6,8-dichloro-2-methyl-1,2,3,4-tetrahydro-isoquinolin-4-yl)-phenyl]-methyl-amide;
174) Morpholine-4-carboxylic acid [4-(6,8-dichloro-2-methyl-1,2,3,4-tetrahydro-isoquinolin-4-yl)-phenyl]-methyl-amide;
175) Pyrrolidine-1-carboxylic acid [4-(6,8-dichloro-2-methyl-1,2,3,4-tetrahydro-isoquinolin-4-yl)-phenyl]-methyl-amide;
176) 1-[4-(6,8-Dichloro-2-methyl-1,2,3,4-tetrahydro-isoquinolin-4-yl)-phenyl]-3-(2-dimethylamino-ethyl)-1-methyl-urea;
177) 1-[4-(6,8-Dichloro-2-methyl-1,2,3,4-tetrahydro-isoquinolin-4-yl)-phenyl]-3,3-diethyl-1-methyl-urea;
178) N-[3-(6,8-Dichloro-2-methyl-1,2,3,4-tetrahydro-isoquinolin-4-yl)-phenyl]-formamide;
179) [3-(6,8-Dichloro-2-methyl-1,2,3,4-tetrahydro-isoquinolin-4-yl)-phenyl]-methyl-amine;
180) Pyrrolidine-1-carboxylic acid [3-(6,8-dichloro-2-methyl-1,2,3,4-tetrahydro-isoquinolin-4-yl)-phenyl]-methyl-amide;
181) Piperidine-1-carboxylic acid [3-(6,8-dichloro-2-methyl-1,2,3,4-tetrahydro-isoquinolin-4-yl)-phenyl]-methyl-amide;
182) 1-[3-(6,8-Dichloro-2-methyl-1,2,3,4-tetrahydro-isoquinolin-4-yl)-phenyl]-1,3,3-trimethyl-urea;
183) 1-[3-(6,8-Dichloro-2-methyl-1,2,3,4-tetrahydro-isoquinolin-4-yl)-phenyl]-1,3-dimethyl-urea;
184) Morpholine-4-carboxylic acid [3-(6,8-dichloro-2-methyl-1,2,3,4-tetrahydro-isoquinolin-4-yl)-phenyl]-methyl-amide;
185) 4-Methyl-piperazine-1-carboxylic acid [3-(6,8-dichloro-2-methyl-1,2,3,4-tetrahydro-isoquinolin-4-yl)-phenyl]-methyl-amide;
186) 1-[3-(6,8-Dichloro-2-methyl-1,2,3,4-tetrahydro-isoquinolin-4-yl)-phenyl]-3-(2-dimethylamino-ethyl)-1-methyl-urea;
187) 1-[3-(6,8-Dichloro-2-methyl-1,2,3,4-tetrahydro-isoquinolin-4-yl)-phenyl]-3,3-diethyl-1-methyl-urea;
188) [3-(6,8-Dichloro-2-methyl-1,2,3,4-tetrahydro-isoquinolin-4-yl)-phenyl]-carbamic acid 2-dimethylamino-ethyl ester;
189) [4-(6,8-Dichloro-2-methyl-1,2,3,4-tetrahydro-isoquinolin-4-yl)-phenyl]-carbamic acid 2-dimethylamino-ethyl ester;
190) [2-(6,8-Dichloro-2-methyl-1,2,3,4-tetrahydro-isoquinolin-4-yl)-phenyl]-carbamic acid 2-dimethylamino-ethyl ester;
191) [3-(6,8-Dichloro-2-methyl-1,2,3,4-tetrahydro-isoquinolin-4-yl)-phenyl]-carbamic acid methyl ester;
192) [3-(6,8-Dichloro-2-methyl-1,2,3,4-tetrahydro-isoquinolin-4-yl)-phenyl]-carbamic acid ethyl ester;
193) [3-(6,8-Dichloro-2-methyl-1,2,3,4-tetrahydro-isoquinolin-4-yl)-phenyl]-carbamic acid isopropyl ester;
194) [3-(6,8-Dichloro-2-methyl-1,2,3,4-tetrahydro-isoquinolin-4-yl)-phenyl]-carbamic acid 2,2-dimethyl-propyl ester;
195) [4-(6,8-Dichloro-2-methyl-1,2,3,4-tetrahydro-isoquinolin-4-yl)-phenyl]-carbamic acid methyl ester;
196) [4-(6,8-Dichloro-2-methyl-1,2,3,4-tetrahydro-isoquinolin-4-yl)-phenyl]-carbamic acid isopropyl ester;
197) [4-(6,8-Dichloro-2-methyl-1,2,3,4-tetrahydro-isoquinolin-4-yl)-phenyl]-carbamic acid 2,2-dimethyl-propyl ester;
198) [4-(6,8-Dichloro-2-methyl-1,2,3,4-tetrahydro-isoquinolin-4-yl)-phenyl]-carbamic acid ethyl ester;
199) (+)-N-[3-(6,8-Dichloro-2-methyl-1,2,3,4-tetrahydro-isoquinolin-4-yl)-phenyl]-methanesulfonamide;
200) (−)-N-[3-(6,8-Dichloro-2-methyl-1,2,3,4-tetrahydro-isoquinolin-4-yl)-phenyl]-methanesulfonamide;
201) (+)-1-[2-(6,8-Dichloro-2-methyl-1,2,3,4-tetrahydro-isoquinolin-4-yl)-phenyl]-3-ethyl-urea;
202) (−)-1-[2-(6,8-Dichloro-2-methyl-1,2,3,4-tetrahydro-isoquinolin-4-yl)-phenyl]-3-ethyl-urea;
203) N-[3-(6,8-Difluoro-2-methyl-1,2,3,4-tetrahydro-isoquinolin-4-yl)-phenyl]-acetamide;
204) 4-(3-Bromo-phenyl)-6,8-dichloro-2-methyl-1,2,3,4-tetrahydro-isoquinoline;
205) 1-[3-(6,8-Dichloro-2-methyl-1,2,3,4-tetrahydro-isoquinolin-4-yl)-phenyl]-3-(2-5-hydroxy-ethyl)-urea;
206) 3-(6,8-Dichloro-2-methyl-1,2,3,4-tetrahydro-isoquinolin-4-yl)-benzoic acid ethyl ester;
207) 3-(6,8-Dichloro-2-methyl-1,2,3,4-tetrahydro-isoquinolin-4-yl)-benzoic acid
and the pharmaceutically acceptable salts thereof.

In another embodiment, compounds of the invention are chosen from the following:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 1-[4-(6,8-dichloro-2-methyl-1,2,3,4-tetrahydro-isoquinolin-4-yl)-phenyl]-3-methyl- thiourea;
5) 1-[4-(6,8-dichloro-2-methyl-1,2,3,4-tetrahydro-isoquinolin-4-yl)-phenyl]-3-ethyl-urea;
6) N-[4-(6-bromo-8-chloro-2-methyl-1,2,3,4-tetrahydro-isoquinolin-4-yl)-phenyl]-acetamide;
7) N-[3-(6,8-dichloro-2-methyl-1,2,3,4-tetrahydro-isoquinolin-4-yl)-phenyl]-acetamide;
8) N-[4-(6,8-dichloro-2-methyl-1,2,3,4-tetrahydro-isoquinolin-4-yl)-phenyl]-propionamide;
9) N-[4-(6,8-dichloro-2-methyl-1,2,3,4-tetrahydro-isoquinolin-4-yl)-phenyl]-1-acetyl-piperidine-4-carboxamide;
10) N-[4-(6,8-dichloro-2-methyl-1,2,3,4-tetrahydro-isoquinolin-4-yl)-phenyl]-methane-sulfonamide;
11) N-[4-(6,8-dichloro-2-methyl-1,2,3,4-tetrahydro-isoquinolin-4-yl)-phenyl]-ethanesulfonamide;
12) N',N'-dimethylamino-N-[4-(6,8-dichloro-2-methyl-1,2,3,4-tetrahydro-isoquinolin-4-yl)-phenyl]-sulfamide;
13) N-[3-(6,8-dichloro-2-methyl-1,2,3,4-tetrahydro-isoquinolin-4-yl)-phenyl]-propionamide;
14) N-[3-(6,8-dichloro-2-methyl-1,2,3,4-tetrahydro-isoquinolin-4-yl)-phenyl]-10 butyramide;
15) N-[3-(6,8-dichloro-2-methyl-1,2,3,4-tetrahydro-isoquinolin-4-yl)-phenyl]-isobutyramide;
16) N-[3-(6,8-dichloro-2-methyl-1,2,3,4-tetrahydro-isoquinolin-4-yl)-phenyl]-cyclopropanecarboxamide;
17) N-[3-(6,8-dichloro-2-methyl-1,2,3,4-tetrahydro-isoquinolin-4-yl)-phenyl]-cyclobutanecarboxamide;
18) N-[3-(6,8-dichloro-2-methyl-1,2,3,4-tetrahydro-isoquinolin-4-yl)-phenyl]-2,2,2-trifluoro-acetamide;
19) N-[3-(6,8-dichloro-2-methyl-1,2,3,4-tetrahydro-isoquinolin-4-yl)-phenyl]-1-acetyl-piperidine-4-carboxamide;
20) N-[3-(6,8-dichloro-2-methyl-1,2,3,4-tetrahydro-isoquinolin-4-yl)-phenyl]-nicotinamide;
21) N-[3-(6,8-dichloro-2-methyl-1,2,3,4-tetrahydro-isoquinolin-4-yl)-phenyl]-methane-sulfonamide;
22) N-[3-(6,8-dichloro-2-methyl-1,2,3,4-tetrahydro-isoquinolin-4-yl)-phenyl]-ethanesulfonamide;
23) N',N'-dimethylamino-N-[3-(6,8-dichloro-2-methyl-1,2,3,4-tetrahydro-isoquinolin-4-yl)-phenyl]-sulfamide;
24) N-[2-(6,8-dichloro-2-methyl-1,2,3,4-tetrahydro-isoquinolin-4-yl)-phenyl]-cyclopropanecarboxamide;
25) N-[2-(6,8-dichloro-2-methyl-1,2,3,4-tetrahydro-isoquinolin-4-yl)-phenyl]-1-acetyl-piperidine-4-carboxamide;
26) 1-[3-(6,8-dichloro-2-methyl-1,2,3,4-tetrahydro-isoquinolin-4-yl)-phenyl]-3-ethyl-urea;
27) 1-[3-(6,8-dichloro-2-methyl-1,2,3,4-tetrahydro-isoquinolin-4-yl)-phenyl]-3-methyl-thiourea;
28) 1-[2-(6,8-dichloro-2-methyl-1,2,3,4-tetrahydro-isoquinolin-4-yl)-phenyl]-3-ethyl-urea;
29) 1-[2-(6,8-dichloro-2-methyl-1,2,3,4-tetrahydro-isoquinolin-4-yl)-phenyl]-3-methyl-thiourea;
30) N-{5-[3-(6,8-dichloro-2-methyl-1,2,3,4-tetrahydro-isoquinolin-4-yl)-phenylsulfamoyl]-4-methyl-thiazol-2-yl}-acetamide;
31) N-[3-(6,8-dichloro-2-methyl-1,2,3,4-tetrahydro-isoquinolin-4-yl)-phenyl]-1,2-dimethyl-1H-imidazole-4-sulfonamide;
32) N-[4-(6,8-dichloro-2-methyl-1,2,3,4-tetrahydro-isoquinolin-4-yl)-phenyl]-C,C,C-trifluoro-methanesulfonamide;
33) N-[3-(6,8-dichloro-2-methyl-1,2,3,4-tetrahydro-isoquinolin-4-yl)-phenyl]-C,C,C-trifluoro-methanesulfonamide;
34) N-ethyl-N'-4-(6,8-dichloro-2-methyl-1,2,3,4-tetrahydro-isoquinolin-4-yl)-benzenesulfonylurea;
35) N-[4-(6,8-Dichloro-2-methyl-1,2,3,4-tetrahydro-isoquinolin-4-yl)-phenyl]-2-dimethylamino-acetamide;
36) 2,6-Diamino-hexanoic acid [4-(6,8-dichloro-2-methyl-1,2,3,4-tetrahydro-isoquinolin-4-yl)-phenyl]-amide;
37) 1H-Pyrrole-3-carboxylic acid [4-(6,8-dichloro-2-methyl-1,2,3,4-tetrahydro-isoquinolin-4-yl)-phenyl]-amide;
38) 1-Methyl-piperidine-4-carboxylic acid [4-(6,8-dichloro-2-methyl-1,2,3,4-tetrahydro-isoquinolin-4-yl)-phenyl]-amide;
39) 1-Methanesulfonyl-piperidine-4-carboxylic acid [4-(6,8-dichloro-2-methyl-1,2,3,4-tetrahydro-isoquinolin-4-yl)-phenyl]-amide;
40) 1H-Pyrazole-4-carboxylic acid [4-(6,8-dichloro-2-methyl-1,2,3,4-tetrahydro-isoquinolin-4-yl)-phenyl]-amide;
41) N-[3-(6,8-Dichloro-2-methyl-1,2,3,4-tetrahydro-isoquinolin-4-yl)-phenyl]-2-methylamino-acetamide;
42) N-[3-(6,8-Dichloro-2-methyl-1,2,3,4-tetrahydro-isoquinolin-4-yl)-phenyl]-2-dimethylamino-acetamide;
43) 2-Amino-N-[3-(6,8-dichloro-2-methyl-1,2,3,4-tetrahydro-isoquinolin-4-yl)-phenyl]-propionamide;
44) 2-Amino-N-[3-(6,8-dichloro-2-methyl-1,2,3,4-tetrahydro-isoquinolin-4-yl)-phenyl]-butyramide;
45) 2,6-Diamino-hexanoic acid [3-(6,8-dichloro-2-methyl-1,2,3,4-tetrahydro-isoquinolin-4-yl)-phenyl]-amide;
46) 1-Methyl-piperidine-4-carboxylic acid [3-(6,8-dichloro-2-methyl-1,2,3,4-tetrahydro-isoquinolin-4-yl)-phenyl]-amide;
47) 1H-Imidazole-4-carboxylic acid [3-(6,8-dichloro-2-methyl-1,2,3,4-tetrahydro-isoquinolin-4-yl)-phenyl]-amide;
48) 1-Methanesulfonyl-piperidine-4-carboxylic acid [3-(6,8-dichloro-2-methyl-1,2,3,4-tetrahydro-isoquinolin-4-yl)-phenyl]-amide;
49) 3,5-Dimethyl-1H-pyrazole-4-carboxylic acid [3-(6,8-dichloro-2-methyl-1,2,3,4-tetrahydro-isoquinolin-4-yl)-phenyl]-amide;
50) 1H-Pyrazole-4-carboxylic acid [3-(6,8-dichloro-2-methyl-1,2,3,4-tetrahydro-isoquinolin-4-yl)-phenyl]-amide;
51) 3-[3-(6,8-Dichloro-2-methyl-1,2,3,4-tetrahydro-isoquinolin-4-yl)-phenyl]-1,1-dimethyl-urea;
52) 4-Methyl-piperazine-1-carboxylic acid [3-(6,8-dichloro-2-methyl-1,2,3,4-tetrahydro-isoquinolin-4-yl)-phenyl]-amide;
53) Piperidine-1-carboxylic acid [3-(6,8-dichloro-2-methyl-1,2,3,4-tetrahydro-isoquinolin-4-yl)-phenyl]-amide;
54) Morpholine-4-carboxylic acid [3-(6,8-dichloro-2-methyl-1,2,3,4-tetrahydro-isoquinolin-4-yl)-phenyl]-amide;
55) Pyrrolidine-1-carboxylic acid [3-(6,8-dichloro-2-methyl-1,2,3,4-tetrahydro-isoquinolin-4-yl)-phenyl]-amide;
56) 3-[3-(6,8-Dichloro-2-methyl-1,2,3,4-tetrahydro-isoquinolin-4-yl)-phenyl]-1,1-diethyl-urea;

57) 1-[3-(6,8-Dichloro-2-methyl-1,2,3,4-tetrahydro-isoquinolin-4-yl)-phenyl]-3-methyl-urea;

58) 1-[3-(6,8-Dichloro-2-methyl-1,2,3,4-tetrahydro-isoquinolin-4-yl)-phenyl]-3-(2-dimethylamino-ethyl)-urea;

59) 1-[3-(6,8-Dichloro-2-methyl-1,2,3,4-tetrahydro-isoquinolin-4-yl)-phenyl]-3-(tetrahydro- furan-3-yl)-urea;

60) 1-[3-(6,8-Dichloro-2-methyl-1,2,3,4-tetrahydro-isoquinolin-4-yl)-phenyl]-3-(tetrahydro-pyran-4-yl)-urea;

61) 3-[3-(6,8-Dichloro-2-methyl-1,2,3,4-tetrahydro-isoquinolin-4-yl)-phenyl]-1-methyl-1-(1-methyl-piperidin-4-yl)-urea;

62) 3-[3-(6,8-Dichloro-2-methyl-1,2,3,4-tetrahydro-isoquinolin-4-yl)-phenyl]-1-(3-dimethylamino-propyl)-1-methyl-urea;

63) 3-[3-(6,8-Dichloro-2-methyl-1,2,3,4-tetrahydro-isoquinolin-4-yl)-phenyl]-1-(2-dimethylamino-ethyl)-1-methyl-urea;

64) 1-[3-(6,8-Dichloro-2-methyl-1,2,3,4-tetrahydro-isoquinolin-4-yl)-phenyl]-3-(3-dimethylamino-propyl)-urea;

65) 1-[3-(6,8-Dichloro-2-methyl-1,2,3,4-tetrahydro-isoquinolin-4-yl)-phenyl]-3-(2-methoxy-ethyl)-urea;

66) 1-[3-(6,8-Dichloro-2-methyl-1,2,3,4-tetrahydro-isoquinolin-4-yl)-phenyl]-3-pyridin-3-yl-urea;

67) 1-[3-(6,8-Dichloro-2-methyl-1,2,3,4-tetrahydro-isoquinolin-4-yl)-phenyl]-3-pyridin-4-yl-urea;

68) 4-Methyl-piperazine-1-carboxylic acid [2-(6,8-dichloro-2-methyl-1,2,3,4-tetrahydro-isoquinolin-4-yl)-phenyl]-amide;

69) 1-[2-(6,8-Dichloro-2-methyl-1,2,3,4-tetrahydro-isoquinolin-4-yl)-phenyl]-3-methyl-urea;

70) 1-[2-(6,8-Dichloro-2-methyl-1,2,3,4-tetrahydro-isoquinolin-4-yl)-phenyl]-3-(2-dimethylamino-ethyl)-urea;

71) 4-Methyl-piperazine-1-carboxylic acid [4-(6,8-dichloro-2-methyl-1,2,3,4-tetrahydro-isoquinolin-4-yl)-phenyl]-amide;

72) 1-[4-(6,8-Dichloro-2-methyl-1,2,3,4-tetrahydro-isoquinolin-4-yl)-phenyl]-3-methyl-urea;

73) 3-[4-(6,8-Dichloro-2-methyl-1,2,3,4-tetrahydro-isoquinolin-4-yl)-phenyl]-1,1-dimethyl-urea;

74) 3-[4-(6,8-Dichloro-2-methyl-1,2,3,4-tetrahydro-isoquinolin-4-yl)-phenyl]-1,1-diethyl-urea;

75) 1-[4-(6,8-Dichloro-2-methyl-1,2,3,4-tetrahydro-isoquinolin-4-yl)-phenyl]-3-(2-dimethylamino-ethyl)-urea;

76) Morpholine-4-carboxylic acid [4-(6,8-dichloro-2-methyl-1,2,3,4-tetrahydro-isoquinolin-4-yl)-phenyl]-amide;

77) N-[4-(6,8-Dichloro-2-methyl-1,2,3,4-tetrahydro-isoquinolin-4-yl)-phenyl]-formamide;

78) N-[3-(6,8-Dichloro-2-methyl-1,2,3,4-tetrahydro-isoquinolin-4-yl)-phenyl]-formamide;

79) 1-[3-(6,8-Dichloro-2-methyl-1,2,3,4-tetrahydro-isoquinolin-4-yl)-phenyl]-1,3,3-trimethyl-urea;

80) 1-[3-(6,8-Dichloro-2-methyl-1,2,3,4-tetrahydro-isoquinolin-4-yl)-phenyl]-1,3-dimethyl-urea;

81) Morpholine-4-carboxylic acid [3-(6,8-dichloro-2-methyl-1,2,3,4-tetrahydro-isoquinolin-4-yl)-phenyl]-methyl-amide;

82) 4-Methyl-piperazine-1-carboxylic acid [3-(6,8-dichloro-2-methyl-1,2,3,4-tetrahydro-isoquinolin-4-yl)-phenyl]-methyl-amide;

83) 1-[3-(6,8-Dichloro-2-methyl-1,2,3,4-tetrahydro-isoquinolin-4-yl)-phenyl]-3-(2-dimethylamino-ethyl)-1-methyl-urea;

84) [3-(6,8-Dichloro-2-methyl-1,2,3,4-tetrahydro-isoquinolin-4-yl)-phenyl]-carbamic acid 2-dimethylamino-ethyl ester;

85) [4-(6,8-Dichloro-2-methyl-1,2,3,4-tetrahydro-isoquinolin-4-yl)-phenyl]-carbamic acid 2-dimethylamino-ethyl ester;

86) [2-(6,8-Dichloro-2-methyl-1,2,3,4-tetrahydro-isoquinolin-4-yl)-phenyl]-carbamic acid 2-dimethylamino-ethyl ester;

87) [3-(6,8-Dichloro-2-methyl-1,2,3,4-tetrahydro-isoquinolin-4-yl)-phenyl]-carbamic acid methyl ester;

88) (R or S)-N-[3-(6,8-Dichloro-2-methyl-1,2,3,4-tetrahydro-isoquinolin-4-yl)-phenyl]-methanesulfonamide;

89) (R or S)-1-[2-(6,8-Dichloro-2-methyl-1,2,3,4-tetrahydro-isoquinolin-4-yl)-phenyl]-3-ethyl-urea;

90) 1-[3-(6,8-Dichloro-2-methyl-1,2,3,4-tetrahydro-isoquinolin-4-yl)-phenyl]-3-(2-hydroxy-ethyl)-urea;

and the pharmaceutically acceptable salts thereof.

In one embodiment, the invention encompasses the use of the compounds of the formula I for the treatment of disorders which can be influenced by inhibition of the sodium-proton exchange of subtype III (NHE3), in which:

wherein:

R1, R2, R3 and R4 are independently of one another H, F, Cl, Br, I, CN, $NO_2$, OH, $NH_2$, $C_aH_{2a+1}$, $C_{qq}H_{2qq-1}$, $OC_bH_{2b+1}$, COOR10, OCOR10, COR10 or $O_x$—$(CH_2)_y$-phenyl; wherein a and b are independently of one another 1, 2, 3, 4, 5, 6, 7 or 8, wherein the groups $C_aH_{2a+1}$ and $OC_bH_{2b+1}$ independently of one another are unsubstituted or substituted where one or more H atoms are replaced by F atoms;

qq is 3, 4, 5, 6, 7 or 8, wherein the group $C_{qq}H_{2qq-1}$ is unsubstituted or substituted where one or more H atoms are replaced by F atoms;

R10 is H or $C_cH_{2c+1}$;

c is 1, 2, 3, 4, 5, 6, 7 or 8, wherein the group CcH2c+1 is unsubstituted or substituted where one or more H atoms are replaced by F atoms;

x is zero or 1;

y is zero, 1, 2, 3 or 4; where the phenyl ring in the group $O_x$—$(CH_2)_y$-phenyl is unsubstituted or substituted by 1-3 independently chosen from F, Cl, Br, CN, $NO_2$, OH, $NH_2$ and $C_dH_{2d+1}$, d is 1, 2, 3 or 4, wherein the group $C_dH_{2d+1}$ is unsubstituted or substituted where one or more H atoms are replaced by F atoms;

or

R1, R2, R3 and R4 are independently of one another chosen from a heteroaryl with at least one heteroatom chosen from 1, 2, 3 or 4 N atoms, 1 oxygen atom and 1 S atom, present as ring atoms; or R1, R2, R3 and R4 are independently of one another CONR11R12 or NR11R12; wherein R11 and R12 are independently of one another H, $C_eH_{2e+1}$, $C_{rr}H_{2rr-1}$;

e is 1, 2, 3, 4, 5, 6, 7 or 8;

rr is 3, 4, 5, 6, 7, or 8, wherein the groups $C_eH_{2e+1}$ and $C_{rr}H_{2rr-1}$ independently of one another are unsubstituted or substituted where one or more H atoms are replaced by F atoms and/or one or more $CH_2$ groups are replaced by O or NR13;

R13 is H or $C_fH_{2f+1}$;

f is 1, 2, 3 or 4, wherein the group $C_fH_{2f+1}$ is unsubsitituted or substituted where one or more H atoms are replaced by F atoms;

or

R13 and a CH$_2$ group of R11 or R12 together with the N atom to which they are bonded form a 5- or 6-membered ring;

or

R11 and R12 together with the N atom to which they are bonded form a 5-, 6- or 7-membered ring; or R11 and R12 are independently of one another COR14, CSR14 or SO$_2$R14; wherein R14 is C$_g$H$_{2g+1}$;

g is 1, 2, 3, 4, 5, 6, 7 or 8, wherein the group C$_g$H$_{2g+1}$ is unsubsituted or substituted where one or more H atoms are replaced by F atoms, and/or one or more CH$_2$ groups are replaced by O or NR13;

or

R1, R2, R3 and R4 are independently of one another —O$_h$—SO$_j$—R15, with h is zero or 1;

j is zero, 1 or 2;

R15 is C$_k$H$_{2k+1}$, OH, OC$_l$H$_{2l+1}$ or NR17R18;

k is 1, 2, 3, 4, 5, 6, 7 or 8, wherein the group C$_k$H$_{2k+1}$ is unsubsituted or substituted where one or more H atoms are replaced by F atoms;

l is 1, 2, 3, 4, 5, 6, 7 or 8, wherein the group OC$_l$H$_{2l+1}$ is unsubsituted or substituted where one or more H atoms are replaced by F atoms;

R17 and R18 are independently of one another H or C$_m$H$_{2m+1}$;

m is 1, 2, 3, 4, 5, 6, 7 or 8, wherein the group C$_m$H$_{2m+1}$ is unsubstituted or substituted where one or more H atoms is replaced by F atoms and/or one or more CH$_2$ groups are replaced by O, CO, CS or NR19;

R19 is H or C$_n$H$_{2n+1}$;

n is 1, 2, 3 or 4, wherein the group C$_n$H$_{2n+1}$ is unsubstituted or substituted where one or more H atoms are replaced by F atoms; or R19 and a CH$_2$ group of R17 or R18 together with the N atom to which they are bonded form a 5- or 6-membered ring;

or

R17 and R18 together with the N atom to which they are bonded form a 5-, 6- or 7-membered ring;

R5 is H, C$_p$H$_{2p+1}$, C$_{ss}$H$_{2ss-1}$, COR20 or SO$_2$R20; wherein p is 1, 2, 3, 4, 5, 6, 7 or 8, ss is 3, 4, 5, 6, 7 or 8, R20 is C$_q$H$_{2q+1}$;

q is 1, 2, 3, 4, 5, 6, 7 or 8, wherein the groups C$_p$H$_{2p+1}$, C$_{ss}$H$_{2ss-1}$ and C$_q$H$_{2q+1}$ independently of one another are unsubstituted or substituted where one or more H atoms are replaced by F atoms and/or one or more CH$_2$ groups are replaced by O or NR21;

R21 is H or C$_r$H$_{2r+1}$;

r is 1, 2, 3 or 4; wherein the group C$_r$H$_{2r+1}$ is unsubstituted or substituted where one or more H atoms are replaced by F atoms;

R6 is H, F, Cl, Br, I, C$_s$H$_{2s+1}$, C$_{dd}$H$_{2dd-1}$, OH, OC$_t$H$_{2t+1}$ or OCOR22; wherein s and t are independently of one another 1, 2, 3, 4, 5, 6, 7 or 8;

dd is 3, 4, 5, 6, 7 or 8, wherein the groups C$_s$H$_{2s+1}$, C$_{dd}$H$_{2dd-1}$ and OC$_t$H$_{2t+1}$ independently of one another are unsubstituted or substituted where one or more H atoms are replaced by F atoms;

R22 is C$_u$H$_{2u+1}$;

u 1, 2, 3 or 4, wherein the group C$_u$H$_{2u+1}$ is unsubstituted or substituted where one or more H atoms are replaced by F atoms;

R7, R8 and R9 are independently of one another —O$_v$—SO$_w$—R$^{23}$; wherein v is zero or 1;

w is zero, 1 or 2;

R23 is C$_{nn}$H$_{2nn+1}$, C$_{mm}$H$_{2mm-1}$, OH, OC$_{pp}$H$_{2pp+1}$ or NR25R26;

nn and pp are independently of one another 1, 2, 3, 4, 5, 6, 7 or 8, mm is 3, 4, 5, 6, 7 or 8, wherein the groups C$_{nn}$H$_{2nn+1}$, C$_{mm}$H$_{2mm-1}$ and OC$_{pp}$H$_{2pp+1}$ independently of one another are unsubstituted or substituted where one or more H atoms are replaced by F atoms;

R25 and R26 are independently of one another H, CN, C$_z$H$_{2z+1}$, or C$_{zz}$H$_{2zz-1}$;

z is 1, 2, 3, 4, 5, 6, 7 or 8;

zz is 3, 4, 5, 6, 7 or 8, wherein the group C$_z$H$_{2z+1}$ is unsubstituted or substituted where one or more H atoms are replaced by F atoms and, wherein the group C$_z$H$_{2z+1}$, is unsubstituted or substituted where one or more H atoms are replaced by F atoms and/or one or more CH$_2$ groups are replaced by O, CO, CS or NR27;

R27 is H or C$_{aa}$H$_{2aa+1}$;

aa is 1, 2, 3 or 4, wherein the group C$_{aa}$H$_{2aa+1}$ is unsubstituted or substituted where one or more H atoms are replaced by F atoms;

or

R27 and a CH$_2$ group of R25 or R26 together with the N atom to which they are bonded form a 5- or 6-membered ring;

or

R25 and R26 together with the N atom to which they are bonded form a 5-, 6- or 7-membered ring;

or

R7, R8 and R9 are independently of one another NR32COR30, NR32CSR30 or NR32SO$_{bb}$R30;

R30 is H, C$_{cc}$H$_{2cc+1}$, C$_{yy}$H$_{2yy-1}$, pyrrolidinyl or piperidinyl, wherein the pyrrolidinyl or piperidinyl is unsubstituted or substituted where a CH$_2$ group is replaced by O or NR33;

R32 and R33 are independently of one another H or C$_h$H$_{2h+1}$;

bb is 2 or 3;

cc is 1, 2, 3, 4, 5, 6, 7 or 8;

yy is 3, 4, 5, 6, 7 or 8;

h is 1, 2, 3, 4, 5, 6, 7 or 8, wherein the group C$_h$H$_{2h+1}$ is unsubstituted or substituted where one or more H atoms are replaced by F atoms, and wherein the groups C$_{cc}$H$_{2cc+1}$ and C$_{yy}$H$_{2yy-1}$ independently of one another are unsubstituted or substituted where one or more H atoms are replaced by F atoms and/or one or more CH$_2$ groups are replaced by NR31 and/or one CH$_2$ group are replaced by O;

R31 is H, C$_{kk}$H$_{2kk+1}$, COR65 or SO$_2$ R65;

kk is 1, 2, 3, or 4; wherein the group C$_{kk}$H$_{2kk+1}$ is unsubstituted or substituted where one or more H atoms are replaced by F atoms, R65 is H, or C$_{xx}$H$_{2xx+1}$;

xx is 1, 2, 3 or 4, wherein the group C$_{xx}$H$_{2xx+1}$ is unsubstituted or substituted where one or more H atoms are replaced by F atoms;

or

R31 together with a CH$_2$ group of R30 forms a 5-, 6- or 7-membered ring;

or
R30 is a 5- or 6-membered heteroaryl with at least one hetero atom chosen from 1, 2, 3 or 4 N atoms, zero, 1 S atom and 1 O atom, which is unsubstituted or substituted by up to three substituents chosen from F, Cl, Br, I, $C_{oo}H_{2oo+1}$, and NR70R71;
R70 and R71 are independently of one another H, $C_{uu}H_{2uu+1}$ or COR72;
R72 is H, or $C_{vv}H_{2vv+1}$;
oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;

or
R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42,
ee and ff are independently of one another 1, 2, 3, 4, 5, 6, 7 or 8;
ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are independently of one another H, $C_{tt}H_{2tt+1}$ or $C(NH)NH_2$;
tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;
R44 is H or $C_{gg}H_{2gg+1}$;
gg is 1, 2, 3, 4, 5, 6, 7 or 8, wherein the group $C_{gg}H_{2gg+1}$ is unnsubstituted or substituted where one or more H atoms are replaced by F atoms
or
R44 forms a 5- or 6-membered ring together with a ($CH_2$) group of R40 or R41 and the N atom to which they are bound;
or
R40 and R41 with the N atom to which they are bonded form a 5- or 6-membered ring;
R42 is H or $C_{hh}H_{2hh+1}$;
hh is 1, 2, 3, 4, 5, 6, 7 or 8, wherein the group $C_{hh}H_{2hh+1}$ is unnsubstituted or substituted where one or more H atoms are replaced by F atoms;
and the pharmaceutically acceptable salts thereof.

In another embodiment, the use of the compounds of the formula I for the treatment of disorders which can be influenced by inhibition of the sodium-proton exchange of subtype III (NHE3), are chosen from:
R1, R2, R3 and R4 are independently of one another, H, F, Cl, Br, I, CN, $NO_2$, OH, $NH_2$, $C_aH_{2a+1}$, cycloalkyl with 3, 4, 5 or 6 C atoms, $OC_bH_{2b+1}$, or COOR10; wherein
a and b are independently of one another 1, 2, 3 or 4, wherein the group $C_aH_{2a+1}$ is unsubstituted or substituted where one or more H atoms are replaced by F atoms;
R10 is H or $C_cH_{2c+1}$;
c is 1, 2, 3 or 4, wherein the group $C_cH_{2c+1}$ is unsubstituted or substituted where one or more H atoms are replaced by F atoms;
or
R1, R2, R3 and R4 are independently of one another a 5- or 6-membered heteroaryl choawn from pyridyl, imidazolyl, pyrazolyl, pyrrolyl, triazolyl, tetrazolyl, thiazolyl and oxazolyl;

or
R1, R2, R3 and R4 are independently of one another CONR11R12 or NR11R12; wherein
R11 and R12 are independently of one another H, $C_eH_{2e+1}$, $C_{rr}H_{2rr-1}$;
e is 1, 2, 3 or 4,
rr is 3, 4, 5 or 6, wherein the groups $C_eH_{2e+1}$ and $C_{rr}H_{2rr-1}$ independently of one another are unsubstituted or substituted where one or more H atoms are replaced by F atoms;

or
R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
R11 and R12 together with the N atom to which they are bonded form a pyrrolidine, piperidine, N-methylpiperazine, piperazine or morpholine ring; or
R11 and R12 are independently of one another COR14, CSR14, CONHR14, CSNHR14 or $SO_2R14$; wherein
R14 is $C_gH_{2g+1}$;
g is 1, 2, 3 or 4, wherein the group $C_gH_{2g+1}$ is unsbustituted or substituted where one or more H atoms are replaced by F atoms;

or
R1, R2, R3 and R4 are independently of one another $OSO_3H$, $SO_3H$, $SO_2R_{15}$; wherein
R15 is $C_kH_{2k+1}$, $OC_lH_{2l+1}$ or NR17R18;
k is 1, 2, 3 or 4, wherein the group $C_kH_{2k+1}$ is unsubstituted or substituted where one ore more H atoms are replaced by F atoms;
l is 1, 2, 3 or 4, wherein the group $OC_lH_{2l+1}$ is unsubstituted or substituted where one ore more H atoms are replaced by F atoms;
R17 and R18 are independently of one another H, or $C_mH_{2m+1}$, in which the first $CH_2$ group bonded to the nitrogen of NR17R18 is replaced by CO and the second $CH_2$ group is replaced by NR19;
m 1, 2, 3, 4 or 5, wherein the group $C_mH_{2m+1}$ is unsubstituted or substituted where one or more H atoms is replaced by F atoms;
R19 is H or $C_nH_{2n+1}$;
n is 1, 2, 3 or 4, wherein the group $C_nH_{2n+1}$ is unsubstituted or substituted where one or more H atoms is replaced by F atoms;
or
R17 and R18 together with the N atom to which they are bonded form a 5- or 6-membered ring;
R5 is H, $C_pH_{2p+1}$ or $C_{ss}H_{2ss-1}$;
p is 1, 2, 3 or 4,
ss is 3, 4, 5 or 6, wherein the groups $C_pH_{2p-}$ and $C_{ss}H_{2ss-1}$ independently of one another are unsubstituted or substituted where one or more H atoms is replaced by F atoms;
R6 is H, $C_sH_{2s+1}$, $OC_tH_{2t+1}$ or OCOR22;
s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;
R22 is $C_uH_{2u+1}$;
u is 1, 2, 3 or 4; wherein the group $C_uH_{2u+1}$ is unsubstituted or substituted where one or more H atoms is replaced by F atoms;
R7, R8 and R9 are independently of one another $OSO_3H$, $SO_3H$ or $SO_2R23$; wherein R23 is $C_{nn}H_{2nn+1}$, $C_{mm}H_{2mm-1}$, $OC_{pp}H_{2pp+1}$ or NR25R26;
  nn and pp are independently of one another 1, 2, 3, 4 or 5, mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;
  R25 and R26 are independently of one another H, CN, or $C_zH_{2z+1}$, in which a first $CH_2$ group bonded to the nitrogen of NR25R26 is replaced by CO or CS and a second $CH_2$ is replaced by NR27;
    z is 1, 2, 3, 4, 5 or 6; wherein the group $C_zH_{2z+1}$ is unsubstituted or substituted where one or more H atoms are replaced by F atoms;
    R27 is H or $C_{aa}H_{2aa+1}$;
      aa is 1, 2, 3 or 4, wherein the group $C_{aa}H_{2aa+1}$ is unsubstituted or substituted where one or more H atoms are replaced by F atoms;
    or
    R27 and a $CH_2$ group of R25 or R26 together with the N atom to which they are bonded form a 5- or 6-membered ring;
  or
  R25 and R26 together with the N atom to which they are bonded form a 5- or 6-membered ring;
or
R7, R8 and R9 are independently of one another NR32COR30, NR32CSR30 or $NR32SO_2R30$; wherein
  R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
  R32 and R33 are independently of one another H or $C_hH_{2h+1}$;
    cc is 1, 2, 3, 4, 5, 6, 7 or 8;
    yy is 3,4, 5 or 6;
    h is 1, 2, 3 or 4; wherein the group $C_hH_{2h+1}$ is unsubstituted or substituted where one or more H atoms are replaced by F atoms, and
    wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups to be replaced by NR31 and/or one $CH_2$ group to be replaced by O;
    R31 is H, $C_{kk}H_{2kk+1}$, COR65 or $SO_2$ R65;
      kk is 1, 2, 3, or 4, wherein the group $C_{kk}H_{2kk+1}$ is unsubstituted or substituted where one or more H atoms are replaced by F atoms,
      R65 is H, or $C_{xx}H_{2xx+1}$;
      xx is 1, 2, 3 or 4, wherein the group $C_{xx}H_{2xx+1}$ is unsubstituted where one or more H atoms are replaced by F atoms; or
    R31 together with a $CH_2$ group of R30 and the N atom to which they are jointly bonded form form a 5- or 6-membered ring;
  or
  R30 is a 5- or 6-membered heteroaryl chosen from pyridyl, imidazolyl, pyrazolyl, pyrrolyl, triazolyl, tetrazolyl, thienyl, thiazolyl and oxazolyl, which is unsubstituted or substituted by up to three substituents chosen from F, Cl, Br, I, $C_{oo}H_{2oo+1}$, and NR70R71,
  R70 and R71 are independently of one another H, $C_{uu}H_{2uu+1}$ or COR72;
    R72 is H, or $C_{vv}H_{2vv+1}$;
    oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;
or
R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or O COR42;
  ee and ff are independently of one another 1, 2, 3 or 4;
  ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
  R40 and R41 are independently of one another H, $C_{tt}H_{2tt+1}$, or $C(NH)NH_2$;
    tt is 1, 2, 3, 4, 5, 6, 7 or 8, wherein the group $C_{tt}H_{2tt+1}$ is unsubstituted or substituted where one or more H atoms are replaced by F atoms;
  or
  R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl;
  or
  R40 and R41 together with the N atom to which they are bonded form a ring chosen from pyrrolidine, piperidine, N-methylpiperazine, piperazine and morpholine;
  R42 is H or $C_{hh}H_{2hh+1}$;
    hh is 1, 2, 3 or 4, wherein the group $C_{hh}H_{2hh+1}$ is unsubstituted or substituted where one or more H atoms are replaced by F atoms;
and the pharmaceutically acceptable salts thereof.

In one embodiment, the use of the compounds of the formula I for the treatment of disorders which can be influenced by inhibition of the sodium-proton exchange of subtype III (NHE3), are chosen from:
R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein
  a and b are independently of one another 1, 2, 3 or 4, wherein the groups $C_aH_{2a+1}$ and $OC_bH_{2b+1}$ independenly of one another are unsubstituted or substituted where one or more H atoms are replaced by F atoms;
or
R1, R2, R3 and R4 are independently of one another NR11R12;
  R11 and R12 are independently of one another H, $C_eH_{2e+1}$, or $C_{rr}H_{2rr-1}$;
    e is 1, 2, 3 or 4,
    rr is 3, 4, 5 or 6, wherein the groups $C_eH_{2e+1}$ and $C_{rr}H_{2rr-1}$ independenly of one another are unsubtituted or substituted where one or more H atoms are replaced by F atoms;
  or
  R11 and R12 together with the N atom to which they are bonded form a ring chosen from pyrrolidine, piperidine, N-methylpiperazine, piperazine and morpholine; or
  R11 and R12 are independently of one another COR14, CSR14, CONHR14, CSNHR14 or $SO_2R14$; wherein
  R14 is $C_gH_{2g+1}$;
    g is 1, 2, 3 or 4, wherein the group $C_gH_{2g+1}$ is unsubstituted or substituted where one or more H atoms are replaced by F atoms;

or

R1, R2, R3 and R4 are independently of one another $OSO_3H$, $SO_3H$, or $SO_2R15$;

R15 is $C_kH_{2k+1}$ or NR17R18;

k is 1, 2, 3 or 4, wherein the group $C_kH_{2k+1}$ is unsubstituted or substituted where one or more H atoms are replaced by F atoms;

R17 and R18 are independently of one another H or $C_mH_{2m+1}$;

m is 1, 2, 3, 4 or 5, wherein the group $C_mH_{2m+1}$ is unsubstituted or substituted where one ore more H atoms are replaced by F atoms;

or

R17 and R18 together with the N atom to which they are bonded form a 5- or 6-membered ring;

but where R2 does not equal H in any of the foregoing definitions;

R5 is methyl or trifluoromethyl;

R6 is H;

R7, R8 and R9 are independently of one another $OSO_3H$, $SO_3H$ or $SO_2R23$; wherein R23 is $C_{nn}H_{2nn+1}$ or NR25R26;

nn is 1, 2, 3, 4 or 5, wherein the group $C_{nn}H_{2nn+1}$ is unsubstituted or substituted where one ore more H atoms are replaced by F atoms;

R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;

z is 1, 2, 3, 4, 5 or 6, wherein the group $C_zH_{2z+1}$ is unsubstituted or substituted where one ore more H atoms are replaced by F atoms;

R27 is H or $C_{aa}H_{2aa+1}$;

aa is 1, 2, 3 or 4, wherein the group $C_{aa}H_{2aa+1}$ is unsubstituted or substituted where one ore more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5- or 6-membered ring, or R7, R8 and R9 are independently of one another NR32COR30, NR32CSR30 or NR32SO2R30;

R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are H, methyl or $CF_3$;

cc is 1, 2, 3, 4, 5, 6, 7 or 8;

yy is 3, 4, 5 or 6;

wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group is replaced by O R31 is H, methyl, ethyl, $CF_3$, $CH_2CF_3$, acetyl or propionyl, methanesulfonyl or ethanesulfonyl; or R31 together with a $CH_2$ group of R30 and the N atom to which they are jointly bonded form a 5- or 6-membered ring;

or

R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl;

or

R7, R8 and R9 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are H, $C_{tt}H_{2tt+1}$ or $C(NH)NH_2$;

tt is 1, 2, 3 or 4, wherein the group $C_{tt}H_{2tt+1}$ is unsubstituted or substituted where one or more H atoms are replaced by F atoms;

or

R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;

R42 is H or $C_{hh}H_{2hh+1}$;

hh is 1, 2, 3 or 4, wherein the $C_{hh}H_{2hh+1}$ is unsubstituted or substituted where one or more H atoms are replaced by F atoms;

and the pharmaceutically acceptable salts thereof.

In another embodiment, the invention encompasses the use of the compounds of the formula I for the treatment of disorders which can be influenced by inhibition of the sodium-proton exchange of subtype III (NHE3), chosen from:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-N,N-dimethyl-benzenesulfonamide;
5) 4-(4-bromo-phenyl)-6,8-dichloro-2-methyl-1,2,3,4-tetrahydroisoquinoline;
6) 4-(6,8-dichloro-2-methyl-1,2,3,4-tetrahydro-isoquinolin-4-yl)-benzoic acid;
7) 4-(6,8-dichloro-2-methyl-1,2,3,4-tetrahydroisoquinolin-4-yl)-N-ethyl-benzamide;
8) 4-(6,8-dichloro-2-methyl-1,2,3,4-tetrahydroisoquinolin-4-yl)-N-propyl-benzamide;
9) 4-(6,8-dichloro-2-methyl-1,2,3,4-tetrahydro-isoquinolin-4-yl)-N-(2-dimethylamino-ethyl)-benzamide;
10) 6,8-dichloro-2-methyl-4-(4-morpholin-4-yl-phenyl)-1,2,3,4-tetrahydroisoquinoline;
11) [4-(6,8-dichloro-2-methyl-1,2,3,4-tetrahydroisoquinolin-4-yl)-phenyl]-diethyl-amine
12) 6,8-dichloro-2-methyl-4-(4-piperidin-1-yl-phenyl)-1,2,3,4-tetrahydroisoquinoline;
13) 6,8-dichloro-2-methyl-4-(4-pyrrolidin-1-yl-phenyl)-1,2,3,4-tetrahydroisoquinoline;
14) 6,8-dichloro-2-methyl-4-[4-(4-methyl-piperazin-1-yl)-phenyl]-1,2,3,4-tetrahydroisoquinoline;
16) 4-(6,8-dichloro-2-methyl-1,2,3,4-tetrahydro-isoquinolin-4-yl)-phenylamine;
17) 1-[4-(6,8-dichloro-2-methyl-1,2,3,4-tetrahydro-isoquinolin-4-yl)-phenyl]-3-propylurea;

18) 1-[4-(6,8-dichloro-2-methyl-1,2,3,4-tetrahydro-isoquinolin-4-yl)-phenyl]-3-methyl-thiourea;
19) 1-[4-(6,8-dichloro-2-methyl-1,2,3,4-tetrahydro-isoquinolin-4-yl)-phenyl]-3-ethyl-urea;
20) N-[4-(6-methanesulfonyl-2-methyl-1,2,3,4-tetrahydro-isoquinolin-4-yl)-phenyl]-acetamide;
21) N-[4-(2,6,8-trimethyl-1,2,3,4-tetrahydro-isoquinolin-4-yl)-phenyl]-acetamide;
22) N-[4-(6-bromo-8-chloro-2-methyl-1,2,3,4-tetrahydro-isoquinolin-4-yl)-phenyl]-acetamide;
23) N-[4-(8-chloro-2-methyl-6-pyrrolidin-1-yl-1,2,3,4-tetrahydro-isoquinolin-4-yl)-phenyl]-acetamide;
24) N-[4-(8-chloro-2-methyl-6-morpholin-4-yl-1,2,3,4-tetrahydro-isoquinolin-4-yl) -phenyl]-acetamide;
25) N-{4-[8-chloro-2-methyl-6-(4-methyl-piperazin-1-yl)-1,2,3,4-tetrahydro-isoquinolin 4-yl]-phenyl}-acetamide;
26) N-{4-[8-chloro-6-(cyclopropylmethyl-amino)-2-methyl-1,2,3,4-tetrahydro-isoquinolin-4-yl]-phenyl}-acetamide;
27) 5-(6,8-dichloro-2-methyl-1,2,3,4-tetrahydro-isoquinolin-4-yl)-2-hydroxy-benzoic acid;
28) 5-(6,8-dichloro-2-methyl-1,2,3,4-tetrahydro-isoquinolin-4-yl)-2-hydroxy-N-methyl-benzamide;
29) 5-(6,8-dichloro-2-methyl-1,2,3,4-tetrahydro-isoquinolin-4-yl)-N-ethyl-2-hydroxy-benzamide;
30) 5-(6,8-dichloro-2-methyl-1,2,3,4-tetrahydro-isoquinolin-4-yl)-N-(2-dimethylamino-ethyl)-2-hydroxy-benzamide;
31) N-[5-(6,8-dichloro-2-methyl-1,2,3,4-tetrahydro-isoquinolin-4-yl)-2-hydroxy-benzoyl]-guanidine;
32) N-[3-(6,8-dichloro-2-methyl-1,2,3,4-tetrahydro-isoquinolin-4-yl)-phenyl]-acetamide;
33) 3-(6,8-dichloro-2-methyl-1,2,3,4-tetrahydro-isoquinolin-4-yl)-phenylamine;
34) 2-(6,8-dichloro-2-methyl-1,2,3,4-tetrahydro-isoquinolin-4-yl)-phenylamine;
35) N-[4-(6,8-dichloro-2-methyl-1,2,3,4-tetrahydro-isoquinolin-4-yl)-phenyl]-propionamide;
36) N-[4-(6,8-dichloro-2-methyl-1,2,3,4-tetrahydro-isoquinolin-4-yl)-phenyl]-butyramide;
37) N-[4-(6,8-dichloro-2-methyl-1,2,3,4-tetrahydro-isoquinolin-4-yl)-phenyl]pentanamide;
38) N-[4-(6,8-dichloro-2-methyl-1,2,3,4-tetrahydro-isoquinolin-4-yl)-phenyl]-isobutyramide;
39) N-[4-(6,8-dichloro-2-methyl-1,2,3,4-tetrahydro-isoquinolin-4-yl)-phenyl]-2,2-dimethyl-propionamide;
40) N-[4-(6,8-dichloro-2-methyl-1,2,3,4-tetrahydro-isoquinolin-4-yl)-phenyl]-cyclopropanecarboxamide;
41) N-[4-(6,8-dichloro-2-methyl-1,2,3,4-tetrahydro-isoquinolin-4-yl)-phenyl]-cyclobutanecarboxamide;
42) N-[4-(6,8-dichloro-2-methyl-1,2,3,4-tetrahydro-isoquinolin-4-yl)-phenyl]-cyclopentanecarboxamide;
43) N-[4-(6,8-dichloro-2-methyl-1,2,3,4-tetrahydro-isoquinolin-4-yl)-phenyl]-2,2,2-trifluoro-acetamide;
44) N-[4-(6,8-dichloro-2-methyl-1,2,3,4-tetrahydro-isoquinolin-4-yl)-phenyl]-1-acetyl piperidine-4-carboxamide;
45) N-[4-(6,8-dichloro-2-methyl-1,2,3,4-tetrahydro-isoquinolin-4-yl)-phenyl]-nicotinamide;
46) N-[4-(6,8-dichloro-2-methyl-1,2,3,4-tetrahydro-isoquinolin-4-yl)-phenyl]-methane-sulfonamide;
47) N-[4-(6,8-dichloro-2-methyl-1,2,3,4-tetrahydro-isoquinolin-4-yl)-phenyl]-ethanesulfonamide;
48) N',N'-dimethylamino-N-[4-(6,8-dichloro-2-methyl-1,2,3,4-tetrahydro-isoquinolin-4-yl)-phenyl]-sulfamide;
49) N-[3-(6,8-dichloro-2-methyl-1,2,3,4-tetrahydro-isoquinolin-4-yl)-phenyl]-propionamide;
50) N-[3-(6,8-dichloro-2-methyl-1,2,3,4-tetrahydro-isoquinolin-4-yl)-phenyl]-butyramide;
51) N-[3-(6,8-dichloro-2-methyl-1,2,3,4-tetrahydro-isoquinolin-4-yl)-phenyl]-pentanamide;
52) N-[3-(6,8-dichloro-2-methyl-1,2,3,4-tetrahydro-isoquinolin-4-yl)-phenyl]-isobutyramide;
53) N-[3-(6,8-dichloro-2-methyl-1,2,3,4-tetrahydro-isoquinolin-4-yl)-phenyl]-2,2-dimethyl-propionamide;
54) N-[3-(6,8-dichloro-2-methyl-1,2,3,4-tetrahydro-isoquinolin-4-yl)-phenyl]-cyclopropanecarboxamide;
55) N-[3-(6,8-dichloro-2-methyl-1,2,3,4-tetrahydro-isoquinolin-4-yl)-phenyl]-cyclobutanecarboxamide;
56) N-[3-(6,8-dichloro-2-methyl-1,2,3,4-tetrahydro-isoquinolin-4-yl)-phenyl]-cyclopentanecarboxamide;
57) N-[3-(6,8-dichloro-2-methyl-1,2,3,4-tetrahydro-isoquinolin-4-yl)-phenyl]-2,2,2-trifluoro-acetamide;
58) N-[3-(6,8-dichloro-2-methyl-1,2,3,4-tetrahydro-isoquinolin-4-yl)-phenyl]-1-acetylpiperidine-4-carboxamide;
59) N-[3-(6,8-dichloro-2-methyl-1,2,3,4-tetrahydro-isoquinolin-4-yl)-phenyl]-nicotinamide;
60) N-[3-(6,8-dichloro-2-methyl-1,2,3,4-tetrahydro-isoquinolin-4-yl)-phenyl]-methane-sulfonamide;
61) N-[3-(6,8-dichloro-2-methyl-1,2,3,4-tetrahydro-isoquinolin-4-yl)-phenyl]-ethanesulfonamide;
62) N',N'-dimethylamino-N-[3-(6,8-dichloro-2-methyl-1,2,3,4-tetrahydro-isoquinolin-4-yl)-phenyl]-sulfamide;
63) N-[2-(6,8-dichloro-2-methyl-1,2,3,4-tetrahydro-isoquinolin-4-yl)-phenyl]-propionamide;
64) N-[2-(6,8-dichloro-2-methyl-1,2,3,4-tetrahydro-isoquinolin-4-yl)-phenyl]-butyramide;
65) N-[2-(6,8-dichloro-2-methyl-1,2,3,4-tetrahydro-isoquinolin-4-yl)-phenyl]-pentanamide;
66) N-[2-(6,8-dichloro-2-methyl-1,2,3,4-tetrahydro-isoquinolin-4-yl)-phenyl]-isobutyramide;
67) N-[2-(6,8-dichloro-2-methyl-1,2,3,4-tetrahydro-isoquinolin-4-yl)-phenyl]-2,2-dimethyl-propionamide;
68) N-[2-(6,8-dichloro-2-methyl-1,2,3,4-tetrahydro-isoquinolin-4-yl)-phenyl]-cyclopropanecarboxamide;
69) N-[2-(6,8-dichloro-2-methyl-1,2,3,4-tetrahydro-isoquinolin-4-yl)-phenyl]-cyclobutanecarboxamide;
70) N-[2-(6,8-dichloro-2-methyl-1,2,3,4-tetrahydro-isoquinolin-4-yl)-phenyl]-cyclopentanecarboxamide;
71) N-[2-(6,8-dichloro-2-methyl-1,2,3,4-tetrahydro-isoquinolin-4-yl)-phenyl]-2,2,2-trifluoro-acetamide;
72) N-[2-(6,8-dichloro-2-methyl-1,2,3,4-tetrahydro-isoquinolin-4-yl)-phenyl]-1-acetylpiperidine-4-carboxamide;
73) N-[2-(6,8-Dichloro-2-methyl-1,2,3,4-tetrahydro-isoquinolin-4-yl)-phenyl]-methane-sulfonamide;
74) N-[2-(6,8-dichloro-2-methyl-1,2,3,4-tetrahydro-isoquinolin-4-yl)-phenyl]-ethanesulfonamide;
75) N',N'-dimethylamino-N-[2-(6,8-dichloro-2-methyl-1,2,3,4-tetrahydro-isoquinolin-4-yl)-phenyl]-sulfamide;
76) 1-[3-(6,8-dichloro-2-methyl-1,2,3,4-tetrahydro-isoquinolin-4-yl)-phenyl]-3-ethyl-u
77) 1-[3-(6,8-dichloro-2-methyl-1,2,3,4-tetrahydro-isoquinolin-4-yl)-phenyl]-3-methyl-thiourea;
78) 1-[2-(6,8-dichloro-2-methyl-1,2,3,4-tetrahydro-isoquinolin-4-yl)-phenyl]-3-ethyl-urea;
79) 1-[2-(6,8-dichloro-2-methyl-1,2,3,4-tetrahydro-isoquinolin-4-yl)-phenyl]-2-methyl-thiourea;
80) N-{5-[4-(6,8-dichloro-2-methyl-1,2,3,4-tetrahydro-isoquinolin-4-yl)-phenylsulfamoyl]-4-methyl!-thiazol-2-yl}-acetamide;
81) N-{5-[3-(6,8-dichloro-2-methyl-1,2,3,4-tetrahydro-isoquinolin-4-yl)-phenylsulfamoyl]-4-methyl-thiazol-2-yl}-acetamide;

82) N-[4-(6,8-dichloro-2-methyl-1,2,3,4-tetrahydro-isoquinolin-4-yl)-phenyl]-1,2-dimethyl-1H-imidazole-4-sulfonamide;
83) N-[3-(6,8-dichloro-2-methyl-1,2,3,4-tetrahydro-isoquinolin-4-yl)-phenyl]-1,2-dimethyl-1H-imidazole-4-sulfonamide;
84) N-[4-(6,8-dichloro-2-methyl-1,2,3,4-tetrahydro-isoquinolin-4-yl)-phenyl]-5-chloro-1,3-dimethyl-1H-pyrazole-4-sulfonamide;
85) N-[3-(6,8-dichloro-2-methyl-1,2,3,4-tetrahydro-isoquinolin-4-yl)-phenyl]-5-chloro-1,3-dimethyl-1H-pyrazole-4-sulfonamide;
86) N-[4-(6,8-dichloro-2-methyl-1,2,3,4-tetrahydro-isoquinolin-4-yl)-phenyl]-5-bromo-thiophene-2-sulfonamide;
87) N-[3-(6,8-dichloro-2-methyl-1,2,3,4-tetrahydro-isoquinolin-4-yl)-phenyl]-5-bromo-thiophene-2-sulfonamide;
88) N-[4-(6,8-dichloro-2-methyl-1,2,3,4-tetrahydro-isoquinolin-4-yl)-phenyl]-C,C,C-trifluoro-methanesulfonamide
89) N-[3-(6,8-dichloro-2-methyl-1,2,3,4-tetrahydro-isoquinolin-4-yl)-phenyl]-C,C,C-trifluoro-methanesulfonamide
90) 4-(6,8-dichloro-2-methyl-1,2,3,4-tetrahydro-isoquinolin-4-yl)-phenyl]-2,2,2-trifluoroethanesulfonamide;
91) 3-(6,8-dichloro-2-methyl-1,2,3,4-tetrahydro-isoquinolin-4-yl)-phenyl]-2,2,2-trifluoro-ethanesulfonamide;
92) N-ethyl-N'-4-(6,8-Dichloro-2-methyl-1,2,3,4-tetrahydro-isoquinolin-4-yl)-benzenesulfonylurea;
93) 2-chloro-5-(6,8-dichloro-2-methyl-1,2,3,4-tetrahydro-isoquinolin-4-yl)-benzenesulfonamide;
94) 2-methyl-4-phenyl-1,2,3,4-tetrahydro-isoquinolin-8-ylamine;
95) 6,8-dichloro-2-methyl-4-phenyl-1,2,3,4-tetrahydro-isoquinoline;
96) 4-(8-amino-2-methyl-1,2,3,4-tetrahydro-isoquinolin-4-yl)-phenol;
97) 8-methoxy-2-methyl-4-phenyl-1,2,3,4-tetrahydro-isoquinoline;
98) 2-(8-amino-2-ethyl-1,2,3,4-tetrahydro-isoquinolin-4-yl)-phenol;
99) 2-(8-amino-2-methyl-1,2,3,4-tetrahydro-isoquinolin-4-yl)-phenol;
100) 5-(8-amino-2-methyl-1,2,3,4-tetrahydro-isoquinolin-4-yl)-2-methoxy-phenol;
101) 2-methyl-8-nitro-4-phenyl-1,2,3,4-tetrahydro-isoquinoline;
102) 4-(8-amino-2-methyl-1,2,3,4-tetrahydro-isoquinolin-4-yl)-benzene-1,2-diol;
103) 2,8-dimethyl-4-phenyl-1,2,3,4-tetrahydro-isoquinoline;
104) 4-(3,4-dichloro-phenyl)-2-methyl-1,2,3,4-tetrahydro-isoquinoline;
105) 4-(3,4-dichloro-phenyl)-2-methyl-1,2,3,4-tetrahydro-isoquinolin-8-ylamine;
106) 4-(2,4-dichloro-phenyl)-2-methyl-1,2,3,4-tetrahydro-isoquinolin-8-ylamine;
107) 4-(3-chloro-phenyl)-2-methyl-1,2,3,4-tetrahydro-isoquinolin-8-ylamine;
108) 2,4-dimethyl-4-phenyl-1,2,3,4-tetrahydro-isoquinoline;
109) 2-butyl-4-phenyl-1,2,3,4-tetrahydro-isoquinolin-8-ylamine;
110) N-(2-methyl-4-phenyl-1,2,3,4-tetrahydro-isoquinolin-8-yl)-acetamide;
111) 7-chloro-2-methyl-4-phenyl-1,2,3,4-tetrahydro-isoquinoline;
112) 8-chloro-2-methyl-4-phenyl-1,2,3,4-tetrahydro-isoquinoline;
113) 2,6-dimethyl-4-phenyl-1,2,3,4-tetrahydro-isoquinoline;
114) 6-chloro-2-methyl-4-phenyl-1,2,3,4-tetrahydro-isoquinoline;
115) 6-methoxy-2-methyl-4-phenyl-1,2,3,4-tetrahydro-isoquinoline;
116) 2-ethyl-4-phenyl-1,2,3,4-tetrahydro-isoquinoline;
117) 2-methyl-4-phenyl-1,2,3,4-tetrahydro-isoquinoline;
118) 6,8-dichloro-2-ethyl-4-phenyl-1,2,3,4-tetrahydro-isoquinoline;
119) 4-(4-bromo-phenyl)-6,8-dichloro-2-methyl-1,2,3,4-tetrahydro-isoquinoline;
120) 2-methyl-4-phenyl-6,8-bis-trifluoromethyl-1,2,3,4-tetrahydro-isoquinoline;
121) 6,8-dichloro-2-isopropyl-4-phenyl-1,2,3,4-tetrahydro-isoquinoline;
122) 5,8-dichloro-2-methyl-4-phenyl-1,2,3,4-tetrahydro-isoquinoline;
123) 6,8-dichloro-4-(4-fluoro-phenyl)-2-methyl-1,2,3,4-tetrahydro-isoquinoline;
124) 6,8-Dichloro-2-methyl-4-p-tolyl-1,2,3,4-tetrahydro-isoquinoline;
125) 5,6-dichloro-2-methyl-4-phenyl-1,2,3,4-tetrahydro-isoquinoline;
126) 6,7-dichloro-2-methyl-4-phenyl-1,2,3,4-tetrahydro-isoquinoline;
127) 8-bromo-2-methyl-4-phenyl-1,2,3,4-tetrahydro-isoquinoline;
128) 6,8-dichloro-4-(4-chloro-phenyl)-2-methyl-1,2,3,4-tetrahydro-isoquinoline;
129) 6,8-dichloro-2-cyclopropyl-4-phenyl-1,2,3,4-tetrahydro-isoquinoline;
130) 2-Amino-N-[4-(6,8-dichloro-2-methyl-1,2,3,4-tetrahydro-isoquinolin-4-yl)-phenyl]-acetamide;
131) N-[4-(6,8-Dichloro-2-methyl-1,2,3,4-tetrahydro-isoquinolin-4-yl)-phenyl]-2-methylamino-acetamide;
132) N-[4-(6,8-Dichloro-2-methyl-1,2,3,4-tetrahydro-isoquinolin-4-yl)-phenyl]-2-dimethylamino-acetamide;
133) 2-Amino-N-[4-(6,8-dichloro-2-methyl-1,2,3,4-tetrahydro-isoquinolin-4-yl)-phenyl]-propionamide;
134) 2-Amino-N-[4-(6,8-dichloro-2-methyl-1,2,3,4-tetrahydro-isoquinolin-4-yl)-phenyl]-butyramide;
135) 2,6-Diamino-hexanoic acid [4-(6,8-dichloro-2-methyl-1,2,3,4-tetrahydro-isoquinolin-4-yl)-phenyl]-amide;
136) Pyrrolidine-2-carboxylic acid [4-(6,8-dichloro-2-methyl-1,2,3,4-tetrahydro-isoquinolin-4-yl)-phenyl]-amide;
137) N-[4-(6,8-Dichloro-2-methyl-1,2,3,4-tetrahydro-isoquinolin-4-yl)-phenyl]-isonicotinamide;
138) 1H-Pyrrole-3-carboxylic acid [4-(6,8-dichloro-2-methyl-1,2,3,4-tetrahydro-isoquinolin-4-yl)-phenyl]-amide;
139) 1H-Pyrrole-2-carboxylic acid [4-(6,8-dichloro-2-methyl-1,2,3,4-tetrahydro-isoquinolin-4-yl)-phenyl]-amide;
140) 1-Methyl-piperidine-4-carboxylic acid [4-(6,8-dichloro-2-methyl-1,2,3,4-tetrahydro-isoquinolin-4-yl)-phenyl]-amide;
141) 1,4-Dimethyl-1H-pyrrole-2-carboxylic acid [4-(6,8-dichloro-2-methyl-1,2,3,4-tetrahydro-isoquinolin-4-yl)-phenyl]-amide;
142) 4-Nitro-1H-pyrrole-2-carboxylic acid [4-(6,8-dichloro-2-methyl-1,2,3,4-tetrahydro-isoquinolin-4-yl)-phenyl]-amide;

143) 2,5-Dimethyl-1H-pyrrole-3-carboxylic acid [4-(6,8-dichloro-2-methyl-1,2,3,4-tetrahydro-isoquinolin-4-yl)-phenyl]-amide;
144) 1H-Imidazole-4-carboxylic acid [4-(6,8-dichloro-2-methyl-1,2,3,4-tetrahydro-isoquinolin-4-yl)-phenyl]-amide;
145) 1-Methanesulfonyl-piperidine-4-carboxylic acid [4-(6,8-dichloro-2-methyl-1,2,3,4-tetrahydro-isoquinolin-4-yl)-phenyl]-amide;
146) 3,5-Dimethyl-1H-pyrazole-4-carboxylic acid [4-(6,8-dichloro-2-methyl-1,2,3,4-tetrahydro-isoquinolin-4-yl)-phenyl]-amide;
147) 1H-Pyrazole-4-carboxylic acid [4-(6,8-dichloro-2-methyl-1,2,3,4-tetrahydro-isoquinolin-4-yl)-phenyl]-amide;
148) 3-Trifluoromethyl-1H-pyrazole-4-carboxylic acid [4-(6,8-dichloro-2-methyl-1,2,3,4-tetrahydro-isoquinolin-4-yl)-phenyl]-amide;
149) N-[3-(6,8-Dichloro-2-methyl-1,2,3,4-tetrahydro-isoquinolin-4-yl)-phenyl]-2-methylamino-acetamide;
150) N-[3-(6,8-Dichloro-2-methyl-1,2,3,4-tetrahydro-isoquinolin-4-yl)-phenyl]-2-dimethylamino-acetamide;
151) 2-Amino-N-[3-(6,8-dichloro-2-methyl-1,2,3,4-tetrahydro-isoquinolin-4-yl)-phenyl]-propionamide;
152) 2-Amino-N-[3-(6,8-dichloro-2-methyl-1,2,3,4-tetrahydro-isoquinolin-4-yl)-phenyl]-butyramide;
153) 2,6-Diamino-hexanoic acid [3-(6,8-dichloro-2-methyl-1,2,3,4-tetrahydro-isoquinolin-4-yl)-phenyl]-amide;
154) Pyrrolidine-2-carboxylic acid [3-(6,8-dichloro-2-methyl-1,2,3,4-tetrahydro-isoquinolin-4-yl)-phenyl]-amide;
155) N-[3-(6,8-Dichloro-2-methyl-1,2,3,4-tetrahydro-isoquinolin-4-yl)-phenyl]-isonicotinamide;
156) 1H-Pyrrole-3-carboxylic acid [3-(6,8-dichloro-2-methyl-1,2,3,4-tetrahydro-isoquinolin-4-yl)-phenyl]-amide;
157) 1H-Pyrrole-2-carboxylic acid [3-(6,8-dichloro-2-methyl-1,2,3,4-tetrahydro-isoquinolin-4-yl)-phenyl]-amide;
158) 1-Methyl-piperidine-4-carboxylic acid [3-(6,8-dichloro-2-methyl-1,2,3,4-tetrahydro-isoquinolin-4-yl)-phenyl]-amide;
159) 1,4-Dimethyl-1H-pyrrole-2-carboxylic acid [3-(6,8-dichloro-2-methyl-1,2,3,4-tetrahydro-isoquinolin-4-yl)-phenyl]-amide;
160) 4-Nitro-1H-pyrrole-2-carboxylic acid [3-(6,8-dichloro-2-methyl-1,2,3,4-tetrahydro-isoquinolin-4-yl)-phenyl]-amide;
161) 2,5-Dimethyl-1H-pyrrole-3-carboxylic acid [3-(6,8-dichloro-2-methyl-1,2,3,4-tetrahydro-isoquinolin-4-yl)-phenyl]-amide;
162) 1H-Imidazole-4-carboxylic acid [3-(6,8-dichloro-2-methyl-1,2,3,4-tetrahydro-isoquinolin-4-yl)-phenyl]-amide;
163) 1-Methanesulfonyl-piperidine-4-carboxylic acid [3-(6,8-dichloro-2-methyl-1,2,3,4-tetrahydro-isoquinolin-4-yl)-phenyl]-amide;
164) 3,5-Dimethyl-1H-pyrazole-4-carboxylic acid [3-(6,8-dichloro-2-methyl-1,2,3,4-tetrahydro-isoquinolin-4-yl)-phenyl]-amide;
165) 1H-Pyrazole-4-carboxylic acid [3-(6,8-dichloro-2-methyl-1,2,3,4-tetrahydro-isoquinolin-4-yl)-phenyl]-amide;
166) 3-Trifluoromethyl-1H-pyrazole-4-carboxylic acid [3-(6,8-dichloro-2-methyl-1,2,3,4-tetrahydro-isoquinolin-4-yl)-phenyl]-amide;
167) 1-[2-(6,8-Dichloro-2-methyl-1,2,3,4-tetrahydro-isoquinolin-4-yl)-phenyl]-3-ethyl-thiourea;
168) 1-[4-(6,8-Dichloro-2-methyl-1,2,3,4-tetrahydro-isoquinolin-4-yl)-phenyl]-3-ethyl-thiourea;
169) 1-[3-(6,8-Dichloro-2-methyl-1,2,3,4-tetrahydro-isoquinolin-4-yl)-phenyl]-3-ethyl-thiourea;
170) 3-[3-(6,8-Dichloro-2-methyl-1,2,3,4-tetrahydro-isoquinolin-4-yl)-phenyl]-1,1-dimethyl-urea;
171) 4-Methyl-piperazine-1-carboxylic acid [3-(6,8-dichloro-2-methyl-1,2,3,4-tetrahydro-isoquinolin-4-yl)-phenyl]-amide;
172) Piperidine-1-carboxylic acid [3-(6,8-dichloro-2-methyl-1,2,3,4-tetrahydro -isoquinolin-4-yl)-phenyl]-amide;
173) Morpholine-4-carboxylic acid [3-(6,8-dichloro-2-methyl-1,2,3,4-tetrahydro -isoquinolin-4-yl)-phenyl]-amide;
174) Pyrrolidine-1-carboxylic acid [3-(6,8-dichloro-2-methyl-1,2,3,4-tetrahydro-isoquinolin-4-yl)-phenyl]-amide;
175) 3-[3-(6,8-Dichloro-2-methyl-1,2,3,4-tetrahydro-isoquinolin-4-yl)-phenyl]-1,1-diethyl-urea;
176) 1-[3-(6,8-Dichloro-2-methyl-1,2,3,4-tetrahydro-isoquinolin-4-yl)-phenyl]-3-methyl-urea;
177) 1-[3-(6,8-Dichloro-2-methyl-1,2,3,4-tetrahydro-isoquinolin-4-yl)-phenyl]-3-(2-dimethylamino-ethyl)-urea;
178) 1-[3-(6,8-Dichloro-2-methyl-1,2,3,4-tetrahydro-isoquinolin-4-yl)-phenyl]-3-(tetrahydro-furan-3-yl)-urea;
179) 1-[3-(6,8-Dichloro-2-methyl-1,2,3,4-tetrahydro-isoquinolin-4-yl)-phenyl]-3-(tetrahydro-pyran-4-yl)-urea;
180) 3-[3-(6,8-Dichloro-2-methyl-1,2,3,4-tetrahydro-isoquinolin-4-yl)-phenyl]-1-methyl-1-(1-methyl-piperidin-4-yl)-urea;
181) 3-[3-(6,8-Dichloro-2-methyl-1,2,3,4-tetrahydro-isoquinolin-4-yl)-phenyl]-1-(3-dimethylamino-propyl)-1-methyl-urea;
182) 3-[3-(6,8-Dichloro-2-methyl-1,2,3,4-tetrahydro-isoquinolin-4-yl)-phenyl]-1-(2-dimethylamino-ethyl)-1-methyl-urea;
183) 1-[3-(6,8-Dichloro-2-methyl-1,2,3,4-tetrahydro-isoquinolin-4-yl)-phenyl]-3-(3-dimethylamino-propyl)-urea;
184) 1-[3-(6,8-Dichloro-2-methyl-1,2,3,4-tetrahydro-isoquinolin-4-yl)-phenyl]-3-(2-methoxy-ethyl)-urea;
185) 1-[3-(6,8-Dichloro-2-methyl-1,2,3,4-tetrahydro-isoquinolin-4-yl)-phenyl]-3-pyridin-3-yl-urea;
186) 1-[3-(6,8-Dichloro-2-methyl-1,2,3,4-tetrahydro-isoquinolin-4-yl)-phenyl]-3-pyridin-4-yl-urea;
187) 4-Methyl-piperazine-1-carboxylic acid [2-(6,8-dichloro-2-methyl-1,2,3,4-tetrahydro -isoquinolin-4-yl)-phenyl]-amide;
188) 1-[2-(6,8-Dichloro-2-methyl-1,2,3,4-tetrahydro-isoquinolin-4-yl)-phenyl]-3-methyl-urea;
189) 3-[2-(6,8-Dichloro-2-methyl-1,2,3,4-tetrahydro-isoquinolin-4-yl)-phenyl]-1,1-dimethyl-urea;
190) 3-[2-(6,8-Dichloro-2-methyl-1,2,3,4-tetrahydro-isoquinolin-4-yl)-phenyl]-1,1-diethyl-urea;
191) Piperidine-1-carboxylic acid [2-(6,8-dichloro-2-methyl-1,2,3,4-tetrahydro-isoquinolin-4-yl)-phenyl]-amide;
192) Morpholine-4-carboxylic acid [2-(6,8-dichloro-2-methyl-1,2,3,4-tetrahydro-isoquinolin-4-yl)-phenyl]-amide;
193) Pyrrolidine-1-carboxylic acid [2-(6,8-dichloro-2-methyl-1,2,3,4-tetrahydro-isoquinolin-4-yl)-phenyl]-amide;
194) 1-[2-(6,8-Dichloro-2-methyl-1,2,3,4-tetrahydro-isoquinolin-4-yl)-phenyl]-3-(2-dimethylamino-ethyl)-urea;

195) 4-Methyl-piperazine-1-carboxylic acid [4-(6,8-dichloro-2-methyl-1,2,3,4-tetrahydro-isoquinolin-4-yl)-phenyl]-amide;
196) Pyrrolidine-1-carboxylic acid [4-(6,8-dichloro-2-methyl-1,2,3,4-tetrahydro-isoquinolin-4-yl)-phenyl]-amide;
197) 1-[4-(6,8-Dichloro-2-methyl-1,2,3,4-tetrahydro-isoquinolin-4-yl)-phenyl]-3-methyl-urea;
198) 3-[4-(6,8-Dichloro-2-methyl-1,2,3,4-tetrahydro-isoquinolin-4-yl)-phenyl]-1,1-dimethyl-urea;
199) 3-[4-(6,8-Dichloro-2-methyl-1,2,3,4-tetrahydro-isoquinolin-4-yl)-phenyl]-1,1-diethyl-urea;
200) 1-[4-(6,8-Dichloro-2-methyl-1,2,3,4-tetrahydro-isoquinolin-4-yl)-phenyl]-3-(2-dimethylamino-ethyl)-urea;
201) Piperidine-1-carboxylic acid [4-(6,8-dichloro-2-methyl-1,2,3,4-tetrahydro-isoquinolin-4-yl)-phenyl]-amide;
202) Morpholine-4-carboxylic acid [4-(6,8-dichloro-2-methyl-1,2,3,4-tetrahydro-isoquinolin-4-yl)-phenyl]-amide;
203) N-[4-(6,8-Dichloro-2-methyl-1,2,3,4-tetrahydro-isoquinolin-4-yl)-phenyl]-formamide;
204) [4-(6,8-Dichloro-2-methyl-1,2,3,4-tetrahydro-isoquinolin-4-yl)-phenyl]-methyl-amine;
205) 1-[4-(6,8-Dichloro-2-methyl-1,2,3,4-tetrahydro-isoquinolin-4-yl)-phenyl]-1,3-dimethyl-urea;
206) 4-Methyl-piperazine-1-carboxylic acid [4-(6,8-dichloro-2-methyl-1,2,3,4-tetrahydro-isoquinolin-4-yl)-phenyl]-methyl-amide;
207) 1-[4-(6,8-Dichloro-2-methyl-1,2,3,4-tetrahydro-isoquinolin-4-yl)-phenyl]-1,3,3-trimethyl-urea;
208) Piperidine-1-carboxylic acid [4-(6,8-dichloro-2-methyl-1,2,3,4-tetrahydro-isoquinolin-4-yl)-phenyl]-methyl-amide;
209) Morpholine-4-carboxylic acid [4-(6,8-dichloro-2-methyl-1,2,3,4-tetrahydro-isoquinolin-4-yl)-phenyl]-methyl-amide;
210) Pyrrolidine-1-carboxylic acid [4-(6,8-dichloro-2-methyl-1,2,3,4-tetrahydro-isoquinolin-4-yl)-phenyl]-methyl-amide;
211) 1-[4-(6,8-Dichloro-2-methyl-1,2,3,4-tetrahydro-isoquinolin-4-yl)-phenyl]-3-(2-dimethylamino-ethyl)-1-methyl-urea;
212) 1-[4-(6,8-Dichloro-2-methyl-1,2,3,4-tetrahydro-isoquinolin-4-yl)-phenyl]-3,3-diethyl-1-methyl-urea;
213) N-[3-(6,8-Dichloro-2-methyl-1,2,3,4-tetrahydro-isoquinolin-4-yl)-phenyl]-formamide;
214) [3-(6,8-Dichloro-2-methyl-1,2,3,4-tetrahydro-isoquinolin-4-yl)-phenyl]-methyl-amine;
215) Pyrrolidine-1-carboxylic acid [3-(6,8-dichloro-2-methyl-1,2,3,4-tetrahydro-isoquinolin-4-yl)-phenyl]-methyl-amide;
216) Piperidine-1-carboxylic acid [3-(6,8-dichloro-2-methyl-1,2,3,4-tetrahydro-isoquinolin-4-yl)-phenyl]-methyl-amide;
217) 1-[3-(6,8-Dichloro-2-methyl-1,2,3,4-tetrahydro-isoquinolin-4-yl)-phenyl]-1,3,3-trimethyl-urea;
218) 1-[3-(6,8-Dichloro-2-methyl-1,2,3,4-tetrahydro-isoquinolin-4-yl)-phenyl]-1,3-dimethyl-urea;
219) Morpholine-4-carboxylic acid [3-(6,8-dichloro-2-methyl-1,2,3,4-tetrahydro-isoquinolin-4-yl)-phenyl]-methyl-amide;
220) 4-Methyl-piperazine-1-carboxylic acid [3-(6,8-dichloro-2-methyl-1,2,3,4-tetrahydro-isoquinolin-4-yl)-phenyl]-methyl-amide;
221) 1-[3-(6,8-Dichloro-2-methyl-1,2,3,4-tetrahydro-isoquinolin-4-yl)-phenyl]-3-(2-dimethylamino-ethyl)-1-methyl-urea;
222) 1-[3-(6,8-Dichloro-2-methyl-1,2,3,4-tetrahydro-isoquinolin-4-yl)-phenyl]-3,3-diethyl-1-methyl-urea;
223) [3-(6,8-Dichloro-2-methyl-1,2,3,4-tetrahydro-isoquinolin-4-yl)-phenyl]-carbamic acid 2-dimethylamino-ethyl ester;
224) [4-(6,8-Dichloro-2-methyl-1,2,3,4-tetrahydro-isoquinolin-4-yl)-phenyl]-carbamic acid 2-dimethylamino-ethyl ester;
225) [2-(6,8-Dichloro-2-methyl-1,2,3,4-tetrahydro-isoquinolin-4-yl)-phenyl]-carbamic acid 2-dimethylamino-ethyl ester;
226) [3-(6,8-Dichloro-2-methyl-1,2,3,4-tetrahydro-isoquinolin-4-yl)-phenyl]-carbamic acid methyl ester;
227) [3-(6,8-Dichloro-2-methyl-1,2,3,4-tetrahydro-isoquinolin-4-yl)-phenyl]-carbamic acid ethyl ester;
228) [3-(6,8-Dichloro-2-methyl-1,2,3,4-tetrahydro-isoquinolin-4-yl)-phenyl]-carbamic acid isopropyl ester;
229) [3-(6,8-Dichloro-2-methyl-1,2,3,4-tetrahydro-isoquinolin-4-yl)-phenyl]-carbamic acid 2,2-dimethyl-propyl ester;
230) [4-(6,8-Dichloro-2-methyl-1,2,3,4-tetrahydro-isoquinolin-4-yl)-phenyl]-carbamic acid methyl ester;
231) [4-(6,8-Dichloro-2-methyl-1,2,3,4-tetrahydro-isoquinolin-4-yl)-phenyl]-carbamic acid isopropyl ester;
232) [4-(6,8-Dichloro-2-methyl-1,2,3,4-tetrahydro-isoquinolin-4-yl)-phenyl]-carbamic acid 2,2-dimethyl-propyl ester;
233) [4-(6,8-Dichloro-2-methyl-1,2,3,4-tetrahydro-isoquinolin-4-yl)-phenyl]-carbamic acid ethyl ester;
234) (+)-N-[3-(6,8-Dichloro-2-methyl-1,2,3,4-tetrahydro-isoquinolin-4-yl)-phenyl]-methanesulfonamide;
235) (−)-N-[3-(6,8-Dichloro-2-methyl-1,2,3,4-tetrahydro-isoquinolin-4-yl)-phenyl]-methanesulfonamide;
236) (+)-1-[2-(6,8-Dichloro-2-methyl-1,2,3,4-tetrahydro-isoquinolin-4-yl)-phenyl]-3-ethyl-urea;
237) (−)-1-[2-(6,8-Dichloro-2-methyl-1,2,3,4-tetrahydro-isoquinolin-4-yl)-phenyl]-3-ethyl-urea;
238) N-[3-(6,8-Difluoro-2-methyl-1,2,3,4-tetrahydro-isoquinolin-4-yl)-phenyl]-acetamide;
239) 4-(3-Bromo-phenyl)-6,8-dichloro-2-methyl-1,2,3,4-tetrahydro-isoquinoline;
240) 1-[3-(6,8-Dichloro-2-methyl-1,2,3,4-tetrahydro-isoquinolin-4-yl)-phenyl]-3-(2-hydroxy-ethyl)-urea;
241) 3-(6,8-Dichloro-2-methyl-1,2,3,4-tetrahydro-isoquinolin-4-yl)-benzoic acid ethyl ester;
242) 3-(6,8-Dichloro-2-methyl-1,2,3,4-tetrahydro-isoquinolin-4-yl)-benzoic acid;

and the pharmaceutically acceptable salts thereof.

In one embodiment, the invention encompasses the use of the compounds of the formula I for the treatment of disorders which can be influenced by inhibition of the sodium-proton exchange of subtype III (NHE3), chosen from:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-benzoic acid;
5) 4-(6,8-dichloro-2-methyl-1,2,3,4-tetrahydroisoquinolin-4-yl)-N-ethyl-benzamide;
6) 4-(6,8-dichloro-2-methyl-1,2,3,4-tetrahydroisoquinolin-4-yl)-N-propyl-benzamide;

7) 4-(6,8-dichloro-2-methyl-1,2,3,4-tetrahydro-isoquinolin-4-yl)-N-(2-dimethylamino-ethyl)-benzamide;
8) 6,8-dichloro-2-methyl-4-(4-morpholin-4-yl-phenyl)-1,2,3,4-tetrahydroisoquinoline;
9) 4-(6,8-dichloro-2-methyl-1,2,3,4-tetrahydro-isoquinolin-4-yl)-phenylamine;
10) 1-[4-(6,8-dichloro-2-methyl-1,2,3,4-tetrahydro-isoquinolin-4-yl)-phenyl]-3-methyl-thiourea;
11) 1-[4-(6,8-dichloro-2-methyl-1,2,3,4-tetrahydro-isoquinolin-4-yl)-phenyl]-3-ethyl-urea;
12) N-[4-(6-bromo-8-chloro-2-methyl-1,2,3,4-tetrahydro-isoquinolin-4-yl)-phenyl]-acetamide;
13) 5-(6,8-dichloro-2-methyl-1,2,3,4-tetrahydro-isoquinolin-4-yl)-2-hydroxy-benzoic acid;
14) 5-(6,8-dichloro-2-methyl-1,2,3,4-tetrahydro-isoquinolin-4-yl)-N-(2-dimethylamino-ethyl)-2-hydroxy-benzamide;
15) N-[3-(6,8-dichloro-2-methyl-1,2,3,4-tetrahydro-isoquinolin-4-yl)-phenyl]-acetamide;
16) 3-(6,8-dichloro-2-methyl-1,2,3,4-tetrahydro-isoquinolin-4-yl)-phenylamine;
17) 2-(6,8-dichloro-2-methyl-1,2,3,4-tetrahydro-isoquinolin-4-yl)-phenylamine;
18) N-[4-(6,8-dichloro-2-methyl-1,2,3,4-tetrahydro-isoquinolin-4-yl)-phenyl]-propionamide;
19) N-[4-(6,8-dichloro-2-methyl-1,2,3,4-tetrahydro-isoquinolin-4-yl)-phenyl]-1-acetyl-piperidine-4-carboxamide;
20) N-[4-(6,8-dichloro-2-methyl-1,2,3,4-tetrahydro-isoquinolin-4-yl)-phenyl]-methane-sulfonamide;
21) N-[4-(6,8-dichloro-2-methyl-1,2,3,4-tetrahydro-isoquinolin-4-yl)-phenyl]-ethanesulfonamide;
22) N',N'-dimethylamino-N-[4-(6,8-dichloro-2-methyl-1,2,3,4-tetrahydro-isoquinolin-4-yl)-phenyl]-sulfamide;
23) N-[3-(6,8-dichloro-2-methyl-1,2,3,4-tetrahydro-isoquinolin-4-yl)-phenyl]-propionamide;
24) N-[3-(6,8-dichloro-2-methyl-1,2,3,4-tetrahydro-isoquinolin-4-yl)-phenyl]-butyramide;
25) N-[3-(6,8-dichloro-2-methyl-1,2,3,4-tetrahydro-isoquinolin-4-yl)-phenyl]-isobutyramide;
26) N-[3-(6,8-dichloro-2-methyl-1,2,3,4-tetrahydro-isoquinolin-4-yl)-phenyl]-cyclopropanecarboxamide;
27) N-[3-(6,8-dichloro-2-methyl-1,2,3,4-tetrahydro-isoquinolin-4-yl)-phenyl]-cyclobutanecarboxamide;
28) N-[3-(6,8-dichloro-2-methyl-1,2,3,4-tetrahydro-isoquinolin-4-yl)-phenyl]-2,2,2-trifluoro-acetamide;
29) N-[3-(6,8-dichloro-2-methyl-1,2,3,4-tetrahydro-isoquinolin-4-yl)-phenyl]-1-acetyl-piperidiene-4-carboxamide;
30) N-[3-(6,8-dichloro-2-methyl-1,2,3,4-tetrahydro-isoquinolin-4-yl)-phenyl]-nicotinamide;
31) N-[3-(6,8-dichloro-2-methyl-1,2,3,4-tetrahydro-isoquinolin-4-yl)-phenyl]-methane-sulfonamide;
32) N-[3-(6,8-dichloro-2-methyl-1,2,3,4-tetrahydro-isoquinolin-4-yl)-phenyl]-ethanesulfonamide;
33) N',N'-dimethylamino-N-[3-(6,8-dichloro-2-methyl-1,2,3,4-tetrahydro-isoquinolin-4-yl)-phenyl]-sulfamide;
34) N-[2-(6,8-dichloro-2-methyl-1,2,3,4-tetrahydro-isoquinolin-4-yl)-phenyl]-cyclopropanecarboxamide;
35) N-[2-(6,8-dichloro-2-methyl-1,2,3,4-tetrahydro-isoquinolin-4-yl)-phenyl]-1-acetyl-piperidine-4-carboxamide;
36) 1-[3-(6,8-dichloro-2-methyl-1,2,3,4-tetrahydro-isoquinolin-4-yl)-phenyl]-3-ethyl-urea;
37) 1-[3-(6,8-dichloro-2-methyl-1,2,3,4-tetrahydro-isoquinolin-4-yl)-phenyl]-3-methyl-thiourea;
38) 1-[2-(6,8-dichloro-2-methyl-1,2,3,4-tetrahydro-isoquinolin-4-yl)-phenyl]-3-ethyl-urea;
39) 1-[2-(6,8-dichloro-2-methyl-1,2,3,4-tetrahydro-isoquinolin-4-yl)-phenyl]-3-methyl-thiourea;
40) N-{5-[3-(6,8-dichloro-2-methyl-1,2,3,4-tetrahydro-isoquinolin-4-yl)-phenylsulfamoyl]-4-methyl-thiazol-2-yl}-acetamide;
41) N-[3-(6,8-dichloro-2-methyl-1,2,3,4-tetrahydro-isoquinolin-4-yl)-phenyl]-1,2-dimethyl-1H-imidazole-4-sulfonamide;
42) N-[4-(6,8-dichloro-2-methyl-1,2,3,4-tetrahydro-isoquinolin-4-yl)-phenyl]-C,C,C-trifluoro-methanesulfonamide;
43) N-[3-(6,8-dichloro-2-methyl-1,2,3,4-tetrahydro-isoquinolin-4-yl)-phenyl]-C,C,C-trifluoro-methanesulfonamide;
44) N-ethyl-N'-4-(6,8-dichloro-2-methyl-1,2,3,4-tetrahydro-isoquinolin-4-yl)-benzenesulfonylurea; 45) N-[4-(6,8-Dichloro-2-methyl-1,2,3,4-tetrahydro-isoquinolin-4-yl)-phenyl]-2-dimethylamino-acetamide;
46) 2,6-Diamino-hexanoic acid [4-(6,8-dichloro-2-methyl-1,2,3,4-tetrahydro-isoquinolin-4-yl)-phenyl]-amide;
47) 1H-Pyrrole-3-carboxylic acid [4-(6,8-dichloro-2-methyl-1,2,3,4-tetrahydro-isoquinolin-4-yl)-phenyl]-amide;
48) 1-Methyl-piperidine-4-carboxylic acid [4-(6,8-dichloro-2-methyl-1,2,3,4-tetrahydro-isoquinolin-4-yl)-phenyl]-amide;
49) 1-Methanesulfonyl-piperidine-4-carboxylic acid [4-(6,8-dichloro-2-methyl-1,2,3,4-tetrahydro-isoquinolin-4-yl)-phenyl]-amide;
50) 1H-Pyrazole-4-carboxylic acid [4-(6,8-dichloro-2-methyl-1,2,3,4-tetrahydro-isoquinolin-4-yl)-phenyl]-amide;
51) N-[3-(6,8-Dichloro-2-methyl-1,2,3,4-tetrahydro-isoquinolin-4-yl)-phenyl]-2-methylamino-acetamide;
52) N-[3-(6,8-Dichloro-2-methyl-1,2,3,4-tetrahydro-isoquinolin-4-yl)-phenyl]-2-dimethylamino-acetamide;
53) 2-Amino-N-[3-(6,8-dichloro-2-methyl-1,2,3,4-tetrahydro-isoquinolin-4-yl)-phenyl]-propionamide;
54) 2-Amino-N-[3-(6,8-dichloro-2-methyl-1,2,3,4-tetrahydro-isoquinolin-4-yl)-phenyl]-butyramide;
55) 2,6-Diamino-hexanoic acid [3-(6,8-dichloro-2-methyl-1,2,3,4-tetrahydro-isoquinolin-4-yl)-phenyl]-amide;
56) 1-Methyl-piperidine-4-carboxylic acid [3-(6,8-dichloro-2-methyl-1,2,3,4-tetrahydro-isoquinolin-4-yl)-phenyl]-amide;
57) 1H-Imidazole-4-carboxylic acid [3-(6,8-dichloro-2-methyl-1,2,3,4-tetrahydro-isoquinolin-4-yl)-phenyl]-amide;
58) 1-Methanesulfonyl-piperidine-4-carboxylic acid [3-(6,8-dichloro-2-methyl-1,2,3,4-tetrahydro-isoquinolin-4-yl)-phenyl]-amide;
59) 3,5-Dimethyl-1H-pyrazole-4-carboxylic acid [3-(6,8-dichloro-2-methyl-1,2,3,4-tetrahydro-isoquinolin-4-yl)-phenyl]-amide;
60) 1H-Pyrazole-4-carboxylic acid [3-(6,8-dichloro-2-methyl-1,2,3,4-tetrahydro-isoquinolin-4-yl)-phenyl]-amide;
61) 3-[3-(6,8-Dichloro-2-methyl-1,2,3,4-tetrahydro-isoquinolin-4-yl)-phenyl]-1,1-dimethyl-urea;
62) 4-Methyl-piperazine-1-carboxylic acid [3-(6,8-dichloro-2-methyl-1,2,3,4-tetrahydro-isoquinolin-4-yl)-phenyl]-amide;
63) Piperidine-1-carboxylic acid [3-(6,8-dichloro-2-methyl-1,2,3,4-tetrahydro-isoquinolin-4-yl)-phenyl]-amide;
64) Morpholine-4-carboxylic acid [3-(6,8-dichloro-2-methyl-1,2,3,4-tetrahydro-isoquinolin-4-yl)-phenyl]-amide;

65) Pyrrolidine-1-carboxylic acid [3-(6,8-dichloro-2-methyl-1,2,3,4-tetrahydro-isoquinolin-4-yl)-phenyl]-amide;
66) 3-[3-(6,8-Dichloro-2-methyl-1,2,3,4-tetrahydro-isoquinolin-4-yl)-phenyl]-1,1-diethyl-urea;
67) 1-[3-(6,8-Dichloro-2-methyl-1,2,3,4-tetrahydro-isoquinolin-4-yl)-phenyl]-3-methyl-urea;
68) 1-[3-(6,8-Dichloro-2-methyl-1,2,3,4-tetrahydro-isoquinolin-4-yl)-phenyl]-3-(2-dimethylamino-ethyl)-urea;
69) 1-[3-(6,8-Dichloro-2-methyl-1,2,3,4-tetrahydro-isoquinolin-4-yl)-phenyl]-3-(tetrahydro-furan-3-yl)-urea;
70) 1-[3-(6,8-Dichloro-2-methyl-1,2,3,4-tetrahydro-isoquinolin-4-yl)-phenyl]-3-(tetrahydro-pyran-4-yl)-urea;
71) 3-[3-(6,8-Dichloro-2-methyl-1,2,3,4-tetrahydro-isoquinolin-4-yl)-phenyl]-1-methyl-1-(1-methyl-piperidine-4-yl)-urea;
72) 3-[3-(6,8-Dichloro-2-methyl-1,2,3,4-tetrahydro-isoquinolin-4-yl)-phenyl]-1-(3-dimethylamino-propyl)-1-methyl-urea;
73) 3-[3-(6,8-Dichloro-2-methyl-1,2,3,4-tetrahydro-isoquinolin-4-yl)-phenyl]-1-(2-dimethylamino-ethyl)-1-methyl-urea;
74) 1-[3-(6,8-Dichloro-2-methyl-1,2,3,4-tetrahydro-isoquinolin-4-yl)-phenyl]-3-(3-dimethylamino-propyl)-urea;
75) 1-[3-(6,8-Dichloro-2-methyl-1,2,3,4-tetrahydro-isoquinolin-4-yl)-phenyl]-3-(2-methoxy-ethyl)-urea;
76) 1-[3-(6,8-Dichloro-2-methyl-1,2,3,4-tetrahydro-isoquinolin-4-yl)-phenyl]-3-pyridin-3-yl-urea;
77) 1-[3-(6,8-Dichloro-2-methyl-1,2,3,4-tetrahydro-isoquinolin-4-yl)-phenyl]-3-pyridin-4-yl-urea;
78) 4-Methyl-piperazine-1-carboxylic acid [2-(6,8-dichloro-2-methyl-1,2,3,4-tetrahydro-isoquinolin-4-yl)-phenyl]-amide;
79) 1-[2-(6,8-Dichloro-2-methyl-1,2,3,4-tetrahydro-isoquinolin-4-yl)-phenyl]-3-methyl-urea;
80) 1-[2-(6,8-Dichloro-2-methyl-1,2,3,4-tetrahydro-isoquinolin-4-yl)-phenyl]-3-(2-dimethylamino-ethyl)-urea;
81) 4-Methyl-piperazine-1-carboxylic acid [4-(6,8-dichloro-2-methyl-1,2,3,4-tetrahydro-isoquinolin-4-yl)-phenyl]-amide;
82) 1-[4-(6,8-Dichloro-2-methyl-1,2,3,4-tetrahydro-isoquinolin-4-yl)-phenyl]-3-methyl-urea; 83) 3-[4-(6,8-Dichloro-2-methyl-1,2,3,4-tetrahydro-isoquinolin-4-yl)-phenyl]-1,1-dimethyl-urea;
84) 3-[4-(6,8-Dichloro-2-methyl-1,2,3,4-tetrahydro-isoquinolin-4-yl)-phenyl]-1,1-diethyl-urea;
85) 1-[4-(6,8-Dichloro-2-methyl-1,2,3,4-tetrahydro-isoquinolin-4-yl)-phenyl]-3-(2-dimethylamino-ethyl)-urea;
86) Morpholine-4-carboxylic acid [4-(6,8-dichloro-2-methyl-1,2,3,4-tetrahydro-isoquinolin-4-yl)-phenyl]-amide;
87) N-[4-(6,8-Dichloro-2-methyl-1,2,3,4-tetrahydro-isoquinolin-4-yl)-phenyl]-formamide;
88) [4-(6,8-Dichloro-2-methyl-1,2,3,4-tetrahydro-isoquinolin-4-yl)-phenyl]-methyl-amine;
89) N-[3-(6,8-Dichloro-2-methyl-1,2,3,4-tetrahydro-isoquinolin-4-yl)-phenyl]-formamide;
90) [3-(6,8-Dichloro-2-methyl-1,2,3,4-tetrahydro-isoquinolin-4-yl)-phenyl]-methyl-amine;
91) 1-[3-(6,8-Dichloro-2-methyl-1,2,3,4-tetrahydro-isoquinolin-4-yl)-phenyl]-1,3,3-trimethyl-urea;
92) 1-[3-(6,8-Dichloro-2-methyl-1,2,3,4-tetrahydro-isoquinolin-4-yl)-phenyl]-1,3-dimethyl-urea;
93) Morpholine-4-carboxylic acid [3-(6,8-dichloro-2-methyl-1,2,3,4-tetrahydro-isoquinolin-4-yl)-phenyl]-methyl-amide;
94) 4-Methyl-piperazine-1-carboxylic acid [3-(6,8-dichloro-2-methyl-1,2,3,4-tetrahydro-isoquinolin-4-yl)-phenyl]-methyl-amide;
95) 1-[3-(6,8-Dichloro-2-methyl-1,2,3,4-tetrahydro-isoquinolin-4-yl)-phenyl]-3-(2-dimethylamino-ethyl)-1-methyl-urea;
96) [3-(6,8-Dichloro-2-methyl-1,2,3,4-tetrahydro-isoquinolin-4-yl)-phenyl]-carbamic acid 2-dimethylamino-ethyl ester;
97) [4-(6,8-Dichloro-2-methyl-1,2,3,4-tetrahydro-isoquinolin-4-yl)-phenyl]-carbamic acid 2-dimethylamino-ethyl ester;
98) [2-(6,8-Dichloro-2-methyl-1,2,3,4-tetrahydro-isoquinolin-4-yl)-phenyl]-carbamic acid 2-dimethylamino-ethyl ester;
99) [3-(6,8-Dichloro-2-methyl-1,2,3,4-tetrahydro-isoquinolin-4-yl)-phenyl]-carbamic acid methyl ester;
100) (R or S)-N-[3-(6,8-Dichloro-2-methyl-1,2,3,4-tetrahydro-isoquinolin-4-yl)-phenyl]-methanesulfonamide;
101) (R or S)-1-[2-(6,8-Dichloro-2-methyl-1,2,3,4-tetrahydro-isoquinolin-4-yl)-phenyl]-3-ethyl-urea;
102) 1-[3-(6,8-Dichloro-2-methyl-1,2,3,4-tetrahydro-isoquinolin-4-yl)-phenyl]-3-(2-hydroxy-ethyl)-urea;
103) 3-(6,8-Dichloro-2-methyl-1,2,3,4-tetrahydro-isoquinolin-4-yl)-benzoic acid ethyl-ester;
104) 3-(6,8-Dichloro-2-methyl-1,2,3,4-tetrahydro-isoquinolin-4-yl)-benzoic acid and the pharmaceutically acceptable salts thereof.

If the compounds of the formula I contain one or more centers of asymmetry, these may have both the S and the R configuration. The compounds may be in the form of optical isomers, of diastereomers, of racemates or of mixtures thereof.

The defined alkyl radicals and partly or completely fluorinated alkyl radicals may be both straight-chain and branched. Groups $C_aH_{2a-1}$ and their analogs as far as $C_{yy}H_{2yy-1}$ mean either the corresponding alkenyls, cycloalkyls, cycloalkylalkyls or alkylcycloalkyls.

Appropriate heteroaryls are, for example, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3-or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. The corresponding N-oxides of these compounds are additionally encompassed, that is to say, for example, 1-oxy-2-, 3- or 4-pyridyl.

In one embodiment, the 5- or 6-membered heterocycles are chosen. In a further embodiment, imidazolyl, pyrazolyl, pyrrolyl, triazolyl, tetrazolyl, thiazolyl and oxazolyl are chosen.

The terminal CH₃ groups in an alkyl chain are also regarded as CH₂ units and are in this connection viewed as CH₂ groups.

Methods for preparing the compounds of the invention are also described.

The substances described herein can be prepared, for example, starting from the benzylamine precursors IV. These in turn can, if not obtainable commercially, be synthesized by standard processes from the corresponding benzyl chlorides or bromides III.

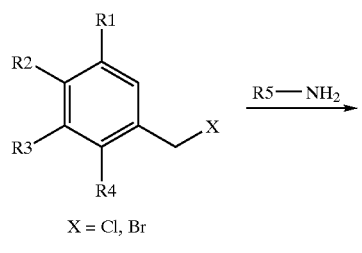

The benzylamines IV obtained in this way may be alkylated in a manner known to the skilled worker with the appropriately substituted alpha-bromoacetophenone compounds V.

The alpha-bromacetophenone compounds V may be obtained from the corresponding acetophenone precursors by bromination in processes known from the literature. The desired tetrahydroisoquinolines I may be obtained by known processes by reduction of the carbonyl group in VI and subsequent acid-catalyzed cyclization of the corresponding alcohols VII (cf. Tetrahedron Lett.; 1989, 30, 5837; Org. Prep. Proced. Int.; 1995, 27, 513).

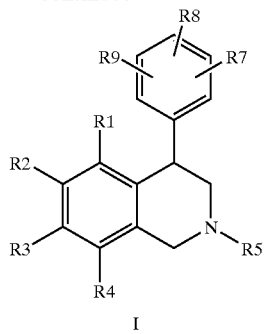

I

When R6 is not equal to H, the desired compounds of the formula I may be prepared for example from the iodides VIII by halogen/metal exchange and subsequent nucleophilic attack of the intermediate organolithium species on the carbonyl group (cf. Chem. Pharm. Bull.; 1995, 43, 1543).

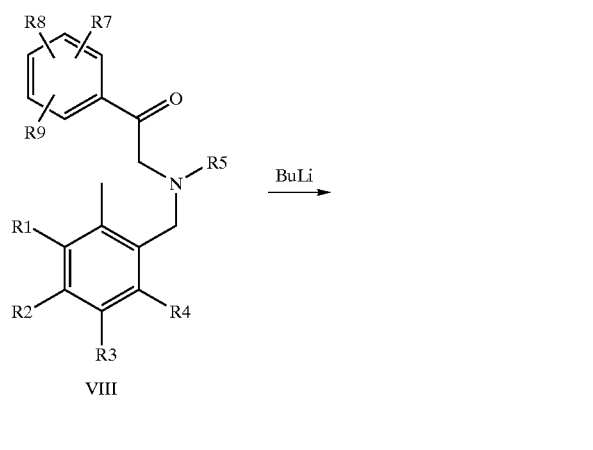

VIII

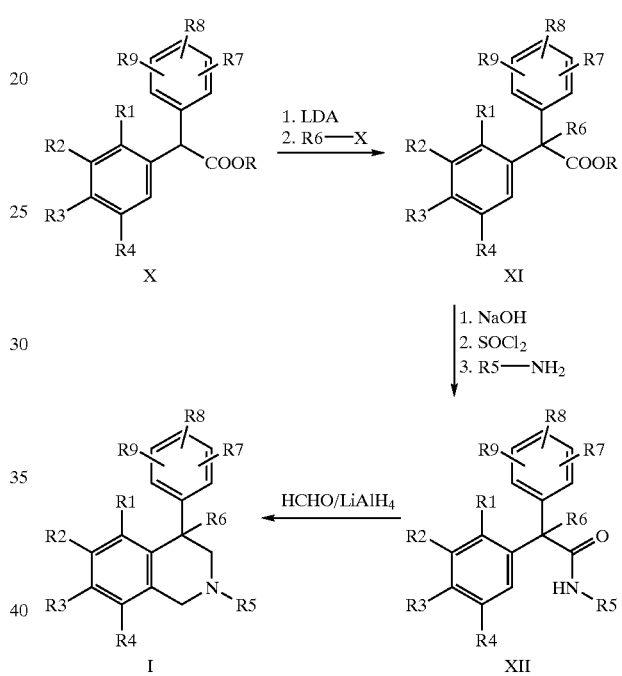

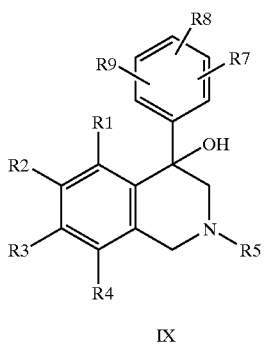

IX

The tertiary alcohols synthesized in this way may be converted by known methods into other derivatives.

Alkyl-branched analogs (I) may be prepared by alkylating the corresponding diphenylacetic esters X in the alpha position by known methods. The desired product XI may be converted by standard processes into the corresponding amides XII, which may be converted into the desired tetrahydroisoquinolines I in a Pictet-Spengler-analogous reaction (cf. Tetrahedron; 1987, 43, 439; Chem. Pharm. Bull.; 1985, 33, 340).

As used herein, treating or treatment includes the treating of, for example, a patient inflicted with a disease or condition, as well as the prevention, prophylaxis, or protective treatment of a patient. Treatment also includes treating a subject susceptible to or predisposed to developing a disease or condition, which could include patients in whom a disease or condition has not yet presented as well as patients in whom the disease has been successfully treated but could redevelop or reoccur.

In one embodiment, the compounds of the formula I may be excellent inhibitors of the sodium-hydrogen exchanger (NHE)—especially of the sodium-hydrogen exchanger of subtype 3 (NHE3).

On the basis of these properties, the compounds may be suitable for the treatment of disorders caused by oxygen deficiency. The compounds may be, as a result of their pharmacological properties, suitable as antiarrhythmic medicaments with a cardioprotective component for prophylaxis of infarction and for treatment of infarction, and for the treatment of angina pectoris, in which connection they may also inhibit or reduce in a preventive manner the pathophysiological processes associated with the development of ischemia-induced damage, in particular in the induction of ischemia-induced cardiac arrhythmias. Because of their possible protective effects against pathological hypoxic and ischemic situations, the compounds of the formula I which are used according to the invention may, as a result of inhibition of the cellular Na$^+$/H$^+$ exchange mechanism, be used as medicaments for the treatment of all acute or chronic damage induced by ischemia or disorders induced primarily or secondarily thereby. This relates to the possible use thereof as medicaments for surgical interventions, e.g. in organ transplantations, in which cases the compounds may be used, for exmple, both to protect the organs in the donor before and during removal, to protect removed organs for example on treatment with or storage thereof in physiological bath fluids, as well as during the transfer into the recipient organism. The compounds may in some embodiments likewise be valuable medicaments with a protective action during the performance of angioplastic surgical interventions, for example on the heart as well as peripheral vessels. In accordance with their possible protective action against ischemia-induced damage, the compounds may also be suitable as medicaments for the treatment of ischemias of the nervous system, especially of the CNS, in which connection they may be suitable for example for the treatment of stroke or of cerebral edema. In addition, the compounds of the formula I which are used according to the invention may likewise be suitable for the treatment of types of shock, such as, for example, of allergic, cardiogenic, hypovolemic and bacterial shock.

In addition, the compounds may induce an improvement in the respiratory drive and may therefore be used to treat respiratory conditions associated with the following clinical conditions and diseases: disturbance of central respiratory drive (e.g. central sleep apnea, sudden infant death, postoperative hypoxia), muscle-related breathing disorders, breathing disorders after long-term ventilation, breathing disorders associated with altitude adaptation, obstructive and mixed type of sleep apnea, acute and chronic pulmonary disorders with hypoxia and hypercapnia.

The compounds additionally may in some embodiments increase the tone of the muscles of the upper airways, so that snoring is suppressed.

A combination of an NHE inhibitor with a carbonic anhydrase inhibitor (e.g. acetazolamide), the latter inducing metabolic acidosis and thus itself increasing respiratory activity, may in some embodiments prove to be advantageous due to an enhanced effect and reduced use of active ingredient.

In one embodiment, the compounds used according to the invention have a mild laxative effect and accordingly may be used advantageously as laxatives or if there is a risk of constipation, in which case the compounds may prevent the ischemic damage associated with constipation in the intestinal region.

In another embodiment, it is possible to prevent the formation of gall stones.

In one embodiment, the compounds of the formula I used according to the invention may demonstrate a strong inhibitory effect on the proliferation of cells, for example of fibroblast cell proliferation and the proliferation of smooth muscular muscle cells. The compounds of the formula I may therefore is some embodiments be suitable as valuable therapeutic agents for diseases in which cell proliferation represents a primary or secondary cause, and may therefore be used as antiatherosclerotic agents, agents to prevent late complications of diabetes, cancers, fibrotic disorders such as pulmonary fibrosis, hepatic fibrosis or renal fibrosis, organ hypertrophies and hyperplasias, in particular for prostate hyperplasia or prostate hypertrophy.

In another embodiment, the compounds used according to the invention may be effective inhibitors of the cellular sodium-proton antiporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention in some embodiments therefore may be suitable as excellent and simple scientific tools, for example in their use as diagnostic agents for determining and distinguishing different types of hypertension, but also of atherosclerosis, of diabetes, proliferative disorders etc. The compounds of the formula I may also be suitable for preventive therapy to prevent the development of high blood pressure, for example of essential hypertension.

In one embodiment, it has additionally been found that NHE inhibitors may show a beneficial effect on serum lipoproteins. It is generally acknowledged that blood lipid levels which are too high, so-called hyperlipoproteinemias, represent a considerable risk factor for the development of arteriosclerotic vascular lesions, especially coronary heart disease. The reduction of elevated serum lipoproteins therefore may have exceptional importance for the prophylaxis and regression of atherosclerotic lesions. The compounds used according to the invention may therefore in some embodiments be used for the prophylaxis and regression of atherosclerotic lesions by eliminating a causal risk factor. With this protection of the vessels against the syndrome of endothelial dysfunction, compounds of the formula I may be valuable medicaments for the prevention and treatment of coronary vasospasms, of atherogenesis and of atherosclerosis, of left-ventricular hypertrophy and of dilated cardiomyopathy, and thrombotic disorders.

In certain embodiment the compounds of the invention may therefore be used for producing a medicament for the prevention and treatment of sleep apneas and muscle-related respiratory disorders; for producing a medicament for the prevention and treatment of snoring; for producing a medicament for lowering blood pressure; for producing a medicament for the prevention and treatment of disorders induced by ischemia and reperfusion of central and peripheral organs, such as acute renal failure, stroke, endogenous states of shock, intestinal disorders etc.; for producing a medicament for the treatment of late damage from diabetes and chronic renal disorders, in particular of all inflammations of the kidneys (nephritides) which are associated with increased protein/albumin excretion; for producing a medicament for the treatment of infection by ectoparasites in human and veterinary medicine; for producing a medicament for the treatment of said disorders in combinations with hypotensive substances, preferably with angiotensin converting enzyme (ACE) inhibitors, with diuretics and saluretics such as furosemide, hydrochlorothiazide, pseudoaldosterone antagonists and aldosterone antagonists; with adenosine receptor modulators, in particular with adenosine receptor activators (A2 agonists); and with angiotensin receptor antagonists.

In another embodiment, at least one sodium-proton exchange inhibitors of the formula I is administered as a medicament for lowering elevated blood lipid levels, including as the combination of sodium-proton exchange inhibitors with hypotensive medicaments and/or medicaments with hypolipidemic activity.

Medicaments which comprise a compound of the invention can in this connection may be administered orally, parenterally, intravenously, rectally, transdermally or by inhalation, the preferred administration being dependent on the particular characteristics of the disorder. The compounds of the invention may moreover may be used alone or together with pharmaceutical excipients, both in veterinary medicine and in human medicine.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds may be mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used include, for example, gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous or intravenous administration, the active compounds used may be converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Compounds of the invention are also suitable as a pharmaceutical formulation for administration in the form of aerosols or sprays are, for example, solutions, suspensions or emulsions of the active ingredient of the formula I in a pharmaceutically acceptable solvent such as, in particular, ethanol or water, or a mixture of such solvents.

The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3, % by weight.

The dosage of the active ingredient of the coumpounds of the invention to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I for a patient weighing about 75 kg is at least 0.001 mg/kg, preferably 0.01 mg/kg, to a maximum of 10 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 200 mg a day may be necessary, in particular on i.v. administration, for example for a patient with infarction in the intensive care unit.

DESCRIPTIONS OF EXPERIMENTS AND EXAMPLES

List of Abbreviations Used:

| | |
|---|---|
| $R_t$ | retention time |
| TFA | trifluoroacetic acid |
| HPLC | high performance liquid chromatography |
| eq | equivalent |
| LCMS | liquid chromatography mass spectroscopy |
| MS | mass spectroscopy |
| CI | chemical ionization |
| RT | room temperature |
| THF | tetrahydrofuran |
| TOTU | O-[(ethoxycarbonyl)-cyanomethyleneamino]-N,N,N',N'-tetramethyluronium tetrafluoroborate |
| DMSO | dimethyl sulfoxide |
| abs. | absolute |
| decomp. | decomposition |
| DMF | dimethylformamid |

General:

The retention times ($R_t$) indicated below relate to LCMS measurements with the following parameters:

Method A:

| | |
|---|---|
| stationary phase: | Merck Purospher 3μ2 × 55 mm |
| mobile phase: | 95% $H_2O$ (0.05% TFA) → 95% acetonitrile; 4 min; 95% acetonitrile; 1.5 min → 5% acetonitrile; 1 min; 0.5 ml/min, 30° C. |

Method B:

| | |
|---|---|
| stationary phase: | Merck Purospher 3μ2 × 55 mm |
| mobile Phase: | 0 min 90% $H_2O$ (0.05% TFA) 2.5 min-95% acetonitrile; 95% acetonitrile to 3.3 min; 10% acetonitrile 3.4 min; 1 ml/min. |

Method B1:

| | |
|---|---|
| stationary phase: | YMC, J'sphere ODS H80 4μ2 × 20 mm |
| mobile phase: | 0 min 90% $H_2O$ (0.05% TFA) 1.9 min-95% acetonitrile; 95% acetonitrile bis 2.4 min; 10% acetonitrile 2.45 min; 1 ml/min. |

Method C:

| | |
|---|---|
| stationary phase: | Merck LiChroCart 55-2 Purospher STAR RP 18e |
| solvent: | solvent A: acetonitrile/water 90:10 + 0.5% HCOOH solvent B: acetonitrile/water 10:90 + 0.5% HCOOH |
| flow rate: | 0.75 ml/min |

| time[min] | solvent B[%] |
|---|---|
| 0.00 | 95.0 |
| 0.50 | 95.0 |
| 1.75 | 5.0 |
| 4.25 | 5.0 |
| 4.50 | 95.0 |
| 5.00 | 95.0 |

| | |
|---|---|
| stop time: | 6.20 min |
| temperature: | 40° C. |

Method D:

| | |
|---|---|
| stationary phase: | Merck RP18 Purospher Star, 55 × 2 mm, 3μ Korngröβe |
| solvent: | Solvent A: acetonitrile + 0.08% HCOOH Solvent B: water + 0.1% HCOOH |
| Flow rate | 0.45 ml/min |

| time [min] | solvent B[%] |
|---|---|
| 0 | 95 |
| 5 | 5 |
| 7 | 5 |

-continued

| 8 | 95 |
| 9 | 5 | temperature: room temperature

Example 1

N-[4-(6,8-Dichloro-2-methyl-1,2,3,4-tetrahydro-isoquinolin-4-yl)-phenyl]-acetamide

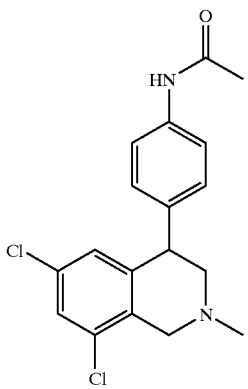

Intermediate 1

2,4-Dichlorobenzyl-(methyl)-amine was prepared by methods known from the literature (J. Med. Chem.; 1984, 27, 1111).

Intermediate 2

N-[4-(2-Bromo-acetyl)-phenyl]-acetamide wais synthesized in a manner known to the skilled worker by bromination of N-(4-acetyl-phenyl)-acetamide.

The starting compound (0.256 mol) was introduced into 300 ml of acetic acid and, at 60° C., a solution of 39.9 g of bromine (1.0 eq) in 60 ml of acetic acid was added dropwise. After 1.5 h, the reaction mixture was allowed to cool to room temperature and was added to 1 l of ice-water. The precipitate was filtered off with suction, washed with water and dried, with 60 g of the title compound being isolated (melting point: 192° C.).

Intermediate 3

N-{4-[2-(2,4-Dichloro-benzylamino)-acetyl]-phenyl}-acetamide;

37.1 g (0.195 mol) of intermediate 1 was introduced into 400 ml of dioxane, and a solution of 60 g (0.234 mol) of intermediate 2 in 600 ml of dioxane was added. 134 ml of triethylamine were added, and the mixture was stirred at room temperature for 4 h. After standing overnight, the precipitate was filtered off and the filtrate was concentrated in vacuo. The residue was taken up in ethyl acetate, washed with NaHCO$_3$ and H$_2$O, dried with MgSO$_4$ and concentrated. The oily residue resulting thereby was triturated with an ethyl acetate/ether mixture, resulting in 36 g of intermediate 3 in the form of a crystalline solid (melting point: 115–117° C.).

Intermediate 4

N-{4-[2-(2,4-Dichloro-benzylamino)-1-hydroxy-ethyl]-phenyl}-acetamide;

36 g (0.099 mol) of intermediate 3 was dissolved in 500 ml of methanol and, at 0° C., 7.8 g (2 eq) of sodium borohydride was added. The mixture was then stirred at 0° C. for 30 min and at room temperature for a further hour. For workup, the reaction mixture was concentrated and the residue was partitioned between 1 N HCl and ethyl acetate. The aqueous phase was separated off, adjusted to pH 9 and extracted twice with ethyl acetate. The combined organic phases were dried with MgSO$_4$ and concentrated. The crude product obtained in this way was reacted further without further purification.

N-[4-(6,8-Dichloro-2-methyl-1,2,3,4-tetrahydro-isoquinolin-4-yl)-phenyl]-acetamide;

20 g (0.054 mol) of intermediate 4 was dissolved in 250 ml of dichloromethane and, at 0° C., 250 ml of conc. H$_2$SO$_4$ was added dropwise. The mixture was stirred at 0° C. for 2 h and at room temperature for 1 h. For workup, the reaction mixture was added to ice-water, and the precipitate was filtered off with suction. The precipitate was taken up in 300 ml of 1 N NaOH and extracted three times with ethyl acetate. Drying of the organic phases and concentration affords a crude product which was triturated with diisopropyl ether, whereupon 11.7 g of the compound of the example were isolated as a crystalline solid (melting point: 205–206° C.).

1a: N-[4-(6,8-Dichloro-2-methyl-1,2,3,4-tetrahydro-isoquinolin-4-yl)-phenyl]-acetamide-hydrochloride;

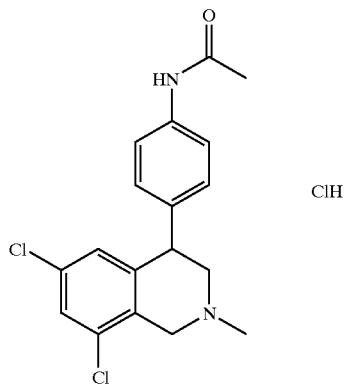

An analytical sample (100 mg) of the title compound from example 1 was suspended in 10 ml of 2 N HCl, and THF was added until a clear solution was produced. It was concentrated in vacuo, and the residue was triturated with ether and filtered off with suction, whereupon the title compound was obtained as a crystalline solid (R$_t$=3.807 min (method A); melting point.: 125° C. with decomposition).

Example 2

2a: (+)-4-(6,8-Dichloro-2-methyl-1,2,3,4-tetrahydro-isoquinolin-4-yl)-benzene-sulfonamide hydrochloride;

2b: (+)-3-(6,8-Dichloro-2-methyl-1,2,3,4-tetrahydro-isoquinolin-4-yl)-benzene-sulfonamide hydrochloride;

2c: (−)-4-(6,8-Dichloro-2-methyl-1,2,3,4-tetrahydro-isoquinolin-4-yl)-benzene-sulfonamide acetate;

2d: (−)-3-(6,8-Dichloro-2-methyl-1,2,3,4-tetrahydro-isoquinolin-4-yl)-benzene-sulfonamide acetate;

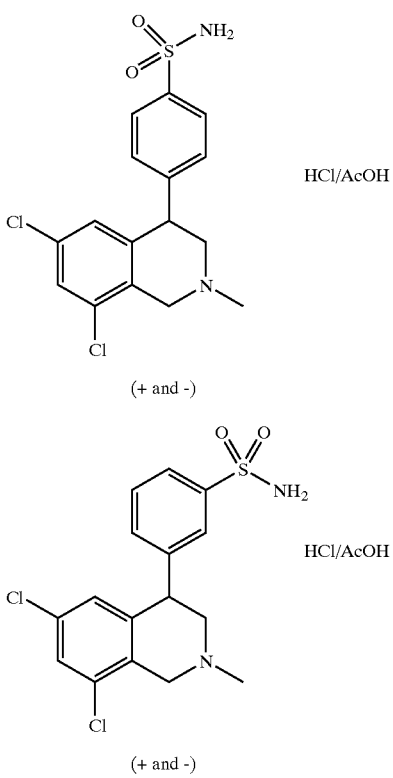

Intermediate 1
2,4-Dichlorobenzyl-(methyl)-amine was prepared by methods known from the literature (J. Med. Chem.; 1984, 27, 1111).

Intermediate 2
2-[(2,4-Dichloro-benzyl)-methyl-amino]-1-phenyl-ethanone;

Intermediate 1 was reacted with 2-bromo-1-phenyl-ethanone in the manner described in example 1, intermediate 3. Workup in an analogous manner and purification on silica gel affords the desired alkylation product in good yield as a yellowish oil ($R_f$=4.188 min (method A); MS($Cl^+$)=308.2/310.2).

Intermediate 3
2-[(2,4-Dichloro-benzyl)-methyl-amino]-1-phenyl-ethanol;

Intermediate 2 was reduced with sodium borohydride in the manner described in example 1, intermediate 4. Once monitoring of the reaction indicates complete conversion, the mixture was concentrated and the residue was taken up in ethyl acetate. It was washed twice with $H_2O$, dried with $MgSO_4$ and freed of solvent. The crude product, which was obtained in quantitative yield, was reacted further without further purification ($R_f$=4.149 min (method A); MS($Cl^+$)=310.2/312.2).

Intermediate 4
6,8-Dichloro-2-methyl-4-phenyl-1,2,3,4-tetrahydro-isoquinoline;

20 g (64.5 mmol) of intermediate 3 were dissolved in 55 ml of dichloromethane and cooled to 0° C. This solution was added dropwise to 55 ml of precooled conc. $H_2SO_4$ and then stirred at room temperature for two hours. For workup, the mixture was poured onto ice and made strongly alkaline with 6 N NaOH. Three extractions with dichloromethane were carried out. The combined organic phases were dried with $MgSO_4$ and concentrated. The oily crude product was purified on silica gel, resulting in intermediate 4 in a yield of 53% ($R_f$=4.444 min (method A); MS($Cl^+$)=292.2/294.2).

4a: (−)-6,8-Dichloro-2-methyl-4-phenyl-1,2,3,4-tetrahydro-isoquinoline trifluoroacetate;
4b: (+)-6,8-Dichloro-2-methyl-4-phenyl-1,2,3,4-tetrahydro-isoquinoline trifluoroacetate;

Intermediate 4 was separated into the two enantiomers by HPLC on a chiral phase.
chiral column: Chiralpak OD 250×4.6 cm;
solvent: n-heptane/isopropanol 7:3+0.1% TFA;
flow rate: 1 ml/min;
$R_f$((−)-enantiomer/4a)=9.340 min;
$R_f$((+)-enantiomer/4b)=20.327 min.

2a: (+)-4-(6,8-Dichloro-2-methyl-1,2,3,4-tetrahydro-isoquinolin-4-yl)-benzenesulfonamide hydrochloride;
2b: (+)-3-(6,8-Dichloro-2-methyl-1,2,3,4-tetrahydro-isoquinolin-4-yl)-benzenesulfonamide hydrochloride;

A suspension of 500 mg (1.7 mmol) of intermediate 4a in 10 ml of dichloromethane was introduced at 0° C. into 1.2 ml of chlorosulfonic acid. The mixture was stirred at 0° C. for one hour and at room temperature for a further hour. A further 5 ml of chlorosulfonic acid was added and the mixture was stirred at room temperature for one hour. For workup, it was poured onto ice and adjusted to pH 8 with $NaHCO_3$. Three extractions with ethyl acetate were carried out. The combined organic phases were dried with $Na_2SO_4$ and freed of solvent. The crude product obtained in this way was heated in 20 ml of conc. $NH_3$ solution at 90° C. for three hours. After the conversion was complete, the reaction solution was concentrated and the residue was partitioned between $H_2O$ and ethyl acetate. The organic phase was separated off and the aqueous phase was extracted once more with ethyl acetate. The combined organic phases were dried with $Na_2SO_4$ and the solvent was removed in vacuo. Subsequent chromatography on silica gel affords 335 mg of a mixture of example 2a and 2b in the form of a yellow amorphous solid. Further purification on a preparative HPLC affords 212 mg of the para-substituted title compound 2a, plus 58 mg of the meta isomer 2b.

Conditions for the preparative HPLC.

chiral column: Chiralpak AS 250×4.6 mm;
solvents: n-heptane/ethanol/methanol/acetonitrile 20:1.5:0.5:0.5
flow rate: 1 ml/min;
$R_f$(main fraction)=14.145 min (→2a);
$R_f$(subsidiary fraction)=11.623 min (→2b).

Both fractions were dissolved in methanol/2 N HCl mixture and freeze dried, and it was possible to obtain the title compounds 2a and 2b in the form of crystalline solids. ($R_f$(2a)=3.630 min (method A); MS(2a),($ES^+$)=371.3/373.3 ($M^+$+H)/412.3/414.3 ($M^+$+$CH_3CN$); $R_f$ (2b)=3.668 min (method A); MS(2b),(ES+)=371.3/373.3 ($M^+$+H)/412.3/414.3 ($M^+$+$CH_3CN$).

2c: (−)-4-(6,8-Dichloro-2-methyl-1,2,3,4-tetrahydro-isoquinolin-4-yl)-benzenesulfonamide acetate;
2d: (−)-3-(6,8-Dichloro-2-methyl-1,2,3,4-tetrahydro-isoquinolin-4-yl)-benzenesulfonamide acetate;

The title compound was synthesized by the method described under 2a/2b, using intermediate 4b as starting compound. The purification and separation from the meta isomer which was to be expected and takes place under the following conditions:

chiral column: Chiralpak AS 250×4.6/12 mm;
solvent: acetonitrile flow rate: 1 ml/min;
R$_t$(main fraction)=4.394 min (→2c);
R$_t$(subsidiary fraction)=4.130 min (→2d).

The purified products were each taken up in a 10% acetic acid solution and freeze dried, resulting in the desired acetates as slightly yellowish solids (R$_t$(2c)=3.656 min (method A); MS(ES$^+$)=371.1/373.1 (M$^+$+H)/412.1/414.1 (M++CH$_3$CN)); (R$_t$(2d)=1.562 min (method B); MS(ES$^+$)= 371.1/373.1 (M$^+$+H)/412.1/414.1 (M$^+$+CH$_3$CN)).

Example 3

4-(6,8-Dichloro-2-methyl-1,2,3,4-tetrahydro-isoquinolin-4-yl)-N,N-dimethyl-benzenesulfonamide, Hydrochloride

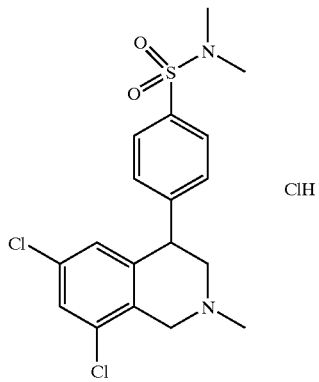

6,8-Dichloro-2-methyl-4-phenyl-1,2,3,4-tetrahydro-isoquinoline (intermediate 4, example 2) was introduced in portions into chlorosulfonic acid (6.6 ml). The mixture was subsequently stirred at 40° C. for one hour. The reaction mixture was then cooled to room temperature and an ice/water mixture was added. The precipitate which separated out during this was filtered off with suction and taken up in ethyl acetate which, after washing with saturated brine was dried over magnesium sulfate. Subsequent concentration afforded 4-(6,8-dichloro-2-methyl-1,2,3,4-tetrahydro-isoquinolin-4-yl)-benzenesulfonyl chloride as a solid crude product, a portion of which (150 mg) was directly introduced in portions into dimethylamine solution (5 ml, approx. 40% in water) cooled to 10° C. The resulting suspension was subsequently stirred at this temperature for 1.5 h. Then ice-water was added and, after extraction three times with ethyl acetate, the combined ethyl acetate phases were washed with saturated brine and dried over magnesium sulfate. The residue was taken up with water and, after addition of 2 N HCl, freeze dried. The crude product obtained in this way was then purified by preparative HPLC.

Conditions:

stationary phase: Merck Purospher RP18 (10 μM) 250×25 mm
mobile phase: 90% H$_2$O (0.05% TFA)→90% acetonitrile; 40 min; flow rate: 25 ml/min The fractions containing the product were combined, the acetonitrile was stripped off in a rotary evaporator, and the aqueous phase was washed with saturated potassium carbonate solution and then extracted three times with ethyl acetate. The combined ethyl acetate phases were washed with saturated brine, dried over magnesium sulfate and concentrated. The residue was taken up in water and, after addition of 2 N HCl, freeze dried. 80 mg of a pale solid were obtained. This consisted of ~80% of the desired compound, in addition to ~20% of a regioisomer (R$_t$=4.000 min (method A); MS(Cl$^+$)=399.1).

Example 4

4a: 4-(6,8-Dichloro-2-methyl-1,2,3,4-tetrahydro-isoquinolin-4-yl)-benzenesulfonamide, Hydrochloride

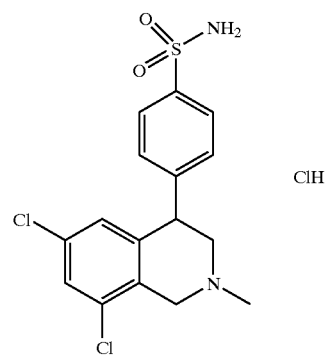

Intermediate 1

4-(6,8-Dichloro-2-methyl-1,2,3,4-tetrahydroisoquinolin-4-yl)-benzenesulfonyl chloride At 0° C., 1 mmol of 6,8-dichloro-2-methyl-4-phenyl-1,2,3,4-tetrahydro-isoquinoline (intermediate 4, example 2) was introduced into 1 ml of chlorosulfonic acid and stirred at room temperature for 3 hours. For workup, the reaction mixture was poured onto ice, adjusted to pH 7 to 8 with 1 N NaOH and extracted twice with ethyl acetate. The combined ethyl acetate phases were dried with Na$_2$SO$_4$ and concentrated in a rotary evaporator. The crude product obtained in this way was reacted further without further purification.

Intermediate 2

4-(6,8-Dichloro-2-methyl-1,2,3,4-tetrahydro-isoquinolin-4-yl)-benzenesulfonamide 319 mg of intermediate 1 were suspended in 6 ml of 25% strength ammonia and heated to 90° C. After 3 h, the mixture was diluted with H$_2$O and extracted with ethyl acetate. The organic phase was separated off and dried with Na$_2$SO$_4$, resulting in 165 mg of the title compound.

4-(6,8-Dichloro-2-methyl-1,2,3,4-tetrahydro-isoquinolin-4-yl)-benzenesulfonamide, Hydrochloride;

145 mg of intermediate 2 were suspended in 15 ml of diethyl ether, and 1 ml of ethereal HCl was added. After stirring at room temperature for 30 minutes, the precipitate was filtered off with suction and dried, resulting in 136 mg of the hydrochloride in the form of a yellowish solid.

4b: 4-(6,8-Dichloro-2-methyl-1,2,3,4-tetrahydro-isoquinolin-4-yl)-benzenesulfonamide, Acetate;

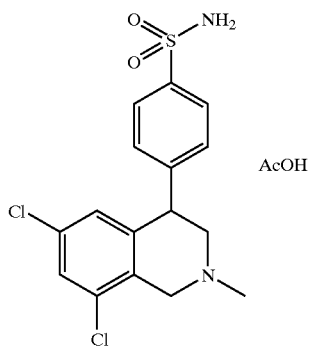

255 mg of intermediate 2, example 8, was mixed with 5 ml of glacial acetic acid, and 50 ml of $H_2O$ was added. Filtration of sparingly soluble constituents was followed by freeze drying, resulting in 250 mg of the title compound.

Example 5

4-(4-Bromo-phenyl)-6,8-dichloro-2-methyl-1,2,3,4-tetrahydroisoquinoline, Hydrochloride

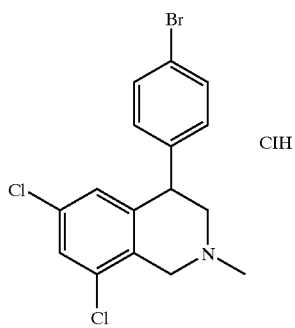

Intermediate 1:
1-(4-Bromo-phenyl)-2-[(2,4-dichloro-benzyl)-methyl-amino]-ethanone;

(2,4-Dichloro-benzyl)-methyl-amine (see example 1, intermediate 1) and 2-bromo-1-(4-bromo-phenyl)-ethanone was reacted in analogy to the method described in example 1, intermediate 3. After analogous workup and chromatography on silica gel, the alkylation product was isolated in a yield of 69%.

Intermediate 2:
1-(4-Bromo-phenyl)-2-[(2,4-dichloro-benzyl)-methyl-amino]-ethanol;

Intermediate 1 was reduced to the corresponding alcohol with 2 equivalents of $NaBH_4$ in analogy to the manner described for intermediate 4, example 1, and the alcohol was isolated in a yield of 86%.

Intermediate 3:
4-(4-Bromo-phenyl)-6,8-dichloro-2-methyl-1,2,3,4-tetrahydro-isoquinoline;

5.45 g (14.0 mmol) of 1-(4-bromo-phenyl)-2-[(2,4-dichloro-benzyl)-methyl-amino]-ethanol was introduced into 15 ml of dichloromethane and, at 0° C., 15 ml of conc. $H_2SO_4$ are added. After stirring at room temperature for 2 hours, the reaction mixture was poured onto ice and made alkaline with 6 N NaOH. Three extractions with dichloromethane were carried out. The combined organic phases were dried with $MgSO_4$ and concentrated. For further purification, the residue was chromatographed on silica gel, resulting in 2.6 g of the title compound as a yellowish oil.
4-(4-Bromo-phenyl)-6,8-dichloro-2-methyl-1,2,3,4-tetrahydroisoquinoline, Hydrochloride;

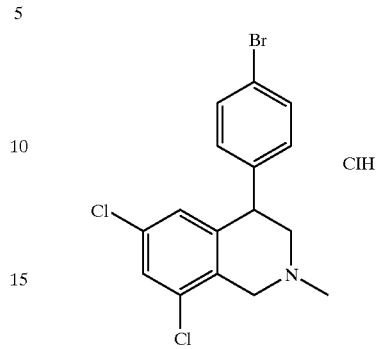

300 mg of 4-(4-bromo-phenyl)-6,8-dichloro-2-methyl-1,2,3,4-tetrahydroisoquinoline was stirred in 2 N HCl at room temperature. The resulting precipitate was filtered off with suction and dried.

Example 6

4-(6,8-Dichloro-2-methyl-1,2,3,4-tetrahydro-isoquinolin-4-yl)-benzoic acid

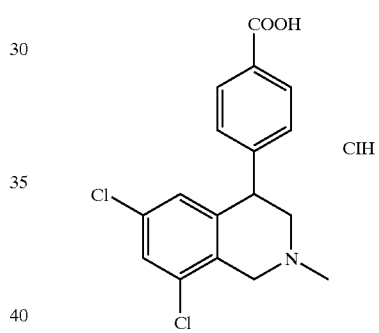

4-(6,8-Dichloro-2-methyl-1,2,3,4-tetrahydro-isoquinolin-4-yl)-benzoic acid; 5.57 g (15 mmol) of 4-(4-bromo-phenyl)-6,8-dichloro-2-methyl-1,2,3,4-tetrahydroisoquinoline (example 5, intermediate 3) was dissolved in 150 ml of abs. DMF/benzene (1:1). After the solution was degassed, under argon 1.18 g (4.5 mmol) of triphenylphosphine and 1.17 g (9 mmol) of $Ca(HCO_2)_2$ were added. After renewed flushing with argon, 867 mg (0.75 mmol) of $Pd(PPh_3)_4$ was added and carbon monoxide was passed into the solution. The mixture was stirred at 120° C. After six hours at 120° C. and standing overnight under argon, a further 867 mg (0.75 mmol) of $Pd(PPh_3)_4$ was added and stirring at 120° C. and passing carbon monoxide into the solution was continued for eight hours. After again standing overnight, 135 mg of $PdCl_2$ was added and reaction was allowed to take place under the same conditions. For workup, the solvent was removed in vacuo and the residue was taken up in ethyl acetate. Three extractions with 2 N NaOH were carried out. The combined aqueous phases were adjusted to pH 6 with 6 N HCl and extracted three times with ethyl acetate. The organic phases were dried with $MgSO_4$ and freed of solvent. The residue was purified on silica gel using a dichloromethane/methanol mixture, resulting in 420 mg of the title compound ($R_f$=4.025 min (method A); MS(CI$^+$)=336.1/338.1).

Example 7

4-(6,8-Dichloro-2-methyl-1,2,3,4-tetrahydroisoquinolin-4-yl)-N-ethyl-benzamide, Trifluoroacetate

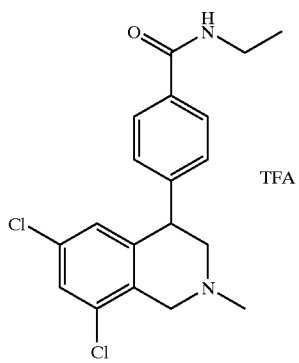

146 mg (0.43 mmol) of 4-(6,8-dichloro-2-methyl-1,2,3,4-tetrahydro-isoquinolin-4-yl)-benzoic acid (see example 6) was dissolved in 5 ml of DMF, and 1.0 equivalent of triethylamine was added. At 0° C., a solution of 141 mg (0.43 mmol) TOTU in 3 ml of DMF was added. The mixture was stirred at 0° C. for 30 min and at room temperature for 30 min. This solution was then added at 0° C. to a solution of 0.28 ml of 2 M ethylamine solution and 0.06 ml (0.043 mmol) of triethylamine in 5 ml of DMF, and the reaction mixture was stirred at room temperature for three hours. For workup, the solvent was distilled off in vacuo, and the residue was taken up in ethyl acetate and washed twice with 1 N KOH and once with $H_2O$. The organic phase was dried with $Na_2SO_4$ and concentrated. Chromatography on silica gel (dichloromethane/methanol 95:5) was used for further purification. Further purification on a preparative HPLC (acetonitrile/$H_2O$/trifluoroacetic acid) afforded the desired carboxamide as trifluoroacetate ($R_t$=4.169 min (method A); MS(Cl$^+$)=363.3/365.3).

Example 8

4-(6,8-Dichloro-2-methyl-1,2,3,4-tetrahydroisoquinolin-4-yl)-N-propyl-benzamide, Trifluoroacetate

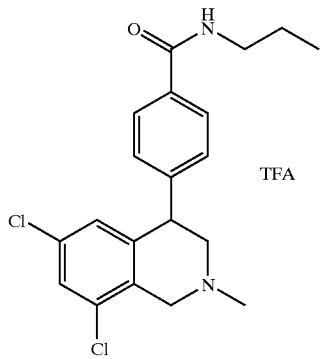

The title compound was prepared by the method described in example 7 starting from n-propylamine and 4-(6,8-dichloro-2-methyl-1,2,3,4-tetrahydro-isoquinolin-4-yl)-benzoic acid (see example 6).
($R_t$=1.881 min (method B); MS(Cl$^+$)=377.3/379.3).

Example 9

4-(6,8-Dichloro-2-methyl-1,2,3,4-tetrahydro-isoquinolin-4-yl)-N-(2-dimethylamino-ethyl)-benzamide, Trifluoroacetate

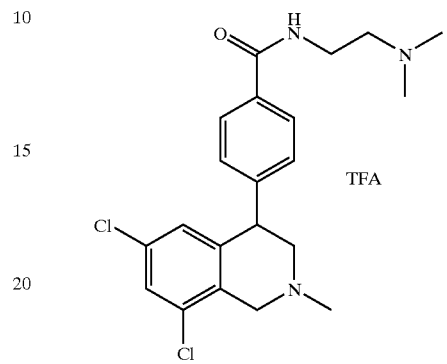

was prepared in analogy to example 7 starting from example 6 and N1,N1-dimethylethane-1,2-diamine by a TOTU-mediated coupling reaction ($R_t$=1.449 min (method B); MS(Cl$^+$)=406.3/408.3).

Example 10

6,8-Dichloro-2-methyl-4-(4-morpholin-4-yl-phenyl)-1,2,3,4-tetrahydroisoquinoline, Trifluoroacetate

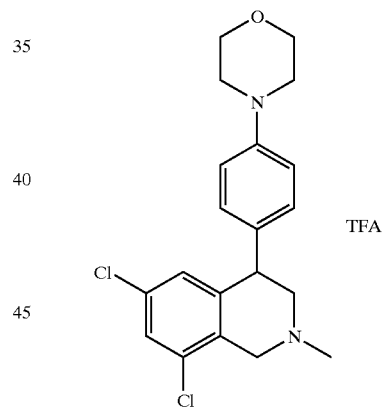

456 mg (1.4 mmol) of $Cs_2CO_3$, 6.75 mg (0.03 mmol) of palladium acetate and 28 mg (0.045 mmol) of 2,2-bis-(diphenylphosphino)-1,1-binaphthyl was introduced into 5 ml of abs. toluene. Under argon, a solution of 0.104 ml (1.2 mmol) of morpholine in 2.5 ml of abs. DMF, and a solution of 371 mg (1.0 mmol) of 4-(4-bromo-phenyl)-6,8-dichloro-2-methyl-1,2,3,4-tetrahydroisoquinoline in 2.5 ml of abs. toluene was added, and the mixture was stirred at 100° C. for a total of 9 hours. For workup, the solvent was removed, the residue was taken up in dichloromethane, and insoluble constituents were filtered off. After concentration of the filtrate, the residue was chromatographed on silica gel ($CH_2Cl_2$/methanol 95:5), resulting in 350 mg of the desired morpholine derivative. After a further purification on a preparative HPLC it was possible to isolate 160 mg of the corresponding trifluoroacetate in the form of a colorless solid.

Example 11

[4-(6,8-Dichloro-2-methyl-1,2,3,4-tetrahydroisoquinolin-4-yl)-phenyl]-diethyl-amine, Trifluoroacetate

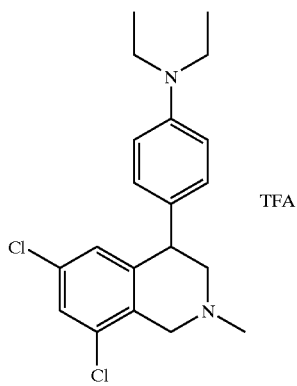

The procedure was analogous to the method described in example 10 starting from diethylamine and 4-(4-bromo-phenyl)-6,8-dichloro-2-methyl-1,2,3,4-tetrahydro-isoquinoline (example 5, intermediate 3). Reaction time: 2 days at 100° C.; three times the amount of Pd catalyst and phosphine ligand. The desired trifluoroacetate can be isolated as a colorless solid after preparative HPLC.

Example 12

6,8-Dichloro-2-methyl-4-(4-piperidin-1-yl-phenyl)-1,2,3,4-tetrahydro-isoquinoline, Trifluoroacetate

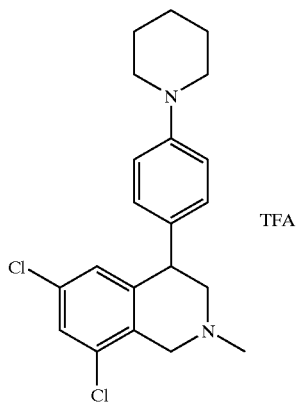

The desired piperidine derivative can be obtained starting from piperidine and 4-(4-bromo-phenyl)-6,8-dichloro-2-methyl-1,2,3,4-tetrahydroisoquinoline (example 5, intermediate 3) in analogy to the method described in example 10.

Example 13

6,8-Dichloro-2-methyl-4-(4-pyrrolidin-1-yl-phenyl)-1,2,3,4-tetrahydroisoquinoline, Hydrochloride

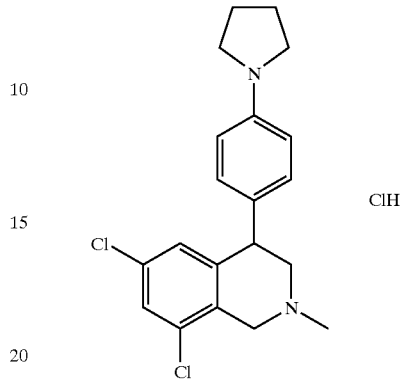

The reaction is carried out in analogy to the method described in example 10, starting from pyrrolidine and 4-(4-bromo-phenyl)-6,8-dichloro-2-methyl-1,2,3,4-tetrahydroisoquinoline (example 5, intermediate 3). The product obtained after purification by chromatography is taken up in the DMSO/acetonitrile mixture, whereupon a precipitate separates out. This is filtered off, dissolved in 2 N HCl and freeze dried, resulting in the title compound of a colorless solid.

Example 14

6,8-Dichloro-2-methyl-4-[4-(4-methyl-piperazin-1-yl)-phenyl]-1,2,3,4-tetrahydro-isoquinoline, Trifluoroacetate

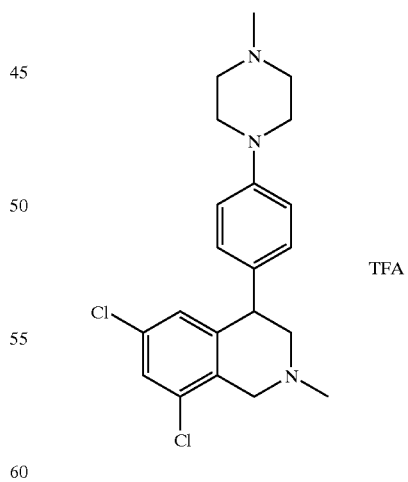

Reaction of N-methyl-piperazine and 4-(4-bromo-phenyl)-6,8-dichloro-2-methyl-1,2,3,4-tetrahydroiso-quinoline (example 5, intermediate 3) by the method described in example 10 affords the title compound in the form of a colorless solid.

Example 15

6,8-Dichloro-2-cyclopropyl-4-phenyl-1,2,3,4-tetrahydroisoquinoline, Trifluoroacetate

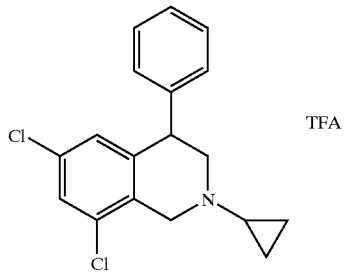

Intermediate 1:
Cyclopropyl-(2,4-dichloro-benzyl)-amine;

5.25 g (30 mmol) of 2,4-dichlorobenzaldehyde was introduced into 140 ml of methanol and, at room temperature, a solution of 1.71 g (30 mmol) of cyclopropylamine was added. The mixture as stirred at room temperature for 40 min and then 1.42 g (37.5 mmol) of NaBH$_4$ was added in portions. After standing overnight, the solvent was removed and the residue was taken up in 2 N HCl. Two extractions with ethyl acetate were carried out. The aqueous phase was made alkaline with NaOH and again extracted twice with ethyl acetate. The organic phases were dried with MgSO$_4$ and concentrated. The crude product obtained in this way, in the form of a slightly yellowish oil, was reacted further without further purification.

Intermediate 2:
2-[Cyclopropyl-(2,4-dichloro-benzyl)-amino]-1-phenyl-ethanone;

Intermediate 1 was reacted with alpha-bromoacetophenone in the presence of triethylamine in dioxane by the method described in example 1, intermediate 3. For workup, the solvent was distilled off, and the residue was taken up in ethyl acetate. It was washed twice with H$_2$O and twice with 2 N HCl, dried with MgSO$_4$ and concentrated. The crude product obtained in this way was reacted further without further purification.

Intermediate 3:
2-[Cyclopropyl-(2,4-dichloro-benzyl)-amino]-1-phenyl-ethanol;

Intermediate 2 was reduced with NaBH$_4$ in analogy to the method described in example 1, intermediate 4. For workup, the mixture was concentrated, and the residue was partitioned between 1 N HCl and ethyl acetate. The aqueous phase was separated off and extracted once more with ethyl acetate. The combined organic phases were dried with MgSO$_4$ and the solvent was removed in vacuo.

6,8-Dichloro-2-cyclopropyl-4-phenyl-1,2,3,4-tetrahydroisoquinoline, trifluoroacetate;

Intermediate 3 (1.9 g) was dissolved without further purification in 10 ml of dichloromethane and cyclized with conc. H$_2$SO$_4$ by the method described in example 1. For workup, the reaction mixture was poured onto ice. The organic phase was separated off, and the aqueous phase was extracted once more with dichloromethane. The combined organic phases were dried with MgSO$_4$ and freed of solvent.

Chromatography on silica gel (n-heptane/ethyl acetate 5:1→3:1) affords 200 mg of a yellowish oil, which was subjected to further purification on a preparative HPLC. This resulted in 184 mg of the title compound as trifluoroacetate.

Example 16

16a: (−)-N-[4-(6,8-Dichloro-2-methyl-1,2,3,4-tetrahydro-isoquinolin-4-yl)-phenyl]-acetamide
16b: (+)-N-[4-(6,8-Dichloro-2-methyl-1,2,3,4-tetrahydro-isoquinolin-4-yl)-phenyl]-acetamide;

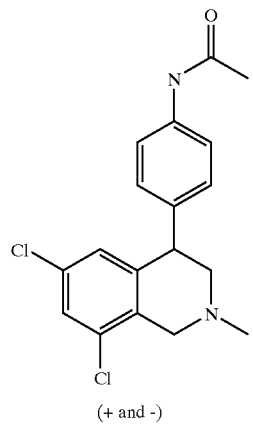

500 mg of the title compound from example 1 was separated on a chiral phase, resulting in about 250 mg of the two enantiomeric acetamides 16a and 16b.

chiral column: Chiralpak OD 250×4.6 mm;
solvent: acetonitrile;
flow rate: 1 ml/min;
R$_t$((−)-enantiomer/16a)=5.856 min;
R$_t$((+)-enantiomer/16b)=8.613 min.

Example 17

4-(6,8-Dichloro-2-methyl-1,2,3,4-tetrahydro-isoquinolin-4-yl)-phenylamine, Hydrochloride

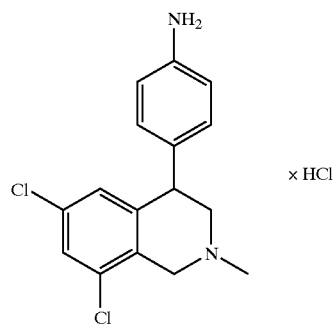

Intermediate 1:
4-(6,8-Dichloro-2-methyl-1,2,3,4-tetrahydro-isoquinolin-4-yl)-phenylamine;

3.0 g (8.6 mmol) of N-[4-(6,8-dichloro-2-methyl-1,2,3,4-tetrahydro-isoquinolin-4-yl)-phenyl]-acetamide (example 1) was dissolved in 100 ml of 20% strength sodium ethanolate solution and heated under reflux for four hours. A further 2.0 g (29.4 mmol) of solid sodium ethanolate was added, and the mixture was heated under reflux for three more hours. For workup, the solvent was removed in vacuo, and the residue was taken up in 200 ml of H$_2$O and extracted twice with dichloromethane. The combined organic phases were dried with MgSO$_4$ and concentrated. Further purification by chromatography on silica gel (ethyl acetate/heptane 1:1) resulted in the aniline as a yellowish oil in quantitative yield.

4-(6,8-Dichloro-2-methyl-1,2,3,4-tetrahydro-isoquinolin-4-yl)-phenylamine, Hydrochloride;

200 mg (0.65 mmol) of 4-(6,8-dichloro-2-methyl-1,2,3,4-tetrahydro-isoquinolin-4-yl)-phenylamine are dissolved in 30 ml of ethanolic HCl. The clear solution was concentrated in vacuo. The residue was triturated in ether, filtered off with suction and dried, whereupon it was possible to isolate 208 mg of the desired hydrochloride.

Example 18

N-Ethyl-N'-4-(6,8-dichloro-2-methyl-1,2,3,4-tetrahydro-isoquinolin-4-yl)-benzenesulfonylurea, Hydrochloride

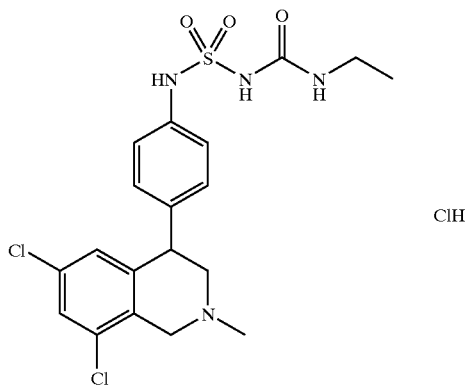

1.0 mmol of 4-(6,8-dichloro-2-methyl-1,2,3,4-tetrahydro-isoquinolin-4-yl)-benzene-sulfonamide (example 4, intermediate 2) as mixed with 350 mg (2.5 eq) of $K_2CO_3$ in 15 ml of dry acetone and stirred at room temperature for 1.5 hours. A solution of 2.5 eq of ethyl isocyanate in acetone was added dropwise at room temperature, and the solution was heated to reflux. For workup, the mixture was concentrated in vacuo, and the residue was taken up in $H_2O$ and extracted twice with ethyl acetate. The aqueous phase was acidified with 6 N HCl, and the resulting precipitate was filtered off with suction. Washing with ethyl acetate and drying in vacuo afforded the title compound in good yield.

Example 19

1-[4-(6,8-Dichloro-2-methyl-1,2,3,4-tetrahydro-isoquinolin-4-yl)-phenyl]-3-propylurea

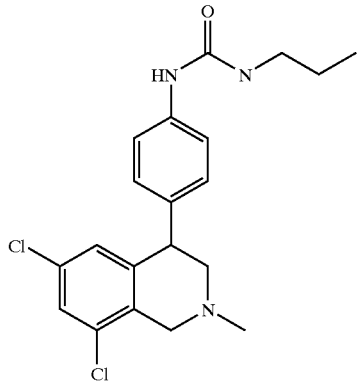

A solution of 0.17 g (2.0 mmol) of n-propyl isocyanate in toluene was added dropwise to a stirred solution of 500 mg (1.63 mmol) of 4-(6,8-dichloro-2-methyl-1,2,3,4-tetrahydro-isoquinolin-4-yl)-phenylamine (see example 17) in 15 ml of toluene. After one hour at 40° C., a further 0.17 g of n-propyl isocyanate was added, and the mixture was stirred at 80° C. for one hour. For workup, the solvent was removed and the residue was triturated with $H_2O$ and ether. Drying affords 503 mg of the desired n-propylurea.

19a: 1-[4-(6,8-Dichloro-2-methyl-1,2,3,4-tetrahydro-isoquinolin-4-yl)-phenyl]-3-propyl-urea, Hydrochloride;

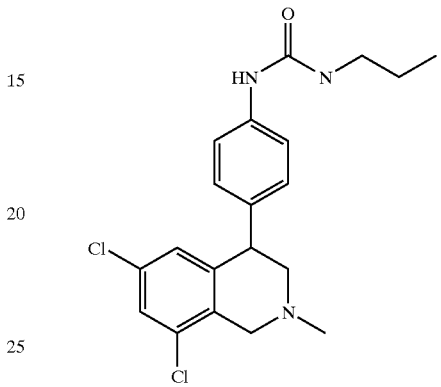

450 mg of 1-[4-(6,8-dichloro-2-methyl-1,2,3,4-tetrahydro-isoquinolin-4-yl)-phenyl]-3-propyl-urea were dissolved in a mixture of 2 N HCl and THF. The clear solution was concentrated in vacuo, and the residue was triturated with ether and filtered off with suction. Drying affords 473 mg of the desired hydrochloride.

Example 20

1-[4-(6,8-Dichloro-2-methyl-1,2,3,4-tetrahydro-isoquinolin-4-yl)-phenyl]-3-methyl-thiourea;

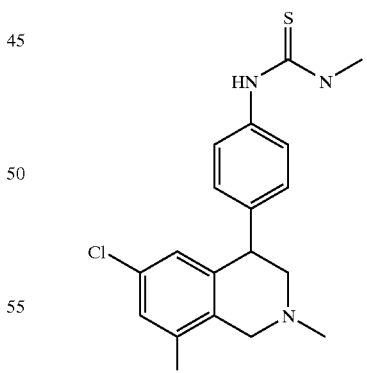

Proceeding in analogy to the method described in example 19 and starting from 500 mg (1.63 mmol) of 4-(6,8-dichloro-2-methyl-1,2,3,4-tetrahydro-isoquinolin-4-yl)-phenylamine (see example 17) and 220 mg (3.0 mmol) of methyl isothiocyanate allowed 245 mg of the desired thiourea to be isolated.

Example 21

1-[4-(6,8-Dichloro-2-methyl-1,2,3,4-tetrahydro-isoquinolin-4-yl)-phenyl]-3-ethylurea;

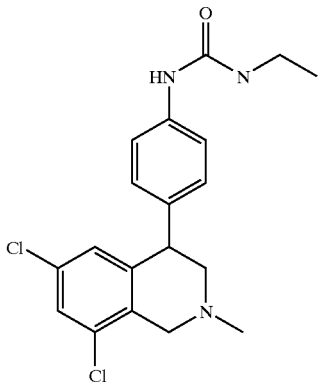

Preparation takes place in analogy to a method described in example 19, starting from 4-(6,8-dichloro-2-methyl-1,2,3,4-tetrahydro-isoquinolin-4-yl)-phenylamine (500 mg; 1.63 mmol) and ethyl isocyanate (284 mg/4 mmol).

21a: 1-[4-(6,8-Dichloro-2-methyl-1,2,3,4-tetrahydro-isoquinolin-4-yl)-phenyl]-3-ethyl-urea, Hydrochloride;

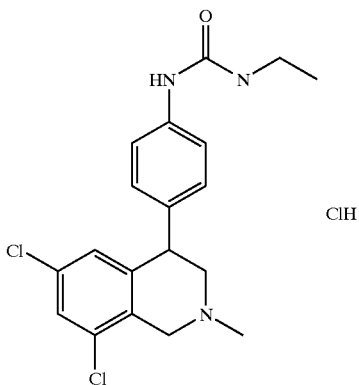

Conversion into the corresponding hydrochloride takes place in analogy to the method described in example 19a.

Example 22

N-[4-(6-Methanesulfonyl-2-methyl-1,2,3,4-tetrahydro-isoquinolin-4-yl)-phenyl]-acetamide;

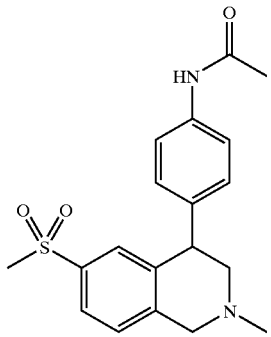

Intermediate 1:

(4-Methanesulfonyl-benzyl)-methyl-amine was synthesized starting from 1-bromomethyl-4-methanesulfonylbenzene and methylamine in a manner known to the skilled worker.

The title compound was prepared in analogy to the synthetic route indicated in example 1, starting from (4-methanesulfonyl-benzyl)-methyl-amine (intermediate 1) and N-[4-(2-bromo-acetyl)-phenyl]-acetamide (example 1, intermediate 2).

Example 23

N-[4-(2,6,8-Trimethyl-1,2,3,4-tetrahydro-isoquinolin-4-yl)-phenyl]-acetamide

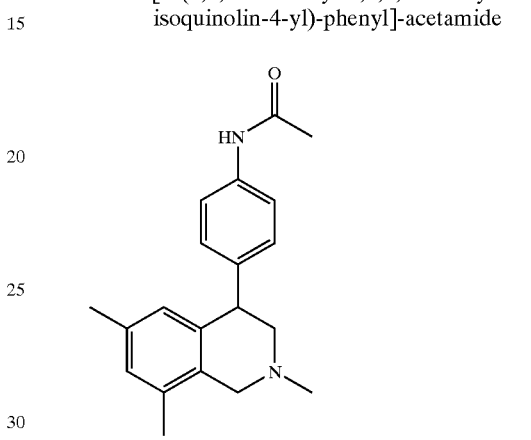

The synthetic route detailed in example 1 was followed, starting from (2,4-dimethyl-benzyl)-methyl-amine, which can be prepared from 1-bromomethyl-2,4-dimethyl-benzene and methylamine in a manner known to the skilled worker, and N-[4-(2-bromo-acetyl)-phenyl]-acetamide (example 1, intermediate 2).

Example 24

N-[4-(6-Bromo-8-chloro-2-methyl-1,2,3,4-tetrahydro-isoquinolin-4-yl)-phenyl]-acetamide

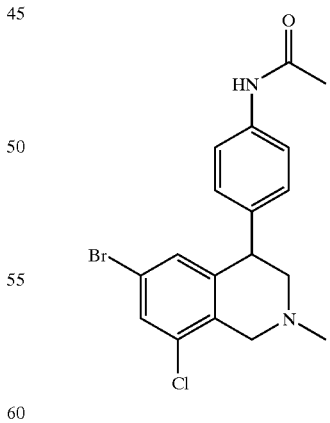

The synthetic route detailed in example 1 was followed, starting from (4-bromo-2-chloro-benzyl)-methyl-amine, which can be prepared from 4-bromo-1-bromomethyl-2-chloro-benzene and methylamine in a manner known to the skilled worker, and N-[4-(2-bromo-acetyl)-phenyl]-acetamide (example 1, intermediate 2).

Example 25

N-[4-(8-Chloro-2-methyl-6-pyrrolidin-1-yl-1,2,3,4-tetrahydro-isoquinolin-4-yl)-phenyl]-acetamide

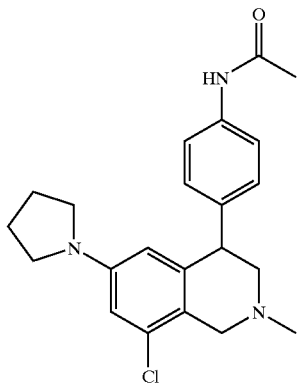

1.02 g (3.12 mmol) of Cs$_2$CO$_3$, 8.8 mg (0.04 mmol) of palladium acetate and 36.1 mg (0.06 mmol) of 2,2-bis-diphenylphosphino-1,1-binaphthyl was introduced into 6.5 ml of abs. toluene under argon. At room temperature, a solution of 512 mg (1.3 mmol) of N-[4-(6-bromo-8-chloro-2-methyl-1,2,3,4-tetrahydro-isoquinolin-4-yl)-phenyl]-acetamide (example 24) in 4 ml of abs. DMF, and a solution of 111 mg (1.56 mmol) of pyrrolidine in 4 ml of DMF were added, and the mixture was heated at 100° C. for 7 hours. For workup, the solvent was removed in vacuo, and the residue was taken up in dichloromethane. Insoluble constituents were filtered off, and the filtrate was concentrated. The residue was chromatographed on silica gel with a dichloromethane/methanol mixture, and it is possible to isolate 360 mg of the compound of the example.

25a: N-[4-(8-Chloro-2-methyl-6-pyrrolidin-1-yl-1,2,3,4-tetrahydro-isoquinolin-4-yl)-phenyl]-acetamide, Hydrochloride;

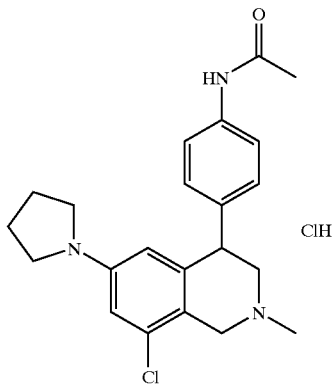

320 mg of N-[4-(8-chloro-2-methyl-6-pyrrolidin-1-yl-1,2,3,4-tetrahydro-isoquinolin-4-yl)-phenyl]-acetamide was dissolved in 20 ml of ethanolic HCl, stirred at room temperature for 30 min and concentrated. The residue was taken up in H$_2$O and freeze dried.

Example 26

N-[4-(8-Chloro-2-methyl-6-morpholin-4-yl-1,2,3,4-tetrahydro-isoquinolin-4-yl)-phenyl]-acetamide, Trifluoroacetate

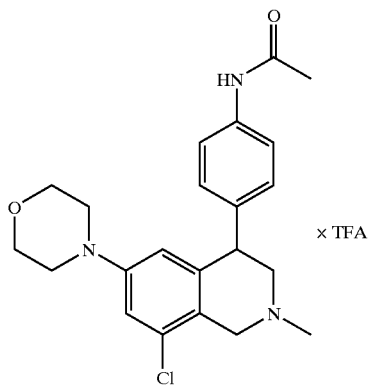

Preparation takes place in analogy to the method described in example 25, starting from N-[4-(6-bromo-8-chloro-2-methyl-1,2,3,4-tetrahydro-isoquinolin-4-yl)-phenyl]-acetamide (example 24) and morpholine. The chromatography on silica gel was followed by a further purification on a preparative HPLC.

Example 27

N-{4-[8-Chloro-2-methyl-6-(4-methyl-piperazin-1-yl)-1,2,3,4-tetrahydro-isoquinolin-4-yl]-phenyl}-acetamide

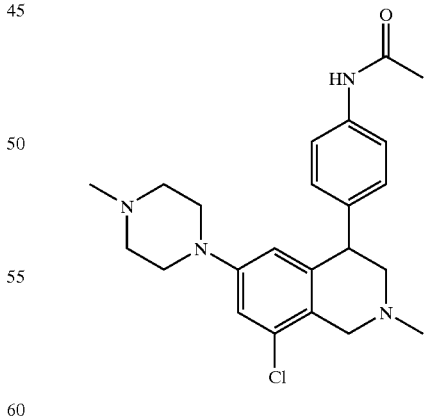

Preparation takes place in analogy to the method described in example 25, starting from N-[4-(6-Bromo-8-chloro-2-methyl-1,2,3,4-tetrahydro-isoquinolin-4-yl)-phenyl]-acetamide (example 24) and N-methyl-piperazine.

27a: N-{4-[8-Chloro-2-methyl-6-(4-methyl-piperazin-1-yl)-1,2,3,4-tetrahydro-isoquinolin-4-yl]-phenyl}-acetamide, Hydrochloride;

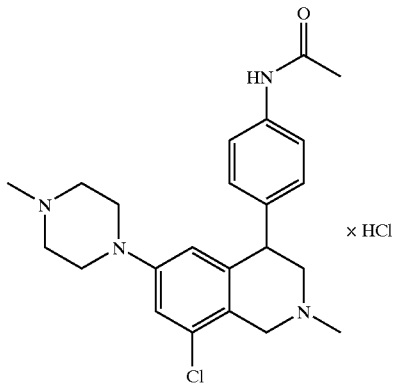

220 mg of N-{4-[8-Chloro-2-methyl-6-(4-methyl-piperazin-1-yl)-1,2,3,4-tetrahydro-isoquinolin-4-yl]-phenyl}-acetamide was dissolved in a little methanol, diluted with 2 N HCl and freeze dried, resulting in 226 mg of the desired hydrochloride.

Example 28

N-{4-[8-Chloro-6-(cyclopropylmethyl-amino)-2-methyl-1,2,3,4-tetrahydro-isoquinolin-4-yl]-phenyl}-acetamide, Hydrochloride

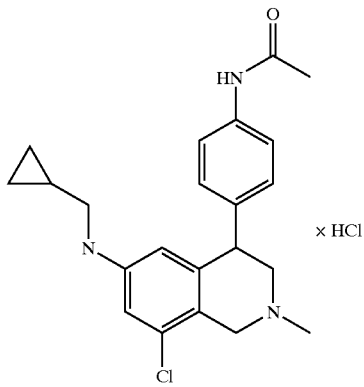

Preparation takes place in analogy to the method described in example 25, starting from N-[4-(6-bromo-8-chloro-2-methyl-1,2,3,4-tetrahydro-isoquinolin-4-yl)-phenyl]-acetamide (example 24) and C-cyclopropyl-methylamine. The chromatography on silica gel was followed by a further purification on a preparative HPLC. The purified compound was dissolved in 1 N HCl, diluted with H₂O and freeze dried.

Example 29

5-(6,8-Dichloro-2-methyl-1,2,3,4-tetrahydro-isoquinolin-4-yl)-2-hydroxy-benzoic acid

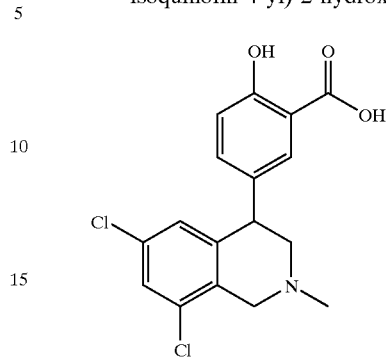

Intermediate 1:

Ethyl 5-acetyl-2-hydroxy-benzoate was prepared from 5-acetyl-2-hydroxy-benzoic acid by acid-catalyzed esterification in a manner known to the skilled worker.

Intermediate 2:

Ethyl 5-(2-bromo-acetyl)-2-hydroxy-benzoate was prepared from ethyl 5-acetyl-2-hydroxy-benzoate by a known method in analogy to the process described in example 1, intermediate 2.

Intermediate 3:

Ethyl 5-(6,8-dichloro-2-methyl-1,2,3,4-tetrahydro-isoquinolin-4-yl)-2-hydroxy-benzoate The title compound was synthesized by the synthetic route described in example 1, starting from ethyl 5-(2-bromo-acetyl)-2-hydroxy-benzoate and 2,4-dichlorobenzyl-(methyl)-amine (see example 1, intermediate 1).

5-(6,8-Dichloro-2-methyl-1,2,3,4-tetrahydro-isoquinolin-4-yl)-2-hydroxy-benzoic acid; 6.8 g (18 mmol) of ethyl 5-(6,8-dichloro-2-methyl-1,2,3,4-tetrahydro-isoquinolin-4-yl)-2-hydroxy-benzoate was hydrolyzed in an ethanol/2 N KOH mixture in a manner known to the skilled worker, resulting in 5.4 g of the free acid.

29a: 5-(6,8-Dichloro-2-methyl-1,2,3,4-tetrahydro-isoquinolin-4-yl)-2-hydroxy-benzoic acid, Sodium Salt;

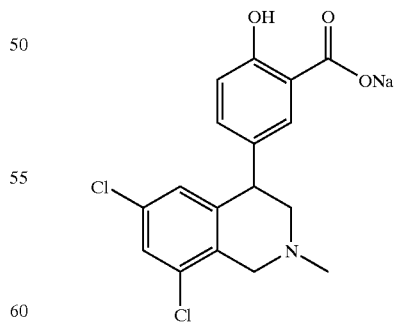

352 mg (1 mmol) of the free acid 5-(6,8-dichloro-2-methyl-1,2,3,4-tetrahydro-isoquinolin-4-yl)-2-hydroxy-benzoic acid was dissolved in 10 ml of 0.1 M NaOH, diluted with H₂O and freeze dried, resulting in 375 mg of the title compound.

Example 30

5-(6,8-Dichloro-2-methyl-1,2,3,4-tetrahydro-isoquinolin-4-yl)-2-hydroxy-N-methyl-benzamide, Trifluoroacetate

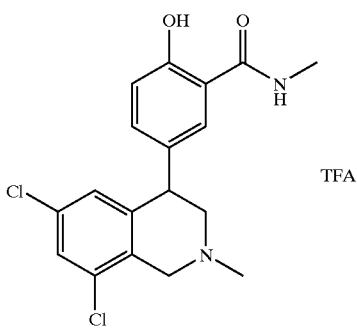

The title compound was prepared starting from 5-(6,8-dichloro-2-methyl-1,2,3,4-tetrahydro-isoquinolin-4-yl)-2-hydroxy-benzoic acid in a TOTU-mediated reaction with methylamine in analogy to the method described in example 7.

Example 31

5-(6,8-Dichloro-2-methyl-1,2,3,4-tetrahydro-isoquinolin-4-yl)-N-ethyl-2-hydroxy-benzamide, Trifluoroacetate

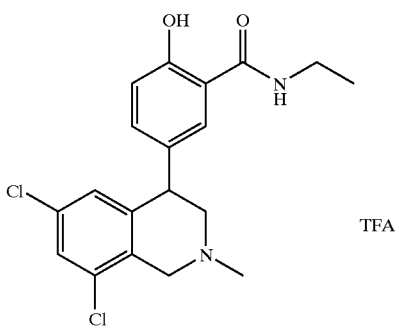

The title compound was prepared starting from 5-(6,8-dichloro-2-methyl-1,2,3,4-tetrahydro-isoquinolin-4-yl)-2-hydroxy-benzoic acid in a TOTU-mediated reaction with ethylamine in analogy to the method described in example 7.

Example 32

5-(6,8-Dichloro-2-methyl-1,2,3,4-tetrahydro-isoquinolin-4-yl)-N-(2-dimethylamino-ethyl)-2-hydroxy-benzamide, Trifluoroacetate

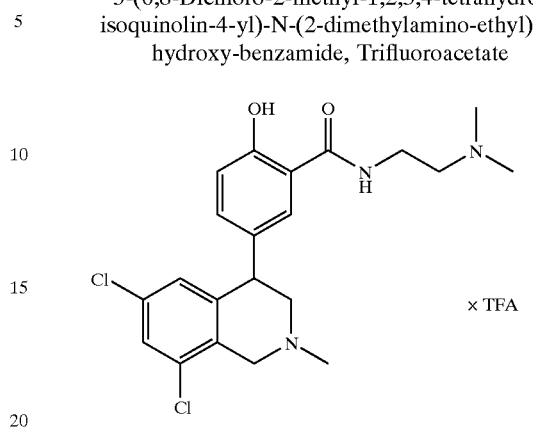

The title compound was prepared starting from 5-(6,8-dichloro-2-methyl-1,2,3,4-tetrahydro-isoquinolin-4-yl)-2-hydroxy-benzoic acid in a TOTU-mediated reaction with N1,N1-dimethyl-ethane-1,2-diamine in analogy to the method described in example 7.

Example 33

N-[5-(6,8-Dichloro-2-methyl-1,2,3,4-tetrahydro-isoquinolin-4-yl)-2-hydroxy-benzoyl]-guanidine

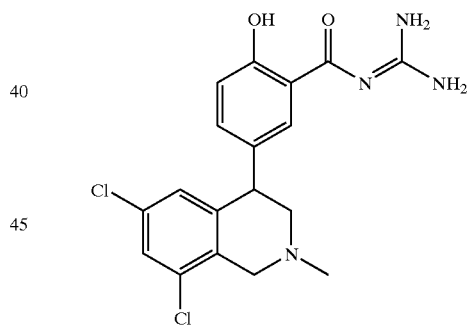

2.52 g of potassium tert-butoxide was added to a solution of 2.39 g (25 mmol) of guanidine hydrochloride in 15 ml of abs. DMF and stirred at room temperature for 45 min. A solution of 950 mg (2.5 mmol) of ethyl 5-(6,8-dichloro-2-methyl-1,2,3,4-tetrahydro-isoquinolin-4-yl)-2-hydroxy-benzoate (example 29, intermediate 3) in 10 ml of abs. DMF was added, and the mixture was stirred at room temperature for four hours. After no further increase in conversion was detectable, the precipitate was removed by filtration with suction and the solvent was removed in vacuo. The residue was taken up in 2 N HCl and extracted twice with dichloromethane. The aqueous phase was adjusted to a pH of about 10 with KOH, whereupon the desired acylguanidine separates out as a colorless precipitate. Filtration with suction and drying affords 793 mg of the title compound.

Example 34

N-[3-(6,8-Dichloro-2-methyl-1,2,3,4-tetrahydro-isoquinolin-4-yl)-phenyl]-acetamide

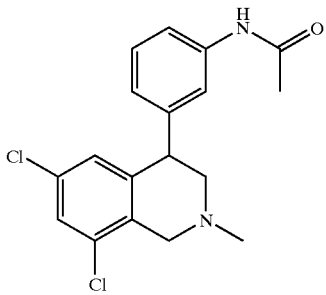

N-[3-(6,8-Dichloro-2-methyl-1,2,3,4-tetrahydro-isoquinolin-4-yl)-phenyl]-acetamide; The desired meta-substituted acetanilide was prepared in analogy to the synthetic route indicated for example 1, starting from N-(3-acetyl-phenyl)-acetamide and 2,4-dichlorobenzyl-(methyl)-amine (example 1, intermediate 1) in four analogous stages.

Example 35

3-(6,8-Dichloro-2-methyl-1,2,3,4-tetrahydro-isoquinolin-4-yl)-phenylamine

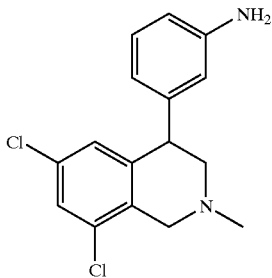

Acetyl was eliminated from N-[3-(6,8-dichloro-2-methyl-1,2,3,4-tetrahydro-isoquinolin-4-yl)-phenyl]-acetamide (example 34) by the method described in example 17, intermediate 1, in the presence of sodium ethanolate.

Example 36

2-(6,8-Dichloro-2-methyl-1,2,3,4-tetrahydro-isoquinolin-4-yl)-phenylamine

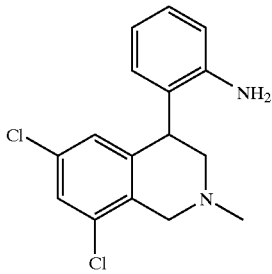

Intermediate 1:
N-[2-(2-Bromo-acetyl)-phenyl]-acetamide;
31 g (0.175 mol) of N-(2-Acetylphenyl)-acetamide (prepared by acylation of 2-aminoacetophenone with acetyl chloride as described by Fuerstner, Alois; Jumbam, Denis N.; Tetrahedron; 48; 29; 5991–6010, (1992)) was dissolved in 200 ml of glacial acetic acid. 127 ml of 33% strength HBr in glacial acetic acid was added and then, at room temperature, 8.75 ml (0.175 mol) of bromine was slowly run in. The mixture was stirred at room temperature overnight. The mixture was stirred into 1.5 l of ice-water, and the precipitated product was filtered off with suction, thoroughly washed with ice-water and dried in vacuo. The crude product contained, according to HPLC and NMR, some precursor and dibrominated product, but was pure enough (about 85% strength) for further reaction.
Yield: 43 g
Intermediate 2:
N-(2-{2-[(2,4-Dichloro-benzyl)-methyl-amino]-acetyl}-phenyl)-acetamide;
12.4 g (65.24 mmol) of 2,4-dichloro-N-methylbenzylamine (example 1, intermediate 1) was dissolved in 200 ml of dioxane. To this was added 19.96 g of the crude product from the preceding bromination, likewise dissolved in 200 ml of dioxane, and 45 ml of triethylamine. The mixture was stirred at room temperature overnight and then filtered. The filtrate was evaporated, and the residue was taken up in ethyl acetate and washed with saturated sodium bicarbonate solution and brine, dried over sodium sulfate and concentrated in a rotary evaporator. The crude product (20.4 g) was pure enough according to NMR for further reaction.
Intermediate 3:
N-(2-{2-[(2,4-Dichloro-benzyl)-methyl-amino]-1-hydroxy-ethyl}-phenyl)-acetamide;
20 g of the crude product from the preceding stage (about 50 mmol) was dissolved in 200 ml of methanol and cooled to <5° C. in an icebath. To this were added, while stirring vigorously, 4.3 g (109 mmol) of sodium borohydride in portions so that the internal temperature does not exceed 10° C. The mixture as then stirred in the icebath for 30 min and at RT for 1 h. After standing overnight, the mixture was evaporated, and the residue was taken up in ethyl acetate, washed 3× with water and 1× with brine, dried over sodium sulfate and concentrated in a rotary evaporator. The crude product (19.4 g) was reacted further without purification.
Intermediate 4:
1-(2-Amino-phenyl)-2-[(2,4-dichloro-benzyl)-methyl-amino]-ethanol;
10 g of the crude product from the preceding stage ere dissolved in 300 ml of methanol. 200 ml of conc. hydrochloric acid were added, and the mixture was stirred at 50° C. for 10 h. The mixture was allowed to cool and was poured into water, and the pH was adjusted to 10–12 with 20% strength NaOH. The product was extracted with ethyl acetate, and the combined extracts were washed with brine, dried over sodium sulfate and evaporated. The crude product (9.9 g) contained some sodium chloride, but this does not interfere with further reaction.
2-(6,8-Dichloro-2-methyl-1,2,3,4-tetrahydro-isoquinolin-4-yl)-phenylamine;
9.9 g of the crude product from the preceding stage was dissolved in 350 ml of chloroform. While cooling in an icebath, 123 ml of conc. sulfuric acid were added dropwise. The mixture was stirred in the icebath for 2 h and was then allowed slowly to reach RT and was finally heated at 50° C. overnight. The cooled mixture was poured onto ice and made alkaline (pH>10) with sodium hydroxide solution. The organic phase was separated off, the aqueous phase was back-extracted 2× with methylene chloride, and the combined organic phases were washed with water and NaCl, dried over sodium sulfate and evaporated.

General Method for Preparing the Compounds of Examples 37 to 77:

154 mg (0.5 mmol) of the title compounds from example 35, example 36 or example 17, intermediate 1, were introduced into 5 ml of dichloromethane, and 0.076 ml (0.55 mmol) of triethylamine was added. At 0° C., a solution of 1.1 equivalents (0.55 mmol,) of an acid chloride in 5 ml of dichloromethane was added, and the mixture was stirred overnight while warming up. For workup, it was filtered and freed of solvent. The residue was dissolved in 20 ml of ethyl acetate and washed once each with 5% strength NaHCO₃ solution and 5% strength NaCl solution, and dried. Evaporation of the solvent was followed by final purification on a preparative HPLC.

TABLE 1

| Example | Precursor 1/<br>aniline | Precursor 2/<br>acid chloride | Product |
|---|---|---|---|
| 37 | 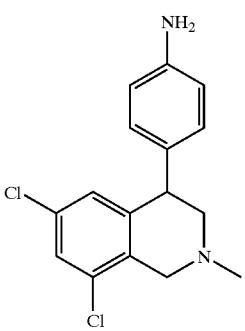<br>Ex. 17, Int. 1 | 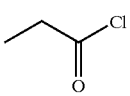 | 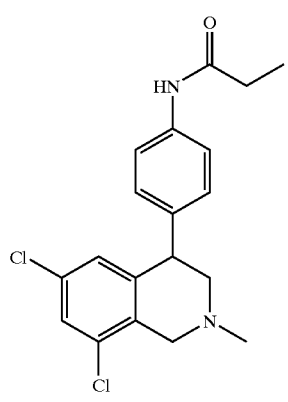 TFA |
| 38 | 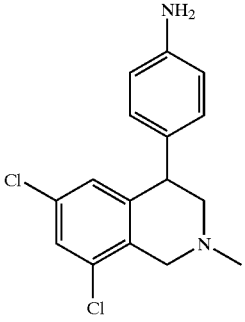<br>Ex. 17, Int. 1 | 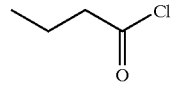 | 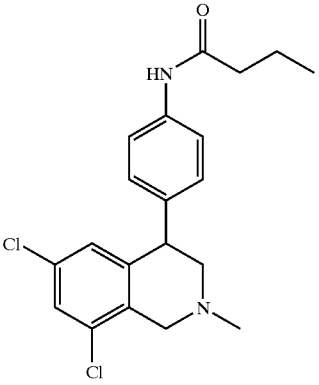 TFA |
| 39 | 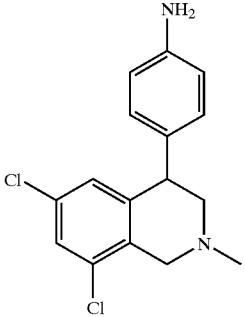<br>Ex. 17, Int. 1 | 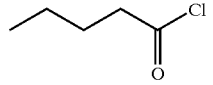 | 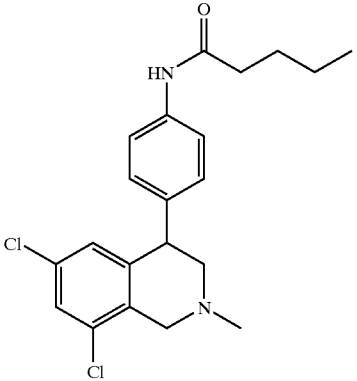 TFA |

TABLE 1-continued
| Example | Precursor 1/ aniline | Precursor 2/ acid chloride | Product |
|---|---|---|---|
| 40 | 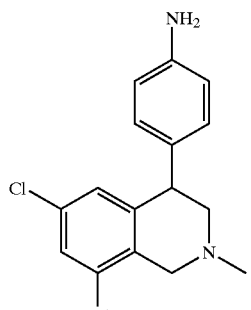 Ex. 17, Int. 1 |  |  TFA |
| 41 | 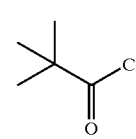 Ex. 17, Int. 1 | 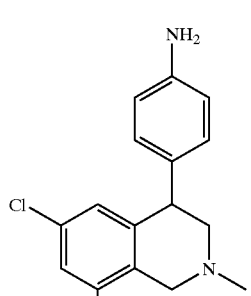 | 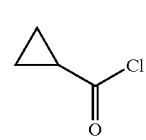 TFA |
| 42 | 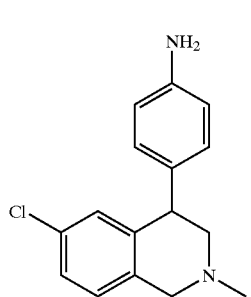 Ex. 17, Int. 1 | 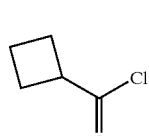 | (cyclopropyl amide product) TFA |
| 43 | (Ex. 17, Int. 1 aniline) | (cyclobutanecarbonyl chloride) | (cyclobutyl amide product) TFA |

TABLE 1-continued
| Example | Precursor 1/ aniline | Precursor 2/ acid chloride | Product |
|---|---|---|---|
| 44 | 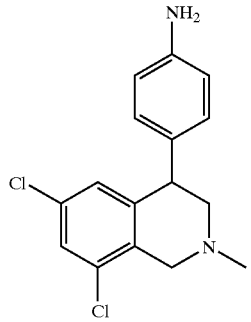 Ex. 17, Int. 1 | 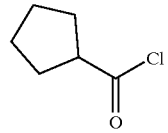 | 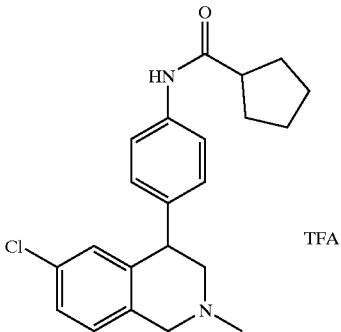 TFA |
| 45 | 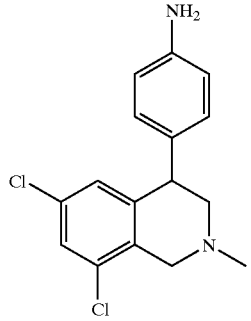 Ex. 17, Int. 1 | 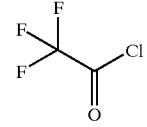 | 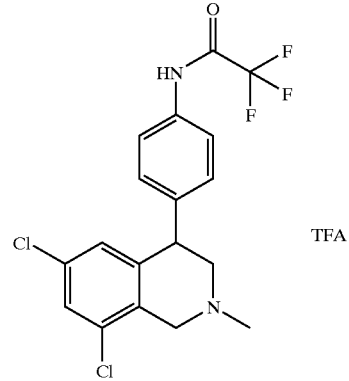 TFA |
| 46* | 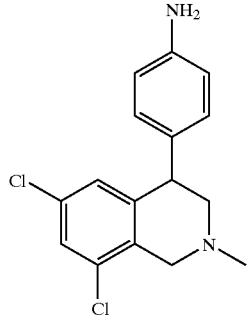 Ex. 17, Int. 1 | 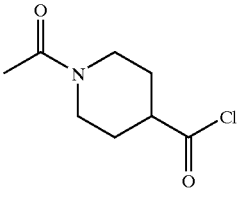 | 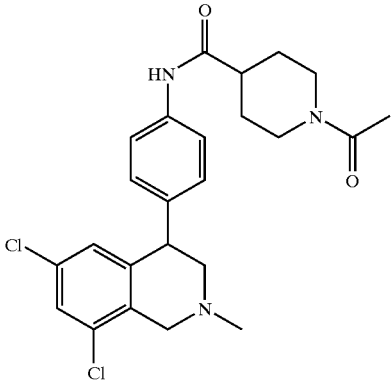 |

TABLE 1-continued

| Example | Precursor 1/ aniline | Precursor 2/ acid chloride | Product |
|---------|----------------------|----------------------------|---------|
| 47 | Ex. 17, Int. 1 | nicotinoyl chloride | nicotinamide product · TFA |
| 48 | Ex. 17, Int. 1 | methanesulfonyl chloride | methanesulfonamide product · TFA |
| 49 | Ex. 17, Int. 1 | ethanesulfonyl chloride | ethanesulfonamide product · TFA |
| 50 | Ex. 17, Int. 1 | dimethylsulfamoyl chloride | dimethylsulfamide product · TFA |

TABLE 1-continued
| Example | Precursor 1/ aniline | Precursor 2/ acid chloride | Product |
|---|---|---|---|
| 51 | 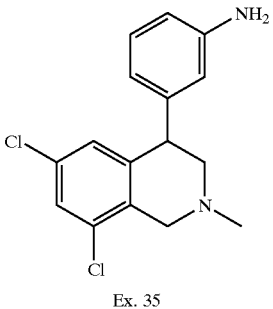 Ex. 35 | 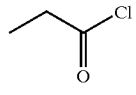 | 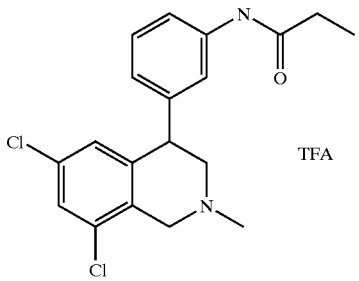 TFA |
| 52 | 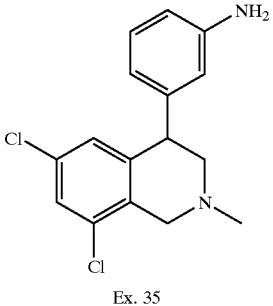 Ex. 35 | 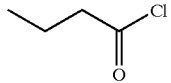 | 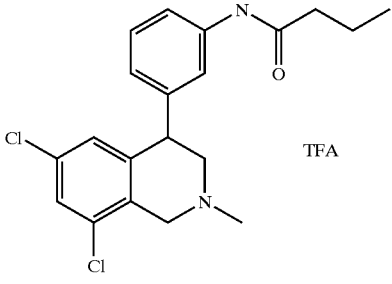 TFA |
| 53 | 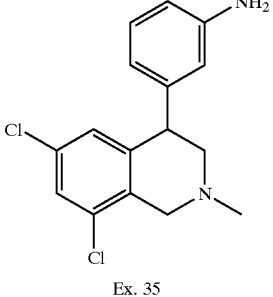 Ex. 35 | 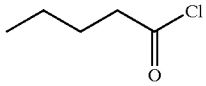 | 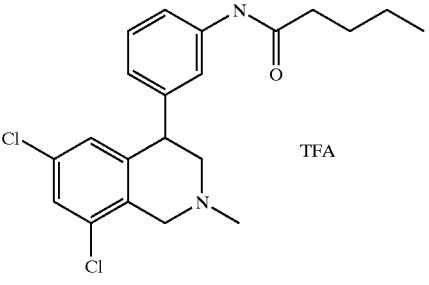 TFA |
| 54 | 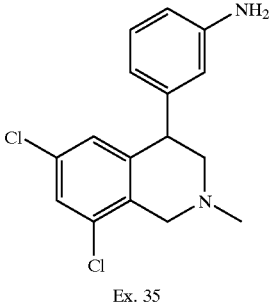 Ex. 35 | 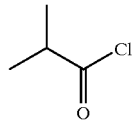 | 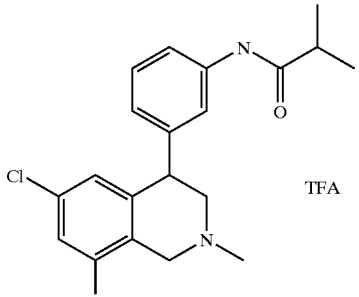 TFA |

TABLE 1-continued
| Example | Precursor 1/ aniline | Precursor 2/ acid chloride | Product |
|---|---|---|---|
| 55 | 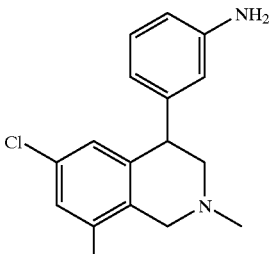 Ex. 35 | 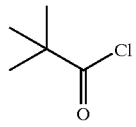 | 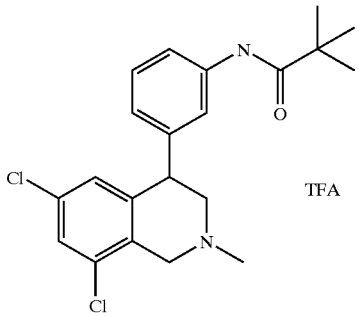 TFA |
| 56 | 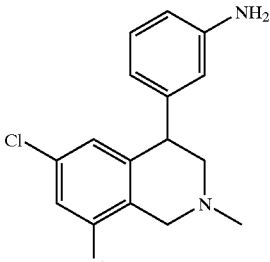 Ex. 35 | 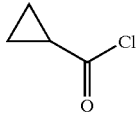 | 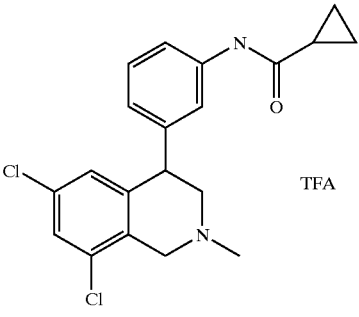 TFA |
| 57 | 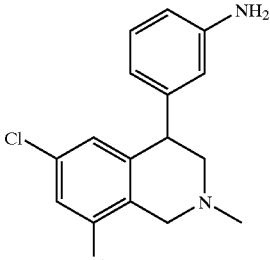 Ex. 35 | 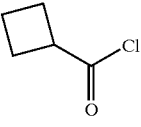 | 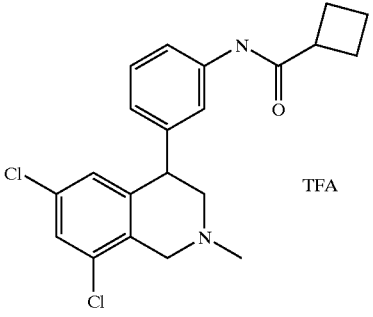 TFA |
| 58 | 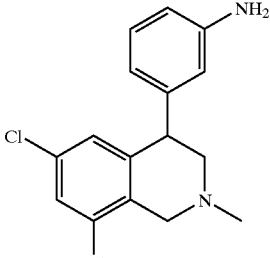 Ex. 35 | 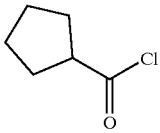 | 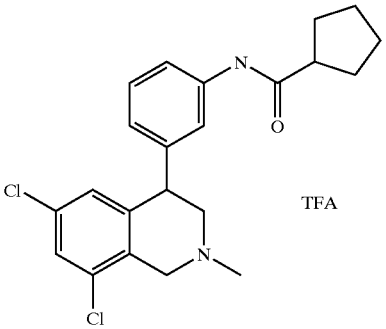 TFA |

TABLE 1-continued
| Example | Precursor 1/aniline | Precursor 2/acid chloride | Product |
|---|---|---|---|
| 59 | 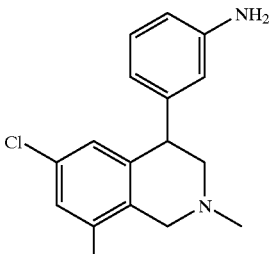 Ex. 35 | 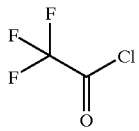 | 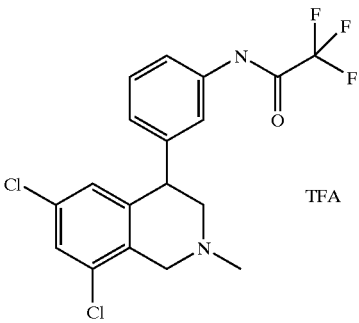 TFA |
| 60 | 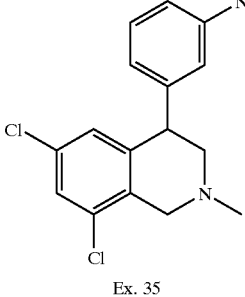 Ex. 35 | 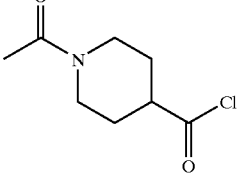 | 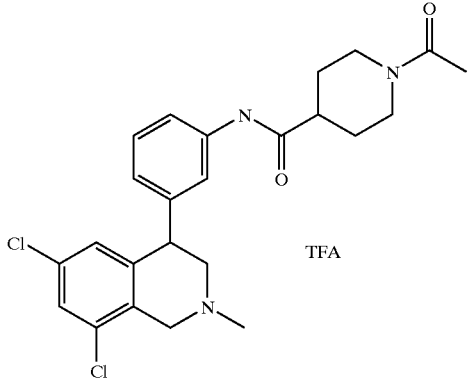 TFA |
| 61 | 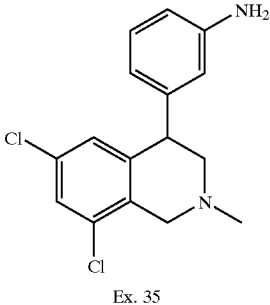 Ex. 35 | 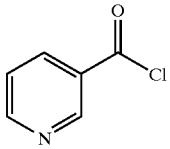 | 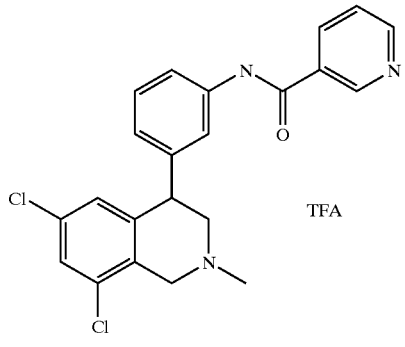 TFA |
| 62 | 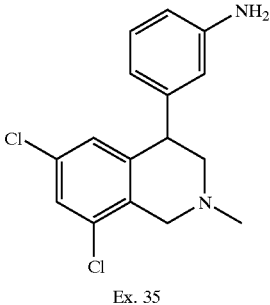 Ex. 35 |  | 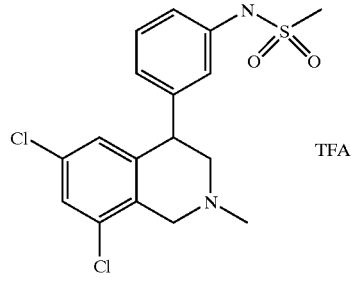 TFA |

TABLE 1-continued
| Example | Precursor 1/ aniline | Precursor 2/ acid chloride | Product |
|---|---|---|---|
| 63 | 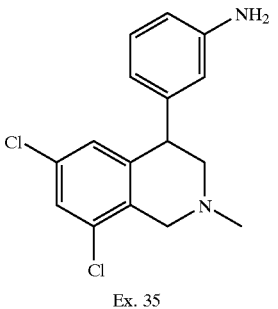 Ex. 35 | 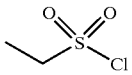 | 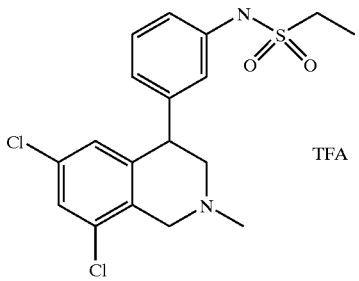 TFA |
| 64 | 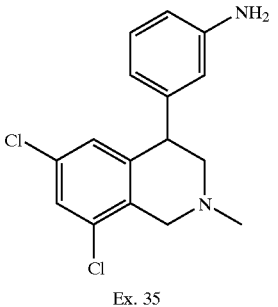 Ex. 35 | 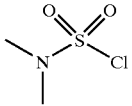 | 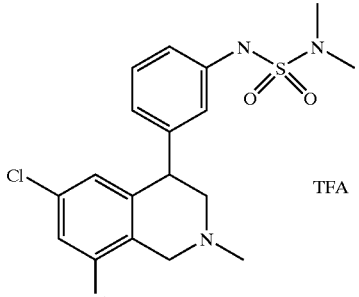 TFA |
| 65 | 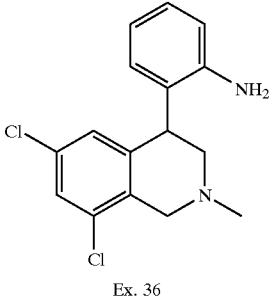 Ex. 36 | 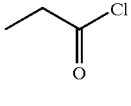 | 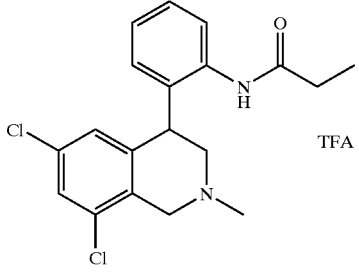 TFA |
| 66 | 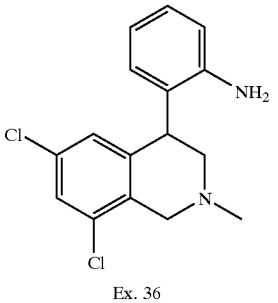 Ex. 36 | 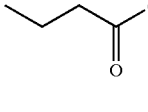 | 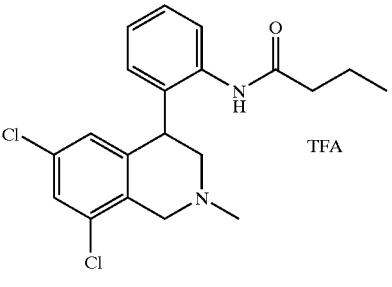 TFA |

TABLE 1-continued

| Example | Precursor 1/ aniline | Precursor 2/ acid chloride | Product |
|---|---|---|---|
| 67 | Ex. 36 | | TFA |
| 68 | Ex. 36 | | TFA |
| 69 | Ex. 36 | | TFA |
| 70 | Ex. 36 | | TFA |

TABLE 1-continued

TABLE 1-continued

| Example | Precursor 1/ aniline | Precursor 2/ acid chloride | Product |
|---|---|---|---|
| 75 | 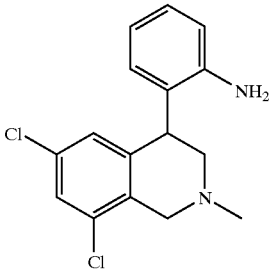 Ex. 36 |  | 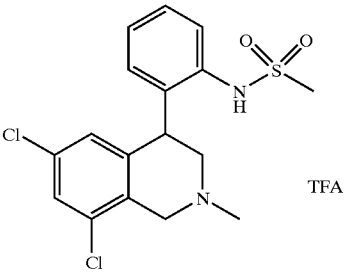 TFA |
| 76 | 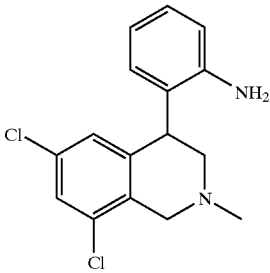 Ex. 36 | 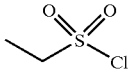 | 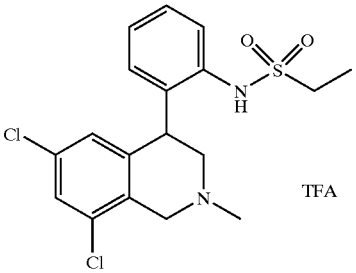 TFA |
| 77 | 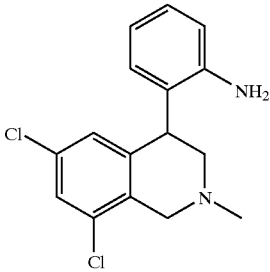 Ex. 36 | 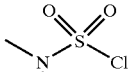 | 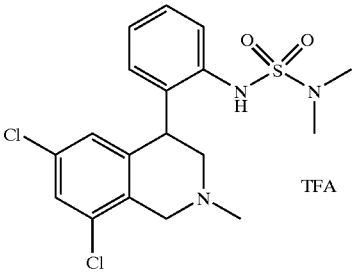 TFA |

*Product precipitates from the reaction solution and requires no further purification

Example 78

1-[3-(6,8-Dichloro-2-methyl-1,2,3,4-tetrahydro-isoquinolin-4-yl)-phenyl]-3-ethyl-urea, Trifluoroacetate

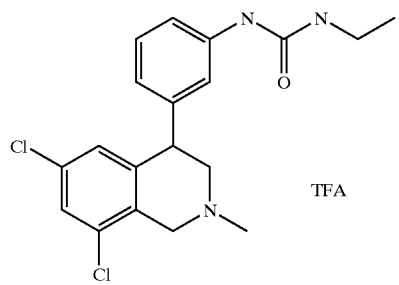

0.355 mmol of the compound of example 35 was dissolved in 5 ml of dry acetonitrile, and 0.39 mmol of ethyl isocyanate was added. After standing overnight with exclusion of moisture, the solvent was removed and the crude product was purified on a preparative HPLC, resulting in the title compound as a colorless solid.

Example 79

1-[3-(6,8-Dichloro-2-methyl-1,2,3,4-tetrahydro-isoquinolin-4-yl)-phenyl]-3-methyl-thiourea, Trifluoroacetate

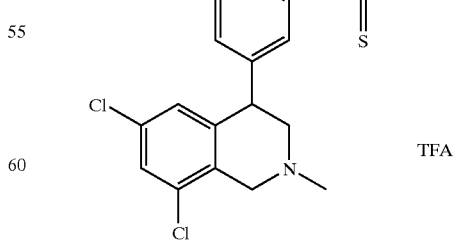

The title compound was synthesized starting from the compound of example 35 and methyl isothiocyanate by the method described in example 78.

Example 80

1-[2-(6,8-Dichloro-2-methyl-1,2,3,4-tetrahydro-isoquinolin-4-yl)-phenyl]-3-ethyl-urea

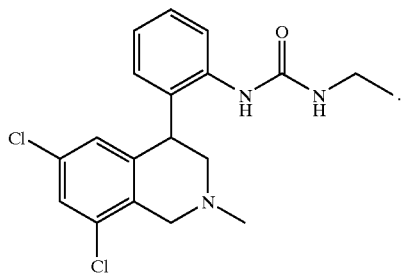

The process is analogous to example 78, starting from the compound of example 36 and ethyl isocyanate. For workup, the resulting precipitate was filtered off with suction and washed with acetonitrile, resulting in the desired ethylurea as a colorless solid.

Example 81

1-[2-(6,8-Dichloro-2-methyl-1,2,3,4-tetrahydro-isoquinolin-4-yl)-phenyl]-3-methyl-thiourea, Trifluoroacetate

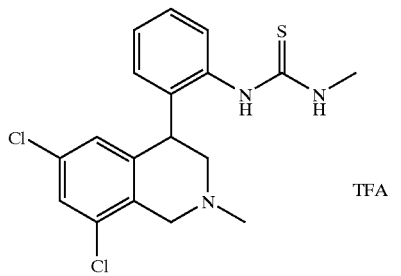

TFA

The compound of example 36 and methyl isothiocyanate are reacted in analogy to the method described in example 78.

Example 82

N-[3-(6,8-Dichloro-2-methyl-1,2,3,4-tetrahydro-isoquinolin-4-yl)-phenyl]-ethanesulfonamide, Hydrochloride

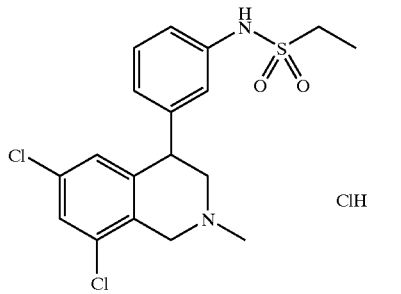

ClH 307.1 mg (1 mmol) of the compound of example 35 was dissolved in 10 ml of pyridine and at 0° C., 0.19 g (1.5 mmol) of ethanesulfonyl chloride, and a catalytic amount of DMAP are added. The mixture was stirred at room temperature.

For workup, the solvent was removed in vacuo, the residue was taken up in ethyl acetate and washed with $H_2O$. The organic phase was dried with $MgSO_4$ and concentrated. The crude product was chromatographed on silica gel. The sulfonamide obtained in this way was dissolved in a THF/2 N HCl mixture and again concentrated in vacuo, resulting in 208 mg of the desired hydrochloride.

Example 83

N-[3-(6,8-Dichloro-2-methyl-1,2,3,4-tetrahydro-isoquinolin-4-yl)-phenyl]-methanesulfonamide, Hydrochloride

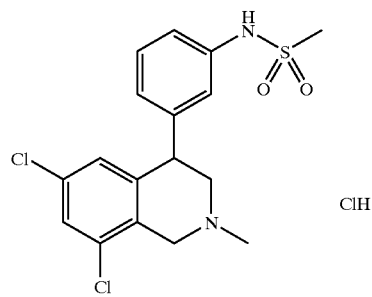

ClH

The process is analogous to the method described in example 82, starting from the compound of example 35 and methanesulfonyl chloride.

Example 84

N-[4-(6,8-dichloro-2-methyl-1,2,3,4-tetrahydro-isoquinolin-4-yl)-phenyl]-ethanesulfonamide, Hydrochloride

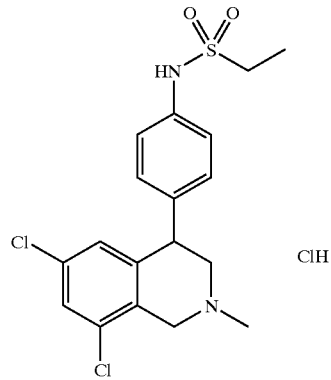

ClH

The process is analogous to the method described in example 82, starting from the compound of example 17, intermediate 1, and ethanesulfonyl chloride.

Example 85

N-[4-(6,8-Dichloro-2-methyl-1,2,3,4-tetrahydro-isoquinolin-4-yl)-phenyl]-methanesulfonamide, Hydrochloride

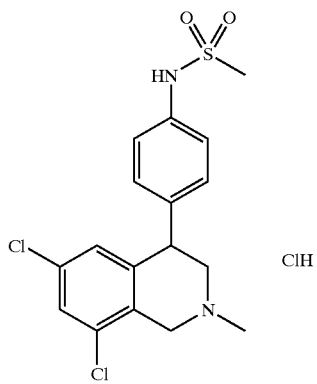

The process is analogous to the method described in example 82, starting from the compound of example 17, intermediate 1, and methanesulfonyl chloride.

Example 86

86a: (−)-N-[3-(6,8-Dichloro-2-methyl-1,2,3,4-tetrahydro-isoquinolin-4-yl)-phenyl]-acetamide
86b: (+)-N-[3-(6,8-Dichloro-2-methyl-1,2,3,4-tetrahydro-isoquinolin-4-yl)-phenyl]-acetamide;

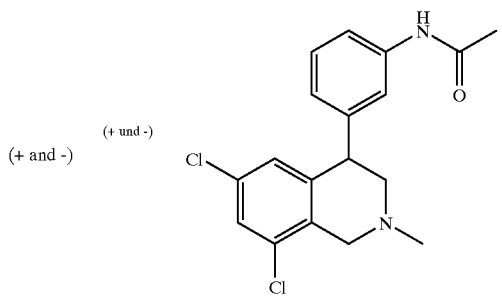

2.0 g of the title compound from example 34 were separated on a chiral phase, resulting in about 1.0 g of the two enantiomeric acetamides 86a and 86b.

chiral column: Chiralpak ADH/31 250×4.6 mm;
solvent: acetonitrile;
flow rate: 1 ml/min;
$R_t$((−)-enantiomer/86a)=5.541 min;
$R_t$((+)-enantiomer/86b)=7.033 min.

General Method for Preparing the Compound of Examples 87 to 98

1.0 mmol of 4-(6,8-dichloro-2-methyl-1,2,3,4-tetrahydro-isoquinolin-4-yl)-phenylamine (example 17, intermediate 1) or -3-(6,8-dichloro-2-methyl-1,2,3,4-tetrahydro-isoquinolin-4-yl)-phenylamine (example 35) was introduced into 10 ml of pyridine and, at 0° C., a solution of 1.2 equivalents of the appropriate sulfonyl chloride (see table 2) in 5 ml of dichloromethane was added dropwise. The mixture as stirred at room temperature. A catalytic amount of DMAP was added depending on the progress of the reaction and, where appropriate, the reaction temperature was increased to 50° C. until no further increase in conversion can be detected. For workup, the mixture was concentrated and the residue was partitioned between ethyl acetate and saturated $NaHCO_3$ solution. The organic phase was separated off and washed once more with saturated $NaHCO_3$ solution and $H_2O$, dried with $Na_2SO_4$ and concentrated. For further purification, the crude product obtained in this way was chromatographed on silica gel. The products obtained in this way were converted into the corresponding hydrochlorides by dissolving the substances in 2 N HCl or ethanolic HCl and freeing off solvent, resulting in the desired HCl salts.

Purification in a preparative HPLC system results in the corresponding products as trifluoroacetates.

TABLE 2

| Example | Precursor 1/ aniline | Precursor 2/ acid chloride | Product |
|---|---|---|---|
| 87 | ![structure with NH2, Ex. 17, Int. 1] | ![F3C-SO2Cl] | ![TFA product] |

TABLE 2-continued

| Example | Precursor 1/ aniline | Precursor 2/ acid chloride | Product |
|---|---|---|---|
| 88 | Ex. 17, Int. 1 | | |
| 88a | Ex. 17, Int. 1 | | ClH |
| 89 | Ex. 17, Int. 1 | | |
| 89a | Ex. 17, Int. 1 | | ClH |

TABLE 2-continued

| Example | Precursor 1/ aniline | Precursor 2/ acid chloride | Product |
|---|---|---|---|
| 90 | Ex. 17, Int. 1 | | |
| 90a | Ex. 17, Int. 1 | | ClH |
| 91 | Ex. 17, Int. 1 | | |
| 91a | Ex. 17, Int. 1 | | ClH |

TABLE 2-continued

| Example | Precursor 1/ aniline | Precursor 2/ acid chloride | Product |
|---|---|---|---|
| 92 | Ex. 17, Int. 1 | | |
| 92a | Ex. 17, Int. 1 | | ClH |
| 93 | Ex. 35 | | TFA |
| 94 | Ex. 35 | | |

TABLE 2-continued

| Example | Precursor 1/ aniline | Precursor 2/ acid chloride | Product |
|---------|----------------------|----------------------------|---------|
| 94a | Ex. 35 | | ClH |
| 95 | Ex. 35 | | |
| 96 | Ex. 35 | | |
| 96a | Ex. 35 | | ClH |

TABLE 2-continued

| Example | Precursor 1/ aniline | Precursor 2/ acid chloride | Product |
|---|---|---|---|
| 97 | Ex. 35 | | |
| 97a | Ex. 35 | | ClH |
| 98 | Ex. 35 | | |

General Method for Synthesizing the Compounds of Examples 99 to 110

Preparation of the Amine Component 4.0 mmol of the aromatic amine (see table 3) was stirred with 8.0 mmol of the aliphatic aldehyde (see table 3) in methanol at room temperature for 2 hours and then, depending on the progress of the reaction, 0.67 to 2.0 eq of NaBH$_4$ was added in portions. After standing at room temperature overnight, the solvent was removed and the residue was taken up in 1 N HCl. It was extracted with dichloromethane. The aqueous phase was adjusted to a pH of 11 to 12 with NaOH and again extracted with dichloromethane. The organic phases were dried with MgSO$_4$ and concentrated in a rotary evaporator. Further purification takes place by chromatography on silica gel or on a preparative HPLC.

Preparation of the Bromo Ketone Component

The bromo ketone building blocks was synthesized by methods known from the literature, starting from commercial acetophenones by treatment with bromine in glacial acetic acid in analogy to example 1, intermediate 2.

The compounds of examples 100 to 111 were prepared starting from the amine and bromo ketone components shown in table 3 in analogy to the synthetic route shown in example 1 (alkylation of the amine component by the bromo ketone component, subsequent reduction with NaBH$_4$ and final H$_2$SO$_4$-mediated cyclization).

The resulting tetrahydroisoquinolines was converted into the corresponding salts in a manner known to the skilled worker.

TABLE 3

| Example No. | Aromatic aldehyde | Aliphatic amine | Amine component | Bromo ketone component | Compound of example |
|---|---|---|---|---|---|
| 99 | 2,4-dichlorobenzaldehyde | —NH₂ | N-methyl-2,4-dichlorobenzylamine | 2-chloro-5-(bromoacetyl)benzenesulfonamide *) | 4-(4-chloro-3-sulfamoylphenyl)-6,8-dichloro-2-methyl-1,2,3,4-tetrahydroisoquinoline |
| 100 | 2,4-dichlorobenzaldehyde | —NH₂ | N-methyl-2,4-dichlorobenzylamine | phenacyl bromide £ | 6,8-dichloro-2-methyl-4-phenyl-1,2,3,4-tetrahydroisoquinoline · HCl |
| 101 | 2,4-dichlorobenzaldehyde | —NH₂ | N-methyl-2,4-dichlorobenzylamine | 4-chlorophenacyl bromide | 4-(4-chlorophenyl)-6,8-dichloro-2-methyl-1,2,3,4-tetrahydroisoquinoline · HCl |
| 102 | 2,4-dichlorobenzaldehyde | ethylamine | N-ethyl-2,4-dichlorobenzylamine | phenacyl bromide | 6,8-dichloro-2-ethyl-4-phenyl-1,2,3,4-tetrahydroisoquinoline · HCl |

TABLE 3-continued

| Example No. | Aromatic aldehyde | Aliphatic amine | Amine component | Bromo ketone component | Compound of example |
|---|---|---|---|---|---|
| 103 | 2,4-bis(trifluoromethyl)benzaldehyde | —NH₂ | N-methyl-2,4-bis(trifluoromethyl)benzylamine | 2-bromo-1-phenylethanone | 6,8-bis(trifluoromethyl)-2-methyl-4-phenyl-1,2,3,4-tetrahydroisoquinoline formate |
| 104 | 2,4-dichlorobenzaldehyde | isopropylamine | N-isopropyl-2,4-dichlorobenzylamine | 2-bromo-1-phenylethanone | 6,8-dichloro-2-isopropyl-4-phenyl-1,2,3,4-tetrahydroisoquinoline formate |
| 105 | 2,5-dichlorobenzaldehyde | —NH₂ | N-methyl-2,5-dichlorobenzylamine | 2-bromo-1-phenylethanone | 5,8-dichloro-2-methyl-4-phenyl-1,2,3,4-tetrahydroisoquinoline formate |
| 106 | 2,4-dichlorobenzaldehyde | —NH₂ | N-methyl-2,4-dichlorobenzylamine | 2-bromo-1-(4-fluorophenyl)ethanone | 6,8-dichloro-2-methyl-4-(4-fluorophenyl)-1,2,3,4-tetrahydroisoquinoline hydrochloride |

TABLE 3-continued

| Example No. | Aromatic aldehyde | Aliphatic amine | Amine component | Bromo ketone component | Compound of example |
|---|---|---|---|---|---|
| 107 | 2,4-dichlorobenzaldehyde | —NH₂ | N-methyl-2,4-dichlorobenzylamine | 2-bromo-1-(4-methylphenyl)ethanone | 6,8-dichloro-2-methyl-4-(4-methylphenyl)-1,2,3,4-tetrahydroisoquinoline · ClH |
| 108 | 3,4-dichlorobenzaldehyde | —NH₂ | N-methyl-2,4-dichlorobenzylamine | 2-bromo-1-phenylethanone | 5,6-dichloro-2-methyl-4-phenyl-1,2,3,4-tetrahydroisoquinoline · ClH |
| 109 | 3,4-dichlorobenzaldehyde | —NH₂ | N-methyl-2,4-dichlorobenzylamine | 2-bromo-1-phenylethanone | 6,7-dichloro-2-methyl-4-phenyl-1,2,3,4-tetrahydroisoquinoline · ClH |
| 110 | 2-bromobenzaldehyde | —NH₂ | N-methyl-2,4-dichlorobenzylamine | 2-bromo-1-phenylethanone | 8-bromo-2-methyl-4-phenyl-1,2,3,4-tetrahydroisoquinoline · ClH |

*) Synthesis described in: Lang et al., DE-A 24 36 263

Standard Procedure for the Preparation of the Example Compounds 111 to 124:

0.358 mmol of the acid component, which are listed in table 4, were dissolved in 1 ml DMF and 0.221 ml (1.30 mmol) of Diisopropylethylamine were added. At 0° C. a solution of 128 mg (0.390 mmol) TOTU was added followed by a solution of the amine component, listed in table 4. After the resulting solution was kept at room temperature overnight, the reaction mixture was filtered and the filter was washed with 20 ml of ethyl acetate. The filtrate was washed twice with sat. NaHCO₃-sol., followed by 5% NaCl-sol. The organic layers were dried using MgSO₄ and the solvent evaporated i. vac. The obtained crude products, which still contained Boc-protecting groups, were deprotected following the procedure given below, without further purification. The above obtained crude products, which were not Boc-protected were purified on a HPLC, by which the example compounds were obtained as the corresponding Trifluoroacetates.

Standard Procedure for the Preparation of the Example Compounds 125 to 147:

0.358 mmol of the acid component, which were listed in table 4, were dissolved in 1 ml DMF and 0.221 ml (1.30 mmol) of Diisopropylethylamine were added. At 0° C., 151 mg (0.975 mmol) Diethylcarbodiimide, a solution of 132 mg (0.975 mmol) HOBt in 1 ml DMF and 20 mg (0.162 mmol) DMAP were added, followed by a solution of the amine component, listed in table 4, in 2 ml DMF. The solution was kept at room temperature overnight. For the working up, the reaction mixture was filtered and the filter was washed with 20 ml of ethyl acetate. The filtrate was washed twice with sat. NaHCO₃-sol., followed by 5% NaCl-sol. The organic layers were dried using MgSO$_4$ and the solvent evaporated i. vac. The obtained crude products, which still contained Boc-protecting groups, were deprotected following the procedure given below, without further purification. The above obtained crude products, which were not Boc-protected were purified on a HPLC, by which the example compounds were obtained as the corresponding Trifluoroacetates.

Standard Procedure for the Deprotection of the Boc-Groups:

The obtained crude products were dissolved in 5 ml of a 10% solution of Trifluoro-acetic acid in Dichloromethane for 1 h at room temperature. The reaction mixture was evaporated i. vac. and the resulting residues were purified by HPLC. The example compounds were obtained as Trifluoro acetates.

TABLE 4

| Example-No. | Acid component | Amine component | Example compound |
|---|---|---|---|
| 111 | [structure: Boc-NH-CH$_2$-COOH] | [structure: 4-(6,8-dichloro-2-methyl-1,2,3,4-tetrahydroisoquinolin-4-yl)aniline] | [structure: corresponding glycinamide] TFA |
| 112 | [structure: Boc-N(Me)-CH$_2$-COOH] | [structure: 4-(6,8-dichloro-2-methyl-1,2,3,4-tetrahydroisoquinolin-4-yl)aniline] | [structure: corresponding N-methyl glycinamide] TFA |
| 113 | [structure: Me$_2$N-CH$_2$-COOH] | [structure: 4-(6,8-dichloro-2-methyl-1,2,3,4-tetrahydroisoquinolin-4-yl)aniline] | [structure: corresponding N,N-dimethyl glycinamide] TFA |

TABLE 4-continued

| Example-No. | Acid component | Amine component | Example compound |
|---|---|---|---|
| 114 | | | TFA |
| 115 | | | TFA |
| 116 | | | TFA |
| 117 | | | TFA |

TABLE 4-continued

| Example-No. | Acid component | Amine component | Example compound |
| --- | --- | --- | --- |
| 118 | isonicotinic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]isonicotinamide TFA |
| 119 | 1H-pyrrole-3-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-1H-pyrrole-3-carboxamide TFA |
| 120 | 1H-pyrrole-2-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-1H-pyrrole-2-carboxamide TFA |
| 121 | 1-methylpiperidine-4-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-1-methylpiperidine-4-carboxamide TFA |

TABLE 4-continued

| Example-No. | Acid component | Amine component | Example compound |
|---|---|---|---|
| 122 | 1-methyl-4-amino-pyrrole-2-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-4-amino-1-methyl-pyrrole-2-carboxamide TFA |
| 123 | 4-nitro-1H-pyrrole-2-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-4-nitro-1H-pyrrole-2-carboxamide TFA |
| 124 | 2,5-dimethyl-1H-pyrrole-3-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-2,5-dimethyl-1H-pyrrole-3-carboxamide TFA |
| 125 | 1H-imidazole-4-carboxylic acid | 4-(6,8-dichloro-2-methyl-1,2,3,4-tetrahydroisoquinolin-4-yl)aniline | N-[4-(6,8-dichloro-2-methyl-1,2,3,4-tetrahydroisoquinolin-4-yl)phenyl]-1H-imidazole-4-carboxamide TFA |

TABLE 4-continued

| Example-No. | Acid component | Amine component | Example compound |
|---|---|---|---|
| 126 | | | TFA |
| 127 | | | TFA |
| 128 | | | TFA |
| 129 | | | TFA |

TABLE 4-continued

| Example-No. | Acid component | Amine component | Example compound |
|---|---|---|---|
| 130 | | | TFA |
| 131 | | | TFA |
| 132 | | | TFA |
| 133 | | | TFA |

TABLE 4-continued

| Example-No. | Acid component | Amine component | Example compound |
|---|---|---|---|
| 134 | N-Boc-lysine | 3-(6,8-dichloro-2-methyl-1,2,3,4-tetrahydroisoquinolin-4-yl)aniline | Lysine amide of the aniline · TFA |
| 135 | N-Boc-proline | 3-(6,8-dichloro-2-methyl-1,2,3,4-tetrahydroisoquinolin-4-yl)aniline | Proline amide of the aniline · TFA |
| 136 | isonicotinic acid | 3-(6,8-dichloro-2-methyl-1,2,3,4-tetrahydroisoquinolin-4-yl)aniline | Isonicotinamide of the aniline · TFA |
| 137 | 1H-pyrrole-3-carboxylic acid | 3-(6,8-dichloro-2-methyl-1,2,3,4-tetrahydroisoquinolin-4-yl)aniline | Pyrrole-3-carboxamide of the aniline · TFA |

TABLE 4-continued
| Example-No. | Acid component | Amine component | Example compound |
|---|---|---|---|
| 138 | 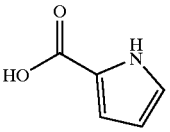 | 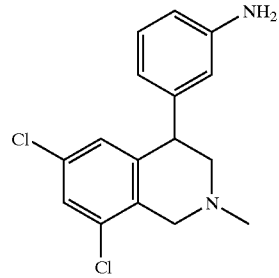 | 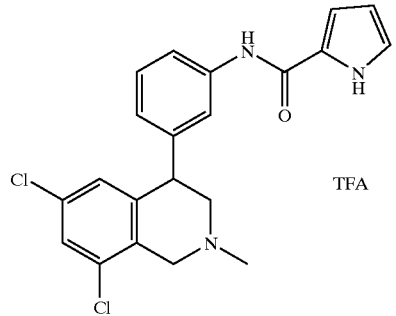 TFA |
| 139 | 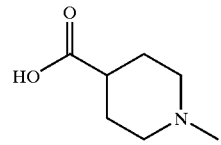 | 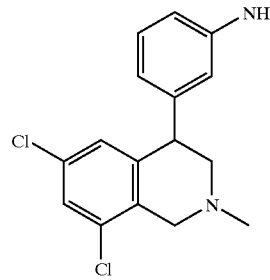 | 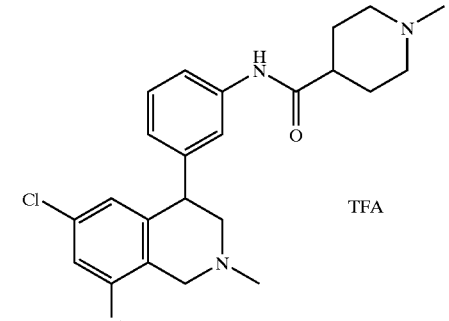 TFA |
| 140 | 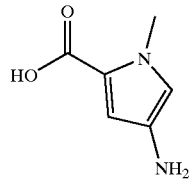 | 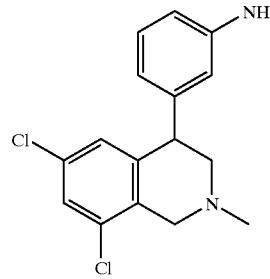 | 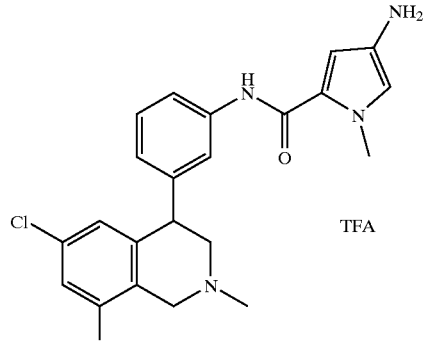 TFA |
| 141 | 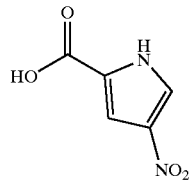 | 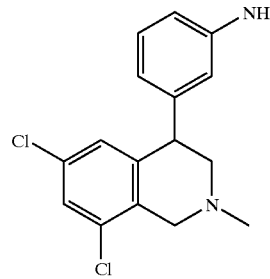 | 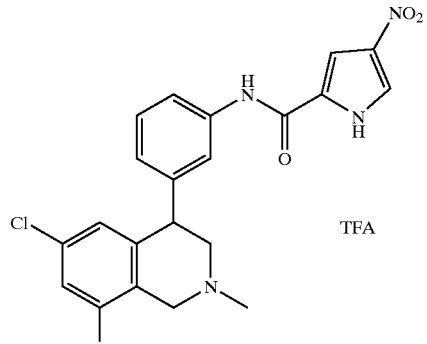 TFA |

TABLE 4-continued
| Example-No. | Acid component | Amine component | Example compound |
|---|---|---|---|
| 142 | 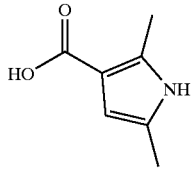 | 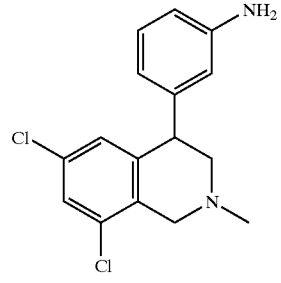 | 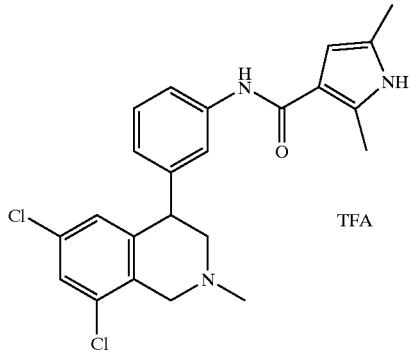 TFA |
| 143 | 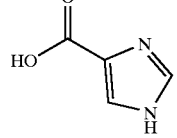 | 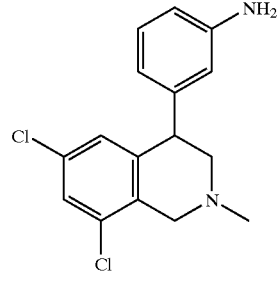 | 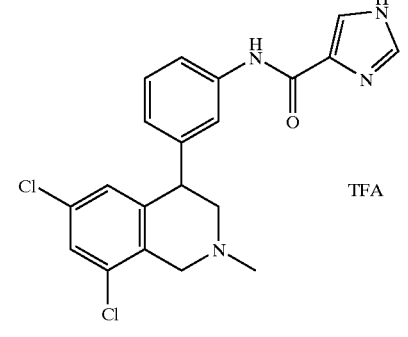 TFA |
| 144 | 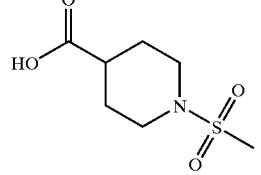 | 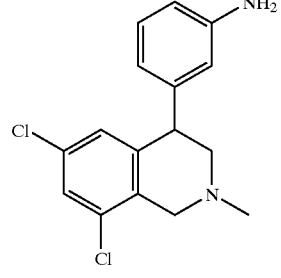 | 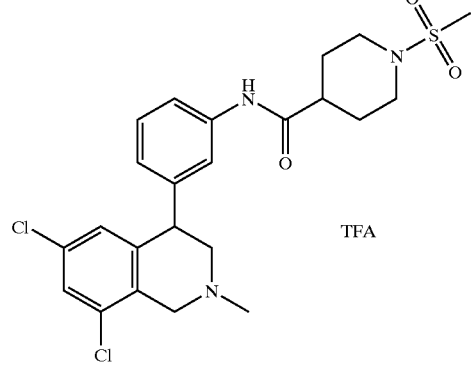 TFA |
| 145 | 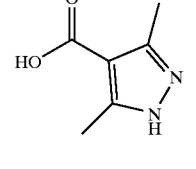 | 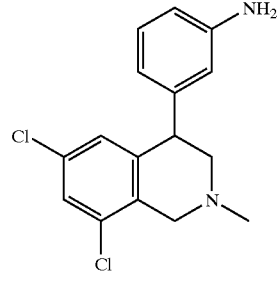 | 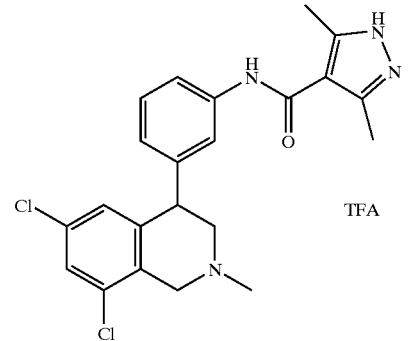 TFA |

TABLE 4-continued

| Example-No. | Acid component | Amine component | Example compound |
|---|---|---|---|
| 146 | | | |
| 147 | | | |

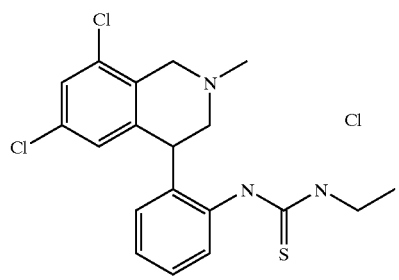

Example 148

1-[2-(6,8-Dichloro-2-methyl-1,2,3,4-tetrahydro-isoquinolin-4-yl)-phenyl]-3ethyl-thiourea-Hydrochloride salt 2-(6,8-Dichloro-2-methyl-1,2,3,4-tetrahydro-isoquinolin-4-yl)-phenylamine (95 mg, example 36) was dissolved in acetonitrile (4 ml) and isothiocyanato-ethane (27 mg) was added to the stirred solution. After standing for 15 h at room temperature the solvent was removed and the residue purified by preparative HPLC. The product containing fractions were combined and the acetonitrile was removed in vaccuo. After addition of potassium carbonate the aqueous phase was extracted with ethyl acetate. The organic layer was separated, dried (magnesium sulphate), filtered and concentrated in vaccuo. The residue was dissolved in water/2N hydrochloric acid and freeze dried to give 36 mg of the title compound.

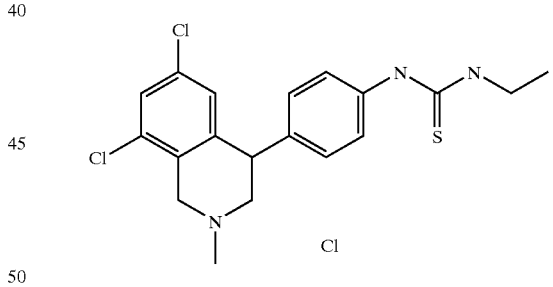

Example 149

1-[4-(6,8-Dichloro-2-methyl-1,2,3,4-tetrahydro-isoquinolin-4-yl)-phenyl]-3-ethyl-thiourea-Hydrochloride salt 4-(6,8-Dichloro-2-methyl-1,2,3,4-tetrahydro-isoquinolin-4-yl)-phenylamine (50 mg, example 17, intermediate 1) was dissolved in tetrahydrofurane (4 ml) and isothiocyanato-ethane (14 mg) was added to the stirred solution. After 2 h at reflux temperature the solution was concentrated and the residue kept for 2 h at 85° C. The crude product was purified by preparative HPLC. The product containing fractions were combined and the acetonitrile was removed in vaccuo. After addition of potassium carbonate the aqueous phase was extracted with ethyl acetate. The organic layer was separated, dried (magnesium sulphate), filtered and concentrated in vaccuo. The residue was dissolved in water/2N hydrochloric acid and freeze dried to give 33 mg of the title compound.

Example 150
1-[3-(6,8-Dichloro-2-methyl-1,2,3,4-tetrahydro-isoquinolin-4-yl)-phenyl]-3-ethyl-thiourea—Trifluoroacetic Acid Salt

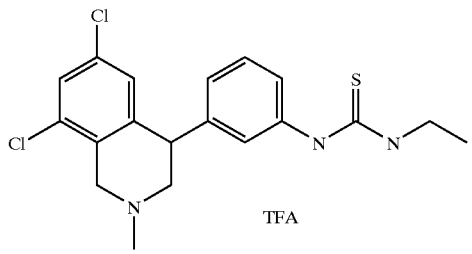

3-(6,8-Dichloro-2-methyl-1,2,3,4-tetrahydro-isoquinolin-4-yl)-phenylamine (50 mg, example 35) was dissolved in tetrahydrofurane (3 ml) and isothiocyanato-ethane (14 mg) was added to the stirred solution. After 2 h at reflux temperature the solution was concentrated and the residue kept for 2 h at 85° C. The crude product was purified by preparative HPLC. The product containing fractions were combined and the solvent was removed in vaccuo to give 66 mg of the title compound.

Example 151
3-[3-(6,8-Dichloro-2-methyl-1,2,3,4-tetrahydro-isoquinolin-4-yl)-phenyl]-1,1-dimethyl-urea-Hydrochloride Salt

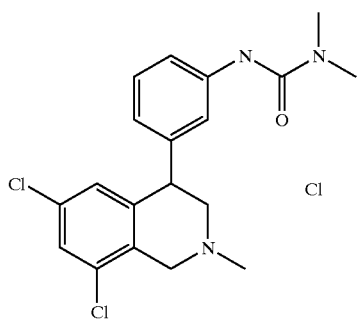

Intermediate 1:
[3-(6,8-Dichloro-2-methyl-1,2,3,4-tetrahydro-isoquinolin-4-yl)-phenyl]-carbamic Acid 4-nitro-phenyl Ester—Hydrochloride Salt 3-(6,8-Dichloro-2-methyl-1,2,3,4-tetrahydro-isoquinolin-4-yl)-phenylamine (350 mg, example 35) was dissolved in dichloromethane (17.5 ml) and 4-nitrophenyl-chloroformate (230 mg) was added to the stirred solution. After 4.5 h an additional 0.1 equivalents of 4-nitrophenyl-chloroformate (23 mg) was added and the mixture stirred over night. The precipitate was removed by suction, washed with dichloromethane and dried under vacuum. The product (545 mg) was used in the next step without further purification.

3-[3-(6,8-Dichloro-2-methyl-1,2,3,4-tetrahydro-isoquinolin-4-yl)-phenyl]-1,1-dimethyl-urea—Hydrochloride Salt

[3-(6,8-Dichloro-2-methyl-1,2,3,4-tetrahydro-isoquinolin-4-yl)-phenyl]-carbamic acid 4-nitro-phenyl ester—Hydrochloride salt (35 mg) was suspended in dichloromethane (3.5 ml). Under stirring dimethylamine (3.7 mg) dissolved in dichloromethane (1 ml) was added. After 1 h dichloromethane, water and saturated potassium carbonate solution were added. The organic layer was separated, washed two times with saturated potassium carbonate solution, dried over magnesium sulphate, filtered and concentrated in vacuo. The residue was dissolved in water/2N hydrochloric acid and freeze dried to give 29 mg of the title compound.

The following examples were synthesised analogously to example 4 using the respective amine. Sometimes preparative HPLC purification was required.

TABLE 5

| Example | Structure |
| --- | --- |
| 152 | 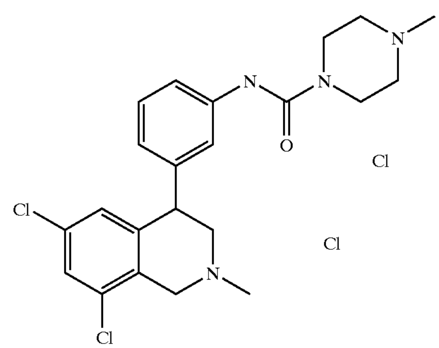 |
| 153 | 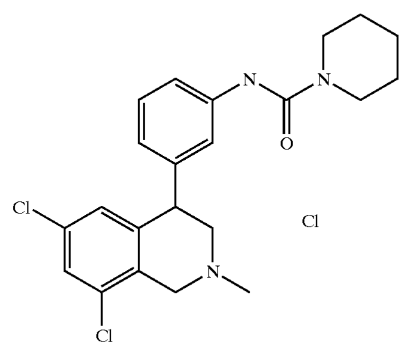 |
| 154 | 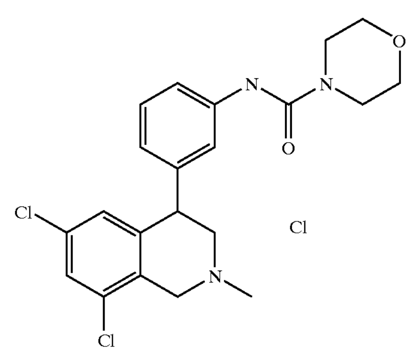 |

141

TABLE 5-continued

| Example | Structure |
|---|---|
| 155 | 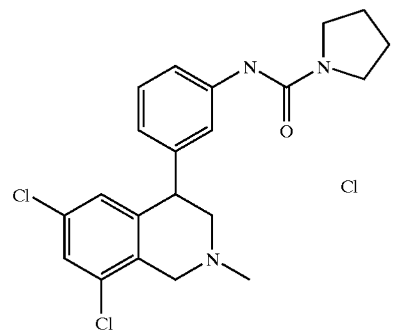 |
| 156 | 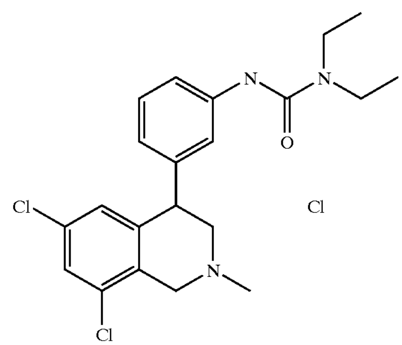 |
| 157 | 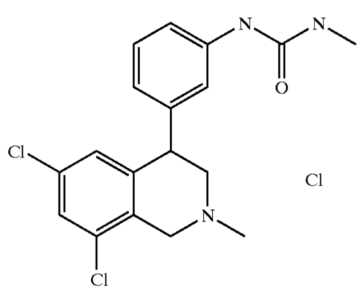 |
| 158 | 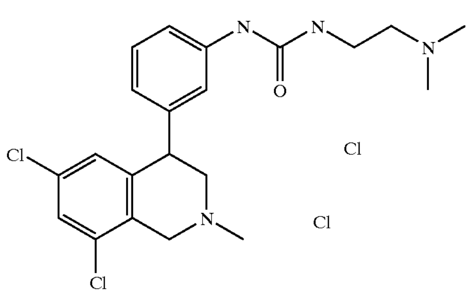 |

The following examples were prepared analogously to example 151. But THF was used as solvent in a closed vial. For examples 159 and 166 a reaction temperature of 85° C. was required. Example 20 required preparative HPLC purification.

142

TABLE 6

| Example | Structure |
|---|---|
| 159 | Chiral |
| 160 | 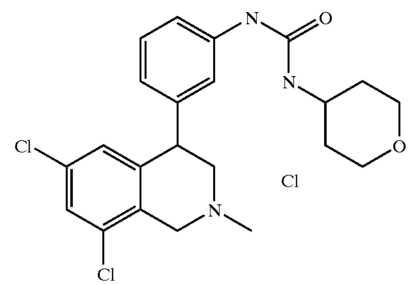 |
| 161 | 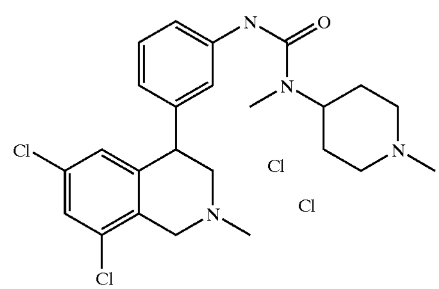 |
| 162 | 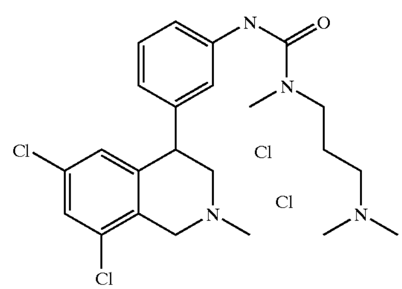 |
| 163 | 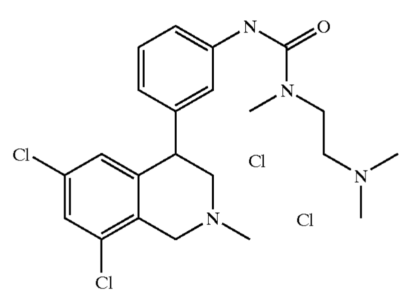 |

TABLE 6-continued

| Example | Structure |
|---------|-----------|
| 164 | 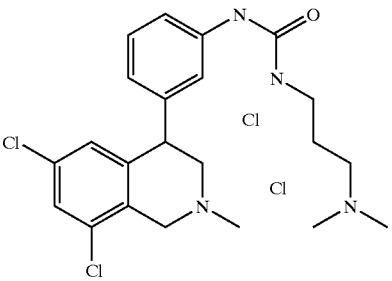 |
| 165 | 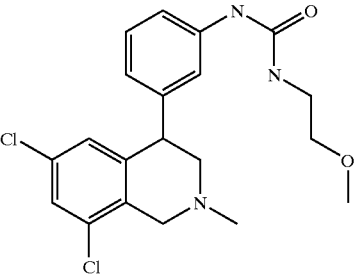 |
| 166 | 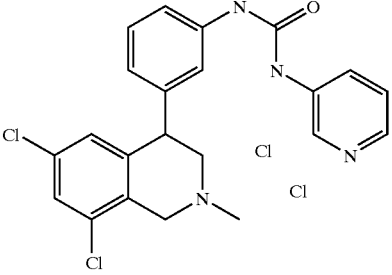 |
| 167 | 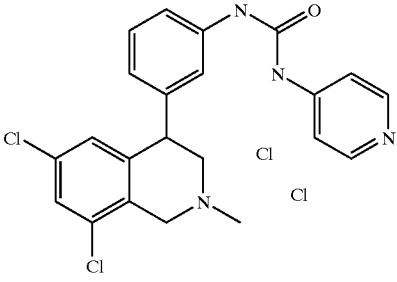 |

Example 168

4-Methyl-piperazine-1-carboxylic acid [2-(6,8-dichloro-2-methyl-1,2,3,4-tetrahydro-isoquinolin-4-yl)-phenyl]-amide—Hydrochloride Salt

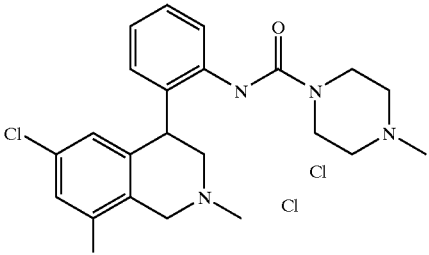

Intermediate 1:

[2-(6,8-Dichloro-2-methyl-1,2,3,4-tetrahydro-isoquinolin-4-yl)-phenyl]-carbamic Acid 4-nitro-phenyl Ester—Hydrochloride Salt 2-(6,8-Dichloro-2-methyl-1,2,3,4-tetrahydro-isoquinolin-4-yl)-phenylamine (200 mg, example 36) was dissolved in dichloromethane (10 ml) and 4-nitrophenyl-chloroformate (131 mg) was added to the stirred solution. After 3.5 h the precipitate was removed by suction, washed with dichloromethane and dried. The crude material was re-crystalized from dichloromethane to give 159 mg of the title compound.

4-Methyl-piperazine-1-carboxylic acid [2-(6,8-dichloro-2-methyl-1,2,3,4-tetrahydro-isoquinolin-4-yl)-phenyl]-amide—Hydrochloride Salt

[2-(6,8-Dichloro-2-methyl-1,2,3,4-tetrahydro-isoquinolin-4-yl)-phenyl]-carbamic acid 4-nitro-phenyl ester—Hydrochloride salt (15 mg) was suspended in dichloromethane (2 ml). Under stirring 1-methyl-piperazine (3.2 mg) dissolved in dichloromethane (1 ml) was added. After 1 h dichloromethane, water and saturated potassium carbonate solution were added. The organic layer was separated, washed two times with saturated potassium carbonate solution, dried over magnesium sulphate, filtered and concentrated in vacuo. The residue was dissolved in water/2N hydrochloric acid and freeze dried to give 13 mg of the title compound.

The Following Examples were Synthesised Analogously to Example 168:

TABLE 7

| Example | Structure |
|---------|-----------|
| 169 | 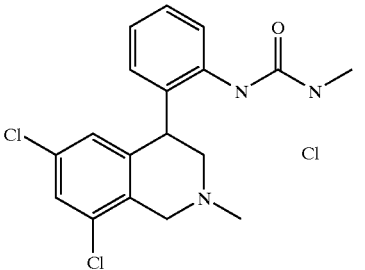 |

TABLE 7-continued

| Example | Structure |
|---|---|
| 170 | 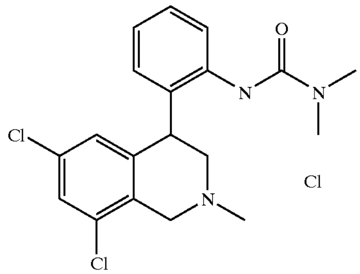 |
| 171 | 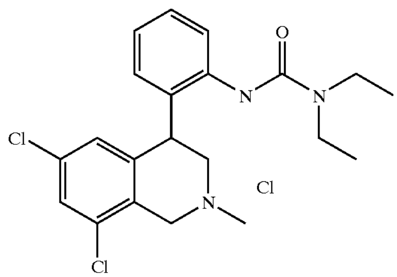 |
| 172 | 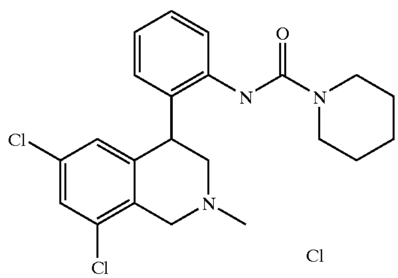 |
| 173 | 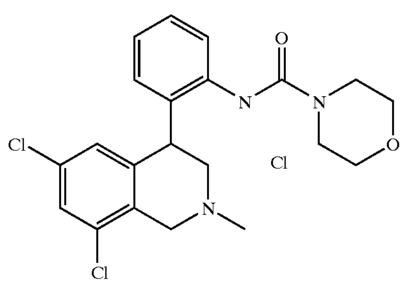 |
| 174 | 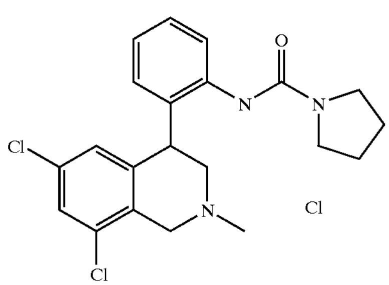 |
| 175 | |

Example 176

4-Methyl-piperazine-1-carboxylic acid [4-(6,8-dichloro-2-methyl-1,2,3,4-tetrahydro-isoquinolin-4-yl)-phenyl]-amide—Hydrochloride Salt Intermediate 1:

[4-(6,8-Dichloro-2-methyl-1,2,3,4-tetrahydro-isoquinolin-4-yl)-phenyl]-carbamic acid 4-nitro-phenyl Ester—Hydrochloride Salt 4-(6,8-Dichloro-2-methyl-1,2,3,4-tetrahydro-isoquinolin-4-yl)-phenylamine (200 mg, example 17, intermediate 1) was dissolved in dichloromethane (10 ml) and 4-nitrophenyl-chloroformate (131 mg) was added to the stirred solution. After 4.5 h the precipitate was removed by suction, washed with dichloromethane and dried. The crude material was re-crystalized twice from dichloromethane to give 254 mg of the title compound.

4-Methyl-piperazine-1-carboxylic acid [4-(6,8-dichloro-2-methyl-1,2,3,4-tetrahydro-isoquinolin-4-yl)-phenyl]-amide—Hydrochloride Salt

[4-(6,8-Dichloro-2-methyl-1,2,3,4-tetrahydro-isoquinolin-4-yl)-phenyl]-carbamic acid 4-nitro-phenyl ester—Hydrochloride salt (15 mg) was suspended in dichloromethane (2 ml). Under stirring 1-methyl-piperazine (3.2 mg) dissolved in dichloromethane (1 ml) was added. After 5 h of stirring and standing over night dichloromethane, water and saturated potassium carbonate solution were added. The organic layer was separated, washed two times with saturated potassium carbonate solution, dried over magnesium sulphate, filtered and concentrated in vacuo. The residue was dissolved in water/2N hydrochloric acid and freeze dried to give 13 mg of the title compound.
The Following Examples Were Synthesised Analogously to Example 176:
TABLE 8
| Example | Structure |
|---------|-----------|
| 177 | 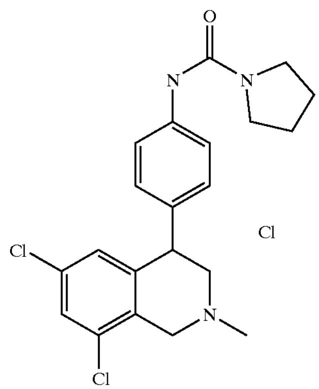 |
| 178 | 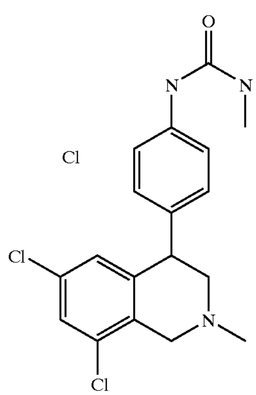 |
| 179 | 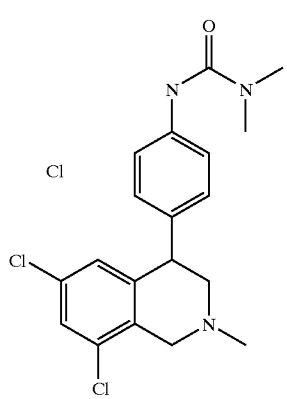 |
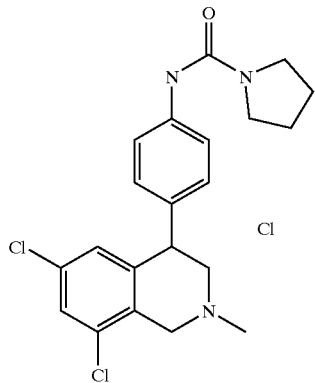
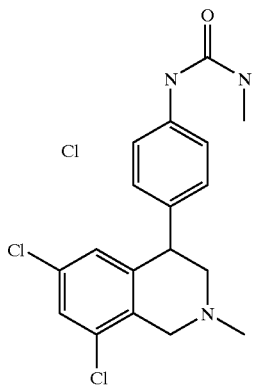
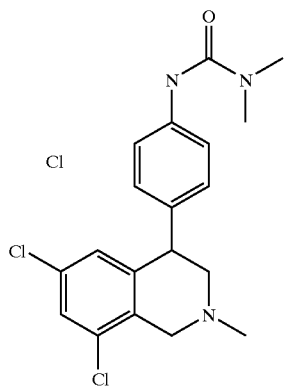
TABLE 8-continued
| Example | Structure |
|---------|-----------|
| 180 | 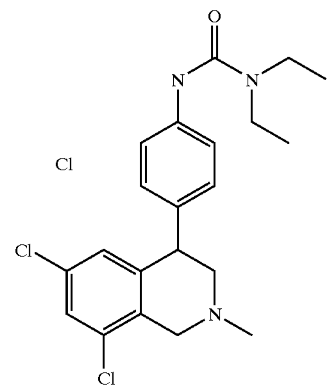 |
| 181 | 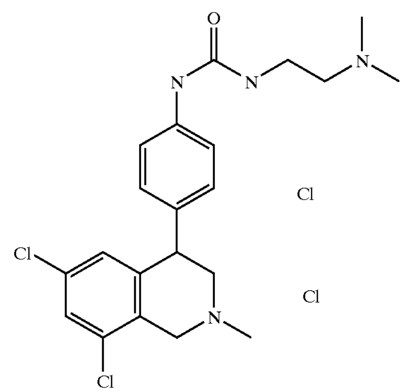 |
| 182 | 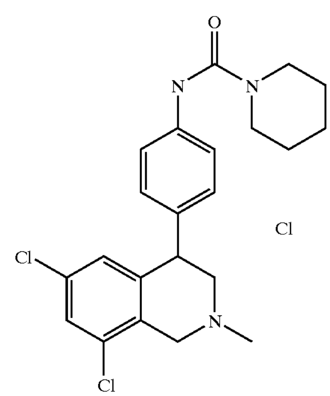 |
| 183 | 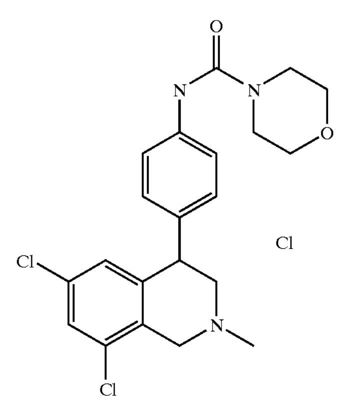 |

Example 184

N-[4-(6,8-Dichloro-2-methyl-1,2,3,4-tetrahydro-isoquinolin-4-yl)-phen^-yl]-formamide—Hydrochloride Salt

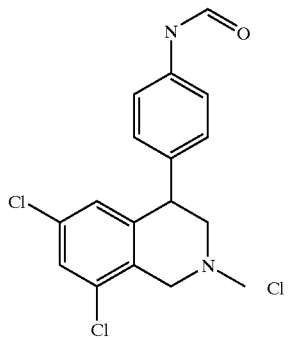

4-(6,8-Dichloro-2-methyl-1,2,3,4-tetrahydro-isoquinolin-4-yl)-phenylamine (200 mg, example 17, intermediate 1) was dissolved in formic acid (1 ml) and kept for 15 min at reflux temperature. After standing over night an ice/water mixture was added followed by ethyl acetate. After separating the organic layer the aqueous phase was again extracted with ethyl acetate. The combined organic layers were dried (magnesium sulphate), filtered and concentrated in vacuo. The residue was dissolved in a mixture of dichloromethane and saturated sodium bicarbonate solution. The organic layer was separated and the aqueous phase was extracted 3 times with dichloromethane. The organic layers were combined, dried (magnesium sulphate), filtered and concentrated in vacuo to yield 167 mg crude material. 10 mg of this material was dissolved in water/2N hydrochloric acid and freeze dried to give 11 mg of the title compound.

Example 185

[4-(6,8-Dichloro-2-methyl-1,2,3,4-tetrahydro-isoquinolin-4-yl)-phenyl]-methyl-amine—Hydrochloride Salt

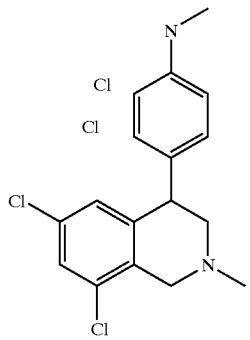

At 50° C. under stirring and argon atmosphere N-[4-(6,8-dichloro-2-methyl-1,2,3,4-tetrahydro-isoquinolin-4-yl)-phenyl]-formamide (150 mg, example 27) dissolved in tetrahydrofurane (2.5 ml) was added to a 1 M solution of lithium aluminiumhydride in tetrahydrofurane (0.45 ml) diluted with tetrahydrofurane (2.5 ml). After the addition the mixture was heated to reflux temperature for 1 h. After standing over night at room temperature the mixture was heated to 50° C. and further lithium aluminiumhydride solution (0.22 ml) was added. The mixture was heated to reflux temperature and after 1 h the mixture was cooled, ice added and the tetrahydrofurane removed in vaccuo. The residue was dissolved in dichloromethane and hydrochloric acid. The aqueous layer was extracted three times with dichloromethane, the organic layers were combined, dried (magnesium sulphate) and concentrated. The crude material was purified by preparative HPLC. The product containing fractions were combined and the acetonitrile was removed in vaccuo. After addition of sodium bicarbonate the aqueous phase was extracted with dichloromethane. The organic layer was separated, dried (magnesium sulphate), filtered and concentrated in vaccuo to yield 80 mg of the salt free base. 10 mg of the base was dissolved in water/2N hydrochloric acid and freeze dried to give 10 mg of the title compound.

Example 186

1-[4-(6,8-Dichloro-2-methyl-1,2,3,4-tetrahydro-isoquinolin-4-yl)-phenyl]-1,3-dimethyl-urea—Hydrochloride Salt

A002955438A

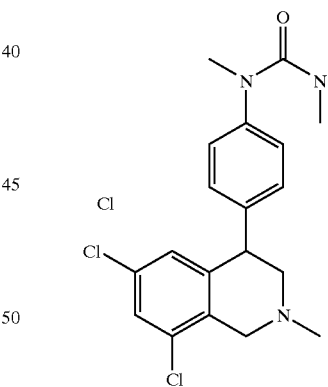

Following the procedure described in example 151 using [4-(6,8-dichloro-2-methyl-1,2,3,4-tetrahydro-isoquinolin-4-yl)-phenyl]-methyl-amine, 4-nitrophenyl-chloroformate and methylamine (20 µl, 2 molar in THF) 9 mg of the title compound was obtained.

The following examples were synthesised analogously to example 186:

TABLE 9

| Example | Structure |
|---|---|
| 187 | *N-methyl-N-(4-(6,8-dichloro-2-methyl-1,2,3,4-tetrahydroisoquinolin-4-yl)phenyl)-4-methylpiperazine-1-carboxamide* |
| 188 | *1,3-dimethyl-1-(4-(6,8-dichloro-2-methyl-1,2,3,4-tetrahydroisoquinolin-4-yl)phenyl)-3-methylurea · HCl* |
| 189 | *N-methyl-N-(4-(6,8-dichloro-2-methyl-1,2,3,4-tetrahydroisoquinolin-4-yl)phenyl)piperidine-1-carboxamide · HCl* |
| 190 | *N-methyl-N-(4-(6,8-dichloro-2-methyl-1,2,3,4-tetrahydroisoquinolin-4-yl)phenyl)morpholine-4-carboxamide · HCl* |

TABLE 9-continued

| Example | Structure |
|---|---|
| 191 | *N-methyl-N-(4-(6,8-dichloro-2-methyl-1,2,3,4-tetrahydroisoquinolin-4-yl)phenyl)pyrrolidine-1-carboxamide · Cl* |
| 192 | *urea derivative · ClH ClH* |
| 193 | *N,N-diethyl urea derivative · ClH* |

Example 194
N-[3-(6,8-Dichloro-2-methyl-1,2,3,4-tetrahydro-isoquinolin-4-yl)-phenyl]-formamide

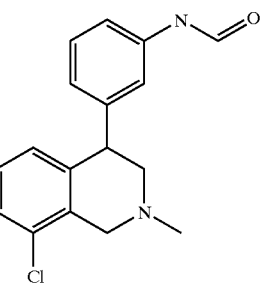

3-(6,8-Dichloro-2-methyl-1,2,3,4-tetrahydro-isoquinolin-4-yl)-phenylamine (600 mg, example 35) was dissolved in formic acid (2.4 ml) and kept for 15 min at reflux temperature. After standing over night an ice/water mixture was added followed by ethyl acetate and saturated sodium bicarbonate solution. The organic layer was separated and the aqueous phase was extracted 3 times with dichloromethane. The organic layers were combined, dried (magnesium sulphate), filtered and concentrated in vacuo to yield 588 mg of the title compound.

Example 195

[3-(6,8-Dichloro-2-methyl-1,2,3,4-tetrahydro-isoquinolin-4-yl)-phenyl]-methyl-amine—Hydrochloride Salt

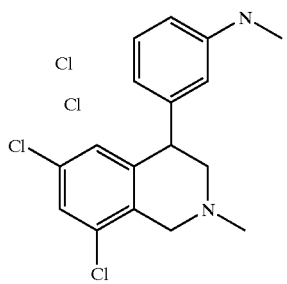

At 50° C. under stirring and argon atmosphere N-[3-(6,8-dichloro-2-methyl-1,2,3,4-tetrahydro-isoquinolin-4-yl)-phenyl]-formamide (588 mg, example 194) dissolved in tetrahydrofurane (10 ml) was added to a 1 M solution of lithium aluminiumhydride in tetrahydrofurane (1.8 ml). After the addition the mixture was heated to reflux temperature for 1 h. After standing over night at room temperature the mixture was heated to 50° C. and further lithium aluminiumhydride solution (2 ml) added. The mixture was heated to reflux temperature and after 0.5 h the mixture was cooled and ice added. The aqueous phase was 4 times extracted with ethyl acetate. The organic layers were combined, dried (magnesium sulphate) and concentrated. The crude material was purified by preparative HPLC. The product containing fractions were combined and the acetonitrile was removed in vaccuo. After addition of sodium bicarbonate the aqueous phase was extracted with ethyl acetate. The organic layer was separated, dried (magnesium sulphate), filtered and concentrated in vaccuo to yield 270 mg of the salt free base. 45 mg of the base was dissolved in water/2N hydrochloric acid and freeze dried to give 45 mg of the title compound.

Following the procedure described in example 151 using [3-(6,8-dichloro-2-methyl-1,2,3,4-tetrahydro-isoquinolin-4-yl)-phenyl]-methyl-amine, 4-nitrophenyl-chloroformate and the respective amine the following urea derivatives were prepared:

TABLE 10

| Example | Structure |
|---------|-----------|
| 196 | 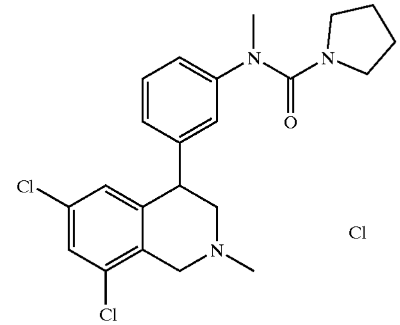 |
| 197 | 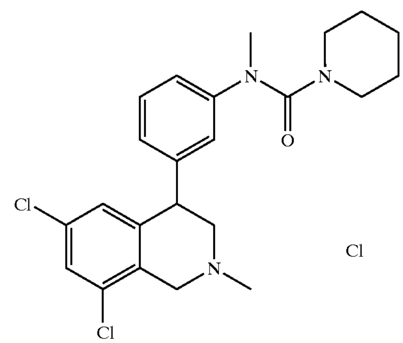 |
| 198 | 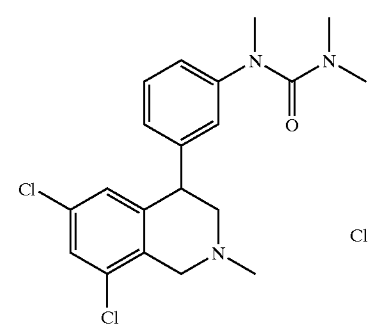 |
| 199 | 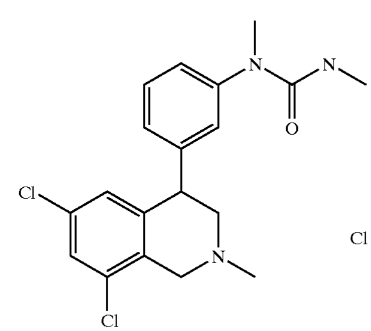 |

TABLE 10-continued

| Example | Structure |
|---|---|
| 200 | 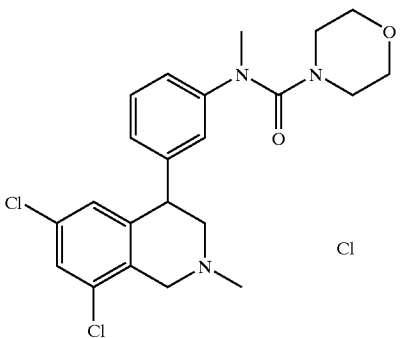 |
| 201 | 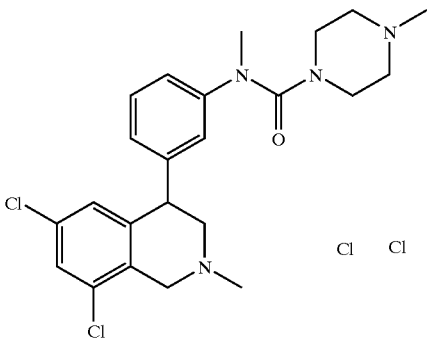 |
| 202 | 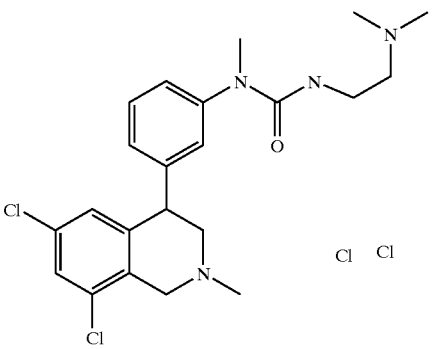 |
| 203 | 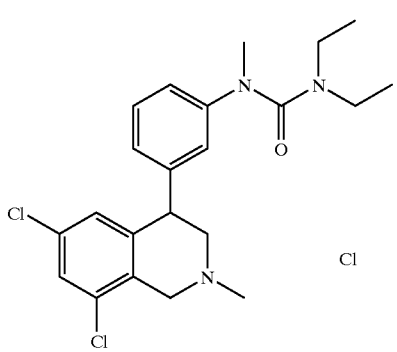 |

Example 204

[3-(6,8-Dichloro-2-methyl-1,2,3,4-tetrahydro-isoquinolin-4-yl)-phenyl]-carbamic Acid 2-dimethylamino-ethyl Ester—Hydrochloride Salt

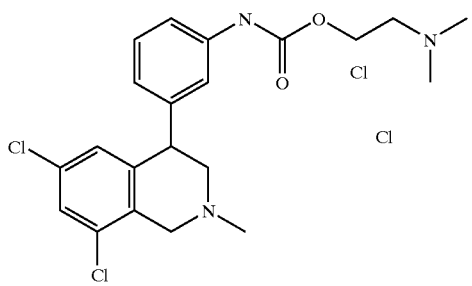

Under stirring and argon atmosphere [3(6,8-dichloro-2-methyl-1,2,3,4-tetrahydro-isoquinolin-4-yl)-phenyl]-carbamic acid 4-nitro-phenyl ester—hydrochloride salt (15 mg, example 151, intermediate 1) was suspended in dichloromethane (1.5 ml) and 2-dimethylamino-ethanol (3 mg) dissolved in dichloromethane (0.5 ml) was added. After stirring for 6 h and standing over night dichloromethane, water and saturated potassium carbonate solution were added. The organic layer was separated, washed three times with saturated potassium carbonate solution, dried over magnesium sulphate, filtered and concentrated in vacuo. The crude material was purified by preparative HPLC. The product containing fractions were combined and the acetonitrile was removed in vaccuo. After addition of sodium bicarbonate the aqueous phase was extracted with ethyl acetate. The organic layer was separated, dried (magnesium sulphate), filtered and concentrated in vaccuo. The residue was dissolved in water/2N hydrochloric acid and freeze dried to give 5 mg of the title compound.

Following the procedure described in the example above the following carbamates were prepared starting from 2-(6,8-Dichloro-2-methyl-1,2,3,4-tetrahydro-isoquinolin-4-yl)-phenylamine and 4-(6,8-Dichloro-2-methyl-1,2,3,4-tetrahydro-isoquinolin-4-yl)-phenylamine, respectively.

TABLE 11

| Example | Structure |
|---|---|
| 205 | 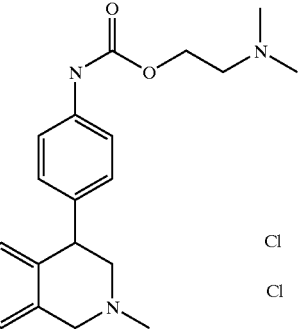 |

TABLE 11-continued

| 206 | 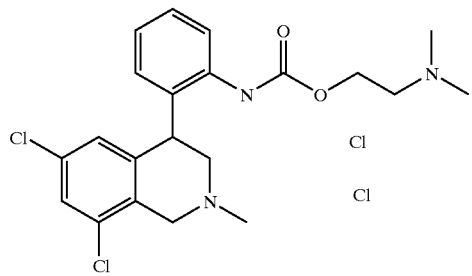 |

Example 207

[3-(6,8-Dichloro-2-methyl-1,2,3,4-tetrahydro-isoquinolin-4-yl)-phenyl]-carbamic acid methyl Ester—Hydrochloride Salt

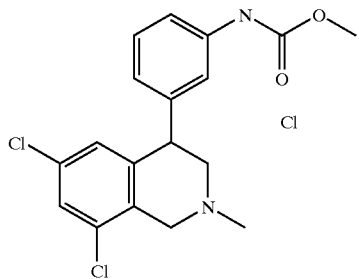

Under stirring and argon 3-(6,8-dichloro-2-methyl-1,2,3,4-tetrahydro-isoquinolin-4-yl)-phenylamine (15 mg, example 35) was dissolved in dichloromethane (1.5 ml) and methyl chloroformate (4.6 mg) dissolved in dichloromethane (0.5 ml) was added. After stirring for 6 h and standing over night additional chloro formate (2.3 mg) was added. Stirring was continued for 5 h, then the solvent was removed and the residue was dissolved in water/2N hydrochloric acid and freeze dried to give 20 mg of the title compound.

Following the procedure described in the example above the following carbamates were prepared starting from 3-(6,8-Dichloro-2-methyl-1,2,3,4-tetrahydro-isoquinolin-4-yl)-phenylamine and 4-(6,8-Dichloro-2-methyl-1,2,3,4-tetrahydro-isoquinolin-4-yl)-phenylamine, respectively.

TABLE 12

| Example | Structure |
|---------|-----------|
| 208 | 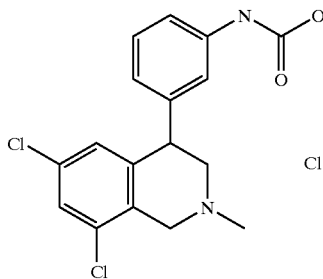 |

TABLE 12-continued

| Example | Structure |
|---------|-----------|
| 209 | 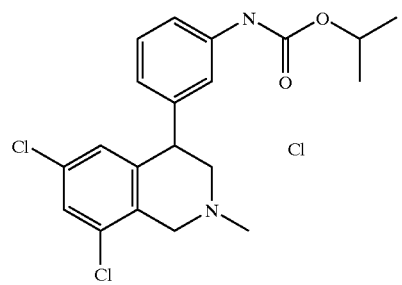 |
| 210 | 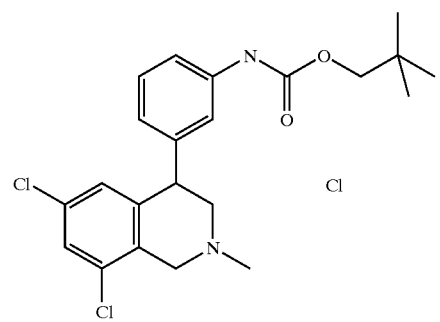 |
| 211 | 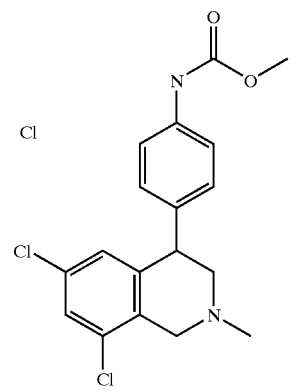 |
| 212 | 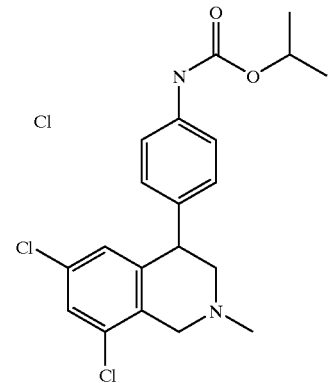 |

TABLE 12-continued

| Example | Structure |
|---|---|
| 213 | 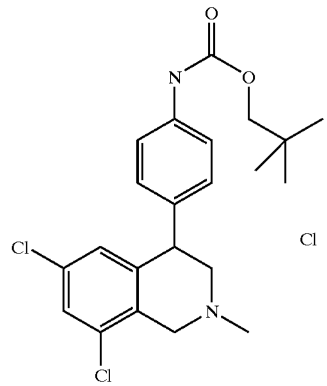 |
| 214 | 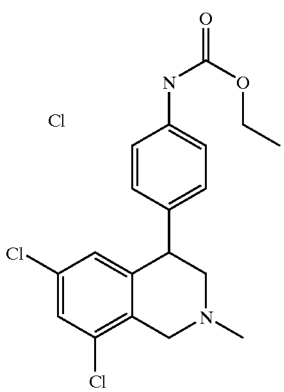 |

Example

215a: (+)-N-[3-(6,8-Dichloro-2-methyl-1,2,3,4-tetrahydro-isoquinolin-4-yl)-phenyl]-methanesulfonamide—Hydrochloride Salt 215b: (−)-N-[3-(6,8-dichloro-2-methyl-1,2,3,4-tetrahydro-isoquinolin-4-yl)-phenyl]-methanesulfonamide—Hydrochloride Salt

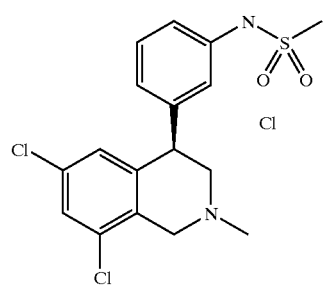

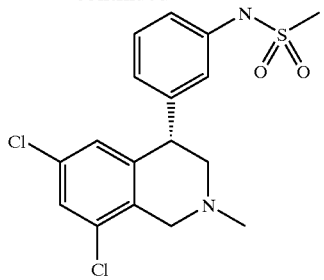

Racemic N-[3-(6,8-dichloro-2-methyl-1,2,3,4-tetrahydro-isoquinolin-4-yl)-phenyl]-methanesulfonamide (96 mg, example 83) was resolved by chiral preparative HPLC.

Chiral phase: Chiralpak AD 250×50 mm; 20μ;

Solvent: Heptane:Ethanol:Methanol: 10:1:1;

Flow rate: 50 ml/min

The residue was dissolved in water/2N hydrochloric acid and freeze dried to give 37 mg of the first eluting and 37 mg of the second eluting enantiomer.

The enantiomeric purity was determined by analytical HPLC.

column: Chiralpak AD-H/31 250×4.6 mm mobile Phase: heptane:ethanol:methanol 10:1:1, flow: 1 ml/min.

| First eluting enantiomer: | 6.84 min, 100% ee, MS (ES$^+$, M + H$^+$): 385.2 |
|---|---|
| Second eluting enantiomer: | 8.02 min, 100% ee, MS (ES$^+$, M + H$^+$): 385.2 |

Example

216a: (+)-1-[2-(6,8-Dichloro-2-methyl-1,2,3,4-tetrahydro-isoquinolin-4-yl)-phenyl]-3-ethyl-urea—Hydrochloride Salt 216b: (−)-1-[2-(6,8-dichloro-2-methyl-1,2,3,4-tetrahydro-isoquinolin-4-yl)-phenyl]-3-ethyl-urea—Hydrochloride Salt

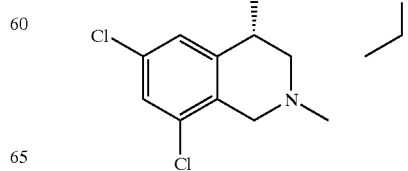

Racemic 1-[2-(6,8-dichloro-2-methyl-1,2,3,4-tetrahydro-isoquinolin-4-yl)-phenyl]-3-ethyl-urea (316 mg, example 80) were resolved by chiral preparative HPLC.

Chiral phase: Chiralpak OD 250×50 mm; 20μ;

Solvent: Heptane:Ethanol:iso-Propanol: 10:1:1; 0,3% Diethylamine;

Flow rate: 50 ml/min

The enantiomers were separately further purified using preparative HPLC. The product containing fractions were combined and the acetonitrile was removed in vaccuo. After addition of sodium bicarbonate the aqueous phase was extracted with ethyl acetate. The organic layer was separated, dried (magnesium sulphate), filtered and concentrated in vaccuo. The residue was dissolved in water/2N hydrochloric acid and freeze dried to give 37 mg of the first eluting and 58 mg of the second eluting enantiomer.

The enantiomeric purity was determined by analytical HPLC.

column: Chiralpak OD-20 250×4.6 mm mobile Phase: heptane:ethanol:iso-propanol 50:2:1 (+0.3% diethylamine), flow: 1 ml/min.

| | |
|---|---|
| First eluting enantiomer: | 9.22 min, 100% ee, MS (ES$^+$, M + H$^+$): 378.1 |
| Second eluting enantiomer: | 9.96 min, 98% ee, MS (ES$^+$, M + H$^+$): 378.1 |

Example 217

N-[3-(6,8-Difluoro-2-methyl-1,2,3,4-tetrahydro-isoquinolin-4-yl)-phenyl]-acetamide—Hydrochloride Salt

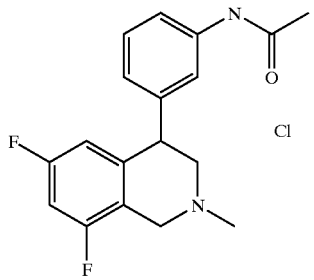

Intermediate 1:

2,4-Difluorobenzyl-methyl-amine was prepared starting from 2,4-Difluoro-benzaldehyd by standart procedures.

N-[3-(6,8-Difluoro-2-methyl-1,2,3,4-tetrahydro-isoquinolin-4-yl)-phenyl]-acetamide—Hydrochloride Salt;

Starting from N-(3-Acetyl-phenyl)-acetamide and 2,4-Difluorobenzyl-methyl-amine (intermediate 1) the title compound was prepared following the procedure described in example 1.

Example 218

4-(3-Bromo-phenyl)-6,8-dichloro-2-methyl-1,2,3,4-tetrahydro-isoquinoline—Hydrochloride Salt

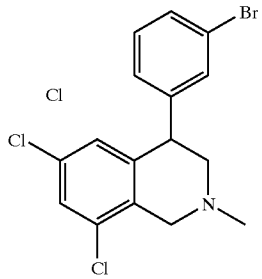

Following the procedure described in example 1 starting from 2,4-dichloro-benzaldehyde and using 2-bromo-1-(3-bromo-phenyl)-ethanone as alkylating reagent 780 mg of the title compound was obtained.

Example 219

1-[3-(6,8-Dichloro-2-methyl-1,2,3,4-tetrahydro-isoquinoline-4-yl)-phenyl]-3-(2-hydroxy-ethyl)-urea;

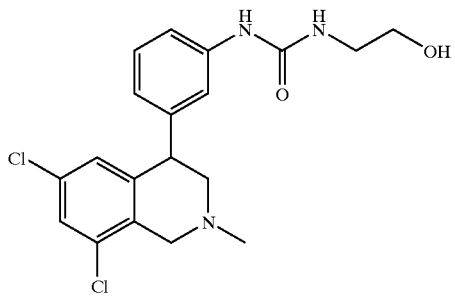

509 mg (1,0 mmol) [3-(6,8-Dichloro-2-methyl-1,2,3,4-tetrahydro-isoquinolin-4-yl)-phenyl]-carbamic-acid 4-nitro-phenyl-ester-Hydrochloride (example 151, intermediate 1) were dissolved in 15 ml DMF and at 0° C. a solution of 67,2 mg (1,1 mmol) of 2-Aminoethanol in 10 ml DMF was added. After stirring for 3 h at room temperature the solvent was removed i. vac. The residue was dissolved in ethylacetate and washed with sat. NaHCO$_3$-solution. The organic layer was separated and the aqueous layer was extracted twice with ethylacetate. The combined organic layers were washed with sat. NaCl-solution, dried (MgSO4) and concentrated. Purification by silica gel chromatography (dichloromethane/methanol) yielded 265 mg of the title compound.

Example 220

3-(6,8-Dichloro-2-methyl-1,2,3,4-tetrahydro-isoquinoline-4-yl)-benzoic-acid-ethyl-ester

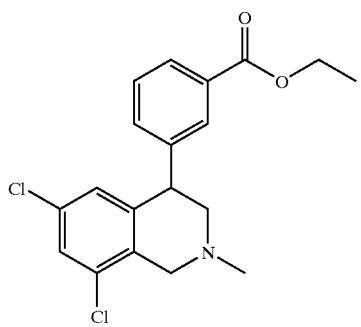

Interrmediate 1:
3-Acetyl-benzoic-acid can be prepared by literature procedures.

Intermediate 2:
3-Acetyl-benzoic-acid-ethyl-ester can be synthesized starting from Intermediate 1 by standart procedures.

Intermediate 3:
3-(2-Bromo-acetyl)-benzoic-acid-ethyl-ester was prepared analoguosly to Example 1, Intermediate 2, starting from 3-Acetyl-benzoic-acid-ethyl-ester (Intermediate 2).

3-(6,8-Dichloro-2-methyl-1,2,3,4-tetrahydro-isoquinoline-4-yl)-benzoic-acid-ethyl-ester Starting from 3-(2-Bromo-acetyl)-benzoic-acid-ethyl-ester (Intermediate 3) and Dichloro-benzyl-methyl-amine (Example 1, Intermediate 1), the title compound can be prepared by the methode described in example 1.

Example 221

3-(6,8-Dichloro-2-methyl-1,2,3,4-tetrahydro-isoquinoline-4-yl)-benzoic-acid

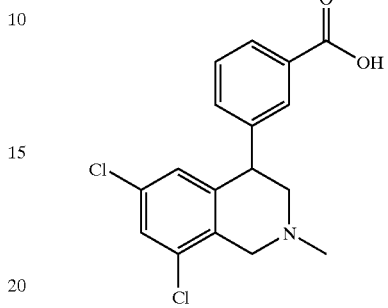

500 mg 3-(6,8-Dichloro-2-methyl-1,2,3,4-tetrahydro-isoquinoline-4-yl)-benzoic-acid-ethyl-ester (Example 220) were dissolved in 15 ml methanol and treated with 10 ml of a 2 N KOH-solution. After 1 h at 50° C. the solvent was removed i. vac. The residue was taken up in water and was washed with ether. The aqueous phase was seperated and 2 N HCl was added until a pH-value of about 6 was reached. The precipitate was filtered off by suction and dried to give 304 mg of the title compound.

Analytical Data for the Compounds of Examples 1 to 221:

Table 13

TABLE 13

| Ex. | Structure | $R_t$[min] | Method | MS [M + H⁺] | MS-Method | |
|---|---|---|---|---|---|---|
| 1 | 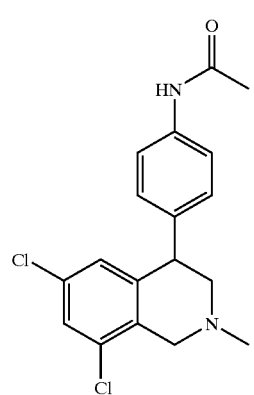 | 1.60 | B | 349.1/350.1/351.0 | ESI | m.p.: 205–206° C. |

TABLE 13-continued
| Ex. | Structure | $R_t$[min] | Method | MS [M + H$^+$] | MS-Method | |
|---|---|---|---|---|---|---|
| 1a | 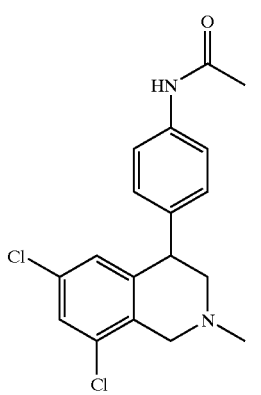 | 1.60 | B | 349.2/351.2 | ESI | m.p.: 125° C. (decomp.) |
| 2a | 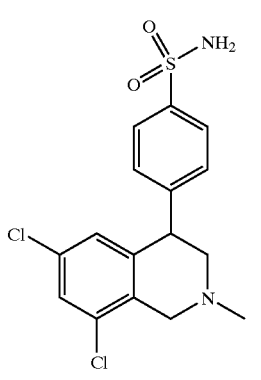 | 3.63 | A | 371.3/373.3 412.3/414.3 | ESI | (+)-enantiomer |
| 2b | 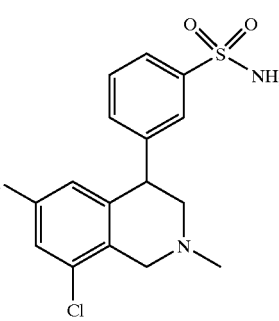 | 3.67 | A | 371.3/373.3 412.3/414.3 | ESI | (+)-enantiomer |
| 2c | 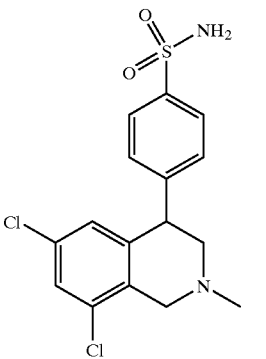 | 3.66 | A | 371.1/373.1 412.1/414.1 | ESI | (−)-enantiomer |

TABLE 13-continued
| Ex. | Structure | $R_t$[min] | Method | MS [M + H$^+$] | MS-Method | |
|---|---|---|---|---|---|---|
| 2d | 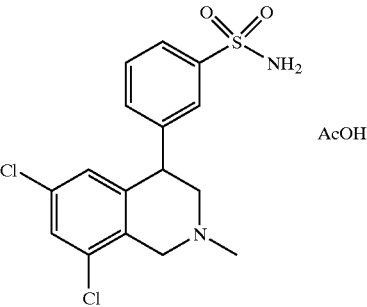 AcOH | 1.56 | B | 371.1/373.1 412.1/414.1 | ESI | (−)-enantiomer |
| 3 | 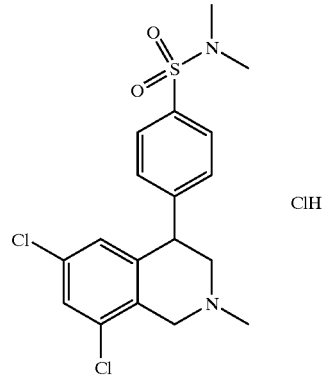 ClH | 4.00 | A | 399.1/401.1 | CI | |
| 4a | 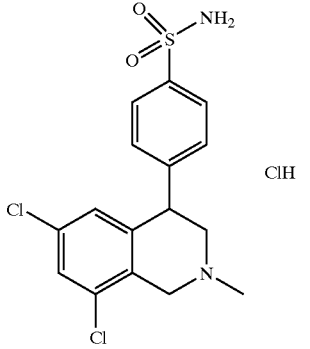 ClH | 3.59 | A | 371.2/373.2 412.2/414.2 | ESI | |
| 4b | 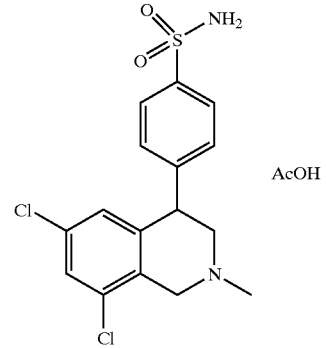 AcOH | 1.58 | B | 371.0/372.0/ 373.0/373.9 | ESI | |

TABLE 13-continued
| Ex. | Structure | R$_t$[min] | Method | MS [M + H$^+$] | MS-Method |
|---|---|---|---|---|---|
| 5 | 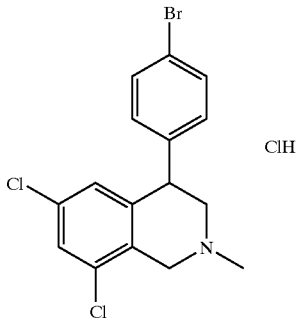 | 4.57 | A | 369.9/371.9/373.9 | Cl |
| 6 | 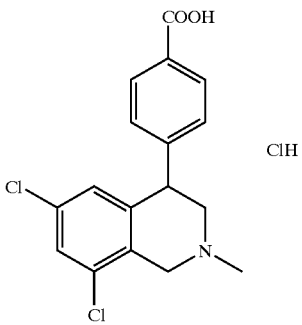 | 4.03 | A | 336.1/338.1 | Cl |
| 7 | 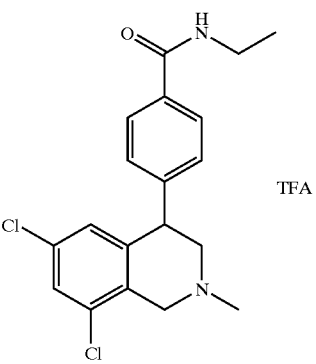 | 4.17 | A | 363.3/365.3 | Cl |
| 8 | 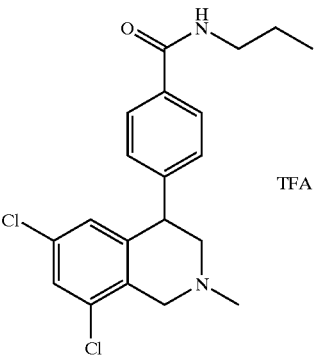 | 1.88 | B | 377.3/379.3 | Cl |

TABLE 13-continued
| Ex. | Structure | R$_t$[min] | Method | MS [M + H$^+$] | MS-Method |
|---|---|---|---|---|---|
| 9 | 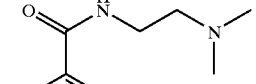 TFA | 1.45 | B | 406.3/408.3 | CI |
| 10 | 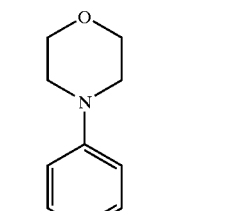 TFA | 4.37 | A | 377.1/379.1 | CI |
| 11 | 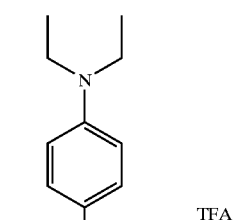 TFA | 4.05 | A | 363.2/365.2 | ESI |
| 12 | 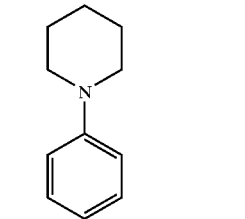 TFA | 3.79 | A | 375.2/377.2 | ESI |

TABLE 13-continued

| Ex. | Structure | $R_t$[min] | Method | MS [M + H$^+$] | MS-Method | |
|---|---|---|---|---|---|---|
| 13 | (pyrrolidine-phenyl-dichloro-N-methyl-tetrahydroisoquinoline) · ClH | 4.92 | A | 361.2/363.2 | ESI | |
| 14 | (N-methylpiperazine-phenyl-dichloro-N-methyl-tetrahydroisoquinoline) · TFA | 4.08 | A | 390.2/392.2 | ESI | |
| 15 | (phenyl-dichloro-N-cyclopropyl-tetrahydroisoquinoline) · TFA | 4.80 | A | 318.2/320.2 | Cl | |
| 16a | (acetamido-phenyl-dichloro-N-methyl-tetrahydroisoquinoline) | 1.61 | B | 349.1/350.1/351.1 | ESI | (−)-enantiomer |

TABLE 13-continued

| Ex. | Structure | R$_t$[min] | Method | MS [M + H$^+$] | MS-Method | |
|---|---|---|---|---|---|---|
| 16b | 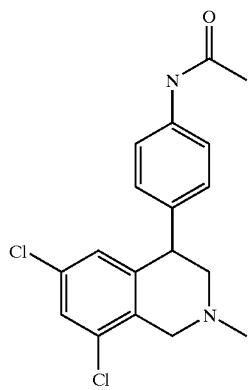 | 1.61 | B | 349.1/350.1/351.1 | ESI | (+)-enantiomer |
| 17 | x HCl | 0.91 | B | 307.1/309.0 | ESI | |
| 18 | ClH | 1.63 | B | 442.0/444.0 | ESI | |
| 19 | 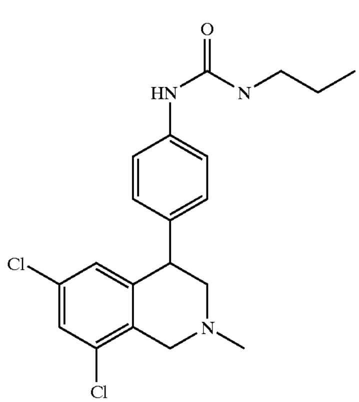 | 4.00 | A | 392.2/394.2 | ESI | |

TABLE 13-continued
| Ex. | Structure | R_t[min] | Method | MS [M + H+] | MS-Method | |
|---|---|---|---|---|---|---|
| 19a | 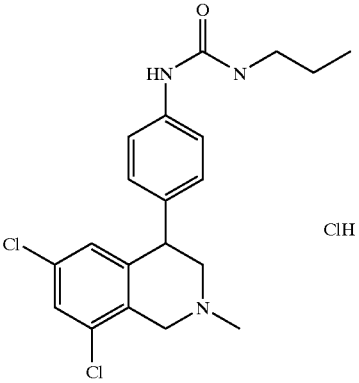 ClH | 1.80 | B | 392.1/394.1 | ESI | |
| 20 | 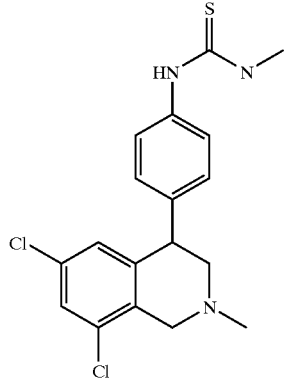 | 1.67 | B | 380.1/382.2 | ESI | |
| 21 | 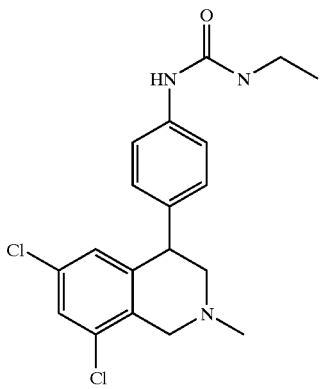 | 1.68 | B | 378.3/380.2 | ESI | m.p.: 218–220° C. |
| 21a | 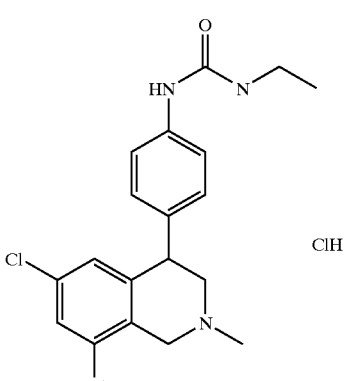 ClH | 1.68 | B | 378.1/379.1/ 380.1 | ESI | |

TABLE 13-continued

| Ex. | Structure | R$_t$[min] | Method | MS [M + H$^+$] | MS-Method |
|---|---|---|---|---|---|
| 22 | 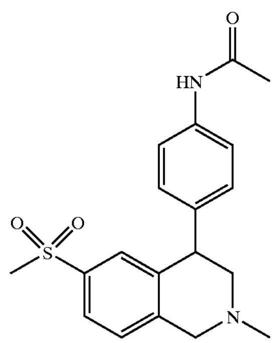 | 0.32 | B | 359.1<br>717.3/718.3/<br>719.3 | ESI |
| 23 | 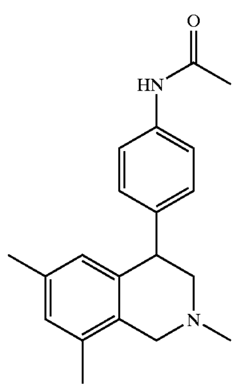 | 1.60 | B | 309.2/310.1 | ESI |
| 24 | 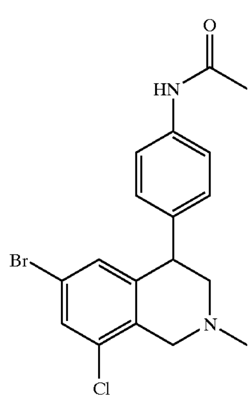 | 1.67 | B | 393.0/394.0/<br>396.0/397.0 | ESI |
| 25 | 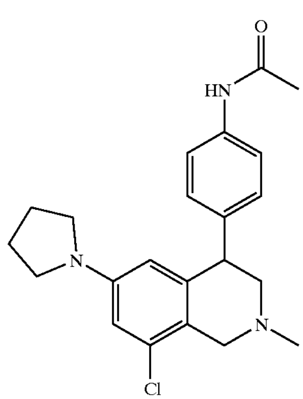 | 1.85 | B | 384.1/386.1 | ESI |

TABLE 13-continued
| Ex. | Structure | $R_t$[min] | Method | MS [M + H⁺] | MS-Method |
|---|---|---|---|---|---|
| 25a | 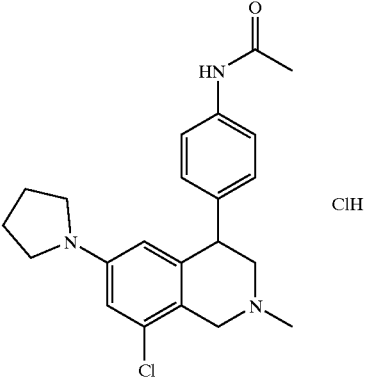 ClH | 1.78 | B | 384.1/385.1/386.2 | ESI |
| 26 | 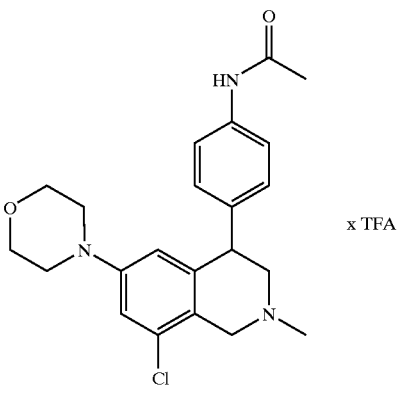 x TFA | 1.46 | B | 400.1/401.2/401.2 | ESI |
| 27 | 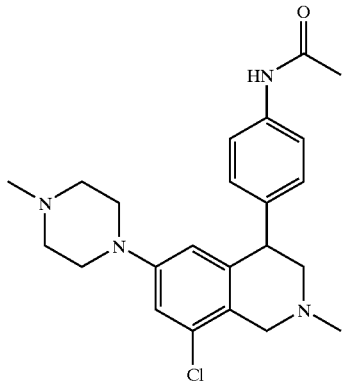 | 0.27 | B | 413.2/414.2/415.2 | ESI |
| 27a | 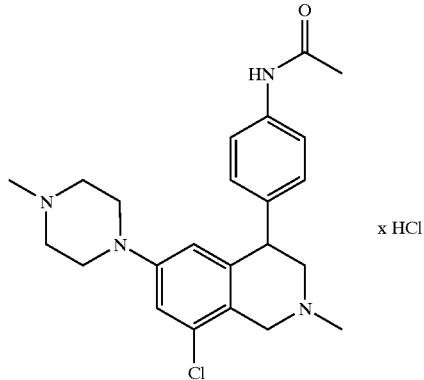 x HCl | 0.25 | B | 413.2/414.2/415.2 | ESI |

TABLE 13-continued
| Ex. | Structure | R$_t$[min] | Method | MS [M + H$^+$] | MS-Method |
|---|---|---|---|---|---|
| 28 | 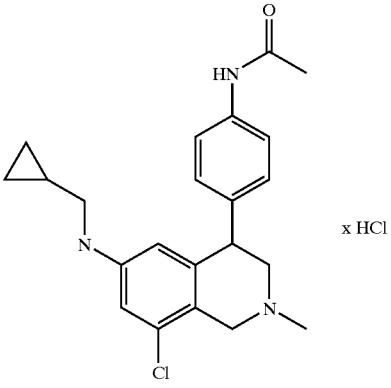 x HCl | 1.65 | B | 384.2/385.2 386.2 | ESI |
| 29 | 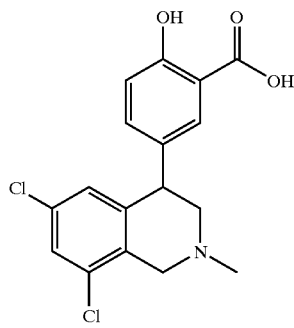 | 1.67 | B | 352.0/353.0/ 354.0 | ESI |
| 29a | 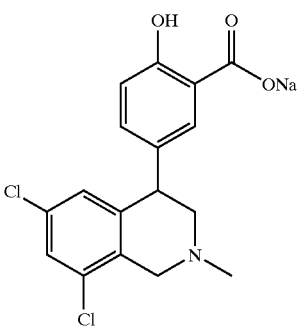 | 1.68 | B | 352.0/353.0/ 354.0 | ESI |
| 30 | 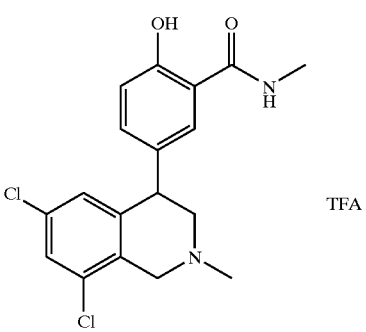 TFA | 1.68 | B | 365.1/366.1/ 367.0/368.0 | ESI |

TABLE 13-continued
| Ex. | Structure | R$_t$[min] | Method | MS [M + H$^+$] | MS-Method |
|---|---|---|---|---|---|
| 31 | 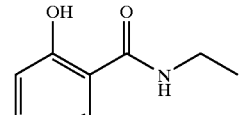 TFA | 1.79 | B | 379.1/380.1/381.1 | ESI |
| 32 | 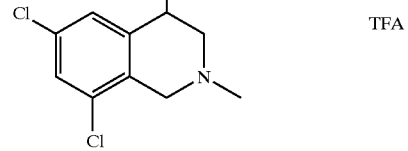 x TFA | 1.47 | B | 422.1/423.1/424.1/425.1 | ESI |
| 33 | 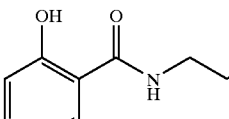 | 1.46 | B | 393.1/394.1/395.1 | ESI |
| 34 | 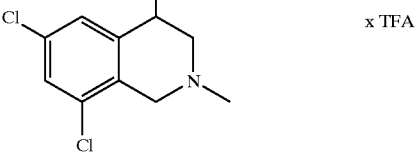 | 1.63 | B | 349.0/350.1/351.0 | ESI |
| 35 | 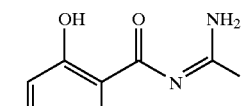 | 1.17 | B | 307.0/308.1/309.1 | ESI |

TABLE 13-continued

| Ex. | Structure | R$_t$[min] | Method | MS [M + H$^+$] | MS-Method |
|---|---|---|---|---|---|
| 36 | 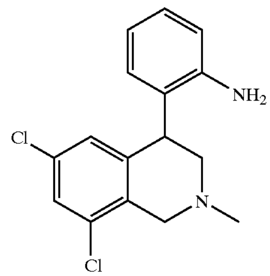 | 1.66 | B | 307.0/308.0/309.1 | ESI |
| 37 | TFA | 2.35 | C | 363.3/365.3 | ESI |
| 38 | TFA | 2.43 | C | 377.3/379.3 | ESI |
| 39 | TFA | 2.49 | C | 391.3/393.3 | ESI |

TABLE 13-continued
| Ex. | Structure | R$_t$[min] | Method | MS [M + H$^+$] | MS-Method |
|---|---|---|---|---|---|
| 40 | 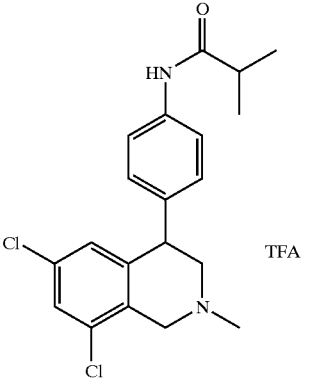 TFA | 2.43 | C | 377.3/379.3 | ESI |
| 41 | 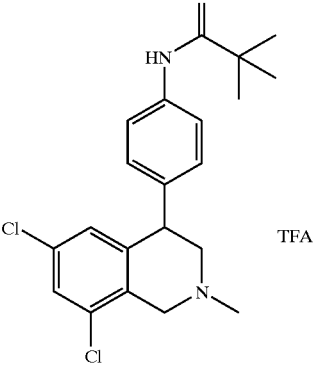 TFA | 2.48 | C | 391.3/393.3 | ESI |
| 42 | 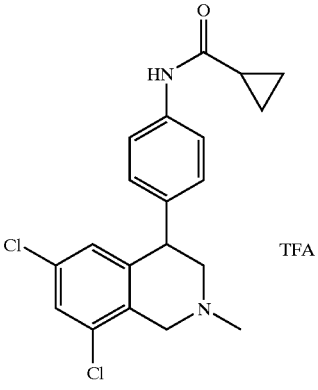 TFA | 2.40 | C | 375.3/377.3 | ESI |
| 43 | 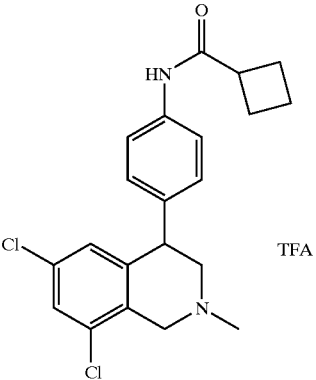 TFA | 2.45 | C | 389.3/391.3 | ESI |

TABLE 13-continued
| Ex. | Structure | R_t[min] | Method | MS [M + H+] | MS-Method |
|---|---|---|---|---|---|
| 44 | 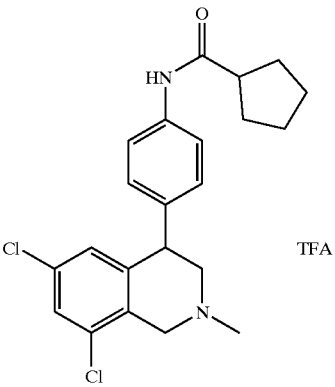 | 2.52 | C | 403.4/405.4 | ESI |
| 45 | 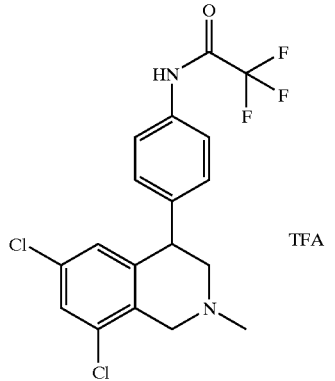 | 2.49 | C | 403.2/404.2 | ESI |
| 46 | 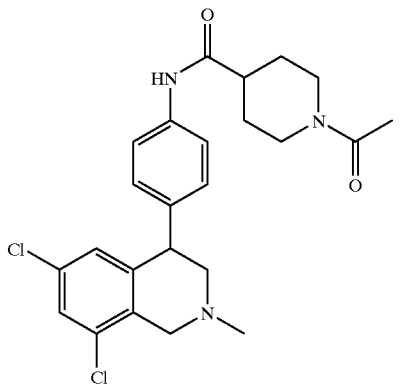 | 2.36 | C | 460.4/462.4 | ESI |

TABLE 13-continued
| Ex. | Structure | R$_t$[min] | Method | MS [M + H$^+$] | MS-Method |
|---|---|---|---|---|---|
| 47 | 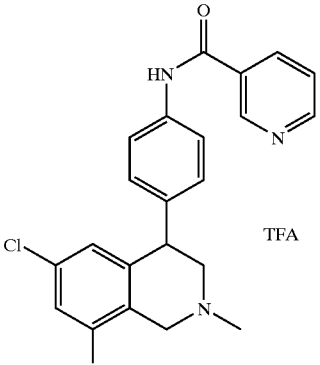 | 2.35 | C | 412.2/414.3 | ESI |
| 48 | 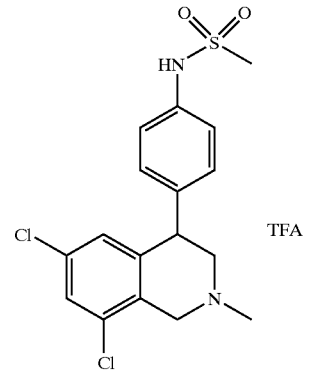 | 2.29 | C | 385.3/387.3 | ESI |
| 49 | 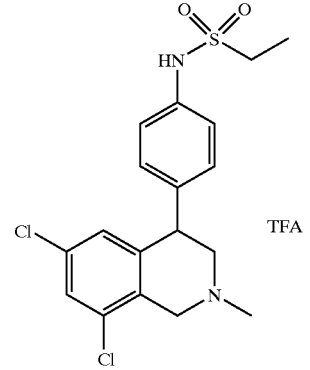 | 2.37 | C | 399.3/401.3 | ESI |
| 50 | 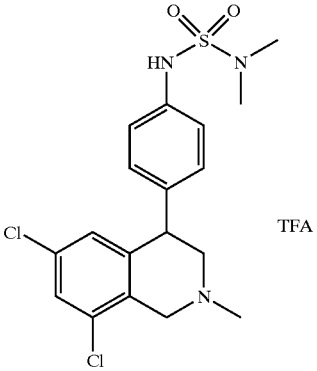 | 2.42 | C | 414.4/416.4 | ESI |

TABLE 13-continued
| Ex. | Structure | R_t[min] | Method | MS [M + H+] | MS-Method |
|---|---|---|---|---|---|
| 51 | 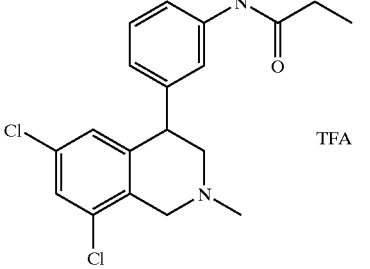 TFA | 2.37 | C | 363.3/365.3 | ESI |
| 52 | 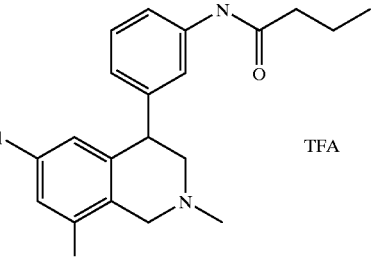 TFA | 2.44 | C | 377.3/379.3 | ESI |
| 53 | 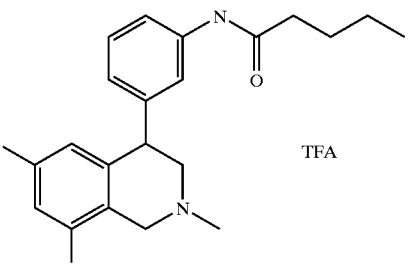 TFA | 2.51 | C | 391.3/393.3 | ESI |
| 54 | 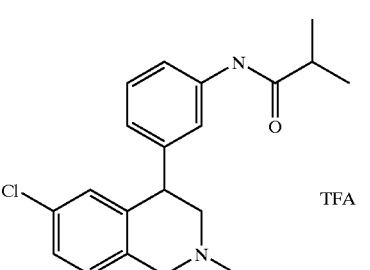 TFA | 2.44 | C | 377.3/379.3 | ESI |
| 55 | 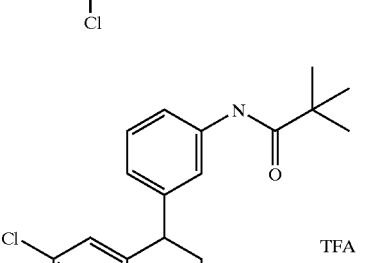 TFA | 2.49 | C | 391.3/393.3 | ESI |

TABLE 13-continued
| Ex. | Structure | R$_t$[min] | Method | MS [M + H$^+$] | MS-Method |
|---|---|---|---|---|---|
| 56 | 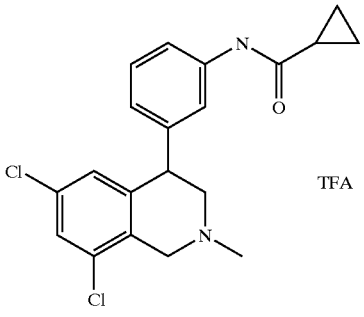 TFA | 2.41 | C | 375.3/377.3 | ESI |
| 57 | 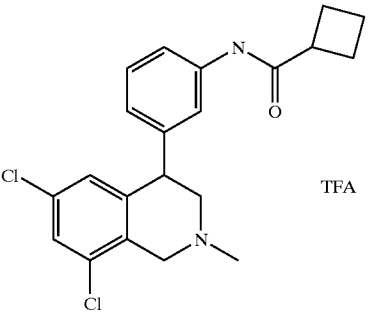 TFA | 2.47 | C | 389.3/391.3 | ESI |
| 58 | 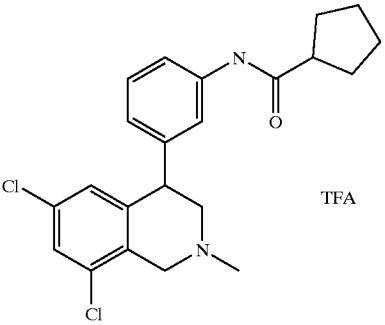 TFA | 2.52 | C | 403.4/405.4 | ESI |
| 59 | 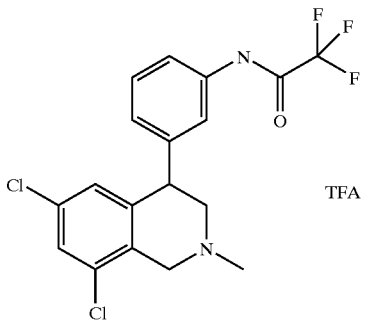 TFA | 2.48 | C | 403.2/404.2 | ESI |

TABLE 13-continued
| Ex. | Structure | R$_t$[min] | Method | MS [M + H$^+$] | MS-Method |
|---|---|---|---|---|---|
| 60 | 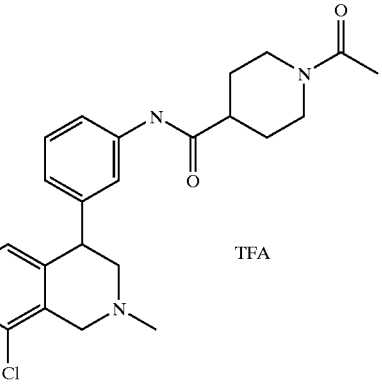 TFA | 2.34 | C | 460.4/462.4 | ESI |
| 61 | 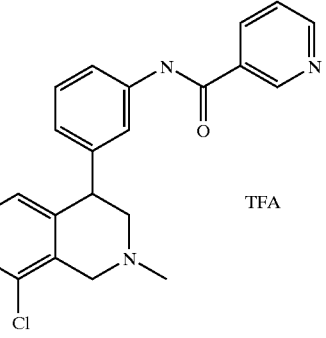 TFA | 2.36 | C | 412.2/414.3 | ESI |
| 62 | 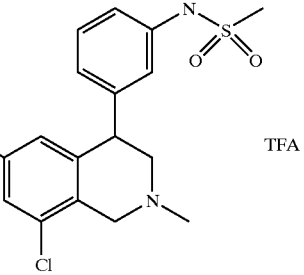 TFA | 2.32 | C | 385.3/387.3 | ESI |
| 63 | 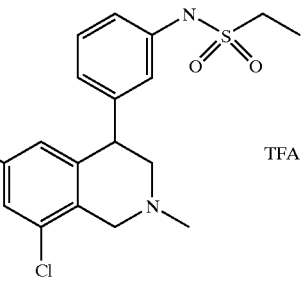 TFA | 2.38 | C | 399.3/401.3 | ESI |

US 6,911,453 B2
TABLE 13-continued
| Ex. | Structure | $R_t$[min] | Method | MS [M + H$^+$] | MS-Method |
|---|---|---|---|---|---|
| 64 | 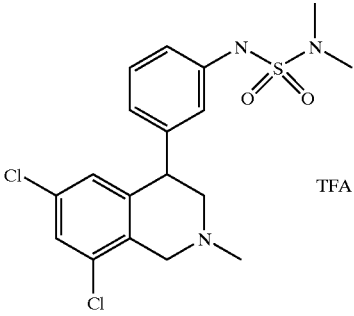 TFA | 2.41 | C | 414.4/416.4 | ESI |
| 65 | 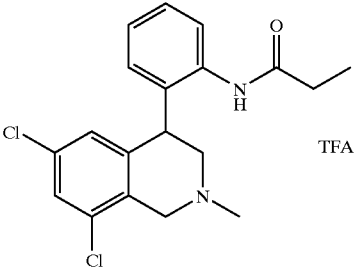 TFA | 2.30 | C | 363.3/365.3 | ESI |
| 66 | 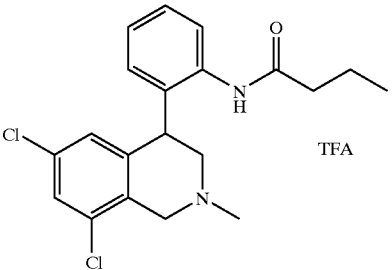 TFA | 2.41 | C | 377.3/379.3 | ESI |
| 67 | 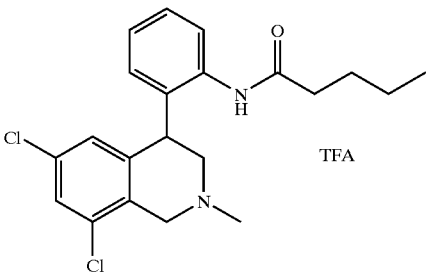 TFA | 2.52 | C | 391.3/393.3 | ESI |
| 68 | 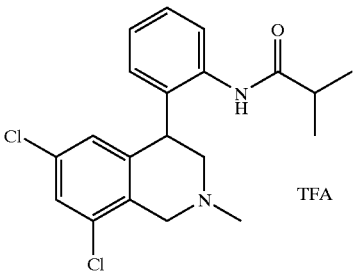 TFA | 2.41 | C | 377.3/379.3 | ESI |

TABLE 13-continued
| Ex. | Structure | $R_t$[min] | Method | MS [M + H+] | MS-Method |
|---|---|---|---|---|---|
| 69 | 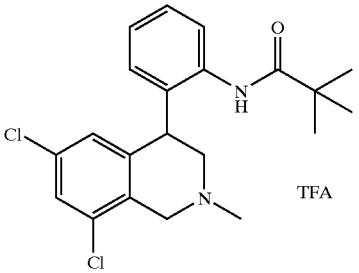 TFA | 2.45 | C | 391.3/393.3 | ESI |
| 70 | 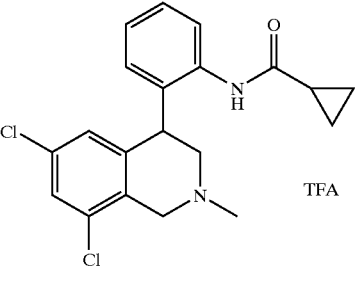 TFA | 2.36 | C | 375.3/377.3 | ESI |
| 71 | 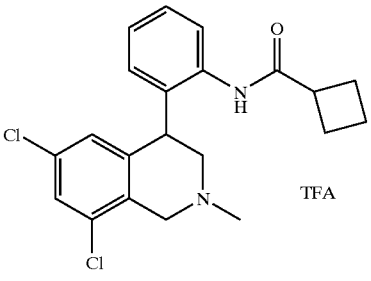 TFA | 2.44 | C | 389.3/391.3 | ESI |
| 72 | 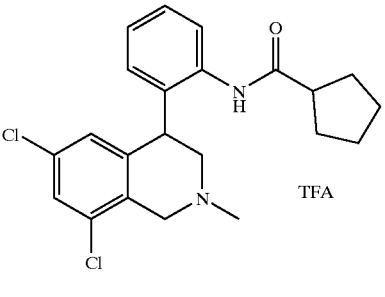 TFA | 2.51 | C | 403.4/405.4 | ESI |
| 73 | 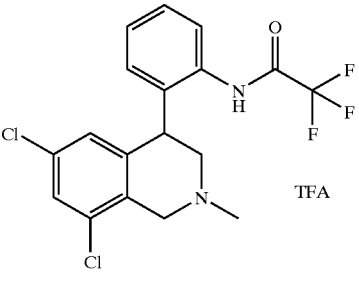 TFA | 2.70 | C | 403.2/404.2 | ESI |

TABLE 13-continued
| Ex. | Structure | R$_t$[min] | Method | MS [M + H$^+$] | MS-Method |
|---|---|---|---|---|---|
| 74 | 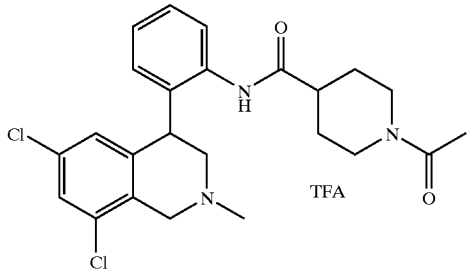 TFA | 2.30 | C | 460.4/462.4 | ESI |
| 75 | 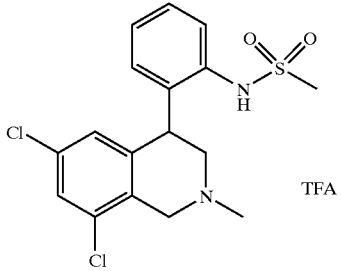 TFA | 2.41 | C | 385.3/387.3 | ESI |
| 76 | 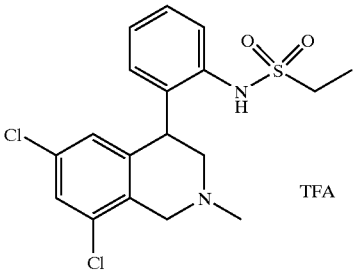 TFA | 2.49 | C | 399.3/401.3 | ESI |
| 77 | 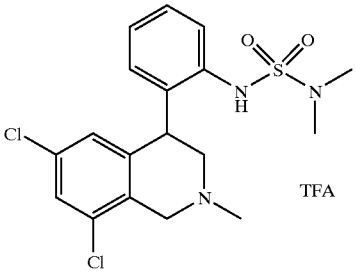 TFA | 2.55 | C | 414.4/416.4 | ESI |
| 78 | 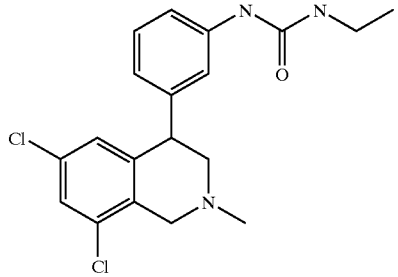 | 1.72 | B | 378.3/380.3 | ESI |

TABLE 13-continued

| Ex. | Structure | R$_t$[min] | Method | MS [M + H$^+$] | MS-Method |
|---|---|---|---|---|---|
| 79 | TFA | 1.74 | B | 380.3/382.3 | ESI |
| 80 | 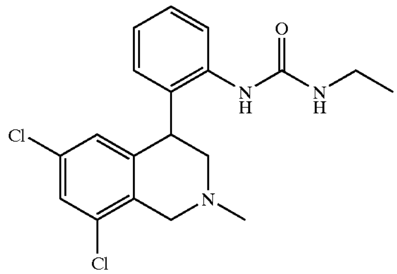 | 1.75 | B | 378.3/380.3 | ESI |
| 81 | TFA | 1.68 | B | 380.3/382.3 | ESI |
| 82 | ClH | 1.71 | B | 399.0/400.0/ 401.0/402.0/ 403.0 | ESI |
| 83 | ClH | 1.66 | B | 385.0/386.0/ 387.0 | ESI |

TABLE 13-continued

| Ex. | Structure | R$_t$[min] | Method | MS [M + H$^+$] | MS-Method | |
|---|---|---|---|---|---|---|
| 84 | (structure) ClH | 1.69 | B | 399.0/400.0/401.0/402.0 | ESI | |
| 85 | (structure) ClH | 1.64 | B | 385.0/386.0/387.0/388.0 | ESI | |
| 86a | (structure) | 1.64 | B | 349.3/351.3 | ESI | (−)-enantiomer |
| 86b | (structure) | 1.63 | B | 349.3/351.3 | ESI | (+)-enantiomer |

TABLE 13-continued
| Ex. | Structure | R$_t$[min] | Method | MS [M + H$^+$] | MS-Method |
|---|---|---|---|---|---|
| 87 | 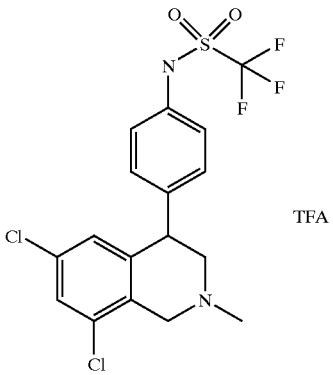 TFA | 1.97 | B | 439.0/441.1 | ESI |
| 88 | 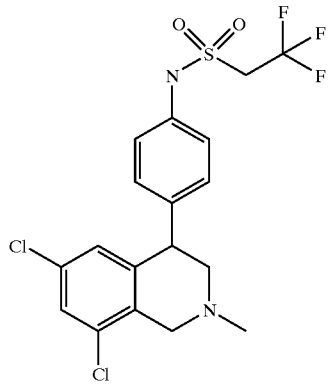 | 1.83 | B | 453.0/455.0 | ESI |
| 88a | 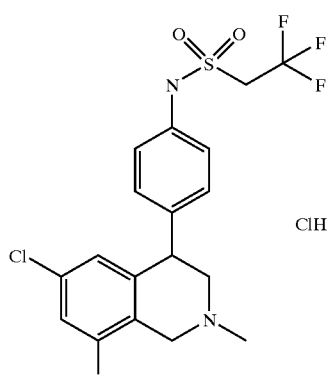 ClH | 1.83 | B | 453.0/455.0 | ESI |
| 89 | 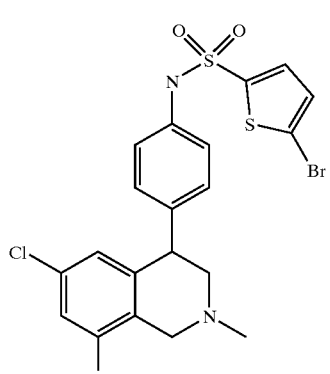 | 2.01 | B | 531.0/533.0/ 534.9 | ESI |

TABLE 13-continued
| Ex. | Structure | R$_t$[min] | Method | MS [M + H$^+$] | MS-Method |
|---|---|---|---|---|---|
| 89a | 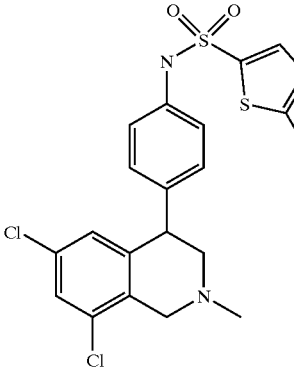 | 2.02 | B | 531.0/533.0/534.9 | ESI |
| 90 | 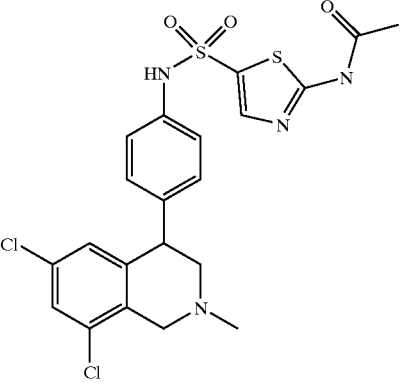 | 1.78 | B | 525.1/527.1 | ESI |
| 90a | 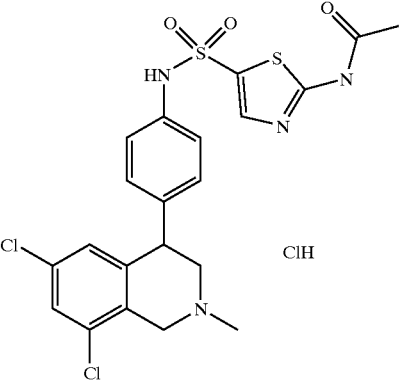 | 1.79 | B | 525.1/527.1 | ESI |
| 91 | 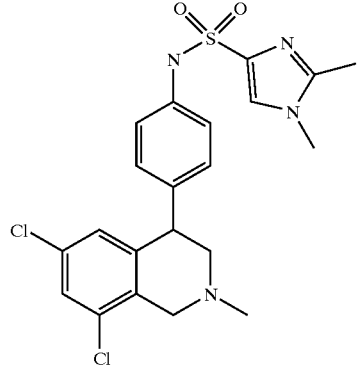 | 1.63 | B | 465.1/467.1 | ESI |

TABLE 13-continued
| Ex. | Structure | R$_t$[min] | Method | MS [M + H$^+$] | MS-Method |
|---|---|---|---|---|---|
| 91a | 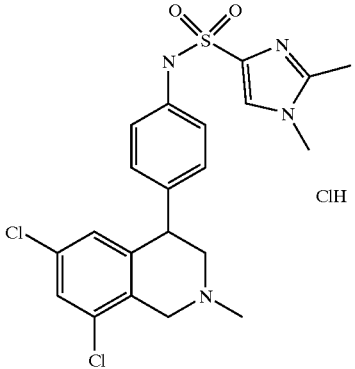 ClH | 1.64 | B | 465.1/467.1 | ESI |
| 92 | 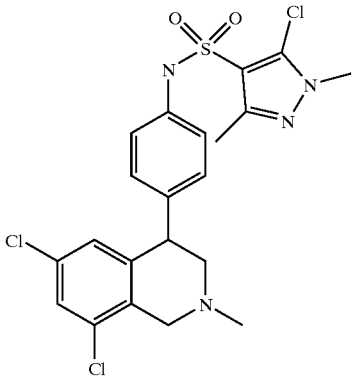 | 1.81 | B | 499.1/501.1/503.1 | ESI |
| 92a | 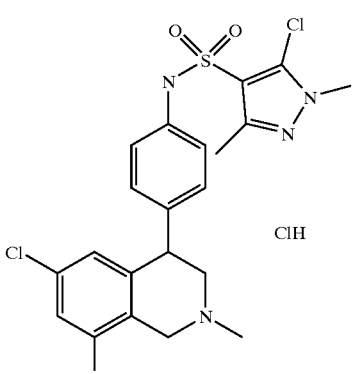 ClH | 1.82 | B | 499.1/501.1/503.1 | ESI |
| 93 | 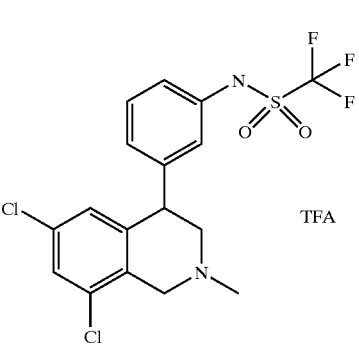 TFA | 1.99 | B | 439.0/441.1 | ESI |

TABLE 13-continued

| Ex. | Structure | R$_t$[min] | Method | MS [M + H$^+$] | MS-Method |
|---|---|---|---|---|---|
| 94 | 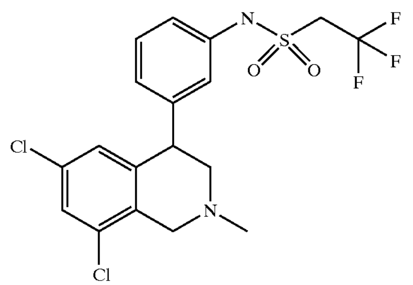 | 1.87 | B | 453.0/455.0 | ESI |
| 94a | (ClH salt) | 1.87 | B | 453.0/455.0 | ESI |
| 95 | 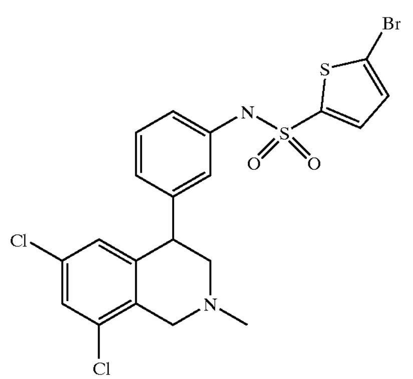 | 2.01 | B | 531.0/533.0/535.0 | ESI |
| 96 | 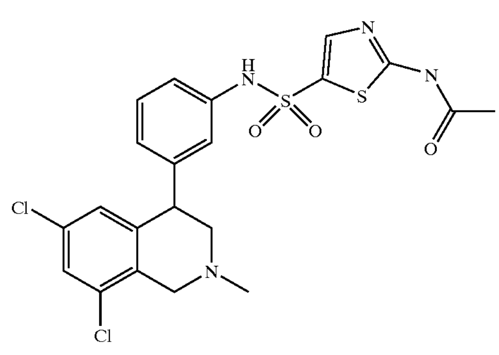 | 1.75 | B | 525.0/527.0 | ESI |

TABLE 13-continued
| Ex. | Structure | R$_t$[min] | Method | MS [M + H$^+$] | MS-Method |
|---|---|---|---|---|---|
| 96a | 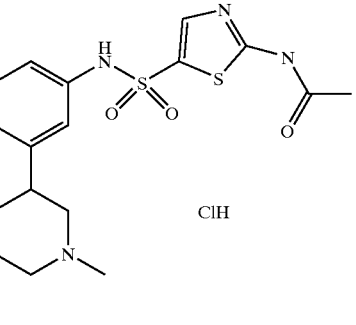 ClH | 1.75 | B | 525.0/527.0 | ESI |
| 97 | 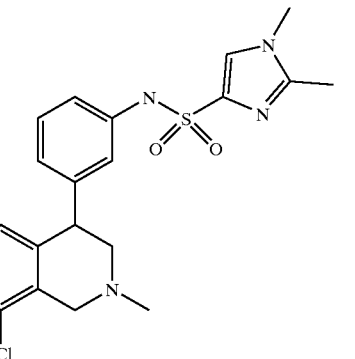 | 1.66 | B | 465.0/467.0 | ESI |
| 97a | 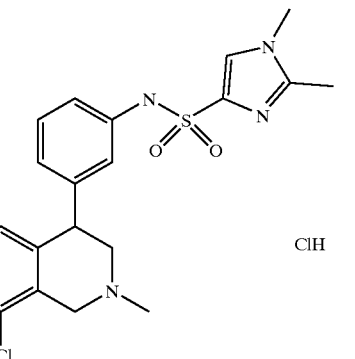 ClH | 1.66 | B | 465.0/467.0 | ESI |
| 98 | 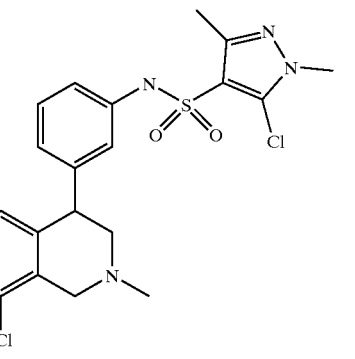 | 1.81 | B | 499.1/501.1/503.1 | ESI |

TABLE 13-continued

| Ex. | Structure | R$_t$[min] | Method | MS [M + H$^+$] | MS-Method | |
|---|---|---|---|---|---|---|
| 99 | 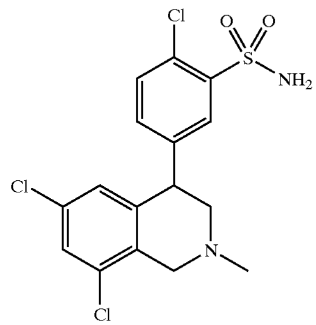 | | | 405.1/407.1 | ESI | m.p.: 122° C. |
| 100 | 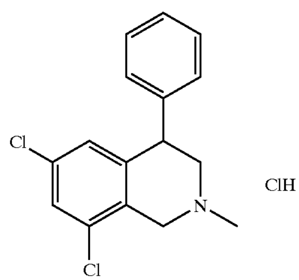 | 4.44 | A | 292.2/294.2 | Cl | s. Ex. 2; Intermediate 4 |
| 100a | 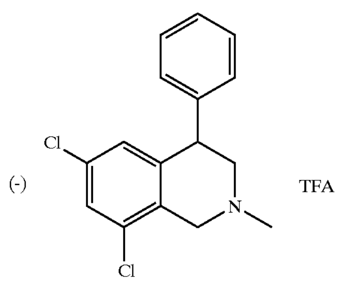 | | | | | s. Ex. 2; Intermediate 4a |
| 100b | 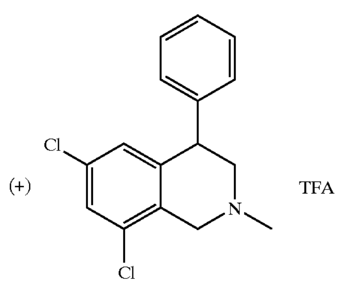 | | | | | s. Ex. 2; Intermediate 4b |
| 101 | 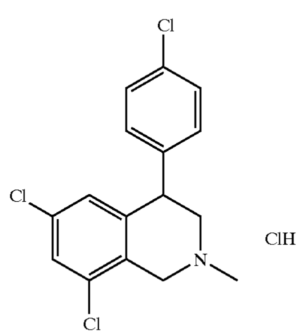 | 4.43 | A | 326.0/328.0 | ESI | |

TABLE 13-continued
| Ex. | Structure | $R_t$[min] | Method | MS [M + H$^+$] | MS-Method |
|---|---|---|---|---|---|
| 102 | 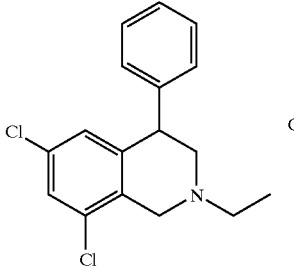 | 4.23 | A | 306.1/308.0 | ESI |
| 103 | 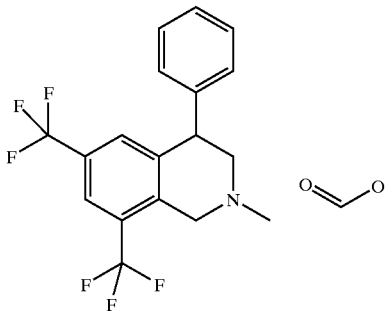 | 2.84 | C | 360.0 | ESI |
| 104 | 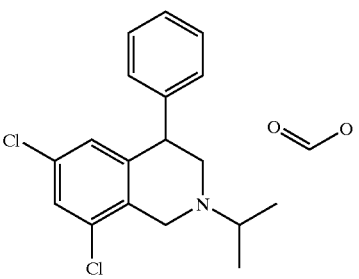 | 2.79 | C | 320.0/322.0 | ESI |
| 105 | 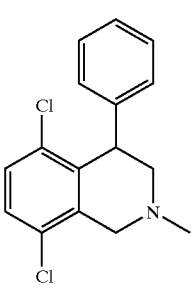 | 2.64 | C | 291.9/293.9 | ESI |
| 106 | 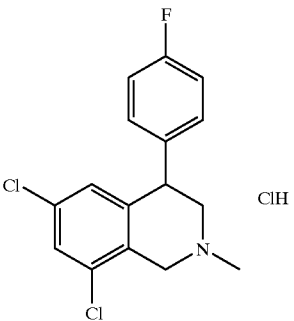 | 4.26 | A | 310.0/312.0 | ESI |

TABLE 13-continued
| Ex. | Structure | R$_t$[min] | Method | MS [M + H$^+$] | MS-Method |
|---|---|---|---|---|---|
| 107 | 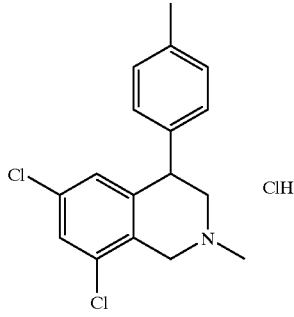 | 4.43 | A | 306.1/308.1 | ESI |
| 108 | 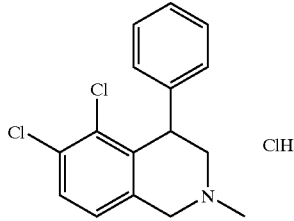 | 4.11 | A | 292.0/294.0 | ESI |
| 109 | 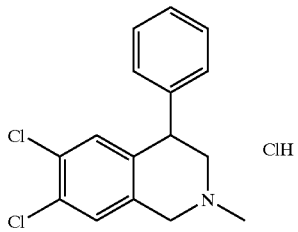 | 4.28 | A | 292.0/294.0 | ESI |
| 110 | 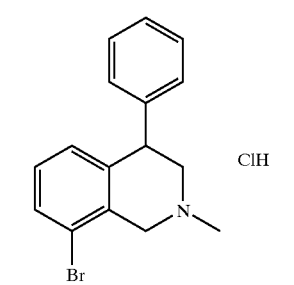 | 4.05 | A | 302.0/304 | ESI |
| 111 | 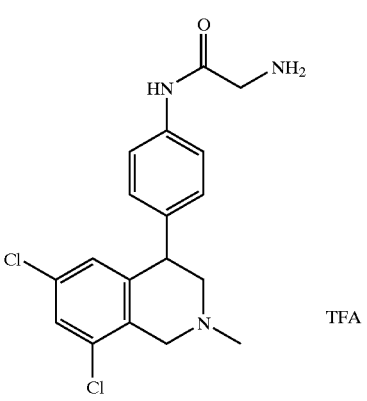 | 1.37 | D | 364.4/366.4 | ESI |

TABLE 13-continued
| Ex. | Structure | R$_t$[min] | Method | MS [M + H$^+$] | MS-Method |
|---|---|---|---|---|---|
| 112 | 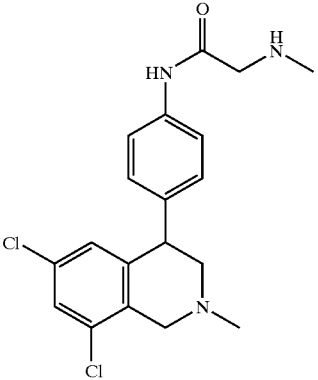 TFA | 1.44 | D | 378.4/380.4 | ESI |
| 113 | 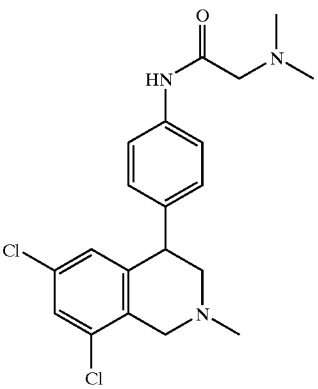 TFA | 1.51 | D | 392.4/394.4 | ESI |
| 114 | 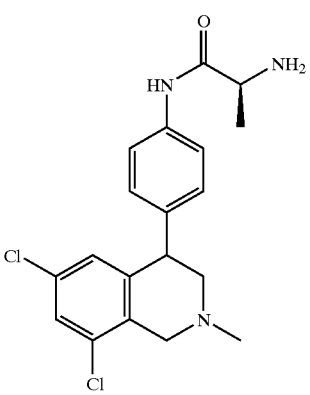 TFA | 1.51 | D | 378.3/380.3 | ESI |
| 115 | 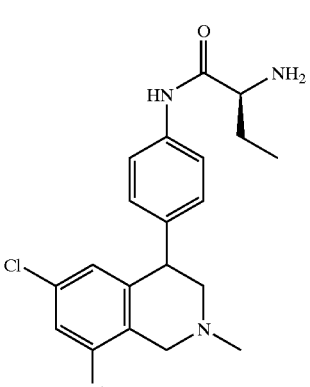 TFA | 1.58 | D | 392.4/394.4 | ESI |

TABLE 13-continued

| Ex. | Structure | R$_t$[min] | Method | MS [M + H$^+$] | MS-Method |
|---|---|---|---|---|---|
| 116 | 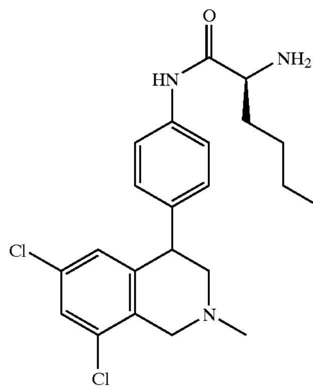 | 1.04 | D | 435.5/437.5 | ESI |
| 117 | 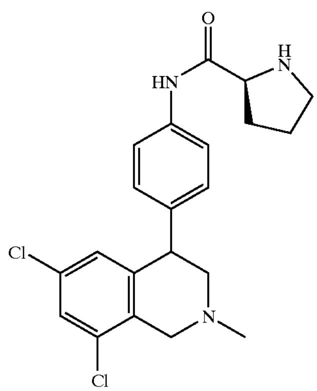 | 1.67 | D | 404.4/406.4 | ESI |
| 118 | 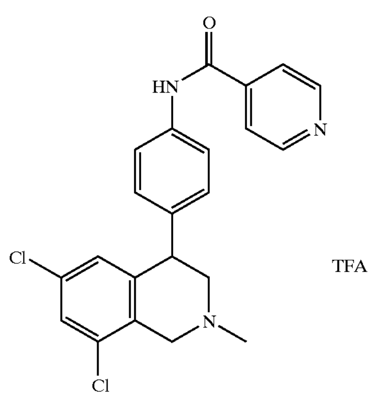 | 2.08 | D | 412.3/414.3 | ESI |

TABLE 13-continued
| Ex. | Structure | R$_t$[min] | Method | MS [M + H$^+$] | MS-Method |
|---|---|---|---|---|---|
| 119 | 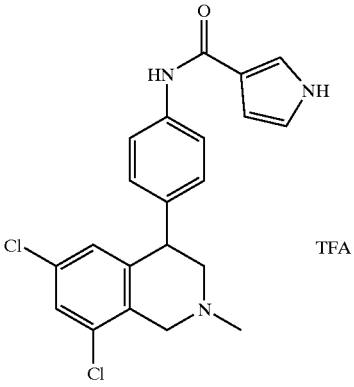 TFA | 2.27 | D | 400.4/402.4 | ESI |
| 120 | 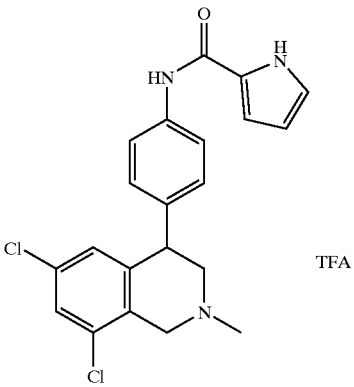 TFA | 2.37 | D | 400.4/402.4 | ESI |
| 121 | 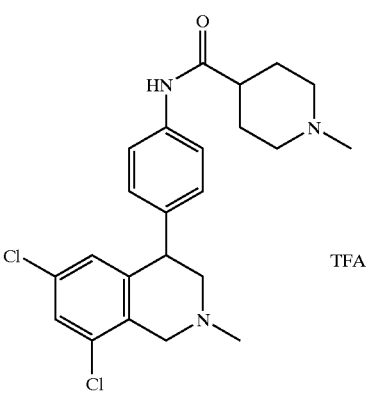 TFA | 1.54 | D | 432.5/434.5 | ESI |
| 122 | 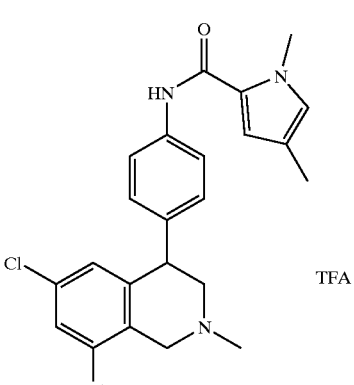 TFA | 1.70 | D | 428.5/430.5 | ESI |

TABLE 13-continued
| Ex. | Structure | R$_t$[min] | Method | MS [M + H$^+$] | MS-Method |
|---|---|---|---|---|---|
| 123 | 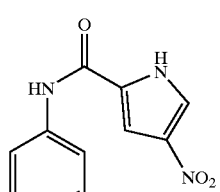 TFA | 2.55 | D | 445.4/447.4 | ESI |
| 124 | 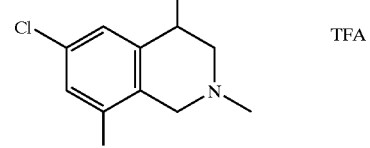 TFA | 2.43 | D | 428.5/430.5 | ESI |
| 125 | 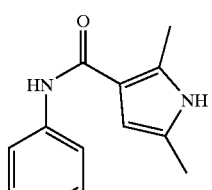 TFA | 1.88 | D | 401.4/403.4 | ESI |

TABLE 13-continued
| Ex. | Structure | $R_t$[min] | Method | MS [M + H$^+$] | MS-Method |
|---|---|---|---|---|---|
| 126 | 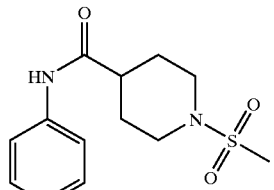 TFA | 2.31 | D | 496.5/498.5 | ESI |
| 127 | 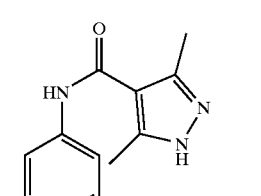 TFA | 2.14 | D | 429.4/431.4 | ESI |
| 128 | 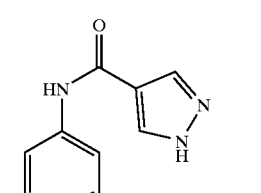 TFA | 2.07 | D | 401.4/403.4 | ESI |

TABLE 13-continued
| Ex. | Structure | R$_t$[min] | Method | MS [M + H$^+$] | MS-Method |
|---|---|---|---|---|---|
| 129 | 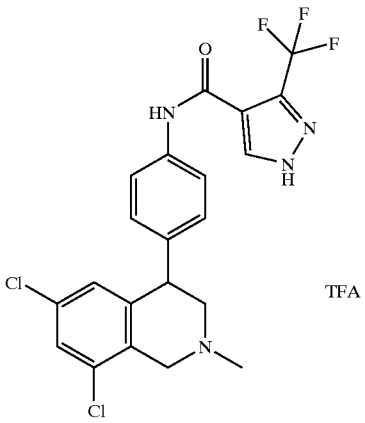 TFA | 2.44 | D | 469.4/471.4 | ESI |
| 130 | 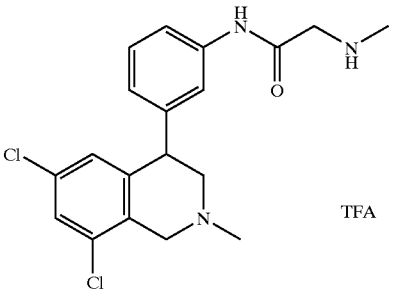 TFA | 1.55 | D | 378.4/380.4 | ESI |
| 131 | 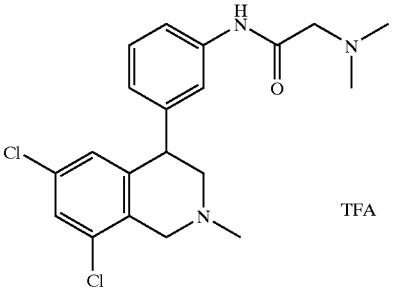 TFA | 1.52 | D | 392.4/394.4 | ESI |
| 132 | 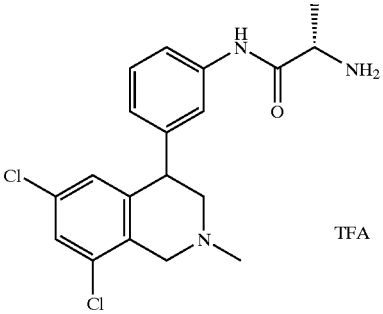 TFA | 1.63 | D | 378.3/380.3 | ESI |

TABLE 13-continued
| Ex. | Structure | $R_t$[min] | Method | MS [M + H$^+$] | MS-Method |
|---|---|---|---|---|---|
| 133 | 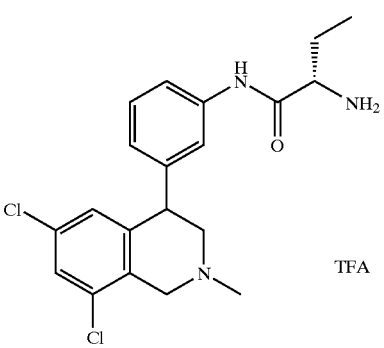 TFA | 1.64 | D | 392.4/394.4 | ESI |
| 134 | 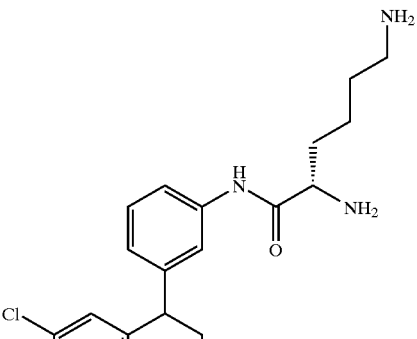 TFA | 1.14 | D | 435.5/437.5 | ESI |
| 135 | 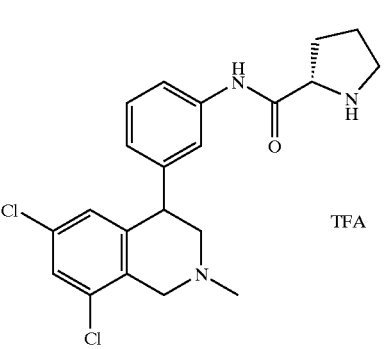 TFA | 1.62 | D | 404.4/406.4 | ESI |
| 136 | 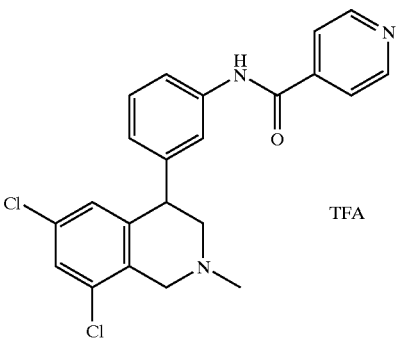 TFA | 2.16 | D | 412.3/414.3 | ESI |

TABLE 13-continued
| Ex. | Structure | R$_t$[min] | Method | MS [M + H$^+$] | MS-Method |
|---|---|---|---|---|---|
| 137 | 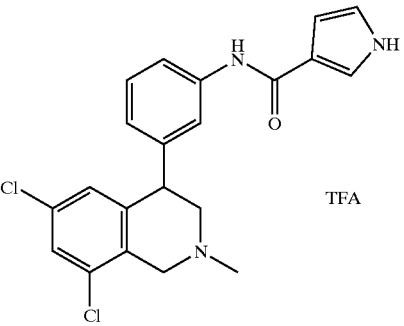 TFA | 2.31 | D | 400.4/402.4 | ESI |
| 138 | 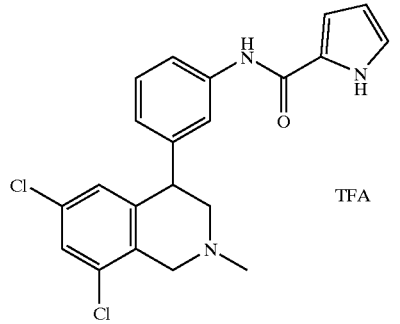 TFA | 2.41 | D | 400.4/402.4 | ESI |
| 139 | 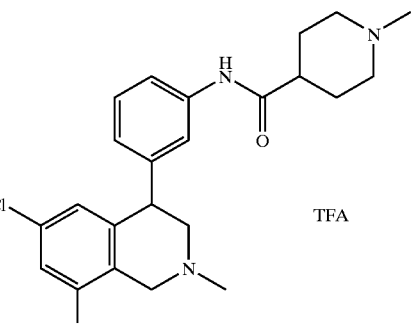 TFA | 1.62 | D | 432.5/434.5 | ESI |
| 140 | 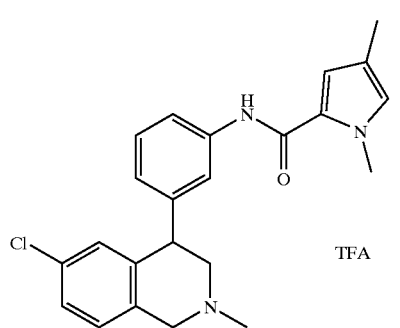 TFA | 1.75 | D | 428.5/430.5 | ESI |

TABLE 13-continued
| Ex. | Structure | $R_t$[min] | Method | MS [M + H+] | MS-Method |
|---|---|---|---|---|---|
| 141 | 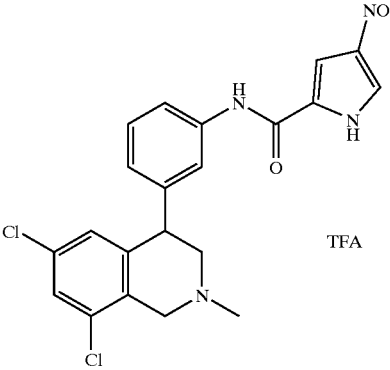 TFA | 2.54 | D | 445.4/447.4 | ESI |
| 142 | 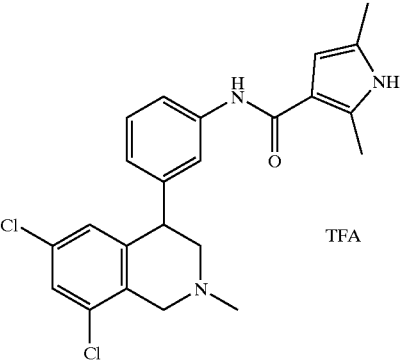 TFA | 2.50 | D | 428.5/430.5 | ESI |
| 143 | 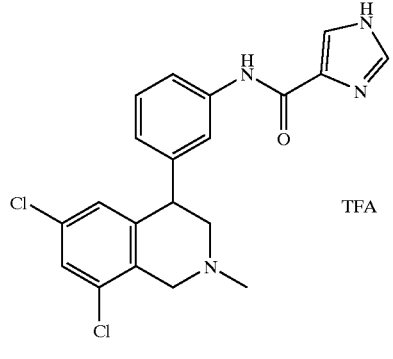 TFA | 1.95 | D | 401.4/403.4 | ESI |
| 144 | 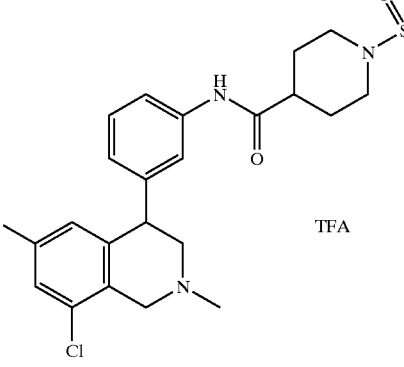 TFA | 2.34 | D | 496.5/498.5 | ESI |

TABLE 13-continued
| Ex. | Structure | R$_t$[min] | Method | MS [M + H$^+$] | MS-Method |
|---|---|---|---|---|---|
| 145 | 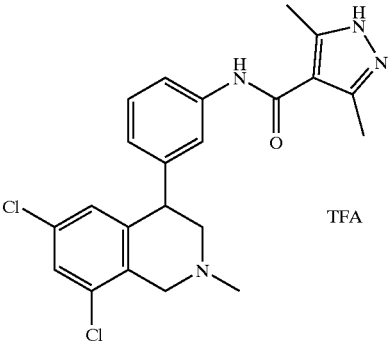 TFA | 2.31 | D | 429.4/431.4 | ESI |
| 146 | 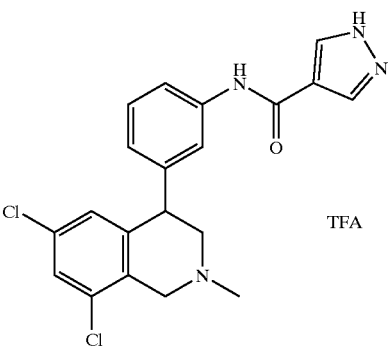 TFA | 2.11 | D | 401.4/403.4 | ESI |
| 147 | 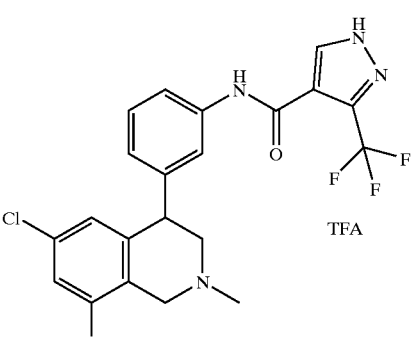 TFA | 2.48 | D | 469.4/471.4 | ESI |
| 148 | 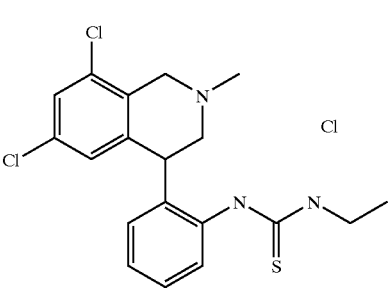 | 2.36 | B | 394.2 | ESI |

TABLE 13-continued
| Ex. | Structure | R$_t$[min] | Method | MS [M + H$^+$] | MS-Method |
|---|---|---|---|---|---|
| 149 | 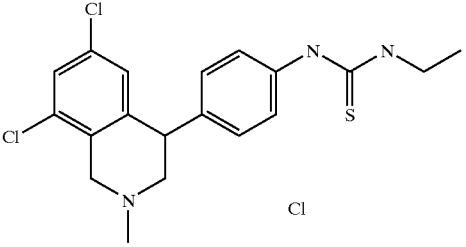 | 2.35 | B | 394.2 | ESI |
| 150 | 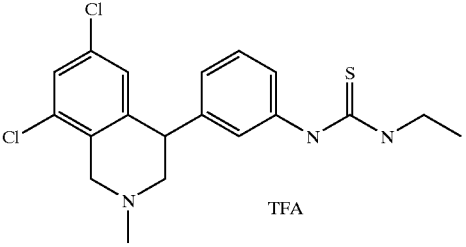 | 2.35 | B | 394.2 | ESI |
| 151 | 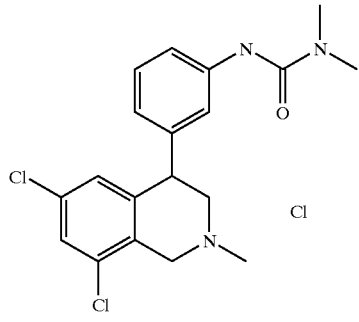 | 2.15 | B | 378.2 | ESI |
| 152 | 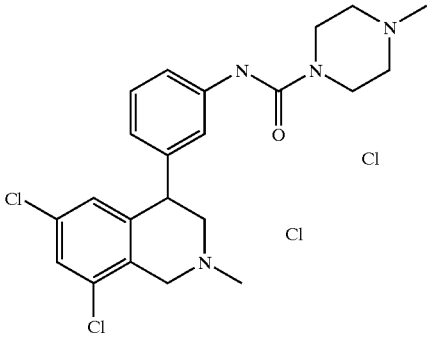 | 1.64 | B | 433.3 | ESI |
| 153 | 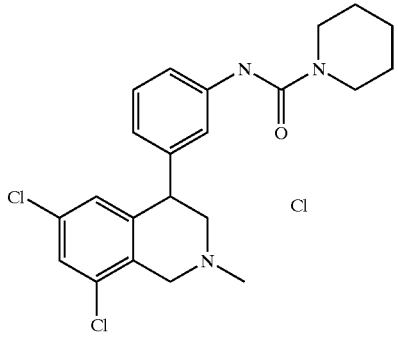 | 2.56 | B | 418.3 | ESI |

TABLE 13-continued
| Ex. | Structure | R$_t$[min] | Method | MS [M + H$^+$] | MS-Method |
|---|---|---|---|---|---|
| 154 | 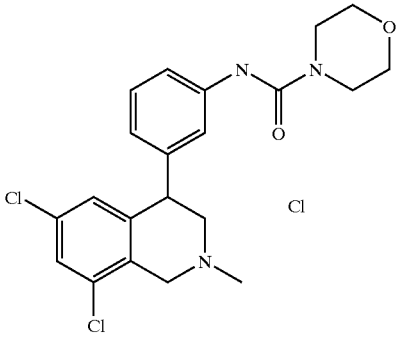 | 2.16 | B | 420.2 | ESI |
| 155 | 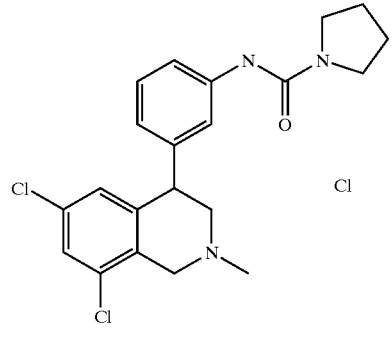 | 2.34 | B | 404.2 | ESI |
| 156 | 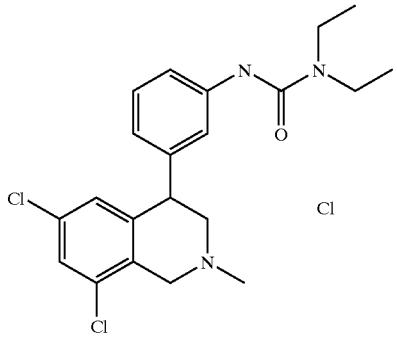 | 2.43 | B | 406.2 | ESI |
| 157 | 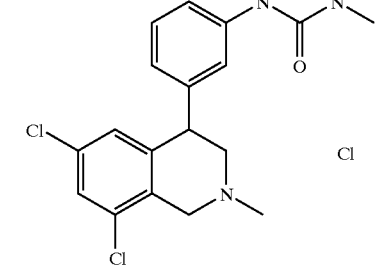 | 2.12 | | 364.2 | ESI |

TABLE 13-continued

| Ex. | Structure | R$_t$[min] | Method | MS [M + H$^+$] | MS-Method |
|---|---|---|---|---|---|
| 158 | 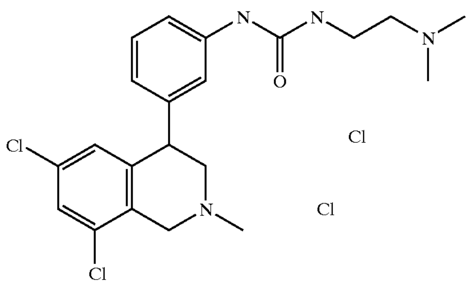 | 1.65 | B | 421.2 | ESI |
| 159 | Chiral | 2.23 | B | 420.3 | ESI |
| 160 | 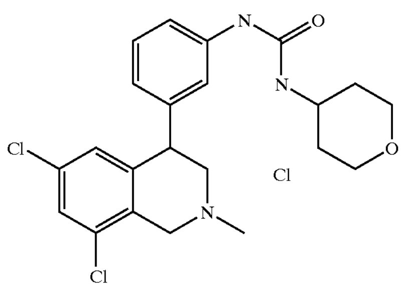 | 2.25 | B | 434.3 | ESI |
| 161 | 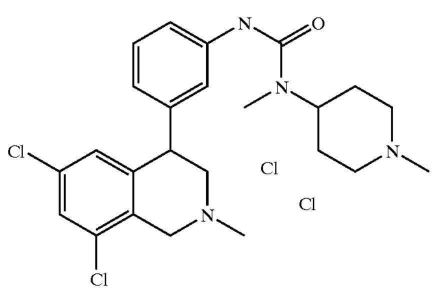 | 1.72 | B | 461.4 | ESI |
| 162 | 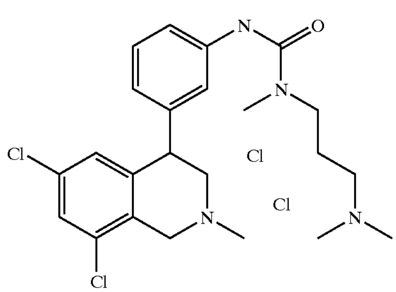 | 1.68 | B | 449.4 | ESI |

TABLE 13-continued

| Ex. | Structure | R$_t$[min] | Method | MS [M + H$^+$] | MS-Method |
|---|---|---|---|---|---|
| 163 | 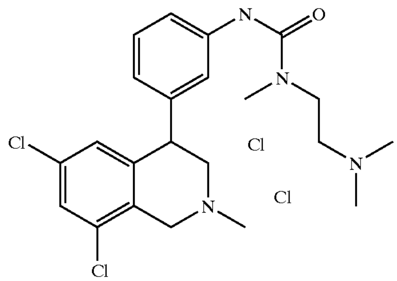 | 1.62 | B | 435.3 | ESI |
| 164 | 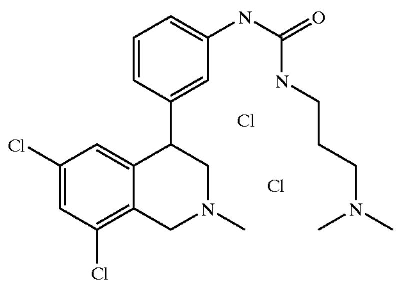 | 1.71 | B | 435.3 | ESI |
| 165 | 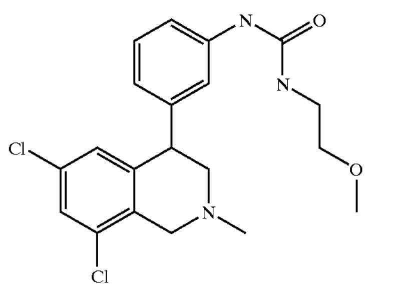 | 2.21 | B | 408.3 | ESI |
| 166 | 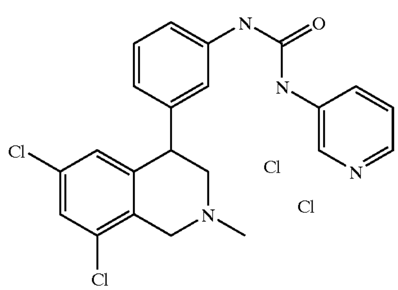 | 1.88 | B | 427.3 | ESI |
| 167 | 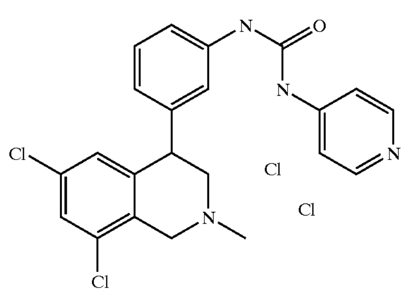 | 1.80 | B | 427.3 | ESI |

TABLE 13-continued

| Ex. | Structure | R$_t$[min] | Method | MS [M + H$^+$] | MS-Method |
|---|---|---|---|---|---|
| 168 | 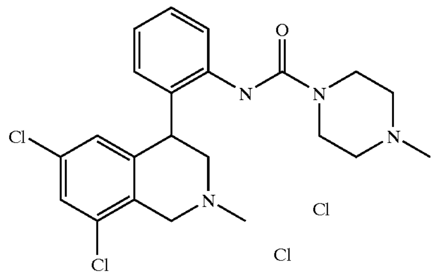 | 1.59 | B | 433.3 | ESI |
| 169 | 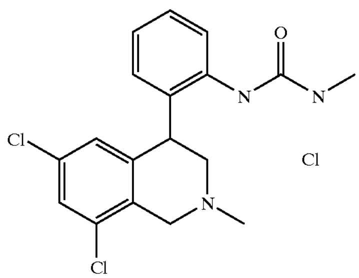 | 2.12 | B | 364.2 | ESI |
| 170 | 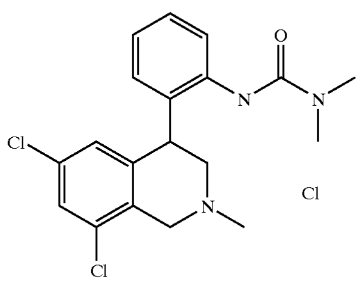 | 2.12 | B | 378.2 | ESI |
| 171 | 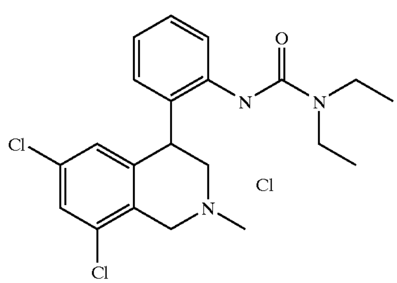 | 2.34 | B | 406.3 | ESI |
| 172 | 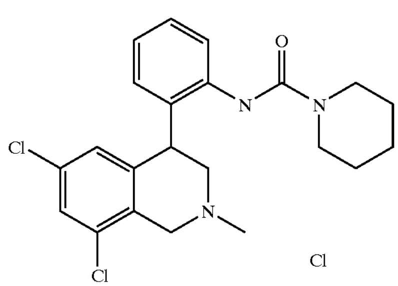 | 2.44 | B | 418.3 | ESI |

TABLE 13-continued

| Ex. | Structure | R$_t$[min] | Method | MS [M + H$^+$] | MS-Method |
|---|---|---|---|---|---|
| 173 | 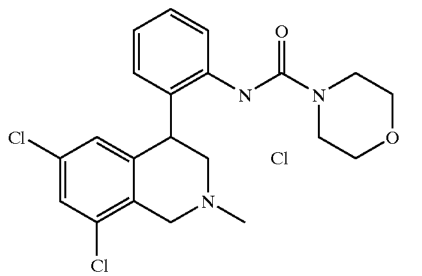 | 2.11 | B | 420.3 | ESI |
| 174 | 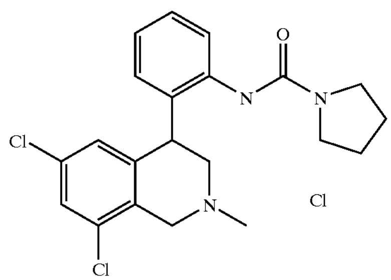 | 2.25 | B | 404.3 | ESI |
| 175 | 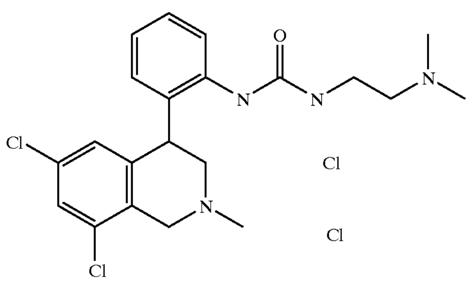 | 0.90 | B | 421.5 | ESI |
| 176 | 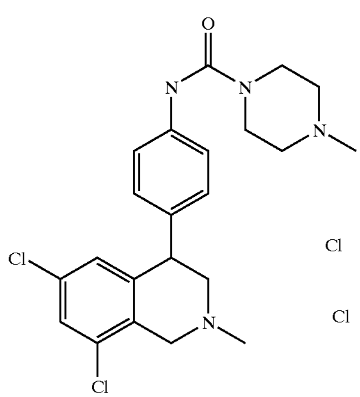 | 1.52 | B | 433.3 | ESI |

TABLE 13-continued

| Ex. | Structure | R$_t$[min] | Method | MS [M + H$^+$] | MS-Method |
|---|---|---|---|---|---|
| 177 | 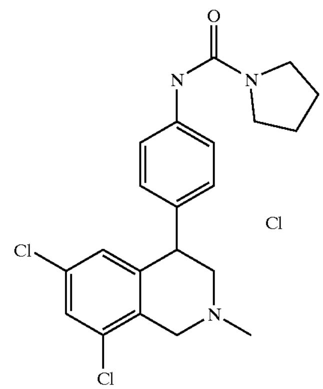 | 2.34 | B | 404.3 | ESI |
| 178 | 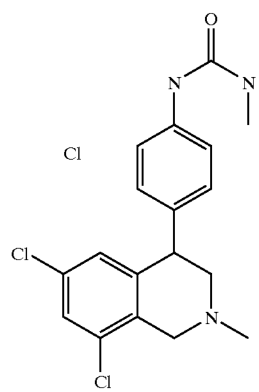 | 2.11 | B | 364.2 | ESI |
| 179 | 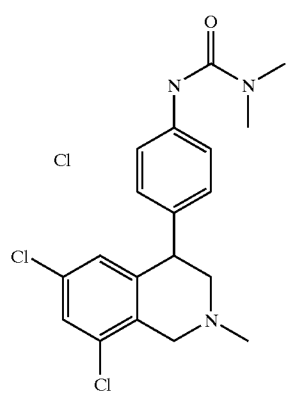 | 2.17 | B | 378.3 | ESI |
| 180 | 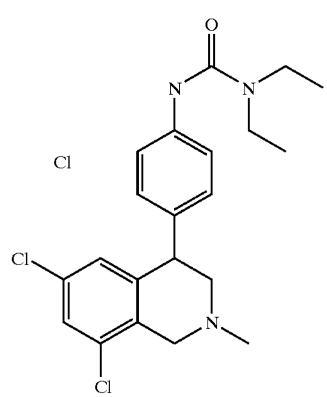 | 2.51 | B | 406.3 | ESI |

TABLE 13-continued

| Ex. | Structure | R$_t$[min] | Method | MS [M + H$^+$] | MS-Method |
|---|---|---|---|---|---|
| 181 | 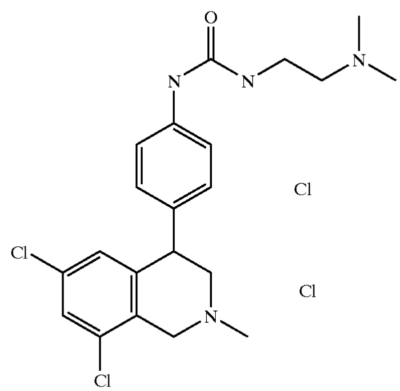 | 1.59 | B | 421.2 | ESI |
| 182 | 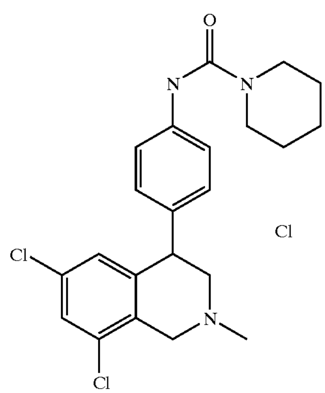 | 2.47 | B | 418.2 | ESI |
| 183 | 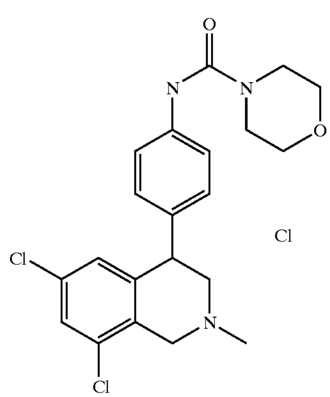 | 2.16 | B | 420.2 | ESI |
| 184 | 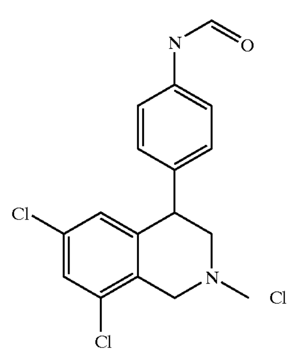 | 2.02 | B | 335.2 | ESI |

TABLE 13-continued

| Ex. | Structure | R$_t$[min] | Method | MS [M + H$^+$] | MS-Method |
|---|---|---|---|---|---|
| 185 | 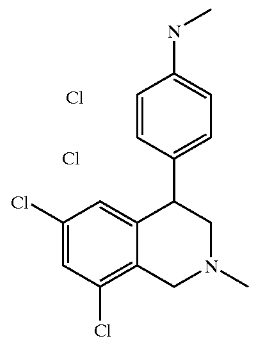 | 1.92 | B | 321.2 | ESI |
| 186 | 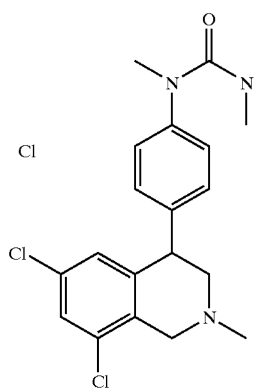 | 1.05 | C | 378.4 | ESI |
| 187 | 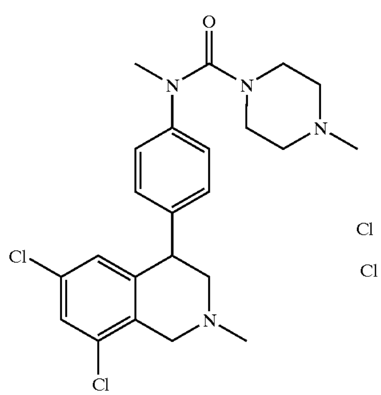 | 0.92 | C | 447.5 | ESI |
| 188 | 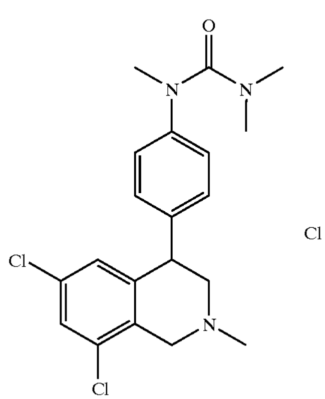 | 1.10 | C | 392.5 | ESI |

TABLE 13-continued
| Ex. | Structure | $R_t$[min] | Method | MS [M + H$^+$] | MS-Method |
|---|---|---|---|---|---|
| 189 | 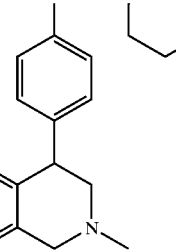 | 1.24 | C | 432.5 | ESI |
| 190 | 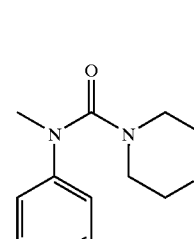 | 1.10 | C | 434.5 | ESI |
| 191 | 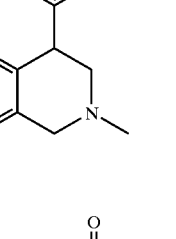 | 1.15 | C | 418.4 | ESI |
| 192 | 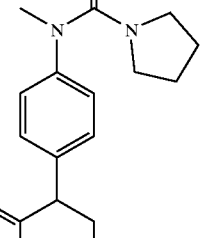 | 0.93 | C | 435.4 | ESI |

TABLE 13-continued
| Ex. | Structure | R$_t$[min] | Method | MS [M + H$^+$] | MS-Method |
|---|---|---|---|---|---|
| 193 | 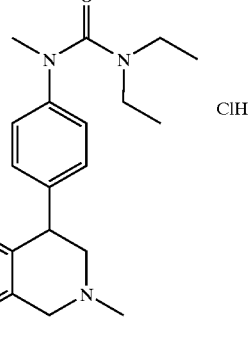 | 1.22 | C | 420.5 | ESI |
| 194 | 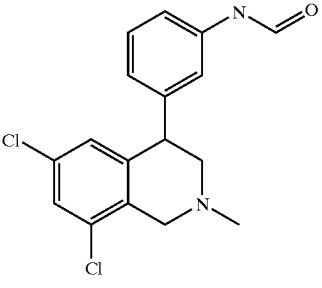 | 2.04 | C | 335.4 | ESI |
| 195 | 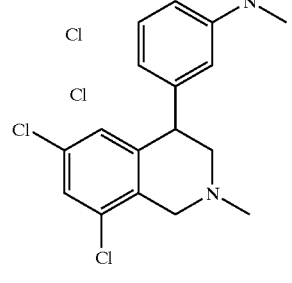 | 0.90 | C | 321.3 | ESI |
| 196 | 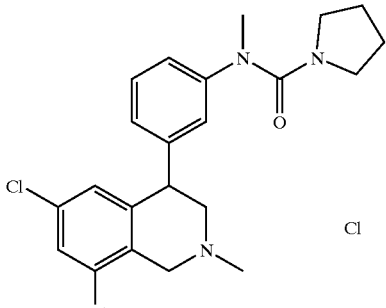 | 2.48 | B | 418.3 | ESI |

TABLE 13-continued
| Ex. | Structure | $R_t$[min] | Method | MS [M + H$^+$] | MS-Method |
|---|---|---|---|---|---|
| 197 | 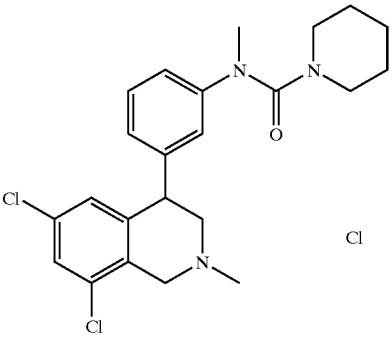 | 2.62 | B | 432.3 | ESI |
| 198 | 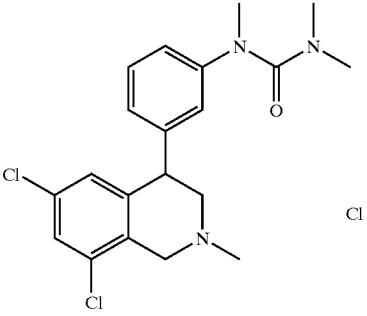 | 2.32 | B | 392.3 | ESI |
| 199 | 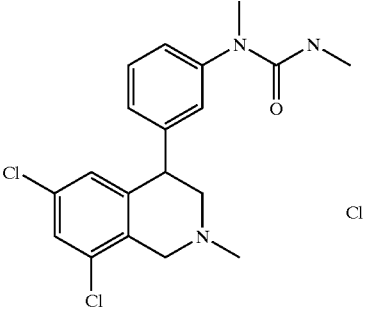 | 2.19 | B | 378.2 | ESI |
| 200 | 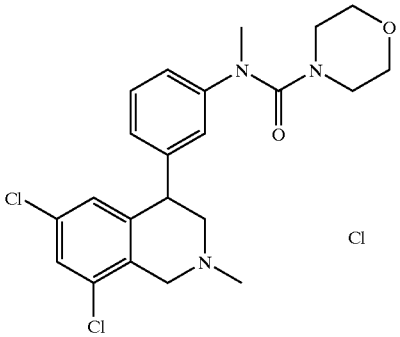 | 2.16 | B | 434.3 | ESI |

TABLE 13-continued
| Ex. | Structure | $R_t$[min] | Method | MS [M + H⁺] | MS-Method |
|---|---|---|---|---|---|
| 201 | 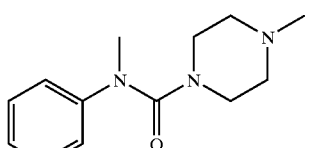 | 1.61 | B | 447.4 | ESI |
| 202 | 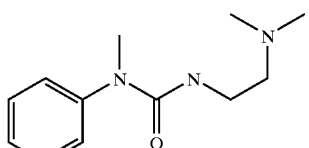 | 1.59 | B | 435.3 | ESI |
| 203 | 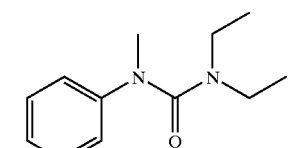 | 2.57 | B | 420.3 | ESI |
| 204 | 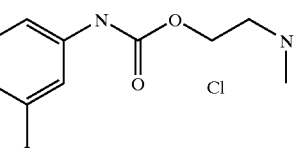 | 1.71 | B | 422.2 | ESI |

TABLE 13-continued

| Ex. | Structure | R$_t$[min] | Method | MS [M + H$^+$] | MS-Method |
|---|---|---|---|---|---|
| 205 | 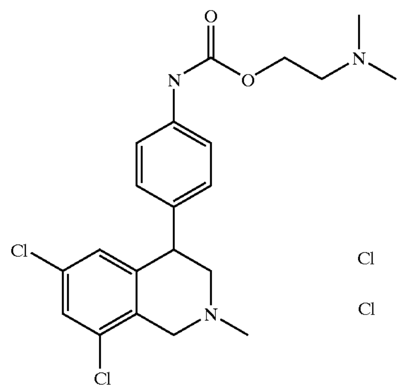 | 1.70 | B | 422.3 | ESI |
| 206 | 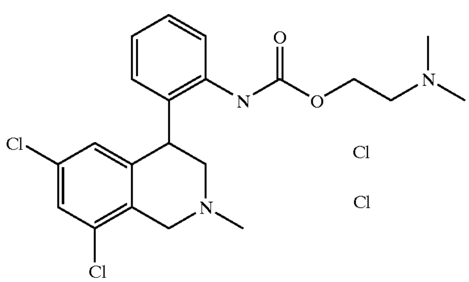 | 1.68 | B | 422.3 | ESI |
| 207 | 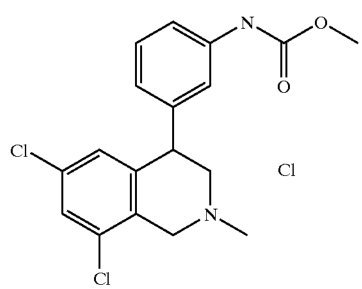 | 2.34 | B | 365.1 | ESI |
| 208 | 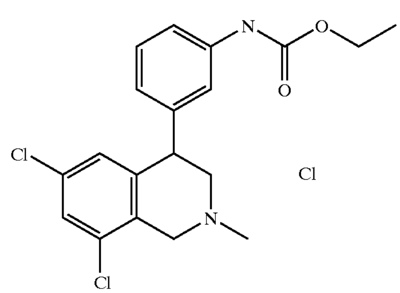 | 1.18 | C | 379.4 | ESI |
| 209 | 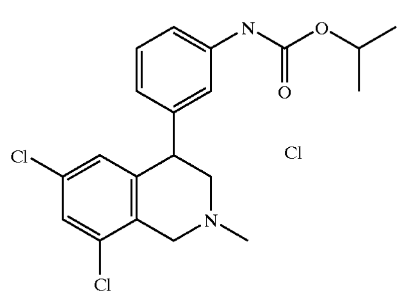 | 1.24 | C | 393.4 | ESI |

TABLE 13-continued
| Ex. | Structure | R$_t$[min] | Method | MS [M + H$^+$] | MS-Method |
|---|---|---|---|---|---|
| 210 | 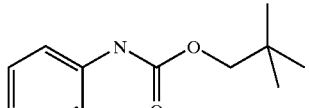 | 1.38 | C | 421.5 | ESI |
| 211 | 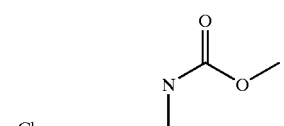 | 1.13 | C | 365.4 | ESI |
| 212 | 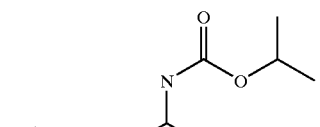 | 1.26 | C | 393.4 | ESI |
| 213 | 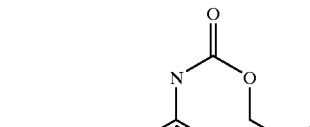 | 1.40 | C | 421.5 | ESI |

TABLE 13-continued

| Ex. | Structure | R$_t$[min] | Method | MS [M + H$^+$] | MS-Method |
|---|---|---|---|---|---|
| 214 | 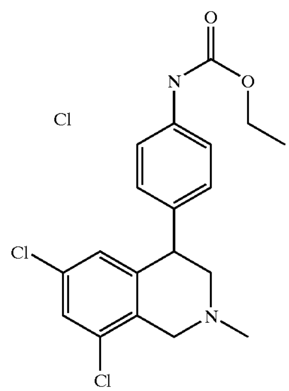 | 1.20 | C | 379.4 | ESI |
| 215a 215b | | | | 385.2 | ESI |
| 216a 216b | | | | 378.1 | ESI |
| 217 | 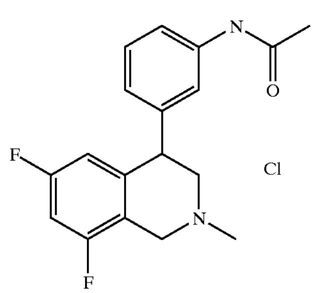 | 1.86 | B | 317.2 | ESI |
| 218 | 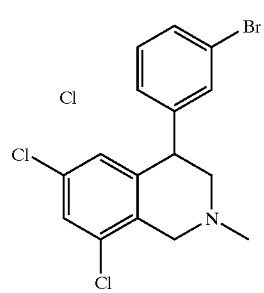 | 1.27 | C | 370.2 | ESI |

TABLE 13-continued

| Ex. | Structure | R$_t$[min] | Method | MS [M + H$^+$] | MS-Method |
|---|---|---|---|---|---|
| 219 | 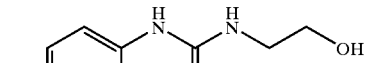 | 0.99 | B1 | 394.1/396.2 | ESI |
| 220 | 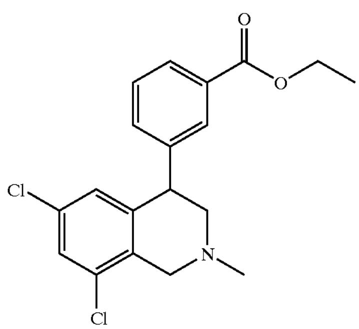 | 1.24 | B1 | 364.1/366.1 | ESI |
| 221 | 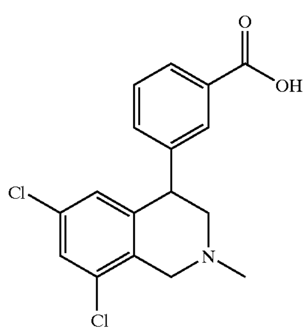 | 1.02 | B1 | 336.1/338.1 | ESI |

Pharmacological Data:

Description of Test:

In this test, the recovery in the intracellular pH (pH$_i$) after an acidification is ascertained, which is initiated if the NHE is capable of functioning, even under bicarbonate-free conditions. For this purpose, the pH$_i$ was determined using the pH-sensitive fluorescent dye BCECF (Calbiochem, the precursor BCECF-AM is employed).

The cells were initially loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the pH$_i$ using calibration curves. The cells were incubated in NH$_4$Cl buffer (pH 7.4) (NH$_4$Cl buffer: 115 mM NaCl, 20 mM NH$_4$Cl, 5 mM KCl, 1 mM CaCl$_2$, 1 mM MgSO$_4$, 20 mM Hepes, 5 mM glucose, 1 mg/ml BSA; a pH of 7.4 is adjusted with 1 M NaOH) even during the BCECF loading. The intracellular acidification was induced by adding 975 µl of an NH$_4$Cl-free buffer (see below) to 25 µl aliquots of the cells incubated in NH$_4$Cl buffer. The subsequent rate of pH recovery was recorded for two minutes with NHE1, five minutes with NHE2 and three minutes with NHE3. To calculate the inhibitory potency of the tested substances, the cells were initially investigated in buffers with which a complete or absolutely no pH recovery took place. For complete pH recovery (100%), the cells were incubated in Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 5 mM Hepes, 5 mM glucose, a pH of 7.0 is adjusted with 1 M NaOH). To determine the 0% value, the cells were incubated in an Na$^+$-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose, a pH of 7.0 is adjusted with 1 M NaOH). The substances to be tested were made up in the Na$^+$-containing buffer. The recovery of the intracellular pH at each test concentration of a substance was expressed as a percentage of the maximum recovery. The IC$_{50}$ value for the particular substance for the individual NHE subtypes was calculated from the pH recovery percentages using the Sigma-Plot program.

Results:

TABLE 14

| Example | IC$_{50}$ [µM], (NHE3) |
|---------|------------------------|
| 1a | 0.075 |
| 2a | 0.082 |
| 2b | 0.026 |
| 6 | 0.670 |
| 7 | 0.250 |
| 10 | 1.000 |
| 17 | 0.049 |
| 21 | 0.814 |
| 23 | 1.507 |
| 24 | 0.340 |
| 29 | 0.318 |
| 36 | 0.274 |
| 48 | 0.349 |
| 51 | 0.215 |
| 60 | 0.202 |
| 64 | 0.507 |
| 81 | 0.730 |
| 87 | 0.418 |
| 97 | 0.308 |
| 113 | 0.279 |
| 119 | 0.682 |
| 144 | 0.695 |
| 146 | 0.024 |
| 153 | 0.602 |
| 183 | 0.597 |
| 199 | 0.252 |
| 207 | 0.186 |

We claim:
1. A compound of the formula I

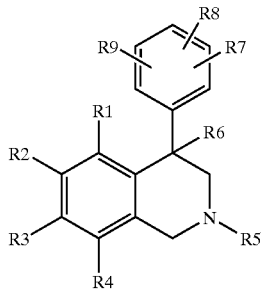

wherein:
R1, R2, R3 and R4 are independently of one another H, F, Cl, Br, I, CN, NO$_2$, OH, NH$_2$, C$_a$H$_{2a+1}$, C$_{qq}$H$_{2qq-1}$, OC$_b$H$_{2b+1}$, COOR10, OCOR10, COR10 or O$_x$—(CH$_2$)$_y$-phenyl; wherein
 a and b are independently of one another 1, 2, 3, 4, 5, 6, 7 or 8, wherein the groups C$_a$H$_{2a+1}$ and OC$_b$H$_{2b+1}$ independently of one another are unsubstituted or substituted where one or more H atoms are replaced by F atoms;
 qq is 3, 4, 5, 6, 7 or 8, wherein the group CqqH2qq−1 is unsubstituted or substituted where one or more H atoms are replaced by F atoms;
 R10 is H or C$_c$H$_{2c+1}$;
  c is 1, 2, 3, 4, 5, 6, 7 or 8, wherein the group C$_c$H2c+1 is unsubstituted or substituted where one or more H atoms are replaced by F atoms;
 x is zero or 1;
 y is zero, 1, 2, 3 or 4; where the phenyl ring in the group O$_x$—(CH$_2$)$_y$-phenyl is unsubstituted or substituted by 1–3 independently chosen from F, Cl, Br, CN, NO$_2$, OH, NH$_2$ and C$_d$H$_{2d+1}$,
 d is 1, 2, 3 or 4, wherein the group C$_d$H$_{2d+1}$ is unsubstituted or substituted where one or more H atoms are replaced by F atoms;
or
R1, R2, R3 and R4 are independently of one another chosen from a heteroaryl with at least one heteroatom chosen from 1, 2, 3 or 4 N atoms, 1 oxygen atom and 1 S atom, present as ring atoms; or
R1, R2, R3 and R4 are independently of one another CONR11R12 or NR11R12; wherein
 R11 and R12 are independently of one another H, C$_e$H$_{2e+1}$, C$_{rr}$H$_{2rr-1}$;
  e is 1, 2, 3, 4, 5, 6, 7 or 8;
  rr is 3, 4, 5, 6, 7, or 8, wherein the groups C$_e$H$_{2e+1}$ and C$_{rr}$H$_{2rr-1}$ independently of one another are unsubstituted or substituted where one or more H atoms are replaced by F atoms and/or one or more CH$_2$ groups are replaced by O or NR13;
   R13 is H or C$_f$H$_{2f+1}$;
    f is 1, 2, 3 or 4, wherein the group C$_f$H$_{2f+1}$ is unsubsitituted or substituted where one or more H atoms are replaced by F atoms;
   or
   R13 and a CH$_2$ group of R11 or R12 together with the N atom to which they are bonded form a 5- or 6-membered ring;
or
 R11 and R12 together with the N atom to which they are bonded form a 5-, 6- or 7-membered ring; or
 R11 and R12 are independently of one another COR14, CSR14 or SO$_2$R14; wherein
  R14 is C$_g$H$_{2g+1}$;
   g is 1, 2, 3, 4, 5, 6, 7 or 8, wherein the group C$_g$H$_{2g+1}$ is unsubsitituted or substituted where one or more H atoms are replaced by F atoms, and/or one or more CH$_2$ groups are replaced by O or NR13;
or
R1, R2, R3 and R4 are independently of one another —O$_h$—SO$_j$-R15, with
 h is zero or 1;
 j is zero, 1 or 2;
 R15 is C$_k$H$_{2k+1}$, OH, OC$_l$H$_{2l+1}$ or NR17R18;
  k is 1, 2, 3, 4, 5, 6, 7 or 8, wherein the group C$_k$H$_{2k+1}$ is unsubsitituted or substituted where one or more H atoms are replaced by F atoms;
  l is 1, 2, 3, 4, 5, 6, 7 or 8, wherein the group OC$_l$H$_{2l+1}$ is unsubsitituted or substituted where one or more H atoms are replaced by F atoms;
  R17 and R18 are independently of one another H or C$_m$H$_{2m+1}$;
   m is 1, 2, 3, 4, 5, 6, 7 or 8, wherein the group C$_m$H$_{2m+1}$ is unsubstituted or substituted where one or more H atoms is replaced by F atoms and/or one or more CH$_2$ groups are replaced by O, CO, CS or NR19;
    R19 is H or C$_n$H$_{2n+1}$;
     n is 1, 2, 3 or 4, wherein the group C$_n$H$_{2n+1}$ is unsubstituted or substituted where one or more H atoms are replaced by F atoms;
    or
    R19 and a CH$_2$ group of R17 or R18 together with the N atom to which they are bonded form a 5- or 6-membered ring;
   or
   R17 and R18 together with the N atom to which they are bonded form a 5-, 6- or 7-membered ring;

but where R2 does not equal H in any of the foregoing definitions,

R5 is H, $C_pH_{2p+1}$, $C_{ss}H_{2ss-1}$, COR20 or $SO_2$R20; wherein
p is 1, 2, 3, 4, 5, 6, 7 or 8,
ss is 3, 4, 5, 6, 7 or 8,
R20 is $C_qH_{2q+1}$;
q is 1, 2, 3, 4, 5, 6, 7 or 8, wherein the groups $C_pH_{2p+1}$, $C_{ss}H_{2ss-1}$ and $C_qH_{2q+1}$ independently of one another are unsubstituted or substituted where one or more H atoms are replaced by F atoms and/or one or more $CH_2$ groups are replaced by O or NR21;
R21 is H or $C_rH_{2r+1}$;
r is 1, 2, 3 or 4; wherein the group $C_rH_{2r+1}$ is unsubstituted or substituted where one or more H atoms are replaced by F atoms;

R6 is H, F, Cl, Br, I, $C_sH_{2s+1}$, $C_{dd}H_{2dd-1}$, OH, $OC_tH_{2t+1}$ or OCOR22; wherein
s and t are independently of one another 1, 2, 3, 4, 5, 6, 7 or 8;
dd is 3, 4, 5, 6, 7 or 8, wherein the groups $C_sH_{2s+1}$, $C_{dd}H_{2dd-1}$ and $OC_tH_{2t+1}$ independently of one another are unsubstituted or substituted where one or more H atoms are replaced by F atoms;
R22 is $C_uH_{2u+1}$;
u 1, 2, 3 or 4, wherein the group $C_uH_{2u+1}$ is unsubstituted or substituted where one or more H atoms are replaced by F atoms;

R7, R8 and R9 are independently of one another —$O_v$—$SO_w$—$R^{23}$; wherein
v is zero or 1;
w is zero, 1 or 2;
R23 is $C_{nn}H_{2nn+1}$, $C_{mm}H_{2mm-1}$, OH, $OC_{pp}H_{2pp+1}$ or NR25R26;
nn and pp are independently of one another 1, 2, 3, 4, 5, 6, 7 or 8,
mm is 3, 4, 5, 6, 7 or 8, wherein the groups $C_{nn}H_{2nn+1}$, $C_{mm}H_{2mm-1}$ and $OC_{pp}H_{2pp+1}$ independently of one another are unsubstituted or substituted where one or more H atoms are replaced by F atoms;
R25 and R26 are independently of one another H, CN, $C_zH_{2z+1}$, or $C_{zz}H_{2zz-1}$;
z is 1, 2, 3, 4, 5, 6, 7 or 8;
zz is 3, 4, 5, 6, 7 or 8, wherein the group $C_zH_{2zz+1}$ is unsubstituted or substituted where one or more H atoms are replaced by F atoms and,
wherein the group $C_zH_{2z+1}$, is unsubstituted or substituted where one or more H atoms are replaced by F atoms and/or one or more $CH_2$ groups are replaced by O, CO, CS or NR27;
R27 is H or $C_{aa}H_{2aa+1}$;
aa is 1, 2, 3 or 4, wherein the group $C_{aa}H_{2aa+1}$ is unsubstituted or substituted where one or more H atoms are replaced by F atoms;
or
R27 and a $CH_2$ group of R25 or R26 together with the N atom to which they are bonded form a 5- or 6-membered ring;
or
R25 and R26 together with the N atom to which they are bonded form a 5-, 6- or 7-membered ring;
or
R7, R8 and R9 are independently of one another NR32COR30, NR32CSR30 or $NR32SO_{bb}R30$;
R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
R32 and R33 are independently of one another H or $C_hH_{2h+1}$;
bb is 2 or 3;
cc is 1, 2, 3, 4, 5, 6, 7 or 8;
yy is 3, 4, 5, 6, 7 or 8;
h is 1, 2, 3, 4, 5, 6, 7 or 8,
wherein the group $C_hH_{2h+1}$ is unsubstituted or substituted where one or more H atoms are replaced by F atoms, and
wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group are replaced by O;
R31 is H, $C_{kk}H_{2kk+1}$, COR65 or $SO_2$ R65;
kk is 1, 2, 3, or 4; wherein the group $C_{kk}H_{2kk+}1$ is unsubstituted or substituted where one or more H atoms are replaced by F atoms,
R65 is H, or $C_{xx}H_{2xx+1}$;
xx is 1, 2, 3 or 4, wherein the group $C_{xx}H_{2xx+1}$ is unsubstituted or substituted where one or more H atoms are replaced by F atoms;
or
R31 together with a $CH_2$ group of R30 forms a 5-, 6- or 7-membered ring; or
R30 is a 5- or 6-membered heteroaryl with at least one hetero atom chosen from 1, 2, 3 or 4 N atoms, zero, 1 S atom and 1 O atom, which is unsubstituted or substituted by up to three substituents chosen from F, Cl, Br, I, $C_{oo}H_{2oo+1}$, and NR70R71;
R70 and R71 are independently of one another H, $C_{uu}H_{2uu+1}$ or COR72;
R72 is H, or $C_{vv}H_{2vv+1}$;
oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;
or
R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42,
ee and ff are independently of one another 1, 2, 3, 4, 5, 6, 7 or 8;
ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are independently of one another H, $C_{tt}H_{2tt+1}$ or $C(NH)NH_2$;
tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;
R44 is H or $C_{gg}H_{2gg+1}$;
gg is 1, 2, 3, 4, 5, 6, 7 or 8, wherein the group $C_{gg}H_{2gg+1}$ is unnsubstituted or substituted where one or more H atoms are replaced by F atoms
or
R44 forms a 5- or 6-membered ring together with a ($CH_2$) group of R40 or R41 and the N atom to which they are bound;

or

R40 and R41 with the N atom to which they are bonded form a 5- or 6-membered ring;

R42 is H or $C_{hh}H_{2hh+1}$;

hh is 1, 2, 3, 4, 5, 6, 7 or 8, wherein the group $C_{hh}H_{2hh+1}$ is unnsubstituted or substituted where one or more H atoms are replaced by F atoms;

with the proviso that two substituents chosen from the group R7, R8 and R9 can not simultaneously be OH and $OCH_3$, and that at least one of the substituents R7, R8 and R9 is chosen from CONR40R41, $-O_v-SO_w-R23$, NR32COR30, NR32CSR30 and $NR32SO_{bb}R30$;

or a pharmaceutically acceptable salt thereof, or a trifluoroacetate thereof in any stereoisomeric form, or a mixture of any such compounds in any ratio.

2. The compound as claimed in claim 1, in which:

R1, R2, R3 and R4 are independently of one another, H, F, Cl, Br, I, CN, $NO_2$, OH, $NH_2$, $C_aH_{2a+1}$, cycloalkyl with 3, 4, 5 or 6 C atoms, $OC_bH_{2b+1}$, or COOR10; wherein a and b are independently of one another 1, 2, 3 or 4, wherein the group $C_aH_{2a+1}$ is unsubstituted or substituted where one or more H atoms are replaced by F atoms;

R10 is H or $C_cH_{2c+1}$;

c is 1, 2, 3 or 4, wherein the group $C_cH_{2c+1}$ is unsubstituted or substituted where one or more H atoms are replaced by F atoms; or R1, R2, R3 and R4 are independently of one another a 5- or 6-membered heteroaryl choawn from pyridyl, imidazolyl, pyrazolyl, pyrrolyl, triazolyl, tetrazolyl, thiazolyl and oxazolyl; or R1, R2, R3 and R4 are independently of one another CONR11R12 or NR11R12; wherein R11 and R12 are independently of one another H, $C_eH_{2e+1}$, $C_{rr}H_{2rr-1}$;

e is 1, 2, 3 or 4, rr is 3, 4, 5 or 6, wherein the groups $C_eH_{2e+1}$ and $C_{rr}H_{2rr-1}$ independently of one another are unsubstituted or substituted where one or more H atoms are replaced by F atoms;

or

R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R11 and R12 together with the N atom to which they are bonded form a pyrrolidine, piperidine, N-methylpiperazine, piperazine or morpholine ring; or R11 and R12 are independently of one another COR14, CSR14, CONHR14, CSNHR14 or $SO_2R14$; wherein R14 is $C_gH_{2g+1}$;

g is 1, 2, 3 or 4, wherein the group $C_gH_{2g+1}$ is unsbustituted or substituted where one or more H atoms are replaced by F atoms;

or

R1, R2, R3 and R4 are independently of one another $OSO_3H$, $SO_3H$, $SO_2R_{15}$; wherein R15 is $C_kH_{2k+1}$, $OC_lH_{2l+1}$ or NR17R18;

k is 1, 2, 3 or 4, wherein the group $C_kH_{2k+1}$ is unsubstituted or substituted where one ore more H atoms are replaced by F atoms;

l is 1, 2, 3 or 4, wherein the group $OC_lH_{2l+1}$ is unsubstituted or substituted where one ore more H atoms are replaced by F atoms;

R17 and R18 are independently of one another H, or $C_mH_{2m+1}$, in which the first $CH_2$ group bonded to the nitrogen of NR17R18 is replaced by CO and the second $CH_2$ group is replaced by NR19;

m 1, 2, 3, 4 or 5, wherein the group $C_mH_{2m+1}$ is unsubstituted or substituted where one or more H atoms is replaced by F atoms;

R19 is H or $C_nH_{2n+1}$;

n is 1, 2, 3 or 4, wherein the group $C_nH_{2n+1}$ is unsubstituted or substituted where one or more H atoms is replaced by F atoms;

or

R17 and R18 together with the N atom to which they are bonded form a 5- or 6-membered ring;

but where R2 does not equal H in any of the foregoing definitions,

R5 is H, or $C_pH_{2p+1}$;

p is 1, 2, 3 or 4, wherein the group $C_pH_{2p+1}$ is unsubstituted or substituted where one or more H atoms is replaced by F atoms;

R6 is H, $C_sH_{2s+1}$, $OC_tH_{2t+1}$ or OCOR22;

s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;

R22 is $C_uH_{2u+1}$;

u is 1, 2, 3 or 4; wherein the group $C_uH_{2u+1}$ is unsubstituted or substituted where one or more H atoms is replaced by F atoms;

R7, R8 and R9 are independently of one another $OSO_3H$, $SO_3H$ or $SO_2R23$; wherein R23 is $C_{nn}H_{2nn+1}$, $C_{mm}H_{2mm-1}$, $OC_{pp}H_{2pp+1}$ or NR25R26;

nn and pp are independently of one another 1, 2, 3, 4 or 5, mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;

R25 and R26 are independently of one another H, CN, or $C_zH_{2z+1}$, in which a first $CH_2$ group bonded to the nitrogen of NR25R26 is replaced by CO or CS and a second $CH_2$ is replaced by NR27;

z is 1, 2, 3, 4, 5 or 6; wherein the group $C_zH_{2z+1}$ is unsubstituted or substituted where one or more H atoms are replaced by F atoms;

R27 is H or $C_{aa}H_{2aa+1}$;

aa is 1, 2, 3 or 4, wherein the group $C_{aa}H_{2aa+}1$ is unsubstituted or substituted where one or more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5- or 6-membered ring;

or

R7, R8 and R9 are independently of one another NR32COR30, NR32CSR30 or $NR32SO_2R30$; wherein R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;

cc is 1, 2, 3, 4, 5, 6, 7 or 8;
yy is 3, 4, 5 or 6;
h is 1, 2, 3 or 4; wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups to be replaced by NR31 and/or one $CH_2$ group to be replaced by O;
R31 is H, $C_{kk}H_{2kk+1}$, COR65 or $SO_2$ R65;
kk is 1, 2, 3, or 4, wherein the group $C_{kk}H_{2kk+1}$ is unsubstituted or substituted where one or more H atoms are replaced by F atoms,
R65 is H, or $C_{xx}H_{2xx+1}$;
xx is 1, 2, 3 or 4, wherein the group $C_{xx}H_{2xx+1}$ is unsubstituted where one or more H atoms are replaced by F atoms;

or

R31 together with a $CH_2$ group of R30 and the N atom to which they are jointly bonded form form a 5- or 6-membered ring; or R30 is a 5- or 6-membered heteroaryl chosen from pyridyl, imidazolyl, pyrazolyl, pyrrolyl, triazolyl, tetrazolyl, thienyl, thiazolyl and oxazolyl,
which is unsubstituted or substituted by up to three substituents chosen from F, Cl, Br, I, $C_{oo}H_{2oo+1}$, and NR70R71,
R70 and R71 are independently of one another H, $C_{uu}H_{2uu+1}$ or COR72;
R72 is H, or $C_{vv}H_{2vv+1}$;
oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;

or

R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;
ee and ff are independently of one another 1, 2, 3 or 4;
ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are independently of one another H, $C_{tt}H_{2tt+1}$, or $C(NH)NH_2$;
tt is 1, 2, 3, 4, 5, 6, 7 or 8, wherein the group $C_{tt}H_{2tt+1}$ is unsubstituted or substituted where one or more H atoms are replaced by F atoms;

or

R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl; or R40 and R41 together with the N atom to which they are bonded form a ring chosen from pyrrolidine, piperidine, N-methylpiperazine, piperazine and morpholine;

R42 is H or $C_{hh}H_{2hh+1}$;
hh is 1, 2, 3 or 4, wherein the group $C_{hh}H_{2hh+1}$ is unsubstituted or substituted where one or more H atoms are replaced by F atoms;

with the proviso that two substituents chosen from the group R7, R8 and R9 can not simultaneously be OH and $OCH_3$, and that at least one of the substituents R7, R8 and R9 is chosen from CONR40R41, $-O_v-SO_w-R^{23}$, NR32COR30, NR32CSR30 and $NR32SO_{bb}R30$;

or a pharmaceutically acceptable salt thereof, or a trifluoroacetate thereof in any stereoisomeric form, or a mixture of any such compounds in any ratio.

3. The compoud as claimed in claim 1, in which:
R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein
a and b are independently of one another 1, 2, 3 or 4, wherein the groups $C_aH_{2a+1}$ and $OC_bH_{2b+1}$ independenly of one another are unsubstituted or substituted where one or more H atoms are replaced by F atoms;

or

R1, R2, R3 and R4 are independently of one another NR11R12;
R11 and R12 are independently of one another H, $C_eH_{2e+1}$, or $C_{rr}H_{2rr-1}$;
e is 1, 2, 3 or 4,
rr is 3, 4, 5 or 6, wherein the groups $C_eH_{2e+1}$ and $C_{rr}H_{2rr-1}$ independenly of one another are unsubstituted or substituted where one or more H atoms are replaced by F atoms; or R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or $SO_2R14$; wherein R14 is $C_gH_{2g+1}$;
g is 1, 2, 3 or 4, wherein the group $C_gH_{2g+1}$ is unsubstituted or substituted where one or more H atoms are replaced by F atoms;

or

R1, R2, R3 and R4 are independently of one another $OSO_3H$, $SO_3H$, or $SO_2R15$;
R15 is $C_kH_{2k+1}$ or NR17R18;
k is 1, 2, 3 or 4, wherein the group $C_kH_{2k+1}$ is unsubstituted or substituted where one or more H atoms are replaced by F atoms;
R17 and R18 are independently of one another H or $C_mH_{2m+1}$;
m is 1, 2, 3, 4 or 5, wherein the group $C_mH_{2m+1}$ is unsubstituted or substituted where one ore more H atoms are replaced by F atoms;

or

R17 and R18 together with the N atom to which they are bonded form a 5- or 6-membered ring;
but where R2 does not equal H in any of the foregoing definitions;
R5 is methyl or trifluoromethyl;
R6 is H;
R7, R8 and R9 are independently of one another $OSO_3H$, $SO_3H$ or $SO_2R23$; wherein
R23 is $C_{nn}H_{2nn+1}$ or NR25R26;
nn is 1, 2, 3, 4 or 5, wherein the group $C_{nn}H_{2nn+1}$ is unsubstituted or substituted where one ore more H atoms are replaced by F atoms;
R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;
z is 1, 2, 3, 4, 5 or 6, wherein the group $C_zH_{2z+1}$ is unsubstituted or substituted where one or more H atoms are replaced by F atoms;

R27 is H or $C_{aa}H_{2aa+1}$;
   aa is 1, 2, 3 or 4, wherein the group $C_{aa}H_{2aa+1}$ is unsubstituted or substituted where one ore more H atoms are replaced by F atoms;
or
R27 and a $CH_2$ group of R25 or R26 together with the N atom to which they are bonded form a 5- or 6-membered ring;
or
R25 and R26 together with the N atom to which they are bonded form a 5- or 6-membered ring,
or
R7, R8 and R9 are independently of one another NR32COR30, NR32CSR30 or $NR32SO_2R30$;
   R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
   R32 and R33 are H, methyl or $CF_3$;
   cc is 1, 2, 3, 4, 5, 6, 7 or 8;
   yy is 3, 4, 5 or 6;
      wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group is replaced by O
      R31 is H, methyl, ethyl, $CF_3$, $CH_2CF_3$, acetyl or propionyl, methanesulfonyl or ethanesulfonyl; or
      R31 together with a $CH_2$ group of R30 and the N atom to which they are jointly bonded form a 5- or 6-membered ring;
   or
   R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl;
or
R7, R8 and R9 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42,
   ee and ff are independently of one another 1, 2, 3 or 4;
      ww is 3, 4, 5 or 6, wherein the groups $C_{ee}H_{2ee+1}$, $C_{ww}H_{2ww}$-1 and $OC_{ff}H_{2ff+1}$ independently of one another are unsubstituted or substituted where one or more H atoms are replaced by F atoms;
   R40 and R41 are H, $C_{tt}H_{2tt+1}$ or $C(NH)NH_2$;
      tt is 1, 2, 3 or 4, wherein the group $C_{tt}H_{2tt+1}$ is unsubstituted or substituted where one or more H atoms are replaced by F atoms;
   or
   R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
   R40 and R41 together with the N atom to which they are bonded form a pyrrolidine, piperidine, N-methylpiperazine, piperazine or morpholine ring;
   R42 is H or $C_{hh}H_{2hh+1}$;
      hh is 1, 2, 3 or 4, wherein the $C_{hh}H_{2hh+1}$ is unsubstituted or substituted where one or more H atoms are replaced by F atoms;
   with the proviso that two substituents chosen from the group R7, R8 and R9 can not simultaneously be OH and $OCH_3$,
   and that at least one of the substituents R7, R8 and R9 is chosen from CONR40R41, $-O_v-SO_w-R^{23}$, NR32COR30, NR32CSR30 and $NR32SO_{bb}R30$;

or a pharmaceutically acceptable salt thereof, or a trifluoroacetate thereof in any stereoisomeric form, or a mixture of any such compounds in any ratio.

4. The compound as claimed in claim 1, in which:
R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$;
   a and b are independently of one another 1, 2, 3 or 4, wherein the groups $C_aH_{2a+1}$ and $OC_bH_{2b+1}$ independently of one another are unsubstituted or substituted where one or more H atoms to be replaced by F atoms;
or
R1, R2, R3 and R4 are independently of one another NR11R12; wherein
   R11 and R12 are independently of one another H, $C_eH_{2e+1}$, or $C_{rr}H_{2rr-1}$;
   e is 1, 2, 3 or 4,
   rr is 3, 4, 5 or 6, wherein the groups $C_eH_{2e+1}$ and $C_{rr}H_{2rr-1}$ independently of one another are unsubstituted or substituted where one or more H atoms are replaced by F atoms;
or
R11 and R12 together with the N atom to which they are bonded form a ring chosen from pyrrolidine, piperidine, N-methylpiperazine, piperazine and morpholine; or
R11 and R12 are independently of one another COR14, CSR14, CONHR14, CSNHR14 or $SO_2R14$;
   R14 is $C_gH_{2g+1}$;
      g is 1, 2, 3 or 4, wherein the group $C_gH_{2g+1}$ is unsubstituted or substituted where one or more H atoms to be replaced by F atoms;
or
R1, R2, R3 and R4 are independently of one another $OSO_3H$, $SO_3H$, or $SO_2R15$; wherein
   R15 is $C_kH_{2k+1}$ or NR17R18;
      k is 1, 2, 3 or 4, wherein the group $C_kH_{2k+1}$ is unsubstituted or substituted where one or more H atoms to be replaced by F atoms;
      R17 and R18 are independently of one another H or $C_mH_{2m+1}$;
         m is 1, 2, 3, 4 or 5, wherein the group $C_mH_{2m+1}$ is unsubstituted or substituted where one or more H atoms to be replaced by F atoms;
      or
      R17 and R18 together with the N atom to which they are bonded form a 5- or 6-membered ring;
but where R2 does not equal H in any of the foregoing definitions,
R5 is methyl or trifluoromethyl;
R6 is H;
R7, R8 and R9 are independently of one another $OSO_3H$, $SO_3H$ or $SO_2R23$;
   R23 is $C_{nn}H_{2nn+1}$ or NR25R26;
      nn is 1, 2, 3, 4 or 5, wherein the group $C_{nn}H_{2nn+1}$ is unsubstituted or substituted where one or more H atoms to be replaced by F atoms;
   R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;
      z is 1, 2, 3, 4, 5 or 6, wherein the group $C_zH_{2z+1}$ is unsubstituted or substituted where one or more H atoms to be replaced by F atoms;
      R27 is H or $C_{aa}H_{2aa+1}$;
         aa is 1, 2, 3 or 4, wherein the group $C_{aa}H_{2aa+1}$ is unsubstituted or substituted where one or more H atoms to be replaced by F atoms;

or
R27 and a CH$_2$ group of R25 or R26 together with the N atom to which they are bonded form a 5- or 6-membered ring;
or
R25 and R26 together with the N atom to which they are bonded form a 5- or 6-membered ring,
or
R7, R8 and R9 are independently of one another NR32COR30, NR32CSR30 or NR32SO$_2$R30;
R30 is H, OH, C$_{cc}$H$_{2cc+1}$, C$_{yy}$H$_{2yy-1}$, pyrrolidinyl or piperidinyl, wherein the pyrrolidinyl or piperidinyl is unsubstituted or substituted where a CH$_2$ group is replaced by O or NR33;
R32 and R33 are independently of one another H, methyl or CF$_3$;
cc is 1, 2, 3, 4, 5, 6, 7 or 8;
yy is 3, 4, 5 or 6; wherein
wherein the groups C$_{cc}$H$_{2cc+1}$ and C$_{yy}$H$_{2yy-1}$ independently of one another are unsubstituted or substituted where one or more H atoms are replaced by F atoms and/or one or more CH$_2$ groups are replaced by NR31 and/or one CH$_2$ group are replaced by O;
R31 is H, methyl, ethyl, CF$_3$, CH$_2$CF$_3$, acetyl or propionyl, methanesulfonyl or ethanesulfonyl; or
R31 together with a CH$_2$ group of R30 and the N atom to which they are jointly bonded form a 5- or 6-membered ring; or
R30 is pyridyl, imidazolyl, pyrazolyl, pyrrolyl, triazolyl, tetrazolyl, thiazolyl or oxazolyl, which are unsubstituted or substituted by up to 3 substituents chosen from F, Cl, methyl, ethyl, trifluoromethyl, NH$_2$, and NHacetyl;
or
R7, R8 and R9 are independently of one another H, F, Cl, OH, NH$_2$, C$_{ee}$H$_{2ee+1}$, C$_{ww}$H$_{2ww-1}$, OC$_{ff}$H$_{2ff+1}$, NR40R41, CONR40R41, COOR42 or OCOR42,
ee and ff are independently of one another 1, 2, 3 or 4;
ww is 3, 4, 5 or 6, wherein the groups C$_{ee}$H$_{2ee+1}$, C$_{ww}$H$_{2ww-1}$ and OC$_{ff}$H$_{2ff+1}$ independently of one another are unsubstituted or substituted where one or more H atoms to be replaced by F atoms;
R40 and R41 is H, C$_{tt}$H$_{2tt+1}$ or C(NH)NH$_2$;
tt is 1, 2, 3 or 4, wherein the group C$_{tt}$H$_{2tt+1}$ is unsubstituted or substituted where one or more H atoms to be replaced by F atoms;
or
R40 and R41 are independently of one another hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
R40 and R41 together with the N atom to which they are bonded form a pyrrolidine, piperidine, N-methylpiperazine, piperazine or morpholine ring;
R42 is H or C$_{hh}$H$_{2hh+1}$;
hh is 1, 2, 3 or 4, wherein the group C$_{hh}$H$_{2hh+1}$ is unsubstituted or substituted where one or more H atoms to be replaced by F atoms;
with the proviso that two substituents chosen from the group R7, R8 and R9 can not simultaneously be OH and OCH$_3$,
and that at least one of the substituents R7, R8 and R9 is chosen from —O$_v$—SO$_w$-R23, NR32COR30, NR32CSR30 and NR32SO$_{bb}$R30;

or a pharmaceutically acceptable salt thereof, or a trifluoroacetate thereof in any stereoisomeric form, or a mixture of any such compounds in any ratio.

5. The compound as claimed in claim 1, chosen from:
1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-N,N-dimethyl-benzenesulfonamide;
5) 4-(4-bromo-phenyl)-6,8-dichloro-2-methyl-1,2,3,4-tetrahydroisoquinoline;
6) 4-(6,8-dichloro-2-methyl-1,2,3,4-tetrahydro-isoquinolin-4-yl)-benzoic acid;
7) 4-(6,8-dichloro-2-methyl-1,2,3,4-tetrahydroisoquinolin-4-yl)-N-ethyl-benzamide;
8) 4-(6,8-dichloro-2-methyl-1,2,3,4-tetrahydroisoquinolin-4-yl)-N-propyl-benzamide;
9) 4-(6,8-dichloro-2-methyl-1,2,3,4-tetrahydro-isoquinolin-4-yl)-N-(2-dimethylamino-ethyl)-benzamide;
10) 6,8-dichloro-2-methyl-4-(4-morpholin-4-yl-phenyl)-1,2,3,4-tetrahydroisoquinoline;
11) [4-(6,8-dichloro-2-methyl-1,2,3,4-tetrahydroisoquinolin-4-yl)-phenyl]-diethyl-amine
12) 6,8-dichloro-2-methyl-4-(4-piperidin-1-yl-phenyl)-1,2,3,4-tetrahydroisoquinoline;
13) 6,8-dichloro-2-methyl-4-(4-pyrrolidin-1-yl-phenyl)-1,2,3,4-tetrahydroisoquinoline;
14) 6,8-dichloro-2-methyl-4-[4-(4-methyl-piperazin-1-yl)-phenyl]-1,2,3,4-tetrahydroisoquinoline;
15) 6,8-dichloro-2-cyclopropyl-4-phenyl-1,2,3,4-tetrahydroisoquinoline;
16) 4-(6,8-dichloro-2-methyl-1,2,3,4-tetrahydro-isoquinolin-4-yl)-phenylamine;
17) 1-[4-(6,8-dichloro-2-methyl-1,2,3,4-tetrahydro-isoquinolin-4-yl)-phenyl]-3-propylurea;
18) 1-[4-(6,8-dichloro-2-methyl-1,2,3,4-tetrahydro-isoquinolin-4-yl)-phenyl]-3-methyl-thiourea;
19) 1-[4-(6,8-dichloro-2-methyl-1,2,3,4-tetrahydro-isoquinolin-4-yl)-phenyl]-3-ethyl-urea;
20) N-[4-(6-methanesulfonyl-2-methyl-1,2,3,4-tetrahydro-isoquinolin-4-yl)-phenyl]-acetamide;
21) N-[4-(2,6,8-trimethyl-1,2,3,4-tetrahydro-isoquinolin-4-yl)-phenyl]-acetamide;
22) N-[4-(6-bromo-8-chloro-2-methyl-1,2,3,4-tetrahydro-isoquinolin-4-yl)-phenyl]-acetamide;
23) N-[4-(8-chloro-2-methyl-6-pyrrolidin-1-yl-1,2,3,4-tetrahydro-isoquinolin-4-yl)-phenyl]-acetamide;
24) N-[4-(8-chloro-2-methyl-6-morpholin-4-yl-1,2,3,4-tetrahydro-isoquinolin-4-yl)-phenyl]-acetamide;
25) N-{4-[8-chloro-2-methyl-6-(4-methyl-piperazin-1-yl)-1,2,3,4-tetrahydro-isoquinolin-4-yl]-phenyl}-acetamide;
26) N-{4-[8-chloro-6-(cyclopropylmethyl-amino)-2-methyl-1,2,3,4-tetrahydro-isoquinolin-4-yl]-phenyl}-acetamide;
27) 5-(6,8-dichloro-2-methyl-1,2,3,4-tetrahydro-isoquinolin-4-yl)-2-hydroxy-benzoic acid;
28) 5-(6,8-dichloro-2-methyl-1,2,3,4-tetrahydro-isoquinolin-4-yl)-2-hydroxy-N-methyl-benzamide;

29) 5-(6,8-dichloro-2-methyl-1,2,3,4-tetrahydro-isoquinolin-4-yl)-N-ethyl-2-hydroxy-benzamide;
30) 5-(6,8-dichloro-2-methyl-1,2,3,4-tetrahydro-isoquinolin-4-yl)-N-(2-dimethylamino-ethyl)-2-hydroxy-benzamide;
31) N-[5-(6,8-dichloro-2-methyl-1,2,3,4-tetrahydro-isoquinolin-4-yl)-2-hydroxy-benzoyl]-guanidine;
32) N-[3-(6,8-dichloro-2-methyl-1,2,3,4-tetrahydro-isoquinolin-4-yl)-phenyl]-acetamide;
33) 3-(6,8-dichloro-2-methyl-1,2,3,4-tetrahydro-isoquinolin-4-yl)-phenylamine;
34) 2-(6,8-dichloro-2-methyl-1,2,3,4-tetrahydro-isoquinolin-4-yl)-phenylamine;
35) N-[4-(6,8-dichloro-2-methyl-1,2,3,4-tetrahydro-isoquinolin-4-yl)-phenyl]-propionamide;
36) N-[4-(6,8-dichloro-2-methyl-1,2,3,4-tetrahydro-isoquinolin-4-yl)-phenyl]-butyramide;
37) N-[4-(6,8-dichloro-2-methyl-1,2,3,4-tetrahydro-isoquinolin-4-yl)-phenyl]pentanamide;
38) N-[4-(6,8-dichloro-2-methyl-1,2,3,4-tetrahydro-isoquinolin-4-yl)-phenyl]-isobutyramide;
39) N-[4-(6,8-dichloro-2-methyl-1,2,3,4-tetrahydro-isoquinolin-4-yl)-phenyl]-2,2-dimethyl-propionamide;
40) N-[4-(6,8-dichloro-2-methyl-1,2,3,4-tetrahydro-isoquinolin-4-yl)-phenyl]-cyclopropanecarboxamide;
41) N-[4-(6,8-dichloro-2-methyl-1,2,3,4-tetrahydro-isoquinolin-4-yl)-phenyl]-cyclobutanecarboxamide;
42) N-[4-(6,8-dichloro-2-methyl-1,2,3,4-tetrahydro-isoquinolin-4-yl)-phenyl]-cyclopentanecarboxamide;
43) N-[4-(6,8-dichloro-2-methyl-1,2,3,4-tetrahydro-isoquinolin-4-yl)-phenyl]-2,2,2-trifluoro-acetamide;
44) N-[4-(6,8-dichloro-2-methyl-1,2,3,4-tetrahydro-isoquinolin-4-yl)-phenyl]-1-acetylpiperidine-4-carboxamide;
45) N-[4-(6,8-dichloro-2-methyl-1,2,3,4-tetrahydro-isoquinolin-4-yl)-phenyl]-nicotinamide;
46) N-[4-(6,8-dichloro-2-methyl-1,2,3,4-tetrahydro-isoquinolin-4-yl)-phenyl]-methanesulfonamide;
47) N-[4-(6,8-dichloro-2-methyl-1,2,3,4-tetrahydro-isoquinolin-4-yl)-phenyl]-ethanesulfonamide;
48) N',N'-dimethylamino-N-[4-(6,8-dichloro-2-methyl-1,2,3,4-tetrahydro-isoquinolin-4-yl)-phenyl]-sulfamide;
49) N-[3-(6,8-dichloro-2-methyl-1,2,3,4-tetrahydro-isoquinolin-4-yl)-phenyl]-propionamide;
50) N-[3-(6,8-dichloro-2-methyl-1,2,3,4-tetrahydro-isoquinolin-4-yl)-phenyl]-butyramide;
51) N-[3-(6,8-dichloro-2-methyl-1,2,3,4-tetrahydro-isoquinolin-4-yl)-phenyl]-pentanamide;
52) N-[3-(6,8-dichloro-2-methyl-1,2,3,4-tetrahydro-isoquinolin-4-yl)-phenyl]-isobutyramide;
53) N-[3-(6,8-dichloro-2-methyl-1,2,3,4-tetrahydro-isoquinolin-4-yl)-phenyl]-2,2-dimethyl-propionamide;
54) N-[3-(6,8-dichloro-2-methyl-1,2,3,4-tetrahydro-isoquinolin-4-yl)-phenyl]-cyclopropanecarboxamide;
55) N-[3-(6,8-dichloro-2-methyl-1,2,3,4-tetrahydro-isoquinolin-4-yl)-phenyl]-cyclobutanecarboxamide;
56) N-[3-(6,8-dichloro-2-methyl-1,2,3,4-tetrahydro-isoquinolin-4-yl)-phenyl]-cyclopentanecarboxamide;
57) N-[3-(6,8-dichloro-2-methyl-1,2,3,4-tetrahydro-isoquinolin-4-yl)-phenyl]-2,2,2-trifluoro-acetamide;
58) N-[3-(6,8-dichloro-2-methyl-1,2,3,4-tetrahydro-isoquinolin-4-yl)-phenyl]-1-acetylpiperidine-4-carboxamide;
59) N-[3-(6,8-dichloro-2-methyl-1,2,3,4-tetrahydro-isoquinolin-4-yl)-phenyl]-nicotinamide;
60) N-[3-(6,8-dichloro-2-methyl-1,2,3,4-tetrahydro-isoquinolin-4-yl)-phenyl]-methanesulfonamide;
61) N-[3-(6,8-dichloro-2-methyl-1,2,3,4-tetrahydro-isoquinolin-4-yl)-phenyl]-ethanesulfonamide;
62) N',N'-dimethylamino-N-[3-(6,8-dichloro-2-methyl-1,2,3,4-tetrahydro-isoquinolin-4-yl)-phenyl]-sulfamide;
63) N-[2-(6,8-dichloro-2-methyl-1,2,3,4-tetrahydro-isoquinolin-4-yl)-phenyl]-propionamide;
64) N-[2-(6,8-dichloro-2-methyl-1,2,3,4-tetrahydro-isoquinolin-4-yl)-phenyl]-butyramide;
65) N-[2-(6,8-dichloro-2-methyl-1,2,3,4-tetrahydro-isoquinolin-4-yl)-phenyl]-pentanamide;
66) N-[2-(6,8-dichloro-2-methyl-1,2,3,4-tetrahydro-isoquinolin-4-yl)-phenyl]-isobutyramide;
67) N-[2-(6,8-dichloro-2-methyl-1,2,3,4-tetrahydro-isoquinolin-4-yl)-phenyl]-2,2-dimethyl-propionamide;
68) N-[2-(6,8-dichloro-2-methyl-1,2,3,4-tetrahydro-isoquinolin-4-yl)-phenyl]-cyclopropanecarboxamide;
69) N-[2-(6,8-dichloro-2-methyl-1,2,3,4-tetrahydro-isoquinolin-4-yl)-phenyl]-cyclobutanecarboxamide;
70) N-[2-(6,8-dichloro-2-methyl-1,2,3,4-tetrahydro-isoquinolin-4-yl)-phenyl]-cyclopentanecarboxamide;
71) N-[2-(6,8-dichloro-2-methyl-1,2,3,4-tetrahydro-isoquinolin-4-yl)-phenyl]-2,2,2-trifluoro-acetamide;
72) N-[2-(6,8-dichloro-2-methyl-1,2,3,4-tetrahydro-isoquinolin-4-yl)-phenyl]-1-acetylpiperidine-4-carboxamide;
73) N-[2-(6,8-Dichloro-2-methyl-1,2,3,4-tetrahydro-isoquinolin-4-yl)-phenyl]-methanesulfonamide;
74) N-[2-(6,8-dichloro-2-methyl-1,2,3,4-tetrahydro-isoquinolin-4-yl)-phenyl]-ethanesulfonamide;
75) N',N'-dimethylamino-N-[2-(6,8-dichloro-2-methyl-1,2,3,4-tetrahydro-isoquinolin-4-yl)-phenyl]-sulfamide;
76) 1-[3-(6,8-dichloro-2-methyl-1,2,3,4-tetrahydro-isoquinolin-4-yl)-phenyl]-3-ethyl-urea;
77) 1-[3-(6,8-dichloro-2-methyl-1,2,3,4-tetrahydro-isoquinolin-4-yl)-phenyl]-3-methyl-thiourea;
78) 1-[2-(6,8-dichloro-2-methyl-1,2,3,4-tetrahydro-isoquinolin-4-yl)-phenyl]-3-ethyl-urea;
79) 1-[2-(6,8-dichloro-2-methyl-1,2,3,4-tetrahydro-isoquinolin-4-yl)-phenyl]-3-methyl-thiourea;
80) N-{5-[4-(6,8-dichloro-2-methyl-1,2,3,4-tetrahydro-isoquinolin-4-yl)-phenylsulfamoyl]-4-methyl-thiazol-2-yl}-acetamide;
81) N-{5-[3-(6,8-dichloro-2-methyl-1,2,3,4-tetrahydro-isoquinolin-4-yl)-phenylsulfamoyl]-4-methyl-thiazol-2-yl}-acetamide;
82) N-[4-(6,8-dichloro-2-methyl-1,2,3,4-tetrahydro-isoquinolin-4-yl)-phenyl]-1,2-dimethyl-1H-imidazole-4-sulfonamide;
83) N-[3-(6,8-dichloro-2-methyl-1,2,3,4-tetrahydro-isoquinolin-4-yl)-phenyl]-1,2-dimethyl-1H-imidazole-4-sulfonamide;
84) N-[4-(6,8-dichloro-2-methyl-1,2,3,4-tetrahydro-isoquinolin-4-yl)-phenyl]-5-chloro-1,3-dimethyl-1H-pyrazole-4-sulfonamide;
85) N-[3-(6,8-dichloro-2-methyl-1,2,3,4-tetrahydro-isoquinolin-4-yl)-phenyl]-5-chloro-1,3-dimethyl-1H-pyrazole-4-sulfonamide;
86) N-[4-(6,8-dichloro-2-methyl-1,2,3,4-tetrahydro-isoquinolin-4-yl)-phenyl]-5-bromo-thiophene-2-sulfonamide;

87) N-[3-(6,8-dichloro-2-methyl-1,2,3,4-tetrahydro-isoquinolin-4-yl)-phenyl]-5-bromo-thiophene-2-sulfonamide;
88) N-[4-(6,8-dichloro-2-methyl-1,2,3,4-tetrahydro-isoquinolin-4-yl)-phenyl]-C,C,C-trifluoro-methanesulfonamide;
89) N-[3-(6,8-dichloro-2-methyl-1,2,3,4-tetrahydro-isoquinolin-4-yl)-phenyl]-C,C,C-trifluoro-methanesulfonamide;
90) 4-(6,8-dichloro-2-methyl-1,2,3,4-tetrahydro-isoquinolin-4-yl)-phenyl]-2,2,2-trifluoroethanesulfonamide;
91) 3-(6,8-dichloro-2-methyl-1,2,3,4-tetrahydro-isoquinolin-4-yl)-phenyl]-2,2,2-trifluoro-ethanesulfonamide;
92) N-ethyl-N'-4-(6,8-Dichloro-2-methyl-1,2,3,4-tetrahydro-isoquinolin-4-yl)-benzenesulfonylurea;
93) 2-chloro-5-(6,8-dichloro-2-methyl-1,2,3,4-tetrahydro-isoquinolin-4-yl)-benzenesulfonamide;
94) 2-methyl-4-phenyl-6,8-bis-trifluoromethyl-1,2,3,4-tetrahydro-isoquinoline;
95) 2-Amino-N-[4-(6,8-dichloro-2-methyl-1,2,3,4-tetrahydro-isoquinolin-4-yl)-phenyl]-acetamide;
96) N-[4-(6,8-Dichloro-2-methyl-1,2,3,4-tetrahydro-isoquinolin-4-yl)-phenyl]-2-methylamino-acetamide;
97) N-[4-(6,8-Dichloro-2-methyl-1,2,3,4-tetrahydro-isoquinolin-4-yl)-phenyl]-2-dimethylamino-acetamide;
98) 2-Amino-N-[4-(6,8-dichloro-2-methyl-1,2,3,4-tetrahydro-isoquinolin-4-yl)-phenyl]-propionamide;
99) 2-Amino-N-[4-(6,8-dichloro-2-methyl-1,2,3,4-tetrahydro-isoquinolin-4-yl)-phenyl]-butyramide;
100) 2,6-Diamino-hexanoic acid [4-(6,8-dichloro-2-methyl-1,2,3,4-tetrahydro-isoquinolin-4-yl)-phenyl]-amide;
101) Pyrrolidine-2-carboxylic acid [4-(6,8-dichloro-2-methyl-1,2,3,4-tetrahydro-isoquinolin-4-yl)-phenyl]-amide;
102) N-[4-(6,8-Dichloro-2-methyl-1,2,3,4-tetrahydro-isoquinolin-4-yl)-phenyl]-isonicotinamide;
103) 1H-Pyrrole-3-carboxylic acid [4-(6,8-dichloro-2-methyl-1,2,3,4-tetrahydro-isoquinolin-4-yl)-phenyl]-amide;
104) 1H-Pyrrole-2-carboxylic acid [4-(6,8-dichloro-2-methyl-1,2,3,4-tetrahydro-isoquinolin-4-yl)-phenyl]-amide;
105) 1-Methyl-piperidine-4-carboxylic acid [4-(6,8-dichloro-2-methyl-1,2,3,4-tetrahydro-isoquinolin-4-yl)-phenyl]-amide;
106) 1,4-Dimethyl-1H-pyrrole-2-carboxylic acid [4-(6,8-dichloro-2-methyl-1,2,3,4-tetrahydro-isoquinolin-4-yl)-phenyl]-amide;
107) 4-Nitro-1H-pyrrole-2-carboxylic acid [4-(6,8-dichloro-2-methyl-1,2,3,4-tetrahydro-isoquinolin-4-yl)-phenyl]-amide;
108) 2,5-Dimethyl-1H-pyrrole-3-carboxylic acid [4-(6,8-dichloro-2-methyl-1,2,3,4-tetrahydro-isoquinolin-4-yl)-phenyl]-amide;
109) 1H-Imidazole-4-carboxylic acid [4-(6,8-dichloro-2-methyl-1,2,3,4-tetrahydro-isoquinolin-4-yl)-phenyl]-amide;
110) 1-Methanesulfonyl-piperidine-4-carboxylic acid [4-(6,8-dichloro-2-methyl-1,2,3,4-tetrahydro-isoquinolin-4-yl)-phenyl]-amide;
111) 3,5-Dimethyl-1H-pyrazole-4-carboxylic acid [4-(6,8-dichloro-2-methyl-1,2,3,4-tetrahydro-isoquinolin-4-yl)-phenyl]-amide;
112) 1H-Pyrazole-4-carboxylic acid [4-(6,8-dichloro-2-methyl-1,2,3,4-tetrahydro-isoquinolin-4-yl)-phenyl]-amide;
113) 3-Trifluoromethyl-1H-pyrazole-4-carboxylic acid [4-(6,8-dichloro-2-methyl-1,2,3,4-tetrahydro-isoquinolin-4-yl)-phenyl]-amide;
114) N-[3-(6,8-Dichloro-2-methyl-1,2,3,4-tetrahydro-isoquinolin-4-yl)-phenyl]-2-methylamino-acetamide;
115) N-[3-(6,8-Dichloro-2-methyl-1,2,3,4-tetrahydro-isoquinolin-4-yl)-phenyl]-2-dimethylamino-acetamide;
116) 2-Amino-N-[3-(6,8-dichloro-2-methyl-1,2,3,4-tetrahydro-isoquinolin-4-yl)-phenyl]-propionamide;
117) 2-Amino-N-[3-(6,8-dichloro-2-methyl-1,2,3,4-tetrahydro-isoquinolin-4-yl)-phenyl]-butyramide;
118) 2,6-Diamino-hexanoic acid [3-(6,8-dichloro-2-methyl-1,2,3,4-tetrahydro-isoquinolin-4-yl)-phenyl]-amide;
119) Pyrrolidine-2-carboxylic acid [3-(6,8-dichloro-2-methyl-1,2,3,4-tetrahydro-isoquinolin-4-yl)-phenyl]-amide;
120) N-[3-(6,8-Dichloro-2-methyl-1,2,3,4-tetrahydro-isoquinolin-4-yl)-phenyl]-isonicotinamide;
121) 1H-Pyrrole-3-carboxylic acid [3-(6,8-dichloro-2-methyl-1,2,3,4-tetrahydro-isoquinolin-4-yl)-phenyl]-amide;
122) 1H-Pyrrole-2-carboxylic acid [3-(6,8-dichloro-2-methyl-1,2,3,4-tetrahydro-isoquinolin-4-yl)-phenyl]-amide;
123) 1-Methyl-piperidine-4-carboxylic acid [3-(6,8-dichloro-2-methyl-1,2,3,4-tetrahydro-isoquinolin-4-yl)-phenyl]-amide;
124) 1,4-Dimethyl-1H-pyrrole-2-carboxylic acid [3-(6,8-dichloro-2-methyl-1,2,3,4-tetrahydro-isoquinolin-4-yl)-phenyl]-amide;
125) 4-Nitro-1H-pyrrole-2-carboxylic acid [3-(6,8-dichloro-2-methyl-1,2,3,4-tetrahydro-isoquinolin-4-yl)-phenyl]-amide;
126) 2,5-Dimethyl-1H-pyrrole-3-carboxylic acid [3-(6,8-dichloro-2-methyl-1,2,3,4-tetrahydro-isoquinolin-4-yl)-phenyl]-amide;
127) 1H-Imidazole-4-carboxylic acid [3-(6,8-dichloro-2-methyl-1,2,3,4-tetrahydro-isoquinolin-4-yl)-phenyl]-amide;
128) 1-Methanesulfonyl-piperidine-4-carboxylic acid [3-(6,8-dichloro-2-methyl-1,2,3,4-tetrahydro-isoquinolin-4-yl)-phenyl]-amide;
129) 3,5-Dimethyl-1H-pyrazole-4-carboxylic acid [3-(6,8-dichloro-2-methyl-1,2,3,4-tetrahydro-isoquinolin-4-yl)-phenyl]-amide;
130) 1H-Pyrazole-4-carboxylic acid [3-(6,8-dichloro-2-methyl-1,2,3,4-tetrahydro-isoquinolin-4-yl)-phenyl]-amide;
131) 3-Trifluoromethyl-1H-pyrazole-4-carboxylic acid [3-(6,8-dichloro-2-methyl-1,2,3,4-tetrahydro-isoquinolin-4-yl)-phenyl]-amide;
132) 1-[2-(6,8-Dichloro-2-methyl-1,2,3,4-tetrahydro-isoquinolin-4-yl)-phenyl]-3-ethyl-thiourea;
133) 1-[4-(6,8-Dichloro-2-methyl-1,2,3,4-tetrahydro-isoquinolin-4-yl)-phenyl]-3-ethyl-thiourea;

134) 1-[3-(6,8-Dichloro-2-methyl-1,2,3,4-tetrahydro-isoquinolin-4-yl)-phenyl]-3-ethyl-thiourea;
135) 3-[3-(6,8-Dichloro-2-methyl-1,2,3,4-tetrahydro-isoquinolin-4-yl)-phenyl]-1,1-dimethyl-urea;
136) 4-Methyl-piperazine-1-carboxylic acid [3-(6,8-dichloro-2-methyl-1,2,3,4-tetrahydro-isoquinolin-4-yl)-phenyl]-amide;
137) Piperidine-1-carboxylic acid [3-(6,8-dichloro-2-methyl-1,2,3,4-tetrahydro-isoquinolin-4-yl)-phenyl]-amide;
138) Morpholine-4-carboxylic acid [3-(6,8-dichloro-2-methyl-1,2,3,4-tetrahydro-isoquinolin-4-yl)-phenyl]-amide;
139) Pyrrolidine-1-carboxylic acid [3-(6,8-dichloro-2-methyl-1,2,3,4-tetrahydro-isoquinolin-4-yl)-phenyl]-amide;
140) 3-[3-(6,8-Dichloro-2-methyl-1,2,3,4-tetrahydro-isoquinolin-4-yl)-phenyl]-1,1-diethyl-urea;
141) 1-[3-(6,8-Dichloro-2-methyl-1,2,3,4-tetrahydro-isoquinolin-4-yl)-phenyl]-3-methyl-urea;
142) 1-[3-(6,8-Dichloro-2-methyl-1,2,3,4-tetrahydro-isoquinolin-4-yl)-phenyl]-3-(2-dimethylamino-ethyl)-urea;
143) 1-[3-(6,8-Dichloro-2-methyl-1,2,3,4-tetrahydro-isoquinolin-4-yl)-phenyl]-3-(tetrahydro-furan-3-yl)-urea;
144) 1-[3-(6,8-Dichloro-2-methyl-1,2,3,4-tetrahydro-isoquinolin-4-yl)-phenyl]-3-(tetrahydro-pyran-4-yl)-urea;
145) 3-[3-(6,8-Dichloro-2-methyl-1,2,3,4-tetrahydro-isoquinolin-4-yl)-phenyl]-1-methyl-1-(1-methyl-piperidin-4-yl)-urea;
146) 3-[3-(6,8-Dichloro-2-methyl-1,2,3,4-tetrahydro-isoquinolin-4-yl)-phenyl]-1-(3-dimethylamino-propyl)-1-methyl-urea;
147) 3-[3-(6,8-Dichloro-2-methyl-1,2,3,4-tetrahydro-isoquinolin-4-yl)-phenyl]-1-(2-dimethylamino-ethyl)-1-methyl-urea;
148) 1-[3-(6,8-Dichloro-2-methyl-1,2,3,4-tetrahydro-isoquinolin-4-yl)-phenyl]-3-(3-dimethylamino-propyl)-urea;
149) 1-[3-(6,8-Dichloro-2-methyl-1,2,3,4-tetrahydro-isoquinolin-4-yl)-phenyl]-3-(2-methoxy-ethyl)-urea;
150) 1-[3-(6,8-Dichloro-2-methyl-1,2,3,4-tetrahydro-isoquinolin-4-yl)-phenyl]-3-pyridin-3-yl-urea;
151) 1-[3-(6,8-Dichloro-2-methyl-1,2,3,4-tetrahydro-isoquinolin-4-yl)-phenyl]-3-pyridin-4-yl-urea;
152) 4-Methyl-piperazine-1-carboxylic acid [2-(6,8-dichloro-2-methyl-1,2,3,4-tetrahydro-isoquinolin-4-yl)-phenyl]-amide;
153) 1-[2-(6,8-Dichloro-2-methyl-1,2,3,4-tetrahydro-isoquinolin-4-yl)-phenyl]-3-methyl-urea;
154) 3-[2-(6,8-Dichloro-2-methyl-1,2,3,4-tetrahydro-isoquinolin-4-yl)-phenyl]-1,1-dimethyl-urea;
155) 3-[2-(6,8-Dichloro-2-methyl-1,2,3,4-tetrahydro-isoquinolin-4-yl)-phenyl]-1,1-diethyl-urea;
156) Piperidine-1-carboxylic acid [2-(6,8-dichloro-2-methyl-1,2,3,4-tetrahydro-isoquinolin-4-yl)-phenyl]-amide;
157) Morpholine-4-carboxylic acid [2-(6,8-dichloro-2-methyl-1,2,3,4-tetrahydro-isoquinolin-4-yl)-phenyl]-amide;
158) Pyrrolidine-1-carboxylic acid [2-(6,8-dichloro-2-methyl-1,2,3,4-tetrahydro-isoquinolin-4-yl)-phenyl]-amide;
159) 1-[2-(6,8-Dichloro-2-methyl-1,2,3,4-tetrahydro-isoquinolin-4-yl)-phenyl]-3-(2-dimethylamino-ethyl)-urea;
160) 4-Methyl-piperazine-1-carboxylic acid [4-(6,8-dichloro-2-methyl-1,2,3,4-tetrahydro-isoquinolin-4-yl)-phenyl]-amide;
161) Pyrrolidine-1-carboxylic acid [4-(6,8-dichloro-2-methyl-1,2,3,4-tetrahydro-isoquinolin-4-yl)-phenyl]-amide;
162) 1-[4-(6,8-Dichloro-2-methyl-1,2,3,4-tetrahydro-isoquinolin-4-yl)-phenyl]-3-methyl-urea;
163) 3-[4-(6,8-Dichloro-2-methyl-1,2,3,4-tetrahydro-isoquinolin-4-yl)-phenyl]-1,1-dimethyl-urea;
164) 3-[4-(6,8-Dichloro-2-methyl-1,2,3,4-tetrahydro-isoquinolin-4-yl)-phenyl]-1,1-diethyl-urea;
165) 1-[4-(6,8-Dichloro-2-methyl-1,2,3,4-tetrahydro-isoquinolin-4-yl)-phenyl]-3-(2-dimethylamino-ethyl)-urea;
166) Piperidine-1-carboxylic acid [4-(6,8-dichloro-2-methyl-1,2,3,4-tetrahydro-isoquinolin-4-yl)-phenyl]-amide;
167) Morpholine-4-carboxylic acid [4-(6,8-dichloro-2-methyl-1,2,3,4-tetrahydro-isoquinolin-4-yl)-phenyl]-amide;
168) N-[4-(6,8-Dichloro-2-methyl-1,2,3,4-tetrahydro-isoquinolin-4-yl)-phenyl]-formamide;
169) [4-(6,8-Dichloro-2-methyl-1,2,3,4-tetrahydro-isoquinolin-4-yl)-phenyl]-methyl-amine;
170) 1-[4-(6,8-Dichloro-2-methyl-1,2,3,4-tetrahydro-isoquinolin-4-yl)-phenyl]-1,3-dimethyl-urea;
171) 4-Methyl-piperazine-1-carboxylic acid [4-(6,8-dichloro-2-methyl-1,2,3,4-tetrahydro-isoquinolin-4-yl)-phenyl]-methyl-amide;
172) 1-[4-(6,8-Dichloro-2-methyl-1,2,3,4-tetrahydro-isoquinolin-4-yl)-phenyl]-1,3,3-trimethyl-urea;
173) Piperidine-1-carboxylic acid [4-(6,8-dichloro-2-methyl-1,2,3,4-tetrahydro-isoquinolin-4-yl)-phenyl]-methyl-amide;
174) Morpholine-4-carboxylic acid [4-(6,8-dichloro-2-methyl-1,2,3,4-tetrahydro-isoquinolin-4-yl)-phenyl]-methyl-amide;
175) Pyrrolidine-1-carboxylic acid [4-(6,8-dichloro-2-methyl-1,2,3,4-tetrahydro-isoquinolin-4-yl)-phenyl]-methyl-amide;
176) 1-[4-(6,8-Dichloro-2-methyl-1,2,3,4-tetrahydro-isoquinolin-4-yl)-phenyl]-3-(2-dimethylamino-ethyl)-1-methyl-urea;
177) 1-[4-(6,8-Dichloro-2-methyl-1,2,3,4-tetrahydro-isoquinolin-4-yl)-phenyl]-3,3-diethyl-1-methyl-urea;
178) N-[3-(6,8-Dichloro-2-methyl-1,2,3,4-tetrahydro-isoquinolin-4-yl)-phenyl]-formamide;
179) [3-(6,8-Dichloro-2-methyl-1,2,3,4-tetrahydro-isoquinolin-4-yl)-phenyl]-methyl-amine;
180) Pyrrolidine-1-carboxylic acid [3-(6,8-dichloro-2-methyl-1,2,3,4-tetrahydro-isoquinolin-4-yl)-phenyl]-methyl-amide;
181) Piperidine-1-carboxylic acid [3-(6,8-dichloro-2-methyl-1,2,3,4-tetrahydro-isoquinolin-4-yl)-phenyl]-methyl-amide;
182) 1-[3-(6,8-Dichloro-2-methyl-1,2,3,4-tetrahydro-isoquinolin-4-yl)-phenyl]-1,3,3-trimethyl-urea;
183) 1-[3-(6,8-Dichloro-2-methyl-1,2,3,4-tetrahydro-isoquinolin-4-yl)-phenyl]-1,3-dimethyl-urea;

184) Morpholine-4-carboxylic acid [3-(6,8-dichloro-2-methyl-1,2,3,4-tetrahydro-isoquinolin-4-yl)-phenyl]-methyl-amide;

185) 4-Methyl-piperazine-1-carboxylic acid [3-(6,8-dichloro-2-methyl-1,2,3,4-tetrahydro-isoquinolin-4-yl)-phenyl]-methyl-amide;

186) 1-[3-(6,8-Dichloro-2-methyl-1,2,3,4-tetrahydro-isoquinolin-4-yl)-phenyl]-3-(2-dimethylamino-ethyl)-1-methyl-urea;

187) 1-[3-(6,8-Dichloro-2-methyl-1,2,3,4-tetrahydro-isoquinolin-4-yl)-phenyl]-3,3-diethyl-1-methyl-urea;

188) [3-(6,8-Dichloro-2-methyl-1,2,3,4-tetrahydro-isoquinolin-4-yl)-phenyl]-carbamic acid 2-dimethylamino-ethyl ester;

189) [4-(6,8-Dichloro-2-methyl-1,2,3,4-tetrahydro-isoquinolin-4-yl)-phenyl]-carbamic acid 2-dimethylamino-ethyl ester;

190) [2-(6,8-Dichloro-2-methyl-1,2,3,4-tetrahydro-isoquinolin-4-yl)-phenyl]-carbamic acid 2-dimethylamino-ethyl ester;

191) [3-(6,8-Dichloro-2-methyl-1,2,3,4-tetrahydro-isoquinolin-4-yl)-phenyl]-carbamic acid methyl ester;

192) [3-(6,8-Dichloro-2-methyl-1,2,3,4-tetrahydro-isoquinolin-4-yl)-phenyl]-carbamic acid ethyl ester;

193) [3-(6,8-Dichloro-2-methyl-1,2,3,4-tetrahydro-isoquinolin-4-yl)-phenyl]-carbamic acid isopropyl ester;

194) [3-(6,8-Dichloro-2-methyl-1,2,3,4-tetrahydro-isoquinolin-4-yl)-phenyl]-carbamic acid 2,2-dimethyl-propyl ester;

195) [4-(6,8-Dichloro-2-methyl-1,2,3,4-tetrahydro-isoquinolin-4-yl)-phenyl]-carbamic acid methyl ester;

196) [4-(6,8-Dichloro-2-methyl-1,2,3,4-tetrahydro-isoquinolin-4-yl)-phenyl]-carbamic acid isopropyl ester;

197) [4-(6,8-Dichloro-2-methyl-1,2,3,4-tetrahydro-isoquinolin-4-yl)-phenyl]-carbamic acid 2,2-dimethyl-propyl ester;

198) [4-(6,8-Dichloro-2-methyl-1,2,3,4-tetrahydro-isoquinolin-4-yl)-phenyl]-carbamic acid ethyl ester;

199) (+)-N-[3-(6,8-Dichloro-2-methyl-1,2,3,4-tetrahydro-isoquinolin-4-yl)-phenyl]-methanesulfonamide;

200) (−)-N-[3-(6,8-Dichloro-2-methyl-1,2,3,4-tetrahydro-isoquinolin-4-yl)-phenyl]-methanesulfonamide;

201) (+)-1-[2-(6,8-Dichloro-2-methyl-1,2,3,4-tetrahydro-isoquinolin-4-yl)-phenyl]-3-ethyl-urea;

202) (−)-1-[2-(6,8-Dichloro-2-methyl-1,2,3,4-tetrahydro-isoquinolin-4-yl)-phenyl]-3-ethyl-urea;

203) N-[3-(6,8-Difluoro-2-methyl-1,2,3,4-tetrahydro-isoquinolin-4-yl)-phenyl]-acetamide;

204) 4-(3-Bromo-phenyl)-6,8-dichloro-2-methyl-1,2,3,4-tetrahydro-isoquinoline;

205) 1-[3-(6,8-Dichloro-2-methyl-1,2,3,4-tetrahydro-isoquinolin-4-yl)-phenyl]-3-(2-hydroxy-ethyl)-urea;

206) 3-(6,8-Dichloro-2-methyl-1,2,3,4-tetrahydro-isoquinolin-4-yl)-benzoic acid ethyl ester;

207) 3-(6,8-Dichloro-2-methyl-1,2,3,4-tetrahydro-isoquinolin-4-yl)-benzoic acid or a pharmaceutically acceptable salt thereof, or a trifluoroacetate thereof in any stereoisomeric form, or a mixture of any such compounds in any ratio.

6. The compound as claimed in claim 1, chosen from:

1) N-[4-(6,8-dichloro-2-methyl-1,2,3,4-tetrahydro-isoquinolin-4-yl)-phenyl]-acetamide;

2) 4-(6,8-dichloro-2-methyl-1,2,3,4-tetrahydro-isoquinolin-4-yl)-benzenesulfonamide;

3) 3-(6,8-dichloro-2-methyl-1,2,3,4-tetrahydro-isoquinolin-4-yl)-benzenesulfonamide;

4) 1-[4-(6,8-dichloro-2-methyl-1,2,3,4-tetrahydro-isoquinolin-4-yl)-phenyl]-3-methyl-thiourea;

5) 1-[4-(6,8-dichloro-2-methyl-1,2,3,4-tetrahydro-isoquinolin-4-yl)-phenyl]-3-ethyl-urea;

6) N-[4-(6-bromo-8-chloro-2-methyl-1,2,3,4-tetrahydro-isoquinolin-4-yl)-phenyl]-acetamide;

7) N-[3-(6,8-dichloro-2-methyl-1,2,3,4-tetrahydro-isoquinolin-4-yl)-phenyl]-acetamide;

8) N-[4-(6,8-dichloro-2-methyl-1,2,3,4-tetrahydro-isoquinolin-4-yl)-phenyl]-propionamide;

9) N-[4-(6,8-dichloro-2-methyl-1,2,3,4-tetrahydro-isoquinolin-4-yl)-phenyl]-1-acetyl-piperidine-4-carboxamide;

10) N-[4-(6,8-dichloro-2-methyl-1,2,3,4-tetrahydro-isoquinolin-4-yl)-phenyl]-methane-sulfonamide;

11) N-[4-(6,8-dichloro-2-methyl-1,2,3,4-tetrahydro-isoquinolin-4-yl)-phenyl]-ethanesulfonamide;

12) N',N'-dimethylamino-N-[4-(6,8-dichloro-2-methyl-1,2,3,4-tetrahydro-isoquinolin-4-yl)-phenyl]-sulfamide;

13) N-[3-(6,8-dichloro-2-methyl-1,2,3,4-tetrahydro-isoquinolin-4-yl)-phenyl]-propionamide;

14) N-[3-(6,8-dichloro-2-methyl-1,2,3,4-tetrahydro-isoquinolin-4-yl)-phenyl]-butyramide;

15) N-[3-(6,8-dichloro-2-methyl-1,2,3,4-tetrahydro-isoquinolin-4-yl)-phenyl]-isobutyramide;

16) N-[3-(6,8-dichloro-2-methyl-1,2,3,4-tetrahydro-isoquinolin-4-yl)-phenyl]-cyclopropanecarboxamide;

17) N-[3-(6,8-dichloro-2-methyl-1,2,3,4-tetrahydro-isoquinolin-4-yl)-phenyl]-cyclobutanecarboxamide;

18) N-[3-(6,8-dichloro-2-methyl-1,2,3,4-tetrahydro-isoquinolin-4-yl)-phenyl]-2,2,2-trifluoro-acetamide;

19) N-[3-(6,8-dichloro-2-methyl-1,2,3,4-tetrahydro-isoquinolin-4-yl)-phenyl]-1-acetyl-piperidine-4-carboxamide;

20) N-[3-(6,8-dichloro-2-methyl-1,2,3,4-tetrahydro-isoquinolin-4-yl)-phenyl]-nicotinamide;

21) N-[3-(6,8-dichloro-2-methyl-1,2,3,4-tetrahydro-isoquinolin-4-yl)-phenyl]-methane-sulfonamide;

22) N-[3-(6,8-dichloro-2-methyl-1,2,3,4-tetrahydro-isoquinolin-4-yl)-phenyl]-ethanesulfonamide;

23) N',N'-dimethylamino-N-[3-(6,8-dichloro-2-methyl-1,2,3,4-tetrahydro-isoquinolin-4-yl)-phenyl]-sulfamide;

24) N-[2-(6,8-dichloro-2-methyl-1,2,3,4-tetrahydro-isoquinolin-4-yl)-phenyl]-cyclopropanecarboxamide;

25) N-[2-(6,8-dichloro-2-methyl-1,2,3,4-tetrahydro-isoquinolin-4-yl)-phenyl]-1-acetyl-piperidine-4-carboxamide;

26) 1-[3-(6,8-dichloro-2-methyl-1,2,3,4-tetrahydro-isoquinolin-4-yl)-phenyl]-3-ethyl-urea;

27) 1-[3-(6,8-dichloro-2-methyl-1,2,3,4-tetrahydro-isoquinolin-4-yl)-phenyl-3-methyl-thiourea;

28) 1-[2-(6,8-dichloro-2-methyl-1,2,3,4-tetrahydro-isoquinolin-4-y)-phenyl]-3-ethyl-urea;

29) 1-[2-(6,8-dichloro-2-methyl-1,2,3,4-tetrahydro-isoquinolin-4-yl)-phenyl]-3-methyl-thiourea;

30) N-{5-[3-(6,8-dichloro-2-methyl-1,2,3,4-tetrahydro-isoquinolin-4-yl)-phenylsulfamoyl]-4-methyl-thiazol-2-yl}-acetamide;

31) N-[3-(6,8-dichloro-2-methyl-1,2,3,4-tetrahydro-isoquinolin-4-yl)-phenyl]-1,2-dimethyl-1H-imidazole-4-sulfonamide;

32) N-[4-(6,8-dichloro-2-methyl-1,2,3,4-tetrahydro-isoquinolin-4-yl)-phenyl]-C,C,C-trifluoro-methanesulfonamide;

33) N-[3-(6,8-dichloro-2-methyl-1,2,3,4-tetrahydro-isoquinolin-4-yl)-phenyl]-C,C,C-trifluoro-methanesulfonamide;

34) N-ethyl-N'-4-(6,8-dichloro-2-methyl-1,2,3,4-tetrahydro-isoquinolin-4-yl)-benzenesulfonylurea;

35) N-[4-(6,8-Dichloro-2-methyl-1,2,3,4-tetrahydro-isoquinolin-4-yl)-phenyl]-2-dimethylamino-acetamide;

36) 2,6-Diamino-hexanoic acid [4-(6,8-dichloro-2-methyl-1,2,3,4-tetrahydro-isoquinolin-4-yl)-phenyl]-amide;

37) 1H-Pyrrole-3-carboxylic acid [4-(6,8-dichloro-2-methyl-1,2,3,4-tetrahydro-isoquinolin-4-yl)-phenyl]-amide;

38) 1-Methyl-piperidine-4-carboxylic acid [4-(6,8-dichloro-2-methyl-1,2,3,4-tetrahydro-isoquinolin-4-yl)-phenyl]-amide;

39) 1-Methanesulfonyl-piperidine-4-carboxylic acid [4-(6,8-dichloro-2-methyl-1,2,3,4-tetrahydro-isoquinolin-4-yl)-phenyl]-amide;

40) 1H-Pyrazole-4-carboxylic acid [4-(6,8-dichloro-2-methyl-1,2,3,4-tetrahydro-isoquinolin-4-yl)-phenyl]-amide;

41) N-[3-(6,8-Dichloro-2-methyl-1,2,3,4-tetrahydro-isoquinolin-4-yl)-phenyl]-2-methylamino-acetamide;

42) N-[3-(6,8-Dichloro-2-methyl-1,2,3,4-tetrahydro-isoquinolin-4-yl)-phenyl]-2-dimethylamino-acetamide;

43) 2-Amino-N-[3-(6,8-dichloro-2-methyl-1,2,3,4-tetrahydro-isoquinolin-4-yl)-phenyl]-propionamide;

44) 2-Amino-N-[3-(6,8-dichloro-2-methyl-1,2,3,4-tetrahydro-isoquinolin-4-yl)-phenyl]-butyramide;

45) 2,6-Diamino-hexanoic acid [3-(6,8-dichloro-2-methyl-1,2,3,4-tetrahydro-isoquinolin-4-yl)-phenyl]-amide;

46) 1-Methyl-piperidine-4-carboxylic acid [3-(6,8-dichloro-2-methyl-1,2,3,4-tetrahydro-isoquinolin-4-yl)-phenyl]-amide;

47) 1H-Imidazole-4-carboxylic acid [3-(6,8-dichloro-2-methyl-1,2,3,4-tetrahydro-isoquinolin-4-yl)-phenyl]-amide;

48) 1-Methanesulfonyl-piperidine-4-carboxylic acid [3-(6,8-dichloro-2-methyl-1,2,3,4-tetrahydro-isoquinolin-4-yl)-phenyl]-amide;

49) 3,5-Dimethyl-1H-pyrazole-4-carboxylic acid [3-(6,8-dichloro-2-methyl-1,2,3,4-tetrahydro-isoquinolin-4-yl)-phenyl]-amide;

50) 1H-Pyrazole-4-carboxylic acid [3-(6,8-dichloro-2-methyl-1,2,3,4-tetrahydro-isoquinolin-4-yl)-phenyl]-amide;

51) 3-[3-(6,8-Dichloro-2-methyl-1,2,3,4-tetrahydro-isoquinolin-4-yl)-phenyl]-1,1-dimethyl-urea;

52) 4-Methyl-piperazine-1-carboxylic acid [3-(6,8-dichloro-2-methyl-1,2,3,4-tetrahydro-isoquinolin-4-yl)-phenyl]-amide;

53) Piperidine-1-carboxylic acid [3-(6,8-dichloro-2-methyl-1,2,3,4-tetrahydro-isoquinolin-4-yl)-phenyl]-amide;

54) Morpholine-4-carboxylic acid [3-(6,8-dichloro-2-methyl-1,2,3,4-tetrahydro-isoquinolin-4-yl)-phenyl]-amide;

55) Pyrrolidine-1-carboxylic acid [3-(6,8-dichloro-2-methyl-1,2,3,4-tetrahydro-isoquinolin-4-yl)-phenyl]-amide;

56) 3-[3-(6,8-Dichloro-2-methyl-1,2,3,4-tetrahydro-isoquinolin-4-yl)-phenyl]-1,1-diethyl-urea;

57) 1-[3-(6,8-Dichloro-2-methyl-1,2,3,4-tetrahydro-isoquinolin-4-yl)-phenyl]-3-methyl-urea;

58) 1-[3-(6,8-Dichloro-2-methyl-1,2,3,4-tetrahydro-isoquinolin-4-yl)-phenyl]-3-(2-dimethylamino-ethyl)-urea;

59) 1-[3-(6,8-Dichloro-2-methyl-1,2,3,4-tetrahydro-isoquinolin-4-yl)-phenyl]-3-(tetrahydro-furan-3-yl)-urea;

60) 1-[3-(6,8-Dichloro-2-methyl-1,2,3,4-tetrahydro-isoquinolin-4-yl)-phenyl]-3-(tetrahydro-pyran-4-yl)-urea;

61) 3-[3-(6,8-Dichloro-2-methyl-1,2,3,4-tetrahydro-isoquinolin-4-yl)-phenyl]-1-methyl-1-(1-methyl-piperidin-4-yl)-urea;

62) 3-[3-(6,8-Dichloro-2-methyl-1,2,3,4-tetrahydro-isoquinolin-4-yl)-phenyl]-1-(3-dimethylamino-propyl)-1-methyl-urea;

63) 3-[3-(6,8-Dichloro-2-methyl-1,2,3,4-tetrahydro-isoquinolin-4-yl)-phenyl]-1-(2-dimethylamino-ethyl)-1-methyl-urea;

64) 1-[3-(6,8-Dichloro-2-methyl-1,2,3,4-tetrahydro-isoquinolin-4-yl)-phenyl]-3-(3-dimethylamino-propyl)-urea;

65) 1-[3-(6,8-Dichloro-2-methyl-1,2,3,4-tetrahydro-isoquinolin-4-yl)-phenyl]-3-(2-methoxy-ethyl)-urea;

66) 1-[3-(6,8-Dichloro-2-methyl-1,2,3,4-tetrahydro-isoquinolin-4-yl)-phenyl]-3-pyridin-3-yl-urea;

67) 1-[3-(6,8-Dichloro-2-methyl-1,2,3,4-tetrahydro-isoquinolin-4-yl)-phenyl]-3-pyridin-4-yl-urea;

68) 4-Methyl-piperazine-1-carboxylic acid [2-(6,8-dichloro-2-methyl-1,2,3,4-tetrahydro-isoquinolin-4-yl)-phenyl]-amide;

69) 1-[2-(6,8-Dichloro-2-methyl-1,2,3,4-tetrahydro-isoquinolin-4-yl)-phenyl]-3-methyl-urea;

70) 1-[2-(6,8-Dichloro-2-methyl-1,2,3,4-tetrahydro-isoquinolin-4-yl)-phenyl]-3-(2-dimethylamino-ethyl)-urea;

71) 4-Methyl-piperazine-1-carboxylic acid [4-(6,8-dichloro-2-methyl-1,2,3,4-tetrahydro-isoquinolin-4-yl)-phenyl]-amide;

72) 1-[4-(6,8-Dichloro-2-methyl-1,2,3,4-tetrahydro-isoquinolin-4-yl)-phenyl]-3-methyl-urea;

73) 3-[4-(6,8-Dichloro-2-methyl-1,2,3,4-tetrahydro-isoquinolin-4-yl)-phenyl]-1,1-dimethyl-urea;

74) 3-[4-(6,8-Dichloro-2-methyl-1,2,3,4-tetrahydro-isoquinolin-4-yl)-phenyl]-1,1-diethyl-urea;

75) 1-[4-(6,8-Dichloro-2-methyl-1,2,3,4-tetrahydro-isoquinolin-4-yl)-phenyl]-3-(2-dimethylamino-ethyl)-urea;

76) Morpholine-4-carboxylic acid [4-(6,8-dichloro-2-methyl-1,2,3,4-tetrahydro-isoquinolin-4-yl)-phenyl]-amide;

77) N-[4-(6,8-Dichloro-2-methyl-1,2,3,4-tetrahydro-isoquinolin-4-yl)-phenyl]-formamide;
78) N-[3-(6,8-Dichloro-2-methyl-1,2,3,4-tetrahydro-isoquinolin-4-yl)-phenyl]-formamide;
79) 1-[3-(6,8-Dichloro-2-methyl-1,2,3,4-tetrahydro-isoquinolin-4-yl)-phenyl]-1,3,3-trimethyl-urea;
80) 1-[3-(6,8-Dichloro-2-methyl-1,2,3,4-tetrahydro-isoquinolin-4-yl)-phenyl]-1,3-dimethyl-urea;
81) Morpholine-4-carboxylic acid [3-(6,8-dichloro-2-methyl-1,2,3,4-tetrahydro-isoquinolin-4-yl)-phenyl]-methyl-amide;
82) 4-Methyl-piperazine-1-carboxylic acid [3-(6,8-dichloro-2-methyl-1,2,3,4-tetrahydro-isoquinolin-4-yl)-phenyl]-methyl-amide;
83) 1-[3-(6,8-Dichloro-2-methyl-1,2,3,4-tetrahydro-isoquinolin-4-yl)-phenyl]-3-(2-dimethylamino-ethyl)-1-methyl-urea;
84) [3-(6,8-Dichloro-2-methyl-1,2,3,4-tetrahydro-isoquinolin-4-yl)-phenyl]-carbamic acid 2-dimethylamino-ethyl ester;
85) [4-(6,8-Dichloro-2-methyl-1,2,3,4-tetrahydro-isoquinolin-4-yl)-phenyl]-carbamic acid 2-dimethylamino-ethyl ester;
86) [2-(6,8-Dichloro-2-methyl-1,2,3,4-tetrahydro-isoquinolin-4-yl)-phenyl]-carbamic acid 2-dimethylamino-ethyl ester;
87) [3-(6,8-Dichloro-2-methyl-1,2,3,4-tetrahydro-isoquinolin-4-yl)-phenyl]-carbamic acid methyl ester;
88) (R or S)-N-[3-(6,8-Dichloro-2-methyl-1,2,3,4-tetrahydro-isoquinolin-4-yl)-phenyl]-methanesulfonamide;
89) (R or S)-1-[2-(6,8-Dichloro-2-methyl-1,2,3,4-tetrahydro-isoquinolin-4-yl)-phenyl]-3-ethyl-urea;
90) 1-[3-(6,8-Dichloro-2-methyl-1,2,3,4-tetrahydro-isoquinolin-4-yl)-phenyl]-3-(2-hydroxy-ethyl)-urea;

or a pharmaceutically acceptable salt thereof, or a trifluoroacetate thereof in any stereoisomeric form, or a mixture of any such compounds in any ratio.

7. A method for the treatment of disorders that can be influenced by inhibition of the sodium-proton exchange of subtype III (NHE3) comprising, administering to a patient in need thereof at least one compound of formula 1

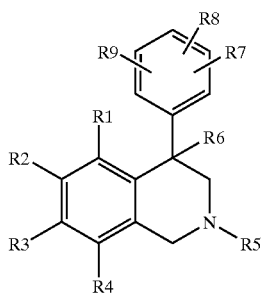

I wherein:
R1, R2, R3 and R4 are independently of one another H, F, Cl, Br, I, CN, $NO_2$, OH, $NH_2$, $C_aH_{2a+1}$, $C_{qq}H_{2qq-1}$, $OC_bH_{2b+1}$, COOR10, OCOR10, COR10 or $O_x$—$(CH_2)_y$-phenyl; wherein
  a and b are independently of one another 1, 2, 3, 4, 5, 6, 7 or 8, wherein the groups $C_aH_{2a+1}$ and $OC_bH_{2b+1}$ independently of one another are unsubstituted or substituted where one or more H atoms are replaced by F atoms;
  qq is 3, 4, 5, 6, 7 or 8, wherein the group $C_{qq}H_{2qq-1}$ is unsubstituted or substituted where one or more H atoms are replaced by F atoms;
  R10 is H or $C_cH_{2c+1}$;
    c is 1, 2, 3, 4, 5, 6, 7 or 8, wherein the group $C_cH_{2c+1}$ is unsubstituted or substituted where one or more H atoms are replaced by F atoms;
  x is zero or 1;
  y is zero, 1, 2, 3 or 4; where the phenyl ring in the group $O_x$-$(CH_2)_y$-phenyl is unsubstituted or substituted by 1-3 independently chosen from F, Cl, Br, CN, $NO_2$, OH, $NH_2$ and $C_dH_{2d+1}$,
    d is 1, 2, 3 or 4, wherein the group $C_dH_{2d+1}$ is unsubstituted or substituted where one or more H atoms are replaced by F atoms;
or
R1, R2, R3 and R4 are independently of one another chosen from a heteroaryl with at least one heteroatom chosen from 1, 2, 3 or 4 N atoms, 1 oxygen atom and 1 S atom, present as ring atoms; or
R1, R2, R3 and R4 are independently of one another CONR11R12 or NR11R12; wherein
  R11 and R12 are independently of one another H, $C_eH_{2e+1}$, $C_{rr}H_{2rr-1}$;
    e is 1, 2, 3, 4, 5, 6, 7 or 8;
    rr is 3, 4, 5, 6, 7, or 8, wherein the groups $C_eH_{2e+1}$ and $C_{rr}H_{2rr-1}$ independently of one another are unsubstituted or substituted where one or more H atoms are replaced by F atoms and/or one or more $CH_2$ groups are replaced by O or NR13;
    R13 is H or $C_fH_{2f+1}$;
      f is 1, 2, 3 or 4, wherein the group $C_fH_{2f+1}$ is unsubsitituted or substituted where one or more H atoms are replaced by F atoms;
  or
    R13 and a $CH_2$ group of R11 or R12 together with the N atom to which they are bonded form a 5- or 6-membered ring;
or
  R11 and R12 together with the N atom to which they are bonded form a 5-, 6- or 7-membered ring; or
  R11 and R12 are independently of one another COR14, CSR14 or $SO_2$R14; wherein
    R14 is $C_gH_{2g+1}$;
      g is 1, 2, 3, 4, 5, 6, 7 or 8, wherein the group $C_gH_{2g+1}$ is unsubsitituted or substituted where one or more H atoms are replaced by F atoms, and/or one or more $CH_2$ groups are replaced by O or NR13;
or
R1, R2, R3 and R4 are independently of one another —$O_h$—$SO_j$-R15, with
  h is zero or 1;
  j is zero, 1 or 2;
  R15 is $C_kH_{2k+1}$, OH, $OC_lH_{2l+1}$ or N R17R18;
    k is 1, 2, 3, 4, 5, 6, 7 or 8, wherein the group $C_kH_{2k+1}$ is unsubsitituted or substituted where one or more H atoms are replaced by F atoms;
    l is 1, 2, 3, 4, 5, 6, 7 or 8, wherein the group $OC_lH_{2l+1}$ is unsubsitituted or substituted where one or more H atoms are replaced by F atoms;
    R17 and R18 are independently of one another H or $C_mH_{2m+1}$;
      m is 1, 2, 3, 4, 5, 6, 7 or 8, wherein the group $C_mH_{2m+1}$ is unsubstituted or substituted where one or more H atoms is replaced by F atoms and/or one or more $CH_2$ groups are replaced by O, CO, CS or NR19;

R19 is H or $C_nH_{2n+1}$;
   n is 1, 2, 3 or 4, wherein the group $C_nH_{2n+1}$ is unsubstituted or substituted where one or more H atoms are replaced by F atoms; or
   R19 and a $CH_2$ group of R17 or R18 together with the N atom to which they are bonded form a 5- or 6-membered ring;
or
R17 and R18 together with the N atom to which they are bonded form a 5-, 6- or 7-membered ring;
R5 is H, $C_pH_{2p+1}$, $C_{ss}H_{2ss-1}$, COR20 or $SO_2R20$; wherein
p is 1, 2, 3, 4, 5, 6, 7 or 8,
ss is 3, 4, 5, 6, 7 or 8,
R20 is $C_qH_{2q+1}$;
   q is 1, 2, 3, 4, 5, 6, 7 or 8, wherein the groups $C_pH_{2p+1}$, $C_{ss}H_{2ss-1}$ and $C_qH_{2q+1}$ independently of one another are unsubstituted or substituted where one or more H atoms are replaced by F atoms and/or one or more $CH_2$ groups are replaced by O or NR21;
   R21 is H or $C_rH_{2r+1}$;
      r is 1, 2, 3 or 4; wherein the group $C_rH_{2r+1}$ is unsubstituted or substituted where one or more H atoms are replaced by F atoms;
R6 is H, F, Cl, Br, I, $C_sH_{2s+1}$, $C_{dd}H_{2dd-1}$, OH, $OC_tH_{2t+1}$ or OCOR22; wherein s and t are independently of one another 1, 2, 3, 4, 5, 6, 7 or 8;
   dd is 3, 4, 5, 6, 7 or 8, wherein the groups $C_sH_{2s+1}$, $C_{dd}H_{2dd-1}$ and $OC_tH_{2t+1}$ independently of one another are unsubstituted or substituted where one or more H atoms are replaced by F atoms;
R22 is $C_uH_{2u+1}$;
   u 1, 2, 3 or 4, wherein the group $C_uH_{2u+1}$ is unsubstituted or substituted where one or more H atoms are replaced by F atoms;
R7, R8 and R9 are independently of one another $—O_v—SO_w-R23$; wherein
v is zero or 1;
w is zero, 1 or 2;
R23 is $C_{nn}H_{2nn+1}$, $C_{mm}H_{2mm-1}$, OH, $OC_{pp}H_{2pp+1}$ or NR25R26;
   nn and pp are independently of one another 1, 2, 3, 4, 5, 6, 7 or 8,
   mm is 3, 4, 5, 6, 7 or 8, wherein the groups $C_{nn}H_{2nn+1}$, $C_{mm}H_{2mm-1}$ and $OC_{pp}H_{2pp+1}$ independently of one another are unsubstituted or substituted where one or more H atoms are replaced by F atoms;
   R25 and R26 are independently of one another H, CN, $C_zH_{2z+1}$, or $C_{zz}H_{2zz-1}$;
   z is 1, 2, 3, 4, 5, 6, 7 or 8;
   zz is 3, 4, 5, 6, 7 or 8, wherein the group $C_zH_{2z+1}$ is unsubstituted or substituted where one or more H atoms are replaced by F atoms and,
      wherein the group $C_zH_{2z+1}$, is unsubstituted or substituted where one or more H atoms are replaced by F atoms and/or one or more $CH_2$ groups are replaced by O, CO, CS or NR27;
      R27 is H or $C_{aa}H_{2aa+1}$;
         aa is 1, 2, 3 or 4, wherein the group $C_{aa}H_{2aa+1}$ is unsubstituted or substituted where one or more H atoms are replaced by F atoms;
      or
      R27 and a $CH_2$ group of R25 or R26 together with the N atom to which they are bonded form a 5- or 6-membered ring;
   or
   R25 and R26 together with the N atom to which they are bonded form a 5-, 6- or 7-membered ring;
or
R7, R8 and R9 are independently of one another NR32COR30, NR32CSR30 or N R32$SO_{bb}$R30;
   R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
   R32 and R33 are independently of one another H or $C_hH_{2h+1}$;
      bb is 2 or 3;
      cc is 1, 2, 3, 4, 5, 6, 7 or 8;
      yy is 3,4,5,6, 7 or 8;
      h is 1, 2, 3,4, 5, 6, 7 or 8,
      wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group are replaced by O;
      R31 is H, $C_{kk}H_{2kk+1}$, COR65 or $SO_2$ R65;
         kk is 1, 2, 3, or 4; wherein the group $C_{kk}H_{2kk+1}$ is unsubstituted or substituted where one or more H atoms are replaced by F atoms,
         R65 is H, or $C_{xx}H_{2xx+1}$;
         xx is 1, 2, 3 or 4, wherein the group $C_{xx}H_{2xx+1}$ is unsubstituted or substituted where one or more H atoms are replaced by F atoms; or
      R31 together with a $CH_2$ group of R30 forms a 5-, 6- or 7-membered ring; or
      R30 is a 5- or 6-membered heteroaryl with at least one hetero atom chosen from 1, 2, 3 or 4 N atoms, zero, 1 S atom and 1 O atom,
      which is unsubstituted or substituted by up to three substituents chosen from F, Cl, Br, I, $C_{oo}H_{2oo+1}$, and NR70R71;
      R70 and R71 are independently of one another H, $C_{uu}H_{2uu+1}$ or COR72;
      R72 is H, or $C_{vv}H_{2vv+1}$;
      oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;
or
R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42,
   ee and ff are independently of one another 1, 2, 3, 4, 5, 6, 7 or 8;
   ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
   R40 and R41 are independently of one another H, $C_{tt}H_{2tt+1}$ or C(NH)$NH_2$;
   tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;
   R44 is H or $C_{gg}H_{2gg+1}$;
      gg is 1, 2, 3, 4, 5, 6, 7 or 8, wherein the group $C_{gg}H_{2gg+1}$ is unnsubstituted or substituted where one or more H atoms are replaced by F atoms or R44 forms a 5- or 6-membered ring together with a ($CH_2$) group of R40 or R41 and the N atom to which they are bound;

or

R40 and R41 with the N atom to which they form a 5- or 6-membered ring;

R42 is H or $C_{hh}H_{2hh+1}$;

hh is 1, 2, 3, 4, 5, 6, 7 or 8, wherein the group $C_{hh}H_{2hh+1}$ is unnsubstituted or substituted where one or more H atoms are replaced by F atoms;

or a pharmaceutically acceptable salt thereof, in any stereoisomeric form, or a mixture of any such compounds in any ratio.

8. The method of claim 7, wherein:

R1, R2, R3 and R4 are independently of one another, H, F, Cl, Br, I, CN, $NO_2$, OH, $NH_2$, $C_aH_{2a+1}$, cycloalkyl with 3, 4, 5 or 6 C atoms, $OC_bH_{2b+1}$, or COOR1; wherein a and b are independently of one another 1, 2, 3 or 4, wherein the group $C_aH_{2a+1}$ is unsubstituted or substituted where one or more H atoms are replaced by F atoms;

R10 is H or $C_cH_{2c+1}$;

c is 1, 2, 3 or 4, wherein the group $C_cH_{2c+1}$ is unsubstituted or substituted where one or more H atoms are replaced by F atoms; or R1, R2, R3 and R4 are independently of one another a 5- or 6-membered heteroaryl choawn from pyridyl, imidazolyl, pyrazolyl, pyrrolyl, triazolyl, tetrazolyl, thiazolyl and oxazolyl; or R1, R2, R3 and R4 are independently of one another CONR11R12 or NR11R12; wherein R11 and R12 are independently of one another H, $C_eH_{2e+1}$, $C_{rr}H_{2rr+1}$;

e is 1, 2, 3 or 4, rr is 3, 4, 5 or 6, wherein the groups $C_eH_{2e+1}$ and $C_{rr}H_{2rr}$-1 independently of one another are unsubstituted or substituted where one or more H atoms are replaced by F atoms;

or

R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R11 and R12 together with the N atom to which they are bonded form a pyrrolidine, piperidine, N-methylpiperazine, piperazine or morpholine ring; or R11 and R12 are independently of one another COR14, CSR14, CONHR14, CSNHR14 or $SO_2$R14; wherein R14 is $C_gH_{2g+1}$;

g is 1, 2, 3 or 4, wherein the group $C_gH_{2g+1}$ is unsbustituted or substituted where one or more H atoms are replaced by F atoms;

or

R1, R2, R3 and R4 are independently of one another $OSO_3H$, $SO_3H$, $SO_2R_{15}$; wherein R15 is $C_kH_{2k+1}$, $OC_lH_{2l+1}$ or NR17R18;

k is 1, 2, 3 or 4, wherein the group $C_kH_{2k+1}$ is unsubstituted or substituted where one ore more H atoms are replaced by F atoms;

l is 1, 2, 3 or 4, wherein the group $OC_lH_{2l+1}$ is unsubstituted or substituted where one ore more H atoms are replaced by F atoms;

R17 and R18 are independently of one another H, or $C_mH_{2m+1}$, in which the first $CH_2$ group bonded to the nitrogen of NR17R18 is replaced by CO and the second $CH_2$ group is replaced by NR19;

m 1, 2, 3, 4 or 5, wherein the group $C_mH_{2m+1}$ is unsubstituted or substituted where one or more H atoms is replaced by F atoms;

R19 is H or $C_nH_{2n+1}$;

n is 1, 2, 3 or 4, wherein the group $C_nH_{2n+1}$ is unsubstituted or substituted where one or more H atoms is replaced by F atoms;

or

R17 and R18 together with the N atom to which they are bonded form a 5- or 6-membered ring;

R5 is H, $C_pH_{2p+1}$ or $C_{ss}H_{2ss-1}$;

p is 1, 2, 3 or 4, ss is 3, 4, 5 or 6, wherein the groups $C_pH_{2p+1}$ and $C_{ss}H_2$ss-1 independently of one another are unsubstituted or substituted where one or more H atoms is replaced by F atoms;

R6 is H, $C_sH_{2s+1}$, $OC_tH_{2t+1}$ or OCOR22;

s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;

R22 is $C_uH_{2u+1}$;

u is 1, 2, 3 or 4; wherein the group $C_uH_{2u+1}$ is unsubstituted or substituted where one or more H atoms is replaced by F atoms;

R7, R8 and R9 are independently of one another $OSO_3H$, $SO_3H$ or $SO_2R23$; wherein R23 is $C_{nn}H_{2nn+1}$, $C_{mm}H_{2mm-1}$, $OC_{pp}H_{2pp+1}$ or NR25R26;

nn and pp are independently of one another 1, 2, 3, 4 or 5, mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;

R25 and R26 are independently of one another H, CN, or $C_zH_{2z+1}$, in which a first $CH_2$ group bonded to the nitrogen of NR25R26 is replaced by CO or CS and a second $CH_2$ is replaced by NR27;

z is 1, 2, 3, 4, 5 or 6; wherein the group $C_zH_{2z+1}$ is unsubstituted or substituted where one or more H atoms are replaced by F atoms;

R27 is H or $C_{aa}H_{2aa+1}$;

aa is 1, 2, 3 or 4, wherein the group $C_{aa}H_{2aa+}1$ is unsubstituted or substituted where one or more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5- or 6-membered ring;

or

R7, R8 and R9 are independently of one another NR32COR30, NR32CSR30 or $NR32SO_2R30$; wherein R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;

cc is 1, 2, 3, 4, 5, 6, 7 or 8;

yy is 3,4, 5 or 6;

h is 1, 2, 3 or 4; wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups to be replaced by NR31 and/or one $CH_2$ group to be replaced by O;

R31 is H, $C_{kk}H_{2kk+1}$, COR65 or $SO_2$ R65;

kk is 1, 2, 3, or 4, wherein the group $C_{kk}H_{2kk+1}$ is unsubstituted or substituted where one or more H atoms are replaced by F atoms, R65 is H, or $C_{xx}H_{2xx+1}$;

xx is 1, 2, 3 or 4, wherein the group $C_{xx}H_{2xx+1}$ is unsubstituted where one or more H atoms are replaced by F atoms;

or

R31 together with a $CH_2$ group of R30 and the N atom to which they are jointly bonded form form a 5- or 6-membered ring;

or

R30 is a 5- or 6-membered heteroaryl chosen from pyridyl, imidazolyl, pyrazolyl, pyrrolyl, triazolyl, tetrazolyl, thienyl, thiazolyl and oxazolyl, which is unsubstituted or substituted by up to three substituents chosen from F, Cl, Br, I, $C_{oo}H_{2oo+1}$, and NR70R71, R70 and R71 are independently of one another H, $C_{uu}H_{2uu+1}$ or COR72;

R72 is H, or $C_{vv}H_{2vv+1}$;

oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;

or

R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;

ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are independently of one another H, $C_{tt}H_{2tt+1}$, or $C(NH)NH_2$;

tt is 1, 2, 3, 4, 5, 6, 7 or 8, wherein the group $C_{tt}H_{2tt+1}$ is unsubstituted or substituted where one or more H atoms are replaced by F atoms;

or

R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl; or R40 and R41 together with the N atom to which they are bonded form a ring chosen from pyrrolidine, piperidine, N-methylpiperazine, piperazine and morpholine;

R42 is H or $C_{hh}H_{2hh+1}$;

hh is 1, 2, 3 or 4, wherein the group $C_{hh}H_{2hh+1}$ is unsubstituted or substituted where one or more H atoms are replaced by F atoms;

or a pharmaceutically acceptable salt thereof, in any stereoisomeric form, or a mixture of any such compounds in any ratio.

9. The method of claim 7, wherein:

R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein a and b are independently of one another 1, 2, 3 or 4, wherein the groups $C_aH_{2a+1}$ and $OC_bH_{2b+1}$ independenly of one another are unsubstituted or substituted where one or more H atoms are replaced by F atoms;

or

R1, R2, R3 and R4 are independently of one another NR11R12;

R11 and R12 are independently of one another H, $C_eH_{2e+1}$, or $C_{rr}H_{2rr-1}$;

e is 1, 2, 3 or 4, rr is 3, 4, 5 or 6, wherein the groups $C_eH_{2e+1}$ and $C_{rr}H_{2rr-1}$ independenly of one another are unsubtituted or substituted where one or more H atoms are replaced by F atoms;

or

R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or $SO_2R14$; wherein R14 is $C_gH_{2g+1}$;

g is 1, 2, 3 or 4, wherein the group $C_gH_{2g+1}$ is unsubstituted or substituted where one or more H atoms are replaced by F atoms;

or

R1, R2, R3 and R4 are independently of one another $OSO_3H$, $SO_3H$, or $SO_2R15$;

R15 is $C_kH_{2k+1}$ or NR17R18;

k is 1, 2, 3 or 4, wherein the group $C_kH_{2k+1}$ is unsubstituted or substituted where one or more H atoms are replaced by F atoms;

R17 and R18 are independently of one another H or $C_mH_{2m+1}$;

m is 1, 2, 3, 4 or 5, wherein the group $C_mH_{2m+1}$ is unsubstituted or substituted where one ore more H atoms are replaced by F atoms;

or

R17 and R18 together with the N atom to which they are bonded form a 5- or 6-membered ring;

but where R2 does not equal H in any of the foregoing definitions;

R5 is methyl or trifluoromethyl;

R6 is H;

R7, R8 and R9 are independently of one another $OSO_3H$, $SO_3H$ or $SO_2R23$; wherein R23 is $C_{nn}H_{2nn+1}$ or NR25R26;

nn is 1, 2, 3, 4 or 5, wherein the group $C_{nn}H_{2nn+1}$ is unsubstituted or substituted where one ore more H atoms are replaced by F atoms;

R25 and R26 are independently of one another H, CN or $C_zH_{2z+1}$ in which a first $CH_2$ group bonded to the nitrogen of NR25R26 is replaced by CO or CS and a second $CH_2$ is replaced by NR27;

z is 1, 2, 3, 4, 5 or 6, wherein the group $C_zH_{2z+1}$ is unsubstituted or substituted where one ore more H atoms are replaced by F atoms;

R27 is H or $C_{aa}H_{2aa+1}$;

aa is 1, 2, 3 or 4, wherein the group $C_{aa}H_{2aa+1}$ is unsubstituted or substituted where one ore more H atoms are replaced by F atoms; or R27 and a $CH_2$ group of R25 or R26 together with the N atom to which they are bonded form a 5- or 6-membered ring;

or
R25 and R26 together with the N atom to which they are bonded form a 5- or 6-membered ring, or R7, R8 and R9 are independently of one another NR32COR30, NR32CSR30 or NR32SO$_2$R30;

R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a CH$_2$ group is replaced by O or NR33;
R32 and R33 are H, methyl or CF$_3$;
cc is 1, 2, 3,4, 5, 6, 7 or 8;
yy is 3,4, 5 or 6;
wherein the groups $C_{cc}H_{2cc+1}$ and $C_{yy}H_{2yy-1}$ independently of one another are unsubstituted or substituted where one or more H atoms are replaced by F atoms and/or one or more CH$_2$ groups are replaced by NR31 and/or one CH$_2$ group is replaced by O
R31 is H, methyl, ethyl, CF$_3$, CH$_2$CF$_3$, acetyl or propionyl, methanesulfonyl or ethanesulfonyl; or
R31 together with a CH$_2$ group of R30 and the N atom to which they are jointly bonded form a 5- or 6-membered ring;

or

R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, NH$_2$, and NHacetyl;

or

R7, R8 and R9 are independently of one another H, F, Cl, OH, NH$_2$, $C_{ee}H_{2ee+1}$, $C_{ww}H_{2ww-1}$, $OC_{ff}H_{2ff+1}$, NR40R41, CONR40R41, COOR42 or OCOR42,
ee and ff are independently of one another 1, 2, 3 or 4;
ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are H, $C_{tt}H_{2tt+1}$ or C(NH)NH$_2$;
tt is 1, 2, 3 or 4, wherein the group $C_{tt}H_{2tt+1}$ is unsubstituted or substituted where one or more H atoms are replaced by F atoms;

or

R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
R40 and R41 together with the N atom to which they are bonded form a pyrrolidine, piperidine, N-methylpiperazine, piperazine or morpholine ring;
R42 is H or $C_{hh}H_{2hh+1}$;
hh is 1, 2, 3 or 4, wherein the $C_{hh}H_{2hh+1}$ is unsubstituted or substituted where one or more H atoms are replaced by F atoms;

or a pharmaceutically acceptable salt thereof, in any stereoisomeric form, or a mixture of any such compounds in any ratio.

10. The method of claim 7, wherein the compound is chosen from:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-N,N-dimethyl-benzenesulfonamide;
5) 4-(4-bromo-phenyl)-6,8-dichloro-2-methyl-1,2,3,4-tetrahydroisoquinoline;
6) 4-(6,8-dichloro-2-methyl-1,2,3,4-tetrahydro-isoquinolin-4-yl)-benzoic acid;
7) 4-(6,8-dichloro-2-methyl-1,2,3,4-tetrahydroisoquinolin-4-yl)-N-ethyl-benzamide;
8) 4-(6,8-dichloro-2-methyl-1,2,3,4-tetrahydroisoquinolin-4-yl)-N-propyl-benzamide;
9) 4-(6,8-dichloro-2-methyl-1,2,3,4-tetrahydro-isoquinolin-4-yl)-N-(2-dimethylamino-ethyl)-benzamide;
10) 6,8-dichloro-2-methyl-4-(4-morpholin-4-yl-phenyl)-1,2,3,4-tetrahydroisoquinoline;
11) [4-(6,8-dichloro-2-methyl-1,2,3,4-tetrahydroisoquinolin-4-yl)-phenyl]-diethyl-amine
12) 6,8-dichloro-2-methyl-4-(4-piperidin-1-yl-phenyl)-1,2,3,4-tetrahydroisoquinoline;
13) 6,8-dichloro-2-methyl-4-(4-pyrrolidin-1-yl-phenyl)-1,2,3,4-tetrahydroisoquinoline;
14) 6,8-dichloro-2-methyl-4-[4-(4-methyl-piperazin-1-yl)-phenyl]-1,2,3,4-tetrahydroisoquinoline;
15) 6,8-dichloro-2-cyclopropyl-4-phenyl-1,2,3,4-tetrahydroisoquinoline;
16) 4-(6,8-dichloro-2-methyl-1,2,3,4-tetrahydro-isoquinolin-4-yl)-phenylamine;
17) 1-[4-(6,8-dichloro-2-methyl-1,2,3,4-tetrahydro-isoquinolin-4-yl)-phenyl]-3-propylurea;
18) 1-[4-(6,8-dichloro-2-methyl-1,2,3,4-tetrahydro-isoquinolin-4-yl)-phenyl]-3-methyl-thiourea;
19) 1-[4-(6,8-dichloro-2-methyl-1,2,3,4-tetrahydro-isoquinolin-4-yl)-phenyl]-3-ethyl-urea;
20) N-[4-(6-methanesulfonyl-2-methyl-1,2,3,4-tetrahydro-isoquinolin-4-yl)-phenyl]-acetamide;
21) N-[4-(2,6,8-trimethyl-1,2,3,4-tetrahydro-isoquinolin-4-yl)-phenyl]-acetamide;
22) N-[4-(6-bromo-8-chloro-2-methyl-1,2,3,4-tetrahydro-isoquinolin-4-yl)-phenyl]-acetamide;
23) N-[4-(8-chloro-2-methyl-6-pyrrolidin-1-yl-1,2,3,4-tetrahydro-isoquinolin-4-yl)-phenyl]-acetamide;
24) N-[4-(8-chloro-2-methyl-6-morpholin-4-yl-1,2,3,4-tetrahydro-isoquinolin-4-yl)-phenyl]-acetamide;
25) N-{4-[8-chloro-2-methyl-6-(4-methyl-piperazin-1-yl)-1,2,3,4-tetrahydro-isoquinolin-4-yl]-phenyl}-acetamide;
26) N-{4-[8-chloro-6-(cyclopropylmethyl-amino)-2-methyl-1,2,3,4-tetrahydro-isoquinolin-4-yl]-phenyl}-acetamide;
27) 5-(6,8-dichloro-2-methyl-1,2,3,4-tetrahydro-isoquinolin-4-yl)-2-hydroxy-benzoic acid;
28) 5-(6,8-dichloro-2-methyl-1,2,3,4-tetrahydro-isoquinolin-4-yl)-2-hydroxy-N-methyl-benzamide;
29) 5-(6,8-dichloro-2-methyl-1,2,3,4-tetrahydro-isoquinolin-4-yl)-N-ethyl-2-hydroxy-benzamide;
30) 5-(6,8-dichloro-2-methyl-1,2,3,4-tetrahydro-isoquinolin-4-yl)-N-(2-dimethylamino-ethyl)-2-hydroxy-benzamide;
31) N-[5-(6,8-dichloro-2-methyl-1,2,3,4-tetrahydro-isoquinolin-4-yl)-2-hydroxy-benzoyl]-guanidine;
32) N-[3-(6,8-dichloro-2-methyl-1,2,3,4-tetrahydro-isoquinolin-4-yl)-phenyl]-acetamide;

33) 3-(6,8-dichloro-2-methyl-1,2,3,4-tetrahydro-isoquinolin-4-yl)-phenylamine;
34) 2-(6,8-dichloro-2-methyl-1,2,3,4-tetrahydro-isoquinolin-4-yl)-phenylamine;
35) N-[4-(6,8-dichloro-2-methyl-1,2,3,4-tetrahydro-isoquinolin-4-yl)-phenyl]-propionamide;
36) N-[4-(6,8-dichloro-2-methyl-1,2,3,4-tetrahydro-isoquinolin-4-yl)-phenyl]-butyramide;
37) N-[4-(6,8-dichloro-2-methyl-1,2,3,4-tetrahydro-isoquinolin-4-yl)-phenyl]pentanamide;
38) N-[4-(6,8-dichloro-2-methyl-1,2,3,4-tetrahydro-isoquinolin-4-yl)-phenyl]-isobutyramide;
39) N-[4-(6,8-dichloro-2-methyl-1,2,3,4-tetrahydro-isoquinolin-4-yl)-phenyl]-2,2-dimethyl-propionamide;
40) N-[4-(6,8-dichloro-2-methyl-1,2,3,4-tetrahydro-isoquinolin-4-yl)-phenyl]-cyclopropanecarboxamide;
41) N-[4-(6,8-dichloro-2-methyl-1,2,3,4-tetrahydro-isoquinolin-4-yl)-phenyl]-cyclobutanecarboxamide;
42) N-[4-(6,8-dichloro-2-methyl-1,2,3,4-tetrahydro-isoquinolin-4-yl)-phenyl]-cyclopentanecarboxamide;
43) N-[4-(6,8-dichloro-2-methyl-1,2,3,4-tetrahydro-isoquinolin-4-yl)-phenyl]-2,2,2-trifluoro-acetamide;
44) N-[4-(6,8-dichloro-2-methyl-1,2,3,4-tetrahydro-isoquinolin-4-yl)-phenyl]-1-acetylpiperidine-4-carboxamide;
45) N-[4-(6,8-dichloro-2-methyl-1,2,3,4-tetrahydro-isoquinolin-4-yl)-phenyl]-nicotinamide;
46) N-[4-(6,8-dichloro-2-methyl-1,2,3,4-tetrahydro-isoquinolin-4-yl)-phenyl]-methanesulfonamide;
47) N-[4-(6,8-dichloro-2-methyl-1,2,3,4-tetrahydro-isoquinolin-4-yl)-phenyl]-ethanesulfonamide;
48) N',N'-dimethylamino-N-[4-(6,8-dichloro-2-methyl-1,2,3,4-tetrahydro-isoquinolin-4-yl)-phenyl]-sulfamide;
49) N-[3-(6,8-dichloro-2-methyl-1,2,3,4-tetrahydro-isoquinolin-4-yl)-phenyl]-propionamide;
50) N-[3-(6,8-dichloro-2-methyl-1,2,3,4-tetrahydro-isoquinolin-4-yl)-phenyl]-butyramide;
51) N-[3-(6,8-dichloro-2-methyl-1,2,3,4-tetrahydro-isoquinolin-4-yl)-phenyl]-pentanamide;
52) N-[3-(6,8-dichloro-2-methyl-1,2,3,4-tetrahydro-isoquinolin-4-yl)-phenyl]-isobutyramide;
53) N-[3-(6,8-dichloro-2-methyl-1,2,3,4-tetrahydro-isoquinolin-4-yl)-phenyl]-2,2-dimethyl-propionamide;
54) N-[3-(6,8-dichloro-2-methyl-1,2,3,4-tetrahydro-isoquinolin-4-yl)-phenyl]-cyclopropanecarboxamide;
55) N-[3-(6,8-dichloro-2-methyl-1,2,3,4-tetrahydro-isoquinolin-4-yl)-phenyl]-cyclobutanecarboxamide;
56) N-[3-(6,8-dichloro-2-methyl-1,2,3,4-tetrahydro-isoquinolin-4-yl)-phenyl]-cyclopentanecarboxamide;
57) N-[3-(6,8-dichloro-2-methyl-1,2,3,4-tetrahydro-isoquinolin-4-yl)-phenyl]-2,2,2-trifluoro-acetamide;
58) N-[3-(6,8-dichloro-2-methyl-1,2,3,4-tetrahydro-isoquinolin-4-yl)-phenyl]-1-acetylpiperidine-4-carboxamide;
59) N-[3-(6,8-dichloro-2-methyl-1,2,3,4-tetrahydro-isoquinolin-4-yl)-phenyl]-nicotinamide;
60) N-[3-(6,8-dichloro-2-methyl-1,2,3,4-tetrahydro-isoquinolin-4-yl)-phenyl]-methanesulfonamide;
61) N-[3-(6,8-dichloro-2-methyl-1,2,3,4-tetrahydro-isoquinolin-4-yl)-phenyl]-ethanesulfonamide;
62) N',N'-dimethylamino-N-[3-(6,8-dichloro-2-methyl-1,2,3,4-tetrahydro-isoquinolin-4-yl)-phenyl]-sulfamide;
63) N-[2-(6,8-dichloro-2-methyl-1,2,3,4-tetrahydro-isoquinolin-4-yl)-phenyl]-propionamide;
64) N-[2-(6,8-dichloro-2-methyl-1,2,3,4-tetrahydro-isoquinolin-4-yl)-phenyl]-butyramide;
65) N-[2-(6,8-dichloro-2-methyl-1,2,3,4-tetrahydro-isoquinolin-4-yl)-phenyl]-pentanamide;
66) N-[2-(6,8-dichloro-2-methyl-1,2,3,4-tetrahydro-isoquinolin-4-yl)-phenyl]-isobutyramide;
67) N-[2-(6,8-dichloro-2-methyl-1,2,3,4-tetrahydro-isoquinolin-4-yl)-phenyl]-2,2-dimethyl-propionamide;
68) N-[2-(6,8-dichloro-2-methyl-1,2,3,4-tetrahydro-isoquinolin-4-yl)-phenyl]-cyclopropanecarboxamide;
69) N-[2-(6,8-dichloro-2-methyl-1,2,3,4-tetrahydro-isoquinolin-4-yl)-phenyl]-cyclobutanecarboxamide;
70) N-[2-(6,8-dichloro-2-methyl-1,2,3,4-tetrahydro-isoquinolin-4-yl)-phenyl]-cyclopentanecarboxamide;
71) N-[2-(6,8-dichloro-2-methyl-1,2,3,4-tetrahydro-isoquinolin-4-yl)-phenyl]-2,2,2-trifluoro-acetamide;
72) N-[2-(6,8-dichloro-2-methyl-1,2,3,4-tetrahydro-isoquinolin-4-yl)-phenyl]-1-acetylpiperidine-4-carboxamide;
73) N-[2-(6,8-Dichloro-2-methyl-1,2,3,4-tetrahydro-isoquinolin-4-yl)-phenyl]-methanesulfonamide;
74) N-[2-(6,8-dichloro-2-methyl-1,2,3,4-tetrahydro-isoquinolin-4-yl)-phenyl]-ethanesulfonamide;
75) N',N'-dimethylamino-N-[2-(6,8-dichloro-2-methyl-1,2,3,4-tetrahydro-isoquinolin-4-yl)-phenyl]-sulfamide;
76) 1-[3-(6,8-dichloro-2-methyl-1,2,3,4-tetrahydro-isoquinolin-4-yl)-phenyl]-3-ethyl-urea;
77) 1-[3-(6,8-dichloro-2-methyl-1,2,3,4-tetrahydro-isoquinolin-4-yl)-phenyl]-3-methyl-thiourea;
78) 1-[2-(6,8-dichloro-2-methyl-1,2,3,4-tetrahydro-isoquinolin-4-yl)-phenyl]-3-ethyl-urea;
79) 1-[2-(6,8-dichloro-2-methyl-1,2,3,4-tetrahydro-isoquinolin-4-yl)-phenyl]-3-methyl-thiourea;
80) N-{5-[4-(6,8-dichloro-2-methyl-1,2,3,4-tetrahydro-isoquinolin-4-yl)-phenylsulfamoyl]-4-methyl-thiazol-2-yl}-acetamide;
81) N-{5-[3-(6,8-dichloro-2-methyl-1,2,3,4-tetrahydro-isoquinolin-4-yl)-phenylsulfamoyl]-4-methyl-thiazol-2-yl}-acetamide;
82) N-[4-(6,8-dichloro-2-methyl-1,2,3,4-tetrahydro-isoquinolin-4-yl)-phenyl]-1,2-dimethyl-1H-imidazole-4-sulfonamide;
83) N-[3-(6,8-dichloro-2-methyl-1,2,3,4-tetrahydro-isoquinolin-4-yl)-phenyl]-1,2-dimethyl-1H-imidazole-4-sulfonamide;
84) N-[4-(6,8-dichloro-2-methyl-1,2,3,4-tetrahydro-isoquinolin-4-yl)-phenyl]-5-chloro-1,3-dimethyl-1H-pyrazole-4-sulfonamide;
85) N-[3-(6,8-dichloro-2-methyl-1,2,3,4-tetrahydro-isoquinolin-4-yl)-phenyl]-5-chloro-1,3-dimethyl-1H-pyrazole-4-sulfonamide;
86) N-[4-(6,8-dichloro-2-methyl-1,2,3,4-tetrahydro-isoquinolin-4-yl)-phenyl]-5-bromo-thiophene-2-sulfonamide;
87) N-[3-(6,8-dichloro-2-methyl-1,2,3,4-tetrahydro-isoquinolin-4-yl)-phenyl]-5-bromo-thiophene-2-sulfonamide;
88) N-[4-(6,8-dichloro-2-methyl-1,2,3,4-tetrahydro-isoquinolin-4-yl)-phenyl]-C,C,C-trifluoro-methanesulfonamide;

89) N-[3-(6,8-dichloro-2-methyl-1,2,3,4-tetrahydro-isoquinolin-4-yl)-phenyl]-C,C,C-trifluoro-methanesulfonamide;
90) 4-(6,8-dichloro-2-methyl-1,2,3,4-tetrahydro-isoquinolin-4-yl)-phenyl]-2,2,2-trifluoroethanesulfonamide;
91) 3-(6,8-dichloro-2-methyl-1,2,3,4-tetrahydro-isoquinolin-4-yl)-phenyl]-2,2,2-trifluoroethanesulfonamide;
92) N-ethyl-N'-4-(6,8-Dichloro-2-methyl-1,2,3,4-tetrahydro-isoquinolin-4-yl)-benzenesulfonylurea;
93) 2-chloro-5-(6,8-dichloro-2-methyl-1,2,3,4-tetrahydro-isoquinolin-4-yl)-benzenesulfonamide;
94) 2-methyl-4-phenyl-1,2,3,4-tetrahydro-isoquinolin-8-ylamine;
95) 6,8-dichloro-2-methyl-4-phenyl-1,2,3,4-tetrahydro-isoquinoline;
96) 4-(8-amino-2-methyl-1,2,3,4-tetrahydro-isoquinolin-4-yl)-phenol;
97) 8-methoxy-2-methyl-4-phenyl-1,2,3,4-tetrahydro-isoquinoline;
98) 2-(8-amino-2-ethyl-1,2,3,4-tetrahydro-isoquinolin-4-yl)-phenol;
99) 2-(8-amino-2-methyl-1,2,3,4-tetrahydro-isoquinolin-4-yl)-phenol;
100) 5-(8-amino-2-methyl-1,2,3,4-tetrahydro-isoquinolin-4-yl)-2-methoxy-phenol;
101) 2-methyl-8-nitro-4-phenyl-1,2,3,4-tetrahydro-isoquinoline;
102) 4-(8-amino-2-methyl-1,2,3,4-tetrahydro-isoquinolin-4-yl)-benzene-1,2-diol;
103) 2,8-dimethyl-4-phenyl-1,2,3,4-tetrahydro-isoquinoline;
104) 4-(3,4-dichloro-phenyl)-2-methyl-1,2,3,4-tetrahydro-isoquinoline;
105) 4-(3,4-dichloro-phenyl)-2-methyl-1,2,3,4-tetrahydro-isoquinolin-8-ylamine;
106) 4-(2,4-dichloro-phenyl)-2-methyl-1,2,3,4-tetrahydro-isoquinolin-8-ylamine;
107) 4-(3-chloro-phenyl)-2-methyl-1,2,3,4-tetrahydro-isoquinolin-8-ylamine;
108) 2,4-dimethyl-4-phenyl-1,2,3,4-tetrahydro-isoquinoline;
109) 2-butyl-4-phenyl-1,2,3,4-tetrahydro-isoquinolin-8-ylamine;
110) N-(2-methyl-4-phenyl-1,2,3,4-tetrahydro-isoquinolin-8-yl)-acetamide;
111) 7-chloro-2-methyl-4-phenyl-1,2,3,4-tetrahydro-isoquinoline;
112) 8-chloro-2-methyl-4-phenyl-1,2,3,4-tetrahydro-isoquinoline;
113) 2,6-dimethyl-4-phenyl-1,2,3,4-tetrahydro-isoquinoline;
114) 6-chloro-2-methyl-4-phenyl-1,2,3,4-tetrahydro-isoquinoline;
115) 6-methoxy-2-methyl-4-phenyl-1,2,3,4-tetrahydro-isoquinoline;
116) 2-ethyl-4-phenyl-1,2,3,4-tetrahydro-isoquinoline;
117) 2-methyl-4-phenyl-1,2,3,4-tetrahydro-isoquinoline;
118) 6,8-dichloro-2-ethyl-4-phenyl-1,2,3,4-tetrahydro-isoquinoline;
119) 4-(4-bromo-phenyl)-6,8-dichloro-2-methyl-1,2,3,4-tetrahydro-isoquinoline;
120) 2-methyl-4-phenyl-6,8-bis-trifluoromethyl-1,2,3,4-tetrahydro-isoquinoline;
121) 6,8-dichloro-2-isopropyl-4-phenyl-1,2,3,4-tetrahydro-isoquinoline;
122) 5,8-dichloro-2-methyl-4-phenyl-1,2,3,4-tetrahydro-isoquinoline;
123) 6,8-dichloro-4-(4-fluoro-phenyl)-2-methyl-1,2,3,4-tetrahydro-isoquinoline;
124) 6,8-Dichloro-2-methyl-4-p-tolyl-1,2,3,4-tetrahydro-isoquinoline;
125) 5,6-dichloro-2-methyl-4-phenyl-1,2,3,4-tetrahydro-isoquinoline;
126) 6,7-dichloro-2-methyl-4-phenyl-1,2,3,4-tetrahydro-isoquinoline;
127) 8-bromo-2-methyl-4-phenyl-1,2,3,4-tetrahydro-isoquinoline;
128) 6,8-dichloro-4-(4-chloro-phenyl)-2-methyl-1,2,3,4-tetrahydro-isoquinoline;
129) 6,8-dichloro-2-cyclopropyl-4-phenyl-1,2,3,4-tetrahydro-isoquinoline;
130) 2-Amino-N-[4-(6,8-dichloro-2-methyl-1,2,3,4-tetrahydro-isoquinolin-4-yl)-phenyl]-acetamide;
131) N-[4-(6,8-Dichloro-2-methyl-1,2,3,4-tetrahydro-isoquinolin-4-yl)-phenyl]-2-methylamino-acetamide;
132) N-[4-(6,8-Dichloro-2-methyl-1,2,3,4-tetrahydro-isoquinolin-4-yl)-phenyl]-2-dimethylamino-acetamide;
133) 2-Amino-N-[4-(6,8-dichloro-2-methyl-1,2,3,4-tetrahydro-isoquinolin-4-yl)-phenyl]-propionamide;
134) 2-Amino-N-[4-(6,8-dichloro-2-methyl-1,2,3,4-tetrahydro-isoquinolin-4-yl)-phenyl]-butyramide;
135) 2,6-Diamino-hexanoic acid [4-(6,8-dichloro-2-methyl-1,2,3,4-tetrahydro-isoquinolin-4-yl)-phenyl]-amide;
136) Pyrrolidine-2-carboxylic acid [4-(6,8-dichloro-2-methyl-1,2,3,4-tetrahydro-isoquinolin-4-yl)-phenyl]-amide;
137) N-[4-(6,8-Dichloro-2-methyl-1,2,3,4-tetrahydro-isoquinolin-4-yl)-phenyl]-isonicotinamide;
138) 1H-Pyrrole-3-carboxylic acid [4-(6,8-dichloro-2-methyl-1,2,3,4-tetrahydro-isoquinolin-4-yl)-phenyl]-amide;
139) 1H-Pyrrole-2-carboxylic acid [4-(6,8-dichloro-2-methyl-1,2,3,4-tetrahydro-isoquinolin-4-yl)-phenyl]-amide;
140) 1-Methyl-piperidine-4-carboxylic acid [4-(6,8-dichloro-2-methyl-1,2,3,4-tetrahydro-isoquinolin-4-yl)-phenyl]-amide;
141) 1,4-Dimethyl-1H-pyrrole-2-carboxylic acid [4-(6,8-dichloro-2-methyl-1,2,3,4-tetrahydro-isoquinolin-4-yl)-phenyl]-amide;
142) 4-Nitro-1H-pyrrole-2-carboxylic acid [4-(6,8-dichloro-2-methyl-1,2,3,4-tetrahydro-isoquinolin-4-yl)-phenyl]-amide;
143) 2,5-Dimethyl-1H-pyrrole-3-carboxylic acid [4-(6,8-dichloro-2-methyl-1,2,3,4-tetrahydro-isoquinolin-4-yl)-phenyl]-amide;
144) 1H-Imidazole-4-carboxylic acid [4-(6,8-dichloro-2-methyl-1,2,3,4-tetrahydro-isoquinolin-4-yl)-phenyl]-amide;
145) 1-Methanesulfonyl-piperidine-4-carboxylic acid [4-(6,8-dichloro-2-methyl-1,2,3,4-tetrahydro-isoquinolin-4-yl)-phenyl]-amide;

146) 3,5-Dimethyl-1H-pyrazole-4-carboxylic acid [4-(6,8-dichloro-2-methyl-1,2,3,4-tetrahydro-isoquinolin-4-yl)-phenyl]-amide;

147) 1H-Pyrazole-4-carboxylic acid [4-(6,8-dichloro-2-methyl-1,2,3,4-tetrahydro-isoquinolin-4-yl)-phenyl]-amide;

148) 3-Trifluoromethyl-1H-pyrazole-4-carboxylic acid [4-(6,8-dichloro-2-methyl-1,2,3,4-tetrahydro-isoquinolin-4-yl)-phenyl]-amide;

149) N-[3-(6,8-Dichloro-2-methyl-1,2,3,4-tetrahydro-isoquinolin-4-yl)-phenyl]-2-methylamino-acetamide;

150) N-[3-(6,8-Dichloro-2-methyl-1,2,3,4-tetrahydro-isoquinolin-4-yl)-phenyl]-2-dimethylamino-acetamide;

151) 2-Amino-N-[3-(6,8-dichloro-2-methyl-1,2,3,4-tetrahydro-isoquinolin-4-yl)-phenyl]-propionamide;

152) 2-Amino-N-[3-(6,8-dichloro-2-methyl-1,2,3,4-tetrahydro-isoquinolin-4-yl)-phenyl]-butyramide;

153) 2,6-Diamino-hexanoic acid [3-(6,8-dichloro-2-methyl-1,2,3,4-tetrahydro-isoquinolin-4-yl)-phenyl]-amide;

154) Pyrrolidine-2-carboxylic acid [3-(6,8-dichloro-2-methyl-1,2,3,4-tetrahydro-isoquinolin-4-yl)-phenyl]-amide;

155) N-[3-(6,8-Dichloro-2-methyl-1,2,3,4-tetrahydro-isoquinolin-4-yl)-phenyl]-isonicotinamide;

156) 1H-Pyrrole-3-carboxylic acid [3-(6,8-dichloro-2-methyl-1,2,3,4-tetrahydro-isoquinolin-4-yl)-phenyl]-amide;

157) 1H-Pyrrole-2-carboxylic acid [3-(6,8-dichloro-2-methyl-1,2,3,4-tetrahydro-isoquinolin-4-yl)-phenyl]-amide;

158) 1-Methyl-piperidine-4-carboxylic acid [3-(6,8-dichloro-2-methyl-1,2,3,4-tetrahydro-isoquinolin-4-yl)-phenyl]-amide;

159) 1,4-Dimethyl-1H-pyrrole-2-carboxylic acid [3-(6,8-dichloro-2-methyl-1,2,3,4-tetrahydro-isoquinolin-4-yl)-phenyl]-amide;

160) 4-Nitro-1H-pyrrole-2-carboxylic acid [3-(6,8-dichloro-2-methyl-1,2,3,4-tetrahydro-isoquinolin-4-yl)-phenyl]-amide;

161) 2,5-Dimethyl-1H-pyrrole-3-carboxylic acid [3-(6,8-dichloro-2-methyl-1,2,3,4-tetrahydro-isoquinolin-4-yl)-phenyl]-amide;

162) 1H-Imidazole-4-carboxylic acid [3-(6,8-dichloro-2-methyl-1,2,3,4-tetrahydro-isoquinolin-4-yl)-phenyl]-amide;

163) 1-Methanesulfonyl-piperidine-4-carboxylic acid [3-(6,8-dichloro-2-methyl-1,2,3,4-tetrahydro-isoquinolin-4-yl)-phenyl]-amide;

164) 3,5-Dimethyl-1H-pyrazole-4-carboxylic acid [3-(6,8-dichloro-2-methyl-1,2,3,4-tetrahydro-isoquinolin-4-yl)-phenyl]-amide;

165) 1H-Pyrazole-4-carboxylic acid [3-(6,8-dichloro-2-methyl-1,2,3,4-tetrahydro-isoquinolin-4-yl)-phenyl]-amide;

166) 3-Trifluoromethyl-1H-pyrazole-4-carboxylic acid [3-(6,8-dichloro-2-methyl-1,2,3,4-tetrahydro-isoquinolin-4-yl)-phenyl]-amide;

167) 1-[2-(6,8-Dichloro-2-methyl-1,2,3,4-tetrahydro-isoquinolin-4-yl)-phenyl]-3-ethyl-thiourea;

168) 1-[4-(6,8-Dichloro-2-methyl-1,2,3,4-tetrahydro-isoquinolin-4-yl)-phenyl]-3-ethyl-thiourea;

169) 1-[3-(6,8-Dichloro-2-methyl-1,2,3,4-tetrahydro-isoquinolin-4-yl)-phenyl]-3-ethyl-thiourea;

170) 3-[3-(6,8-Dichloro-2-methyl-1,2,3,4-tetrahydro-isoquinolin-4-yl)-phenyl]-1,1-dimethyl-urea;

171) 4-Methyl-piperazine-1-carboxylic acid [3-(6,8-dichloro-2-methyl-1,2,3,4-tetrahydro-isoquinolin-4-yl)-phenyl]-amide;

172) Piperidine-1-carboxylic acid [3-(6,8-dichloro-2-methyl-1,2,3,4-tetrahydro-isoquinolin-4-yl)-phenyl]-amide;

173) Morpholine-4-carboxylic acid [3-(6,8-dichloro-2-methyl-1,2,3,4-tetrahydro-isoquinolin-4-yl)-phenyl]-amide;

174) Pyrrolidine-1-carboxylic acid [3-(6,8-dichloro-2-methyl-1,2,3,4-tetrahydro-isoquinolin-4-yl)-phenyl]-amide;

175) 3-[3-(6,8-Dichloro-2-methyl-1,2,3,4-tetrahydro-isoquinolin-4-yl)-phenyl]-1,1-diethyl-urea;

176) 1-[3-(6,8-Dichloro-2-methyl-1,2,3,4-tetrahydro-isoquinolin-4-yl)-phenyl]-3-methyl-urea;

177) 1-[3-(6,8-Dichloro-2-methyl-1,2,3,4-tetrahydro-isoquinolin-4-yl)-phenyl]-3-(2-dimethylamino-ethyl)-urea;

178) 1-[3-(6,8-Dichloro-2-methyl-1,2,3,4-tetrahydro-isoquinolin-4-yl)-phenyl]-3-(tetrahydro-furan-3-yl)-urea;

179) 1-[3-(6,8-Dichloro-2-methyl-1,2,3,4-tetrahydro-isoquinolin-4-yl)-phenyl]-3-(tetrahydro-pyran-4-yl)-urea;

180) 3-[3-(6,8-Dichloro-2-methyl-1,2,3,4-tetrahydro-isoquinolin-4-yl)-phenyl]-1-methyl-1-(1-methyl-piperidin-4-yl)-urea;

181) 3-[3-(6,8-Dichloro-2-methyl-1,2,3,4-tetrahydro-isoquinolin-4-yl)-phenyl]-1-(3-dimethylamino-propyl)-1-methyl-urea;

182) 3-[3-(6,8-Dichloro-2-methyl-1,2,3,4-tetrahydro-isoquinolin-4-yl)-phenyl]-1-(2-dimethylamino-ethyl)-1-methyl-urea;

183) 1-[3-(6,8-Dichloro-2-methyl-1,2,3,4-tetrahydro-isoquinolin-4-yl)-phenyl]-3-(3-dimethylamino-propyl)-urea;

184) 1-[3-(6,8-Dichloro-2-methyl-1,2,3,4-tetrahydro-isoquinolin-4-yl)-phenyl]-3-(2-methoxy-ethyl)-urea;

185) 1-[3-(6,8-Dichloro-2-methyl-1,2,3,4-tetrahydro-isoquinolin-4-yl)-phenyl]-3-pyridin-3-yl-urea;

186) 1-[3-(6,8-Dichloro-2-methyl-1,2,3,4-tetrahydro-isoquinolin-4-yl)-phenyl]-3-pyridin-4-yl-urea;

187) 4-Methyl-piperazine-1-carboxylic acid [2-(6,8-dichloro-2-methyl-1,2,3,4-tetrahydro-isoquinolin-4-yl)-phenyl]-amide;

188) 1-[2-(6,8-Dichloro-2-methyl-1,2,3,4-tetrahydro-isoquinolin-4-yl)-phenyl]-3-methyl-urea;

189) 3-[2-(6,8-Dichloro-2-methyl-1,2,3,4-tetrahydro-isoquinolin-4-yl)-phenyl]-1,1-dimethyl-urea;

190) 3-[2-(6,8-Dichloro-2-methyl-1,2,3,4-tetrahydro-isoquinolin-4-yl)-phenyl]-1,1-diethyl-urea;

191) Piperidine-1-carboxylic acid [2-(6,8-dichloro-2-methyl-1,2,3,4-tetrahydro-isoquinolin-4-yl)-phenyl]-amide;

192) Morpholine-4-carboxylic acid [2-(6,8-dichloro-2-methyl-1,2,3,4-tetrahydro-isoquinolin-4-yl)-phenyl]-amide;

193) Pyrrolidine-1-carboxylic acid [2-(6,8-dichloro-2-methyl-1,2,3,4-tetrahydro-isoquinolin-4-yl)-phenyl]-amide;

194) 1-[2-(6,8-Dichloro-2-methyl-1,2,3,4-tetrahydro-isoquinolin-4-yl)-phenyl]-3-(2-dimethylamino-ethyl)-urea;
195) 4-Methyl-piperazine-1-carboxylic acid [4-(6,8-dichloro-2-methyl-1,2,3,4-tetrahydro-isoquinolin-4-yl)-phenyl]-amide;
196) Pyrrolidine-1-carboxylic acid [4-(6,8-dichloro-2-methyl-1,2,3,4-tetrahydro-isoquinolin-4-yl)-phenyl]-amide;
197) 1-[4-(6,8-Dichloro-2-methyl-1,2,3,4-tetrahydro-isoquinolin-4-yl)-phenyl]-3-methyl-urea;
198) 3-[4-(6,8-Dichloro-2-methyl-1,2,3,4-tetrahydro-isoquinolin-4-yl)-phenyl]-1,1-dimethyl-urea;
199) 3-[4-(6,8-Dichloro-2-methyl-1,2,3,4-tetrahydro-isoquinolin-4-yl)-phenyl]-1,1-diethyl-urea;
200) 1-[4-(6,8-Dichloro-2-methyl-1,2,3,4-tetrahydro-isoquinolin-4-yl)-phenyl]-3-(2-dimethylamino-ethyl)-urea;
201) Piperidine-1-carboxylic acid [4-(6,8-dichloro-2-methyl-1,2,3,4-tetrahydro-isoquinolin-4-yl)-phenyl]-amide;
202) Morpholine-4-carboxylic acid [4-(6,8-dichloro-2-methyl-1,2,3,4-tetrahydro-isoquinolin-4-yl)-phenyl]-amide;
203) N-[4-(6,8-Dichloro-2-methyl-1,2,3,4-tetrahydro-isoquinolin-4-yl)-phenyl]-formamide;
204) [4-(6,8-Dichloro-2-methyl-1,2,3,4-tetrahydro-isoquinolin-4-yl)-phenyl]-methyl-amine;
205) 1-[4-(6,8-Dichloro-2-methyl-1,2,3,4-tetrahydro-isoquinolin-4-yl)-phenyl]-1,3-dimethyl-urea;
206) 4-Methyl-piperazine-1-carboxylic acid [4-(6,8-dichloro-2-methyl-1,2,3,4-tetrahydro-isoquinolin-4-yl)-phenyl]-methyl-amide;
207) 1-[4-(6,8-Dichloro-2-methyl-1,2,3,4-tetrahydro-isoquinolin-4-yl)-phenyl]-1,3,3-trimethyl-urea;
208) Piperidine-1-carboxylic acid [4-(6,8-dichloro-2-methyl-1,2,3,4-tetrahydro-isoquinolin-4-yl)-phenyl]-methyl-amide;
209) Morpholine-4-carboxylic acid [4-(6,8-dichloro-2-methyl-1,2,3,4-tetrahydro-isoquinolin-4-yl)-phenyl]-methyl-amide;
210) Pyrrolidine-1-carboxylic acid [4-(6,8-dichloro-2-methyl-1,2,3,4-tetrahydro-isoquinolin-4-yl)-phenyl]-methyl-amide;
211) 1-[4-(6,8-Dichloro-2-methyl-1,2,3,4-tetrahydro-isoquinolin-4-yl)-phenyl]-3-(2-dimethylamino-ethyl)-1-methyl-urea;
212) 1-[4-(6,8-Dichloro-2-methyl-1,2,3,4-tetrahydro-isoquinolin-4-yl)-phenyl]-3,3-diethyl-1-methyl-urea;
213) N-[3-(6,8-Dichloro-2-methyl-1,2,3,4-tetrahydro-isoquinolin-4-yl)-phenyl]-formamide;
214) [3-(6,8-Dichloro-2-methyl-1,2,3,4-tetrahydro-isoquinolin-4-yl)-phenyl]-methyl-amine;
215) Pyrrolidine-1-carboxylic acid [3-(6,8-dichloro-2-methyl-1,2,3,4-tetrahydro-isoquinolin-4-yl)-phenyl]-methyl-amide;
216) Piperidine-1-carboxylic acid [3-(6,8-dichloro-2-methyl-1,2,3,4-tetrahydro-isoquinolin-4-yl)-phenyl]-methyl-amide;
217) 1-[3-(6,8-Dichloro-2-methyl-1,2,3,4-tetrahydro-isoquinolin-4-yl)-phenyl]-1,3,3-trimethyl-urea;
218) 1-[3-(6,8-Dichloro-2-methyl-1,2,3,4-tetrahydro-isoquinolin-4-yl)-phenyl]-1,3-dimethyl-urea;
219) Morpholine-4-carboxylic acid [3-(6,8-dichloro-2-methyl-1,2,3,4-tetrahydro-isoquinolin-4-yl)-phenyl]-methyl-amide;
220) 4-Methyl-piperazine-1-carboxylic acid [3-(6,8-dichloro-2-methyl-1,2,3,4-tetrahydro-isoquinolin-4-yl)-phenyl]-methyl-amide;
221) 1-[3-(6,8-Dichloro-2-methyl-1,2,3,4-tetrahydro-isoquinolin-4-yl)-phenyl]-3-(2-dimethylamino-ethyl)-1-methyl-urea;
222) 1-[3-(6,8-Dichloro-2-methyl-1,2,3,4-tetrahydro-isoquinolin-4-yl)-phenyl]-3,3-diethyl-1-methyl-urea;
223) [3-(6,8-Dichloro-2-methyl-1,2,3,4-tetrahydro-isoquinolin-4-yl)-phenyl]-carbamic acid 2-dimethylamino-ethyl ester;
224) [4-(6,8-Dichloro-2-methyl-1,2,3,4-tetrahydro-isoquinolin-4-yl)-phenyl]-carbamic acid 2-dimethylamino-ethyl ester;
225) [2-(6,8-Dichloro-2-methyl-1,2,3,4-tetrahydro-isoquinolin-4-yl)-phenyl]-carbamic acid 2-dimethylamino-ethyl ester;
226) [3-(6,8-Dichloro-2-methyl-1,2,3,4-tetrahydro-isoquinolin-4-yl)-phenyl]-carbamic acid methyl ester;
227) [3-(6,8-Dichloro-2-methyl-1,2,3,4-tetrahydro-isoquinolin-4-yl)-phenyl]-carbamic acid ethyl ester;
228) [3-(6,8-Dichloro-2-methyl-1,2,3,4-tetrahydro-isoquinolin-4-yl)-phenyl]-carbamic acid isopropyl ester;
229) [3-(6,8-Dichloro-2-methyl-1,2,3,4-tetrahydro-isoquinolin-4-yl)-phenyl]-carbamic acid 2,2-dimethyl-propyl ester;
230) [4-(6,8-Dichloro-2-methyl-1,2,3,4-tetrahydro-isoquinolin-4-yl)-phenyl]-carbamic acid methyl ester;
231) [4-(6,8-Dichloro-2-methyl-1,2,3,4-tetrahydro-isoquinolin-4-yl)-phenyl]-carbamic acid isopropyl ester;
232) [4-(6,8-Dichloro-2-methyl-1,2,3,4-tetrahydro-isoquinolin-4-yl)-phenyl]-carbamic acid 2,2-dimethyl-propyl ester;
233) [4-(6,8-Dichloro-2-methyl-1,2,3,4-tetrahydro-isoquinolin-4-yl)-phenyl]-carbamic acid ethyl ester;
234) (+)-N-[3-(6,8-Dichloro-2-methyl-1,2,3,4-tetrahydro-isoquinolin-4-yl)-phenyl]-methanesulfonamide;
235) (−)-N-[3-(6,8-Dichloro-2-methyl-1,2,3,4-tetrahydro-isoquinolin-4-yl)-phenyl]-methanesulfonamide;
236) (+)-1-[2-(6,8-Dichloro-2-methyl-1,2,3,4-tetrahydro-isoquinolin-4-yl)-phenyl]-3-ethyl-urea;
237) (−)-1-[2-(6,8-Dichloro-2-methyl-1,2,3,4-tetrahydro-isoquinolin-4-yl)-phenyl]-3-ethyl-urea;
238) N-[3-(6,8-Difluoro-2-methyl-1,2,3,4-tetrahydro-isoquinolin-4-yl)-phenyl]-acetamide;
239) 4-(3-Bromo-phenyl)-6,8-dichloro-2-methyl-1,2,3,4-tetrahydro-isoquinoline;
240) 1-[3-(6,8-Dichloro-2-methyl-1,2,3,4-tetrahydro-isoquinolin-4-yl)-phenyl]-3-(2-hydroxy-ethyl)-urea;
241) 3-(6,8-Dichloro-2-methyl-1,2,3,4-tetrahydro-isoquinolin-4-yl)-benzoic acid ethyl ester;
242) 3-(6,8-Dichloro-2-methyl-1,2,3,4-tetrahydro-isoquinolin-4-yl)-benzoic acid;

or a pharmaceutically acceptable salt thereof, in any stereoisomeric form, or a mixture of any such compounds in any ratio.

11. The method of claim 7, wherein the compound is chosen from:

1) N-[4-(6,8-dichloro-2-methyl-1,2,3,4-tetrahydro-isoquinolin-4-yl)-phenyl]-acetamide;
2) 4-(6,8-dichloro-2-methyl-1,2,3,4-tetrahydro-isoquinolin-4-yl)-benzenesulfonamide;
3) 3-(6,8-dichloro-2-methyl-1,2,3,4-tetrahydro-isoquinolin-4-yl)-benzenesulfonamide;
4) 4-(6,8-dichloro-2-methyl-1,2,3,4-tetrahydro-isoquinolin-4-yl)-benzoic acid;
5) 4-(6,8-dichloro-2-methyl-1,2,3,4-tetrahydroisoquinolin-4-yl)-N-ethyl-benzamide;
6) 4-(6,8-dichloro-2-methyl-1,2,3,4-tetrahydroisoquinolin-4-yl)-N-propyl-benzamide;
7) 4-(6,8-dichloro-2-methyl-1,2,3,4-tetrahydro-isoquinolin-4-yl)-N-(2-dimethylamino-ethyl)-benzamide;
8) 6,8-dichloro-2-methyl-4-(4-morpholin-4-yl-phenyl)-1,2,3,4-tetrahydroisoquinoline;
9) 4-(6,8-dichloro-2-methyl-1,2,3,4-tetrahydro-isoquinolin-4-yl)-phenylamine;
10) 1-[4-(6,8-dichloro-2-methyl-1,2,3,4-tetrahydro-isoquinolin-4-yl)-phenyl]-3-methyl-thiourea;
11) 1-[4-(6,8-dichloro-2-methyl-1,2,3,4-tetrahydro-isoquinolin-4-yl)-phenyl]-3-ethyl-urea;
12) N-[4-(6-bromo-8-chloro-2-methyl-1,2,3,4-tetrahydro-isoquinolin-4-yl)-phenyl]-acetamide;
13) 5-(6,8-dichloro-2-methyl-1,2,3,4-tetrahydro-isoquinolin-4-yl)-2-hydroxy-benzoic acid;
14) 5-(6,8-dichloro-2-methyl-1,2,3,4-tetrahydro-isoquinolin-4-yl)-N-(2-dimethylamino-ethyl)-2-hydroxy-benzamide;
15) N-[3-(6,8-dichloro-2-methyl-1,2,3,4-tetrahydro-isoquinolin-4-yl)-phenyl]-acetamide;
16) 3-(6,8-dichloro-2-methyl-1,2,3,4-tetrahydro-isoquinolin-4-yl)-phenylamine;
17) 2-(6,8-dichloro-2-methyl-1,2,3,4-tetrahydro-isoquinolin-4-yl)-phenylamine;
18) N-[4-(6,8-dichloro-2-methyl-1,2,3,4-tetrahydro-isoquinolin-4-yl)-phenyl]-propionamide;
19) N-[4-(6,8-dichloro-2-methyl-1,2,3,4-tetrahydro-isoquinolin-4-yl)-phenyl]-1-acetyl-piperidine-4-carboxamide;
20) N-[4-(6,8-dichloro-2-methyl-1,2,3,4-tetrahydro-isoquinolin-4-yl)-phenyl]-methanesulfonamide;
21) N-[4-(6,8-dichloro-2-methyl-1,2,3,4-tetrahydro-isoquinolin-4-yl)-phenyl]-ethanesulfonamide;
22) N',N'-dimethylamino-N-[4-(6,8-dichloro-2-methyl-1,2,3,4-tetrahydro-isoquinolin-4-yl)-phenyl]-sulfamide;
23) N-[3-(6,8-dichloro-2-methyl-1,2,3,4-tetrahydro-isoquinolin-4-yl)-phenyl]-propionamide;
24) N-[3-(6,8-dichloro-2-methyl-1,2,3,4-tetrahydro-isoquinolin-4-yl)-phenyl]-butyramide;
25) N-[3-(6,8-dichloro-2-methyl-1,2,3,4-tetrahydro-isoquinolin-4-yl)-phenyl]-isobutyramide;
26) N-[3-(6,8-dichloro-2-methyl-1,2,3,4-tetrahydro-isoquinolin-4-yl)-phenyl]-cyclopropanecarboxamide;
27) N-[3-(6,8-dichloro-2-methyl-1,2,3,4-tetrahydro-isoquinolin-4-yl)-phenyl]-cyclobutanecarboxamide;
28) N-[3-(6,8-dichloro-2-methyl-1,2,3,4-tetrahydro-isoquinolin-4-yl)-phenyl]-2,2,2-trifluoro-acetamide;
29) N-[3-(6,8-dichloro-2-methyl-1,2,3,4-tetrahydro-isoquinolin-4-yl)-phenyl]-1-acetyl-piperidine-4-carboxamide;
30) N-[3-(6,8-dichloro-2-methyl-1,2,3,4-tetrahydro-isoquinolin-4-yl)-phenyl]-nicotinamide;
31) N-[3-(6,8-dichloro-2-methyl-1,2,3,4-tetrahydro-isoquinolin-4-yl)-phenyl]-methanesulfonamide;
32) N-[3-(6,8-dichloro-2-methyl-1,2,3,4-tetrahydro-isoquinolin-4-yl)-phenyl]-ethanesulfonamide;
33) N',N'-dimethylamino-N-[3-(6,8-dichloro-2-methyl-1,2,3,4-tetrahydro-isoquinolin-4-yl)-phenyl]-sulfamide;
34) N-[2-(6,8-dichloro-2-methyl-1,2,3,4-tetrahydro-isoquinolin-4-yl)-phenyl]-cyclopropanecarboxamide;
35) N-[2-(6,8-dichloro-2-methyl-1,2,3,4-tetrahydro-isoquinolin-4-yl)-phenyl]-1-acetyl-piperidine-4-carboxamide;
36) 1-[3-(6,8-dichloro-2-methyl-1,2,3,4-tetrahydro-isoquinolin-4-yl)-phenyl]-3-ethyl-urea;
37) 1-[3-(6,8-dichloro-2-methyl-1,2,3,4-tetrahydro-isoquinolin-4-yl)-phenyl]-3-methyl-thiourea;
38) 1-[2-(6,8-dichloro-2-methyl-1,2,3,4-tetrahydro-isoquinolin-4-yl)-phenyl]-3-ethyl-urea;
39) 1-[2-(6,8-dichloro-2-methyl-1,2,3,4-tetrahydro-isoquinolin-4-yl)-phenyl]-3-methyl-thiourea;
40) N-{5-[3-(6,8-dichloro-2-methyl-1,2,3,4-tetrahydro-isoquinolin-4-yl)-phenylsulfamoyl]-4-methyl-thiazol-2-yl}-acetamide;
41) N-[3-(6,8-dichloro-2-methyl-1,2,3,4-tetrahydro-isoquinolin-4-yl)-phenyl]-1,2-dimethyl-1H-imidazole-4-sulfonamide;
42) N-[4-(6,8-dichloro-2-methyl-1,2,3,4-tetrahydro-isoquinolin-4-yl)-phenyl]-C,C,C-trifluoro-methanesulfonamide;
43) N-[3-(6,8-dichloro-2-methyl-1,2,3,4-tetrahydro-isoquinolin-4-yl)-phenyl]-C,C,C-trifluoro-methanesulfonamide;
44) N-ethyl-N'-4-(6,8-dichloro-2-methyl-1,2,3,4-tetrahydro-isoquinolin-4-yl)-benzenesulfonylurea;
45) N-[4-(6,8-Dichloro-2-methyl-1,2,3,4-tetrahydro-isoquinolin-4-yl)-phenyl]-2-dimethylamino-acetamide;
46) 2,6-Diamino-hexanoic acid [4-(6,8-dichloro-2-methyl-1,2,3,4-tetrahydro-isoquinolin-4-yl)-phenyl]-amide;
47) 1H-Pyrrole-3-carboxylic acid [4-(6,8-dichloro-2-methyl-1,2,3,4-tetrahydro-isoquinolin-4-yl)-phenyl]-amide;
48) 1-Methyl-piperidine-4-carboxylic acid [4-(6,8-dichloro-2-methyl-1,2,3,4-tetrahydro-isoquinolin-4-yl)-phenyl]-amide;
49) 1-Methanesulfonyl-piperidine-4-carboxylic acid [4-(6,8-dichloro-2-methyl-1,2,3,4-tetrahydro-isoquinolin-4-yl)-phenyl]-amide;
50) 1H-Pyrazole-4-carboxylic acid [4-(6,8-dichloro-2-methyl-1,2,3,4-tetrahydro-isoquinolin-4-yl)-phenyl]-amide;
51) N-[3-(6,8-Dichloro-2-methyl-1,2,3,4-tetrahydro-isoquinolin-4-yl)-phenyl]-2-methylamino-acetamide;
52) N-[3-(6,8-Dichloro-2-methyl-1,2,3,4-tetrahydro-isoquinolin-4-yl)-phenyl]-2-dimethylamino-acetamide;
53) 2-Amino-N-[3-(6,8-dichloro-2-methyl-1,2,3,4-tetrahydro-isoquinolin-4-yl)-phenyl]-propionamide;
54) 2-Amino-N-[3-(6,8-dichloro-2-methyl-1,2,3,4-tetrahydro-isoquinolin-4-yl)-phenyl]-butyramide;
55) 2,6-Diamino-hexanoic acid [3-(6,8-dichloro-2-methyl-1,2,3,4-tetrahydro-isoquinolin-4-yl)-phenyl]-amide;

56) 1-Methyl-piperidine-4-carboxylic acid [3-(6,8-dichloro-2-methyl-1,2,3,4-tetrahydro-isoquinolin-4-yl)-phenyl]-amide;
57) 1H-Imidazole-4-carboxylic acid [3-(6,8-dichloro-2-methyl-1,2,3,4-tetrahydro-isoquinolin-4-yl)-phenyl]-amide;
58) 1-Methanesulfonyl-piperidine-4-carboxylic acid [3-(6,8-dichloro-2-methyl-1,2,3,4-tetrahydro-isoquinolin-4-yl)-phenyl]-amide;
59) 3,5-Dimethyl-1H-pyrazole-4-carboxylic acid [3-(6,8-dichloro-2-methyl-1,2,3,4-tetrahydro-isoquinolin-4-yl)-phenyl]-amide;
60) 1H-Pyrazole-4-carboxylic acid [3-(6,8-dichloro-2-methyl-1,2,3,4-tetrahydro-isoquinolin-4-yl)-phenyl]-amide;
61) 3-[3-(6,8-Dichloro-2-methyl-1,2,3,4-tetrahydro-isoquinolin-4-yl)-phenyl]-1,1-dimethyl-urea;
62) 4-Methyl-piperazine-1-carboxylic acid [3-(6,8-dichloro-2-methyl-1,2,3,4-tetrahydro-isoquinolin-4-yl)-phenyl]-amide;
63) Piperidine-1-carboxylic acid [3-(6,8-Dichloro-2-methyl-1,2,3,4-tetrahydro-isoquinolin-4-yl)-phenyl]-amide;
64) Morpholine-4-carboxylic acid [3-(6,8-Dichloro-2-methyl-1,2,3,4-tetrahydro-isoquinolin-4-yl)-phenyl]-amide;
65) Pyrrolidine-1-carboxylic acid [3-(6,8-dichloro-2-methyl-1,2,3,4-tetrahydro-isoquinolin-4-yl)-phenyl]-amide;
66) 3-[3-(6,8-Dichloro-2-methyl-1,2,3,4-tetrahydro-isoquinolin-4-yl)-phenyl]-1,1-diethyl-urea;
67) 1-[3-(6,8-Dichloro-2-methyl-1,2,3,4-tetrahydro-isoquinolin-4-yl)-phenyl]-3-methyl-urea;
68) 1-[3-(6,8-Dichloro-2-methyl-1,2,3,4-tetrahydro-isoquinolin-4-yl)-phenyl]-3-(2-dimethylamino-ethyl)-urea;
69) 1-[3-(6,8-Dichloro-2-methyl-1,2,3,4-tetrahydro-isoquinolin-4-yl)-phenyl]-3-(tetrahydro-furan-3-yl)-urea;
70) 1-[3-(6,8-Dichloro-2-methyl-1,2,3,4-tetrahydro-isoquinolin-4-yl)-phenyl]-3-(tetrahydro-pyran-4-yl)-urea;
71) 3-[3-(6,8-Dichloro-2-methyl-1,2,3,4-tetrahydro-isoquinolin-4-yl)-phenyl]-1-methyl-1-(1-methyl-piperidin-4-yl)-urea;
72) 3-[3-(6,8-Dichloro-2-methyl-1,2,3,4-tetrahydro-isoquinolin-4-yl)-phenyl]-1-(3-dimethylamino-propyl)-1-methyl-urea;
73) 3-[3-(6,8-Dichloro-2-methyl-1,2,3,4-tetrahydro-isoquinolin-4-yl)-phenyl]-1-(2-dimethylamino-ethyl)-1-methyl-urea;
74) 1-[3-(6,8-Dichloro-2-methyl-1,2,3,4-tetrahydro-isoquinolin-4-yl)-phenyl]-3-(3-dimethylamino-propyl)-urea;
75) 1-[3-(6,8-Dichloro-2-methyl-1,2,3,4-tetrahydro-isoquinolin-4-yl)-phenyl]-3-(2-methoxy-ethyl)-urea;
76) 1-[3-(6,8-Dichloro-2-methyl-1,2,3,4-tetrahydro-isoquinolin-4-yl)-phenyl]-3-pyridin-3-yl-urea;
77) 1-[3-(6,8-Dichloro-2-methyl-1,2,3,4-tetrahydro-isoquinolin-4-yl)-phenyl]-3-pyridin-4-yl-urea;
78) 4-Methyl-piperazine-1-carboxylic acid [2-(6,8-dichloro-2-methyl-1,2,3,4-tetrahydro-isoquinolin-4-yl)-phenyl]-amide;
79) 1-[2-(6,8-Dichloro-2-methyl-1,2,3,4-tetrahydro-isoquinolin-4-yl)-phenyl]-3-methyl-urea;
80) 1-[2-(6,8-Dichloro-2-methyl-1,2,3,4-tetrahydro-isoquinolin-4-yl)-phenyl]-3-(2-dimethylamino-ethyl)-urea;
81) 4-Methyl-piperazine-1-carboxylic acid [4-(6,8-dichloro-2-methyl-1,2,3,4-tetrahydro-isoquinolin-4-yl)-phenyl]-amide;
82) 1-[4-(6,8-Dichloro-2-methyl-1,2,3,4-tetrahydro-isoquinolin-4-yl)-phenyl]-3-methyl-urea;
83) 3-[4-(6,8-Dichloro-2-methyl-1,2,3,4-tetrahydro-isoquinolin-4-yl)-phenyl]-1,1-dimethyl-urea;
84) 3-[4-(6,8-Dichloro-2-methyl-1,2,3,4-tetrahydro-isoquinolin-4-yl)-phenyl]-1,1-diethyl-urea;
85) 1-[4-(6,8-Dichloro-2-methyl-1,2,3,4-tetrahydro-isoquinolin-4-yl)-phenyl]-3-(2-dimethylamino-ethyl)-urea;
86) Morpholine-4-carboxylic acid [4-(6,8-dichloro-2-methyl-1,2,3,4-tetrahydro-isoquinolin-4-yl)-phenyl]-amide;
87) N-[4-(6,8-Dichloro-2-methyl-1,2,3,4-tetrahydro-isoquinolin-4-yl)-phenyl]-formamide;
88) [4-(6,8-Dichloro-2-methyl-1,2,3,4-tetrahydro-isoquinolin-4-yl)-phenyl]-methyl-amine;
89) N-[3-(6,8-Dichloro-2-methyl-1,2,3,4-tetrahydro-isoquinolin-4-yl)-phenyl]-formamide;
90) [3-(6,8-Dichloro-2-methyl-1,2,3,4-tetrahydro-isoquinolin-4-yl)-phenyl]-methyl-amine;
91) 1-[3-(6,8-Dichloro-2-methyl-1,2,3,4-tetrahydro-isoquinolin-4-yl)-phenyl]-1,3,3-trimethyl-urea;
92) 1-[3-(6,8-Dichloro-2-methyl-1,2,3,4-tetrahydro-isoquinolin-4-yl)-phenyl]-1,3-dimethyl-urea;
93) Morpholine-4-carboxylic acid [3-(6,8-dichloro-2-methyl-1,2,3,4-tetrahydro-isoquinolin-4-yl)-phenyl]-methyl-amide;
94) 4-Methyl-piperazine-1-carboxylic acid [3-(6,8-dichloro-2-methyl-1,2,3,4-tetrahydro-isoquinolin-4-yl)-phenyl]-methyl-amide;
95) 1-[3-(6,8-Dichloro-2-methyl-1,2,3,4-tetrahydro-isoquinolin-4-yl)-phenyl]-3-(2-dimethylamino-ethyl)-1-methyl-urea;
96) [3-(6,8-Dichloro-2-methyl-1,2,3,4-tetrahydro-isoquinolin-4-yl)-phenyl]-carbamic acid 2-dimethylamino-ethyl ester;
97) [4-(6,8-Dichloro-2-methyl-1,2,3,4-tetrahydro-isoquinolin-4-yl)-phenyl]-carbamic acid 2-dimethylamino-ethyl ester;
98) [2-(6,8-Dichloro-2-methyl-1,2,3,4-tetrahydro-isoquinolin-4-yl)-phenyl]-carbamic acid 2-dimethylamino-ethyl ester;
99) [3-(6,8-Dichloro-2-methyl-1,2,3,4-tetrahydro-isoquinolin-4-yl)-phenyl]-carbamic acid methyl ester;
100) (R or S)-N-[3-(6,8-Dichloro-2-methyl-1,2,3,4-tetrahydro-isoquinolin-4-yl)-phenyl]-methanesulfonamide;
101) (R or S)-1-[2-(6,8-Dichloro-2-methyl-1,2,3,4-tetrahydro-isoquinolin-4-yl)-phenyl]-3-ethyl-urea;
102) 1-[3-(6,8-Dichloro-2-methyl-1,2,3,4-tetrahydro-isoquinolin-4-yl)-phenyl]-3-(2-hydroxy-ethyl)-urea;
103) 3-(6,8-Dichloro-2-methyl-1,2,3,4-tetrahydro-isoquinolin-4-yl)-benzoic acid ethyl-ester;
104) 3-(6,8-Dichloro-2-methyl-1,2,3,4-tetrahydro-isoquinolin-4-yl)-benzoic acid or a pharmaceutically acceptable salt thereof, in any stereoisomeric form, or a mixture of any such compounds in any ratio.

12. The method of claim 7, wherein the disorder is a disorder of respiratory drive.

13. The method of claim 7, wherein the disorder is a sleep-related respiratory disorder.

14. The method of claim 13, wherein the sleep-related respiratory disorder is sleep apneas.

15. The method of claim 7, wherein the disorder is snoring.

16. The method of claim 7, wherein the disorder is acute or chronic renal disorder.

17. The method of claim 16, wherein the acute or chronic renal disorder is acute renal failure or chronic renal failure.

18. The method of claim 7, wherein the disorder is a disorder of intestinal function.

19. The method of claim 7, wherein the disorder is a disorder of biliary function.

20. The method of claim 7, wherein the disorder is a disordes of ischemic states of the peripheral and central nervous system and of stroke.

21. The method of claim 7, wherein the disorder is a disorder of ischemic states of the peripheral organs and limbs.

22. The method of claim 7, wherein the disorder is a state of shock.

23. The method of claim 7, wherein the patient is undergoing a surgical operation or organ transplantations.

24. The method of claim 7, wherein the disorder is a disorder in which cell proliferation represents a primary or secondary cause.

25. The method of claim 7, wherein the disorder is a disorder of lipid metabolism.

26. The method of claim 7, wherein the disorder is an infestation by ectoparasites.

27. A pharmaceutical comprising at least one compound as claimed in claim 1 and at least one pharmaceutical carrier.

28. A method for preserving and storing transplants for surgical interventions comprising: contacting the transplant with at least one compound of formula 1

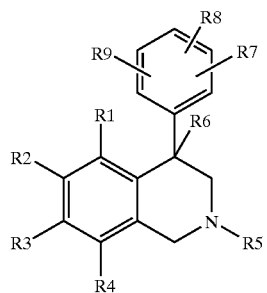

I wherein:
R1, R2, R3 and R4 are independently of one another H, F, Cl, Br, I, CN, $NO_2$, OH, $NH_2$, $C_aH_{2a+1}$, $C_{qq}H_{2qq-1}$, $OC_bH_{2b+1}$, COOR10, OCOR10, COR10 or $O_x$—$(CH_2)_y$-phenyl; wherein
  a and b are independently of one another 1, 2, 3, 4, 5, 6, 7 or 8, wherein the groups $C_aH_{2a+1}$ and $OC_bH_{2b+1}$ independently of one another are unsubstituted or substituted where one or more H atoms are replaced by F atoms;
  qq is 3, 4, 5, 6, 7 or 8, wherein the group $C_{qq}H_{2qq-1}$ is unsubstituted or substituted where one or more H atoms are replaced by F atoms;

R10 is H or $C_cH_{2c+1}$;
  c is 1, 2, 3, 4, 5, 6, 7 or 8, wherein the group $C_cH_{2c+1}$ is unsubstituted or substituted where one or more H atoms are replaced by F atoms;
x is zero or 1;
y is zero, 1, 2, 3 or 4; where the phenyl ring in the group $O_x$—$(CH_2)_y$-phenyl is unsubstituted or substituted by 1-3 independently chosen from F, Cl, Br, CN, $NO_2$, OH, $NH_2$ and $C_dH_{2d+1}$,
  d is 1, 2, 3 or 4, wherein the group $C_dH_{2d+1}$ is unsubstituted or substituted where one or more H atoms are replaced by F atoms;

or
R1, R2, R3 and R4 are independently of one another chosen from a heteroaryl with at least one heteroatom chosen from 1, 2, 3 or 4 N atoms, 1 oxygen atom and 1 S atom, present as ring atoms; or
R1, R2, R3 and R4 are independently of one another CONR11R12 or NR11R12; wherein
  R11 and R12 are independently of one another H, $C_eH_{2e+1}$, $C_{rr}H_{2rr-1}$;
  e is 1, 2, 3, 4, 5, 6, 7 or 8;
  rr is 3, 4, 5, 6, 7, or 8, wherein the groups $C_eH_{2e+1}$ and $C_{rr}H_{2rr-1}$ independently of one another are unsubstituted or substituted where one or more H atoms are replaced by F atoms and/or one or more $CH_2$ groups are replaced by O or NR13;
    R13 is H or $C_fH_{2f+1}$;
      f is 1, 2, 3 or 4, wherein the group $C_fH_{2f+1}$ is unsubsitituted or substituted where one or more H atoms are replaced by F atoms;
    or
    R13 and a $CH_2$ group of R11 or R12 together with the N atom to which they are bonded form a 5- or 6-membered ring;

or
R11 and R12 together with the N atom to which they are bonded form a 5-, 6- or 7-membered ring; or
R11 and R12 are independently of one another COR14, CSR14 or $SO_2R14$; wherein
  R14 is $C_gH_{2g+1}$;
    g is 1, 2, 3, 4, 5, 6, 7 or 8, wherein the group $C_gH_{2g+1}$ is unsubsitituted or substituted where one or more H atoms are replaced by F atoms, and/or one or more $CH_2$ groups are replaced by O or NR13;

or
R1, R2, R3 and R4 are independently of one another —$O_h$—$SO_j$-R15, with
  h is zero or 1;
  j is zero, 1 or 2;
  R15 is $C_kH_{2k+1}$, OH, $OC_lH_{2l+1}$ or NR17R18;
    k is 1, 2, 3, 4, 5, 6, 7 or 8, wherein the group $C_kH_{2k+1}$ is unsubsitituted or substituted where one or more H atoms are replaced by F atoms;
    l is 1, 2, 3, 4, 5, 6, 7 or 8, wherein the group $OC_lH_{2l+1}$ is unsubsitituted or substituted where one or more H atoms are replaced by F atoms;
    R17 and R18 are independently of one another H or $C_mH_{2m+1}$;
      m is 1, 2, 3, 4, 5, 6, 7 or 8, wherein the group $C_mH_{2m+1}$ is unsubstituted or substituted where one or more H atoms is replaced by F atoms and/or one or more $CH_2$ groups are replaced by O, CO, CS or NR19;
        R19 is H or $C_nH_{2n+1}$;
          n is 1, 2, 3 or 4, wherein the group $C_nH_{2n+1}$ is unsubstituted or substituted where one or more H atoms are replaced by F atoms; or R19 and a $CH_2$ group of R17 or R18 together with the N atom to which they are bonded form a 5- or 6-membered ring;

or

R17 and R18 together with the N atom to which they are bonded form a 5-, 6- or 7-membered ring;

R5 is H, $C_pH_{2p+1}$, $C_{ss}H_{2ss-1}$, COR20 or $SO_2R20$; wherein p is 1, 2, 3, 4, 5, 6, 7 or 8, ss is 3, 4, 5, 6, 7 or 8, R20 is $C_qH_{2q+1}$;

q is 1, 2, 3, 4, 5, 6, 7 or 8, wherein the groups $C_pH_{2p+1}$, $C_{ss}H_{2ss-1}$ and $C_qH_{2q+1}$ independently of one another are unsubstituted or substituted where one or more H atoms are replaced by F atoms and/or one or more $CH_2$ groups are replaced by O or NR21;

R21 is H or $C_rH_{2r+1}$;

r is 1, 2, 3 or 4; wherein the group $C_rH_{2r+1}$ is unsubstituted or substituted where one or more H atoms are replaced by F atoms;

R6 is H, F, Cl, Br, I, $C_sH_{2s+1}$, $C_{dd}H_{2dd-1}$, OH, $OC_tH_{2t+1}$ or OCOR22; wherein s and t are independently of one another 1, 2, 3, 4, 5, 6, 7 or 8;

dd is 3, 4, 5, 6, 7 or 8, wherein the groups $C_sH_{2s+1}$, $C_{dd}H_{2dd-1}$ and $OC_tH_{2t+1}$ independently of one another are unsubstituted or substituted where one or more H atoms are replaced by F atoms;

R22 is $C_uH_{2u+1}$;

u 1, 2, 3 or 4, wherein the group $C_uH_{2u+1}$ is unsubstituted or substituted where one or more H atoms are replaced by F atoms;

R7, R8 and R9 are independently of one another —$O_v$—$SO_w$-R23; wherein v is zero or 1;

w is zero, 1 or 2;

R23 is $C_{nn}H_{2nn+1}$, $C_{mm}H_{2mm-1}$, OH, $OC_{pp}H_{2pp+1}$ or NR25R26;

nn and pp are independently of one another 1, 2, 3, 4, 5, 6, 7 or 8, mm is 3, 4, 5, 6, 7 or 8, wherein the groups $C_{nn}H_{2nn+1}$, $C_{mm}H_{2mm}^{-1}$ and $OC_{pp}H_{2pp+1}$ independently of one another are unsubstituted or substituted where one or more H atoms are replaced by F atoms;

R25 and R26 are independently of one another H, CN, $C_zH_{2z+1}$, or $C_{zz}H_{2zz-1}$;

z is 1, 2, 3,4, 5, 6, 7 or 8;

zz is 3, 4, 5, 6, 7 or 8, wherein the group $C_zH_{2z+1}$ is unsubstituted or substituted where one or more H atoms are replaced by F atoms and, wherein the group $C_zH_{2z+1}$, is unsubstituted or substituted where one or more H atoms are replaced by F atoms and/or one or more $CH_2$ groups are replaced by O, CO, CS or NR27;

R27 is H or $C_{aa}H_{2aa+1}$;

aa is 1, 2, 3 or 4, wherein the group $C_{aa}H_{2aa+1}$ is unsubstituted or substituted where one or more H atoms are replaced by F atoms;

or

R27 and a $CH_2$ group of R25 or R26 together with the N atom to which they are bonded form a 5- or 6-membered ring;

or

R25 and R26 together with the N atom to which they are bonded form a 5-, 6- or 7-membered ring;

or

R7, R8 and R9 are independently of one another NR32COR30, NR32CSR30 or $NR32SO_{bb}R30$;

R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;

bb is 2 or 3;

cc is 1, 2, 3, 4, 5, 6, 7 or 8;

yy is 3, 4, 5, 6, 7 or 8;

h is 1, 2, 3, 4, 5, 6, 7 or 8, wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by NR31 and/or one $CH_2$ group are replaced by O;

R31 is H, $C_{kk}H_{2kk+1}$, COR65 or $SO_2$ R65;

kk is 1, 2, 3, or 4; wherein the group $C_{kk}H_{2kk+1}$ is unsubstituted or substituted where one or more H atoms are replaced by F atoms, R65 is H, or $C_{xx}H_{2xx+1}$;

xx is 1, 2, 3 or 4, wherein the group $C_{xx}H_{2xx+1}$ is unsubstituted or substituted where one or more H atoms are replaced by F atoms;

or

R31 together with a $CH_2$ group of R30 forms a 5-, 6- or 7-membered ring;

or

R30 is a 5- or 6-membered heteroaryl with at least one hetero atom chosen from 1, 2, 3 or 4 N atoms, zero, 1 S atom and 1 O atom, which is unsubstituted or substituted by up to three substituents chosen from F, Cl, Br, I, $C_{oo}H_{2oo+1}$, and NR70R71;

R70 and R71 are independently of one another H, $C_{uu}H_{2uu+}1$ or COR72;

R72 is H, or $C_{vv}H_{2vv+1}$;

oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms;

or

R7, R8 and R9 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42, ee and ff are independently of one another 1, 2, 3, 4, 5, 6, 7 or 8;

ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are independently of one another H, $C_{tt}H_{2tt+1}$ or $C(NH)NH_2$;

tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;

R44 is H or $C_{gg}H_{2gg+1}$;

gg is 1, 2, 3, 4, 5, 6, 7 or 8, wherein the group $C_{gg}H_{2gg+1}$ is unnsubstituted or substituted where one or more H atoms are replaced by F atoms or R44 forms a 5- or 6-membered ring together with a (CH$_2$) group of R40 or R41 and the N atom to which they are bound;

or

R40 and R41 with the N atom to which they are bonded form a 5- or 6-membered ring;

R42 is H or $C_{hh}H_{2hh+1}$;

hh is 1, 2, 3, 4, 5, 6, 7 or 8, wherein the group $C_{hh}H_{2hh+1}$ is unnsubstituted or substituted where one or more H atoms are replaced by F atoms;

or a pharmaceutically acceptable salt thereof, in any stereoisomeric form, or a mixture of any such compounds in any ratio.

\* \* \* \* \*